United States Patent
Bailey et al.

(10) Patent No.: US 7,705,146 B2
(45) Date of Patent: Apr. 27, 2010

(54) HEPATITIS C INHIBITOR PEPTIDE ANALOGS

(75) Inventors: Murray D. Bailey, Pierrefonds (CA); Punit Bhardwaj, Laval (CA); Pasquale Forgione, Montreal (CA); Elise Ghiro, Laval (CA); Nathalie Goudreau, St. Laurent (CA); Teddy Halmos, Laval (CA); Montse Llinas-Brunet, Dollard-des-Ormeaux (CA); Marc-Andre Poupart, Laval (CA); Jean Rancourt, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 607 days.

(21) Appl. No.: 10/595,108

(22) PCT Filed: Jun. 22, 2005

(86) PCT No.: PCT/CA2005/000967

§ 371 (c)(1),
(2), (4) Date: Feb. 17, 2006

(87) PCT Pub. No.: WO2006/000085

PCT Pub. Date: Jan. 5, 2006

(65) Prior Publication Data

US 2006/0258868 A1 Nov. 16, 2006

Related U.S. Application Data

(60) Provisional application No. 60/583,543, filed on Jun. 28, 2004.

(51) Int. Cl.
A61K 31/535 (2006.01)
C07D 413/00 (2006.01)
C07D 401/00 (2006.01)

(52) U.S. Cl. .............. 544/141; 514/237.2; 514/253.07; 514/423; 514/312; 514/301; 514/248; 546/155; 546/114; 544/238; 544/363

(58) Field of Classification Search .............. 546/279.1, 546/114, 423, 155; 514/309, 423, 312, 301, 514/248, 237.2, 253.07; 548/536; 544/238, 544/141, 363
See application file for complete search history.

(56) References Cited

U.S. PATENT DOCUMENTS

| | | | |
|---|---|---|---|
| 6,323,180 | B1 | 11/2001 | Bailey et al. |
| 6,869,964 | B2 | 3/2005 | Campbell et al. |
| 7,132,504 | B2 * | 11/2006 | Scola et al. ............ 514/18 |
| 2005/0020503 | A1 * | 1/2005 | Llinas-Brunet et al. ....... 514/18 |
| 2005/0187165 | A1 | 8/2005 | Scola et al. |
| 2007/0243166 | A1 * | 10/2007 | Llinas-Brunet et al. ... 424/85.7 |

FOREIGN PATENT DOCUMENTS

| | | |
|---|---|---|
| CA | 2445938 A1 | 2/2000 |
| WO | WO 00/09543 | 2/2000 |
| WO | WO 02/060926 A2 | 8/2002 |
| WO | WO 03/053349 A2 | 7/2003 |
| WO | WO 03/064416 A1 | 8/2003 |
| WO | WO 03/064456 A1 | 8/2003 |
| WO | WO 03/099274 A1 | 12/2003 |
| WO | WO 03/099316 A1 | 12/2003 |
| WO | WO 2004/032827 A2 | 4/2004 |
| WO | WO 2004/043339 A2 | 5/2004 |
| WO | WO 2004/101602 A2 | 11/2004 |
| WO | WO 2004/101605 A1 | 11/2004 |
| WO | WO 2004/103996 A1 | 12/2004 |
| WO | WO 2005/046712 A1 | 5/2005 |

OTHER PUBLICATIONS

Patani et. al., "Bioisoterism: A Rational Approach in Drug Design", Chem. Rev. 1996, 96, 3147-3176.*

* cited by examiner

*Primary Examiner*—Janet L Andres
*Assistant Examiner*—Binta M Robinson
(74) *Attorney, Agent, or Firm*—Michael P. Morris; Mary-Ellen M. Devlin; Philip I. Datlow

(57) ABSTRACT

The invention relates to compounds of formula (I) wherein $R^1$, $R^2$, $R^3$, $R^4$, $R^5$, $R^6$, Y, n and m are as defined herein. The compounds are useful for the treatment and prevention of hepatitis C viral infections in mammals by inhibiting HCV NS3 protease. The invention further relates to azalactone compounds of the formula (III) which can be reacted with an amide anion to produce the compounds of formula (I).

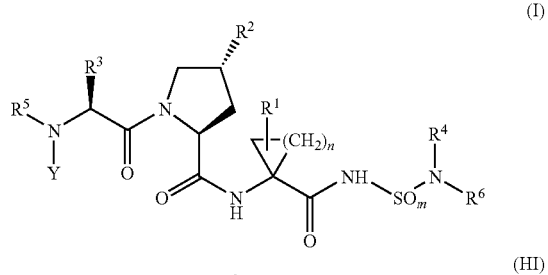

(I)

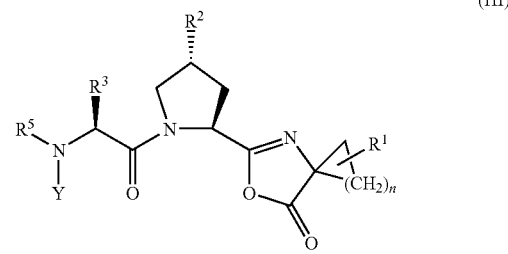

(III)

23 Claims, No Drawings

HEPATITIS C INHIBITOR PEPTIDE ANALOGS

This application is the National Stage of International Application No. PCT/CA2005/000967, filed Jun. 22, 2005, which claims the benefit under 35 USC 119(e) of U.S. Provisional Application No. 60/583,543, filed on Jun. 28, 2004.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulin treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Interferon in combination with ribavirin has been approved for the treatment of patients with chronic hepatitis C. However, side effects caused by IFN (such as retinopathy, thyroiditis, acute pancreatitis, depression) are not alleviated with this combination therapy. Pegylated forms of interferons such as PEG-Intron® and Pegasys® can apparently partially address these deleterious side effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first (generally referred to as the NS2/3 protease) cleaves at the NS2-NS3 junction; the second (the NS3 protease) is a serine protease contained within the N-terminal region of NS3 and mediates all the subsequent cleavages downstream of NS3, both in cis, at the NS3-NS4A cleavage site, and in trans, for the remaining NS4A-NS4B, NS4B—NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus. In a two day clinical trial, it has been shown that the HCV NS3 protease inhibitor BILN 2061 is effective in rapidly reducing viral loads in patients infected with the hepatitis C virus (*Gastroenterology* (2004) 127(5): 1347-1355), thus providing proof of principle of the clinical antiviral activity of HCV NS3 protease inhibitors.

The NS3 protease has been found to potentially have an additional impact by blocking the IFN-mediated cellular antiviral activity in the infected cell (Foy et al., *Science*, 17 Apr. 2003). This lends credence to a hypothesis that the NS3/NS4A protease may represent a dual therapeutic target, the inhibition of which may both block viral replication and restore Interferon response of HCV infected cells.

Inhibitors of the HCV NS3 protease have been described in WO 00/09543 (Boehringer Ingelheim), WO 03/064456 (Boehringer Ingelheim), WO 03/064416 (Boehringer Ingelheim), WO 02/060926 (Bristol-Myers Squibb), WO 03/053349 (Bristol-Myers Squibb), WO 03/099316 (Bristol-Myers Squibb), WO 03/099274 (Bristol-Myers Squibb), WO 2004/032827 (Bristol-Myers Squibb), and WO 2004/043339 (Bristol-Myers Squibb).

Acyl sulfamide inhibitors of the HCV NS3 protease have also been described in WO 2005/046712.

The present invention now provides novel compounds that are inhibitory to the NS3 protease. Furthermore, compounds being active in cell culture are provided.

An advantage of one aspect of the present invention resides in the fact that compounds according to this invention specifically inhibit the NS3 protease and do not show significant inhibitory activity against other serine proteases such as human leukocyte elastase (HLE), or cysteine proteases such as human liver cathepsin B (Cat B).

SUMMARY OF THE INVENTION

Included in the scope of the invention is a compound of formula (I):

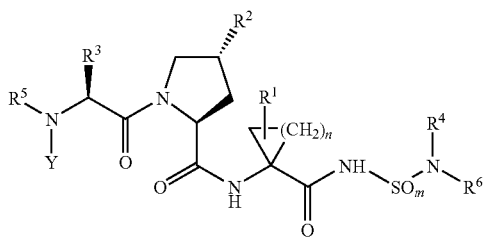

wherein
n is 1 or 2;
m is 1 or 2;
$R^1$ is H, $(C_{1-6})$alkyl, $(C_{2-6})$alkenyl, or $(C_{2-6})$alkynyl, wherein each of said $(C_{1-6})$alkyl, $(C_{2-6})$alkenyl, or $(C_{2-6})$alkynyl are optionally substituted with from one to three halogen atoms;
$R^2$ is selected from —$CH_2$—$R^{20}$, —NH—$R^{20}$, —O—$R^{20}$, —S—$R^{20}$, —SO—$R^{20}$, —$SO_2R^{20}$, —$CH_2O$—$R^{20}$, and —O—X—$R^{20}$, wherein
X is $(C_{2-3})$alkenyl, $(C_{2-3})$alkynyl, or $(C_{1-3})$alkyl; and
$R^{20}$ is $(C_6$ or $C_{10})$aryl or Het, wherein said $(C_6$ or $C_{10})$aryl or Het is optionally substituted with $R^{200}$; wherein
$R^{200}$ is one to four substituents each independently selected from H, halogen, cyano, $(C_{1-6})$alkyl, $(C_{3-7})$cycloalkyl, aryl-$(C_{1-6})$alkyl-, aryl, Het, oxo, thioxo, —$OR^{201}$—$SR^{201}$, —$SOR^{201}$, —$SO_2R^{201}$, —$N(R^{202})R^{201}$, and —$CON(R^{202})R^{201}$; wherein each of said alkyl, cycloalkyl, aryl and Het is optionally further substituted with $R^{2000}$;
$R^{201}$ in each case is independently selected from H, $(C_{1-6})$alkyl, $(C_{2-6})$alkenyl, aryl, —CO—$(C_{1-6})$alkyl and —CO—O—$(C\_6)$alkyl, wherein each of said alkyl and aryl is optionally further substituted with $R^{2000}$;
$R^{202}$ in each case is independently selected from H and $(C_{1-6})$alkyl;
$R^{20000}$ in each case is one to three substituents each independently selected from halogen, aryl, Het, —$OR^{2001}$, —$SR^{2001}$, —$SOR^{2001}$—$SO_2R^{2001}$, cyano, —$N(R^{2002}XR^{2001})$, and $R^{2003}$, wherein said aryl and Het are optionally substituted with one, two or three substituents each independently selected from $(C_{1-6})$alkyl and —O-$(d_{-6})$alkyl;
$R^{2001}$ in each case is independently selected from aryl, aryl-$(C_{1-6})$alkyl-, —C(O)—$R^{2003}$, —C(O)O—$R^{2003}$, —$CON(R^{2002}XR^{2004})$ and $R^{2004}$;
$R^{2002}$ in each case is independently selected from H and $(C_{1-6})$alkyl;
$R^{2003}$ in each case is independently selected from $(C_{1-8})$alkyl, $(C_{3-7})$cycloalkyl and $(C_{3-7})$cycloalkyl-$(C_{1-4})$alkyl-, wherein said $(C_{3-7})$cycloalkyl and $(C_{3-7})$cycloalkyl-$(C_{1-4})$alkyl- are each optionally substituted with one to three substituents each independently selected from $(C_{1-3})$alkyl; and
$R^{2004}$ in each case is independently selected from H and $R^{2003}$;
$R^3$ is $(C_{1-8})$alkyl, $(C_{3-7})$cycloalkyl or $(C_{3-7})$cycloalkyl-$(C_{1-3})$alkyl-, each optionally substituted with one or more substituents each independently selected from $(C_{1-6})$alkyl, $(C_{2-6})$alkenyl, halogen, cyano, —$OR^{30}$, —$SR^{30}$, —C(=O)$OR^{30}$, —C(=O)$NH_2$, —C(=O)$NH(C_{1-6})$alkyl, C(=O)N$((C_{1-6})$alkyl$)_2$, —$NH_2$, —$NH(C_{1-6})$alkyl, —N$((C_{1-6})$alkyl$)_2$, aryl, and aryl$(C_{1-6})$alkyl-, wherein $R^{30}$ is H, $(C_{1-6})$alkyl, aryl, or aryl$(C_{1-6})$alkyl-;
$R^5$ is selected from B, B—C(=O)—, B—O—C(=O)—, B—N($R^{51}$)—C(=O)—; B—N($R^{51}$)—C(=S)—, B—$SO_2$— and B—N($R^{51}$)—$SO_2$—; wherein B is selected from:
(0 $(C_{1-10})$alkyl optionally substituted with one or more substituents each selected independently from —COOH, —COO$(C_{1-6})$alkyl, —OH, halogen, —OC(=O)$(C_{1-6})$alkyl, —O$(C_{1-6})$alkyl, —$NH_2$, —$NH(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;
(ii) $(C_{3-7})$cycloalkyl, or $(C_{3-7})$cycloalkyl-$(C_{1-4})$alkyl-, each optionally substituted with one or more substituents each selected independently from $(C_{1-6})$alkyl, halogen, —COOH, —COO$(C_{1-6})$alkyl, —OH, —O$C_d$alkyl, —$NH_2$, —$NH(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;
(iii) aryl or aryl$(C_{1-6})$alkyl-, each optionally substituted with one or more substituents each selected independently from $(C_{1-6})$alkyl, —OH, —$NH_2$, —$NH(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;
(iv) Het or Het-$(C_{1-6})$alkyl-, each optionally substituted with one or more substituents each selected independently from $(C_{1-6})$alkyl, —OH, —$NH_2$, —$NH(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$; and
(v) $(C_{2-6})$alkenyl, or $(C_{2-6})$alkynyl, each optionally substituted with 1 to 3 halogens; and wherein
$R^{51}$ is selected from H and $(C_{1-6})$alkyl;
Y is H or $(C_{1-6})$alkyl;
$R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl, Het, and aryl-$(C_{1-6})$alkyl-;
wherein said $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one or more substituents each independently selected from halogen, $(C_{1-6})$alkyl, hydroxy, cyano, O—$(C_{1-6})$alkyl, —$NH_2$, —$NH(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl; or
$R^4$ and $R^6$ are linked, together with the nitrogen to which they are bonded, to form a 3- to 7-membered monocyclic saturated or unsaturated heterocycle optionally fused to at least one other cycle to form a heteropolycycle, each of said heterocycle and heteropolycycle optionally containing from one to three additional heteroatoms each independently selected from N, S and O, and each of said heterocycle and heteropolycycle being optionally substituted with one or more substituents each independently selected from halogen, $(C_{1-6})$alkyl, hydroxy, cyano, O—$(C_{1-6})$alkyl, —$NH_2$, —$NH(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl;

with the proviso that when:
$R^5$ is B—O—C(=O)— or B—N($R^{51}$)—C(=O)—, wherein $R^{51}$ is H; and
B is selected from $(C_{1-10})$alkyl, $(C_{3-7})$cycloalkyl, and $(C_{3-7})$cycloalkyl-$(C_{1-4})$alkyl,
a) wherein said alkyl, cycloalkyl, and cycloalkyl-alkyl are optionally mono-, di- or tri-substituted with $(C_{1-3})$alkyl; and b) wherein said alkyl, cycloalkyl, and cycloalkyl-alkyl are optionally mono- or di-substituted with substituents selected from hydroxy and O—(C$_{1-4}$)alkyl; and
c) wherein each of said alkyl groups may be mono-, di- or tri-substituted with halogen; and
d) wherein in each of said cycloalkyl groups being 4-, 5-, 6- or 7-membered, one (for the 4-, 5-, 6-, or 7-membered) or two (for the 5-, 6- or 7-membered) —CH$_2$-groups not directly linked to each other may be replaced by —O— to provide a heterocycle, such that the O-atom is linked to the —O—C(=O) or —N(R$^{51}$)—C(=O) group via at least two carbon atoms; and R$^2$ is O—R$^{20}$; then
R$^{20}$ cannot be

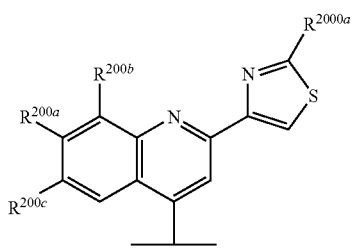

wherein
R$^{200a}$ is H, halogen, (C$_{1-4}$)alkyl, —OH, —O—(C$_{1-4}$)alkyl, —NH$_2$, —NH(C$_{1-4}$)alkyl or —N((C$_{1-4}$)alkyl)$_2$;
R$^{200b}$, R$^{200c}$ are each independently halogen, cyano, (C$_{1-4}$)alkyl, —O—(C$_{1-4}$)alkyl, —S—(C$_{1-4}$)alkyl, —SO—(C$_{1-4}$)alkyl, or —SO$_2$—(C$_{1-4}$)alkyl, wherein each of said alkyl groups is optionally substituted with from one to three halogen atoms; and either R$^{200b}$ or R$^{200c}$ (but not both at the same time) may also be H; or R$^{200a}$ and R$^{200b}$ or
R$^{200a}$ and R$^{200c}$ may be covalently bonded to form, together with the two C-atoms to which they are linked, a 5- or 6-membered carbocyclic ring wherein one or two —CH$_2$-groups not being directly linked to each other may be replaced each independently by —O— or NR$^a$ wherein R$^a$ is H or (C$_{1-4}$)alkyl, and wherein said carbo- or heterocyclic ring is optionally mono- or di-substituted with (C$_{1-4}$)alkyl; and
R$^{2000a}$ is R$^{2003}$, —N(R$^{2002}$)COR$^{2003}$, —N(R$^{2002}$)COOR$^{2003}$, —N(R$^{2002}$)(R$^{2004}$), or —N(R$^{2002}$)CON(R$^{2002}$)(R$^{2004}$), wherein
R$^{2002}$ is H or methyl;
R$^{2003}$ is (C$_{1-8}$)alkyl, (C$_{3-7}$)cycloalkyl or (C$_{3-7}$)cycloalkyl-(C$_{1-4}$)alkyl-, wherein said (C$_{3-7}$)cycloalkyl and (C$_{3-7}$)cycloalkyl-(C$_{1-4}$)alkyl- are optionally mono-, di- or tri-substituted with (C$_{1-3}$)alkyl; and
R$^{2004}$ is H or R$^{2003}$;

wherein Het as used in the above definitions unless otherwise stated is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a diastereomer thereof or a salt thereof.

One aspect of the invention provides a pharmaceutical composition comprising an anti-hepatitis C virally effective amount of a compound of formula (I), or a pharmaceutically acceptable salt thereof; and a pharmaceutically acceptable carrier medium or auxiliary agent.

According to an embodiment of this aspect, the pharmaceutical composition according to this invention additionally comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula (I), a pharmaceutically acceptable salt thereof, or a composition as described above, alone or in combination with at least one other antiviral agent, administered together or separately.

Also within the scope of this invention is the use of a compound of formula (I) as described herein, or a pharmaceutically acceptable salt thereof, for the treatment or prevention of hepatitis C viral infection in a mammal.

Further encompassed within the scope of this invention is the use of a compound of formula (I) as described herein, or a pharmaceutically acceptable salt thereof, for the manufacture of a medicament for the treatment or prevention of hepatitis C viral infection in a mammal.

A further aspect of the invention provides the use of a compound of formula (I), as described herein, or a pharmaceutically acceptable salt thereof, in combination with at least one other antiviral agent, for the manufacture of a medicament for the treatment or prevention of hepatitis C viral infection.

Still another aspect of this invention relates to a method of inhibiting the replication of hepatitis C virus by exposing the virus to a hepatitis C viral NS3 protease inhibiting amount of the compound of formula (I) according to this invention, or a pharmaceutically acceptable salt thereof.

Further included in the scope of the invention is the use of a compound of formula (I) according to this invention, or a pharmaceutically acceptable salt thereof, to inhibit the replication of hepatitis C virus.

An additional aspect of this invention refers to an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of formula (I) according to this invention or a pharmaceutically acceptable salt thereof.

In a further aspect of this invention there is provided a process for the preparation of a compound of formula (I) comprising:

a) reacting a compound of formula (II):

(II)

wherein R$^4$, R$^6$ and m are as defined herein, with a strong base so as to form the corresponding amide anion and b) reacting an azalactone of formula (III):

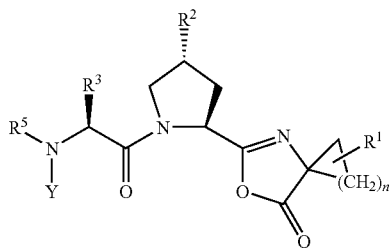
(III)

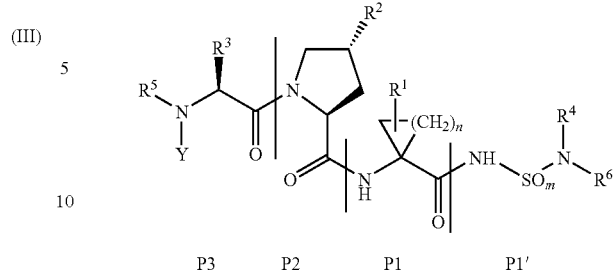

wherein $R^1$, $R^2$, $R^3$, $R^5$, Y and n are as defined herein, with the amide anion formed in step a).

In yet a further aspect of this invention is provided an intermediate azalactone of formula (III):

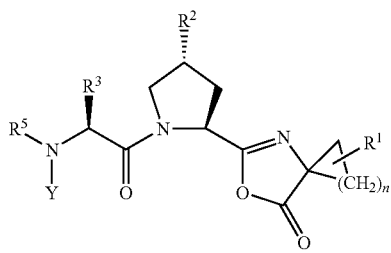
(III)

wherein $R^1$, $R^2$, $R^3$, $R^5$, Y and n are as defined herein.

A further aspect of this invention is the use of the intermediate azalactone of formula (III) as described hereinbefore in the preparation of an HCV NS3 protease inhibitor peptide analog.

DETAILED DESCRIPTION OF PREFERRED EMBODIMENTS

Definitions

As used herein, the following definitions apply unless otherwise noted:

With reference to the instances where (R) or (S) is used to designate the absolute configuration of a substituent or asymmetric center of a compound of formula I, the designation is done in the context of the whole compound and not in the context of the substituent or asymmetric center alone.

The designations "P3, P2, P1 and P1'" as used herein refer to the position of the amino acid residues starting from the N-terminus of the peptide analogs and extending towards and beyond the cleavage site, i.e. the bond in a substrate of the protease enzyme which is normally cleaved by the catalytic action of the protease enzyme. Thus, P3 refers to position 3 from the C-terminal side of the cleavage site, P2: position 2 from the C-terminal side of the cleavage site, etc. The bond between the P1 and P1' residues corresponds to the cleavage site. Thus, the P1' position corresponds to the first position on the N-terminal side of the cleavage site (see Berger A. & Schechter I., Transactions of the Royal Society London series B257, 249-264 (1970)). In the context of the compounds of formula (I) herein described, these positions are as designated in the following formula:

The term "$(C_{1-n})$alkyl" as used herein, wherein n is an integer, either alone or in combination with another substituent, means acyclic, straight or branched chain alkyl substituents containing from 1 to n carbon atoms. "$(C_{1-6})$alkyl" includes, but is not limited to, methyl, ethyl, n-propyl, n-butyl, 1-methylethyl (iso-propyl), 1-methylpropyl, 2-methylpropyl, 1,1-dimethylethyl (tert-butyl), pentyl and hexyl. The abbreviation Me denotes a methyl group and Et denotes an ethyl group.

The term "$(C_{2-n})$alkenyl", as used herein, wherein n is an integer, either alone or in combination with another radical, is intended to mean an unsaturated, acyclic straight chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise.

The term "$(C_{2-n})$alkynyl", as used herein, wherein n is an integer, either alone or in combination with another radical, is intended to mean an unsaturated, acyclic straight chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise.

The term "$(C_{3-m})$ cycloalkyl" as used herein, wherein m is an integer, either alone or in combination with another substituent, means a cycloalkyl substituent containing from 3 to m carbon atoms and includes, but is not limited to, cyclopropyl, cyclobutyl, cyclopentyl, cyclohexyl and cycloheptyl.

The term "$(C3_{-m})$cycloalkyl-$(C_{1-n})$alkyl-" as used herein, wherein n and m are both integers, means an alkyl radical containing from 1 to n carbon atoms to which a cycloalkyl radical containing from 3 to m carbon atoms is directly linked; including, but not limited to, cyclopropylmethyl, cyclobutylmethyl, cyclopentylmethyl, 1-cyclopentylethyl, 2-cyclopentylethyl, cyclohexyl methyl, 1-cyclohexylethyl and 2-cyclohexylethyl. Unless specified otherwise, a $(C_{3-m})$cycloalkyl-$(Ci_{-n})$alkyl-group may be substituted on either the cycloalkyl or the alkyl portion thereof, or both.

The term "aryl" as used herein, either alone or in combination with another radical, means either a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl and 2-naphthyl.

As used herein, the term "aryl-($C_{1-n}$)alkyl-" means an alkyl radical containing from 1 to n carbon atoms, wherein n is an integer, to which an aryl is bonded. Examples of aryl-($C_{1-3}$) alkyl- include, but are not limited to, benzyl (phenylmethyl), 1-phenylethyl, 2-phenylethyl and phenylpropyl. Unless specified otherwise, an aryl-($C_{1-n}$)alkyl-group may be substituted on either the aryl or the alkyl portion thereof, or both.

As used herein, the term "Het" defines a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic, unless specified otherwise.

As used herein the term "heteroatom" means O, S or N.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms selected from nitrogen, oxygen and sulfur. Examples of such heterocycles include, but are not limited to, azetidine, pyrrolidine, tetrahydrofuran, thiazolidine, pyrroline, pyrrole, thiophene, furan, hydantoin, diazepine, 1H-imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, or the following heterocycles:

As used herein, the term "heteropolycycle" either alone or in combination with another radical, means a heterocycle as defined above fused to one or more other cycle, be it a heterocycle or any other cycle. Examples of such heteropolycycles include, but are not limited to, indole, benzimidazole, thiazolo[4,5b]-pyridine, quinoline, isoquinoline, or coumarin, or the following:

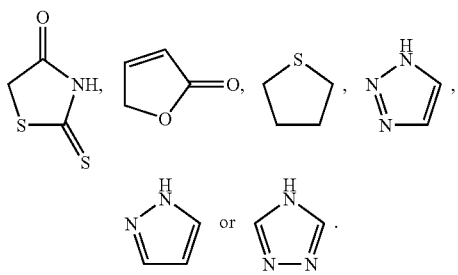

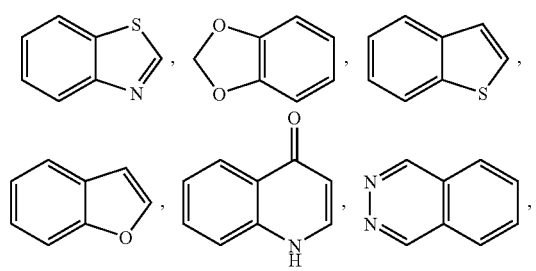

The term "O—($C_{1-n}$)alkyl" or "($C_{1-n}$)alkoxy" as used interchangeably herein, either alone or in combination with another radical, means refers to an oxygen atom further bonded to an alkyl radical as defined above containing from 1 to n carbon atoms, and includes methoxy, ethoxy, propoxy, 1-methylethoxy, butoxy and 1,1-dimethylethoxy. The latter radical is known commonly as tert-butoxy. When an O—($Ci_{-n}$)alkyl group is substituted, it is understood to be substituted on the ($Ci_{-n}$)alkyl portion thereof.

As used herein, the term "—S—($C_{1-n}$)alkyl" or "($Ci_{-n}$) alkylthio", used interchangeably, refers to a sulfur atom further bonded to an alkyl radical as defined above containing from 1 to n carbon atoms. Examples of ($C_{1-6}$)alkylthio include, but are not limited to, methylthio ($CH_3S—$), ethylthio ($CH_3CH_2S—$), propylthio ($CH_3CH_2CH_2S—$), 1-methylethylthio (($CHs)_2CHS—$), 1,1-dimethylethylthio (($CHa)_3CS—$), etc. When an —S—($C_{1-n}$)alkyl group is substituted, it is understood to be substituted on the ($Ci_{-n}$)alkyl portion thereof. Likewise, when an —SO—($C_{1-n}$)alkyl or an —$SO_2$—($C_{1-n}$)alkyl group is substituted, it is understood to be substituted on the ($C_{1-n}$)alkyl portion thereof.

The term "halo" or "halogen" as used interchangeably herein means a halogen substituent selected from fluoro, chloro, bromo or iodo.

The term "oxo" as used herein means an oxygen atom attached as a substituent by a double bond (=O).

The term "thioxo" as used herein means an sulfur atom attached as a substituent by a double bond (=S).

The term "salt thereof means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor. Antiviral agents include, for example, ribavirin, amantadine, VX497 (merimepodib, Vertex Pharmaceuticals), Levovirin, Viramidine, XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ- and omega interferons, tau-interferons, consensus interferons and asialo-interferons), class II interferons (such as γ-interferons), pegylated interferons and conjugated interferons, including but not limited to interferons conjugated with other proteins including but not limited to human albumin.

The term "inhibitor of HCV NS3 protease" as used herein means an agent (compound or biological) that is effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/037855, WO 2004/039833, WO 2004/101602, WO 2004/101605, WO 2004/103996, WO 2005/028501 and co-pending patent application Ser. No. 11/039,698; herein incorporated by reference in its entirety (all by Boehringer Ingelheim), WO 02/060926, WO 03/053349, WO 03/099274, WO 03/099316, WO 2004/032827, WO 2004/043339, WO 2004/094452, WO 2005/046712 (all by BMS), WO 2004/072243, WO 2004/093798, WO 2004/113365, WO 2005/010029 (all by Enanta) and WO 2005/037214 (Intermune), and the Vertex candidate identified as VX-950.

The term "inhibitor of HCV polymerase" as used herein means an agent (compound or biological) that is effective to inhibit the function of an HCV polymerase in a mammal. This includes, but is not limited to, non-nucleoside and nucleoside inhibitors of HCV NS5B polymerase.

Examples of inhibitors of HCV polymerase include but are not limited to those compounds described in: WO 02/04425 (Boehringer Ingelheim) WO 03/007945 (Boehringer Ingelheim), WO 03/010140 (Boehringer Ingelheim), WO 03/010141 (Boehringer Ingelheim), WO 2004/064925 (Boehringer Ingelheim), WO 2004/065367 (Boehringer Ingelheim), WO 2005/012288 (Genelabs), WO 2004/087714 (IRBM), WO 03/101993 (Neogenesis), WO 03/026587 (BMS), WO 03/000254 (Japan Tobacco), and WO 01/47883

(Japan Tobacco), and the clinical candidates JTK-003 (Japan Tobacco), HCV 796 (ViroPharma/Wyeth), R-1626 (Roche) and NM 283 (Idenix/Novartis).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from a helicase, a NS2/3 protease and an internal ribosome entry site (IRES) and agents that interfere with the function of other viral targets including but not limited to an NS5A protein.

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, δ-, ω-interferons, τ-interferons, consensus interferons, asialo-interferons and pegylated forms thereof.

The term "class II interferon" as used herein means an interferon selected from a group of interferons that all bind to receptor type II. Examples of class II interferons include γ-interferons.

Specific preferred examples of some of these agents are listed below:

antiviral agents: ribavirin and amantadine;
immunomodulatory agents: class I interferons, class II interferons, pegylated interferons and conjugated interferons;
HCV polymerase inhibitors: nucleoside analogs and non-nucleosides;
inhibitor of another target in the HCV life cycle: agents that inhibit a target selected from a helicase, a NS2/3 protease and an internal ribosome entry site (IRES) and agents that interfere with the function of other viral targets including but not limited to an NS5A protein;
HIV inhibitors: nucleoside inhibitors, non-nucleoside inhibitors, protease inhibitors, fusion inhibitors and integrase inhibitors; or
HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood.

As used herein, the designation whereby a bond to a substituent R is drawn as emanating from the center of a ring, such as, for example,

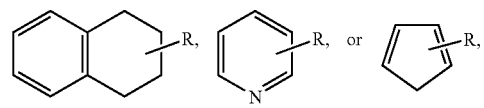

means that the substituent R may be attached to any free position on the ring that would otherwise be substituted with a hydrogen atom, unless specified otherwise.

The following sign

is used in sub-formulas to indicate the bond which is connected to the rest of the molecule as defined.

Preferred Embodiments

In the following preferred embodiments, groups and substituents of the compounds of formula (I) according to this invention are described in detail.

One preferred embodiment of the invention provides a compound of formula (I):

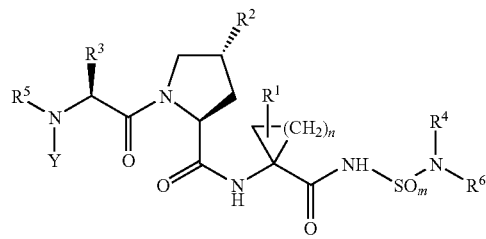

(I)

wherein n is 1 or 2;

m is 1 or 9

$R^1$ is H, $(C_{1-6})$alkyl, $(C_{2-6})$alkenyl, or $(C_{2-6})$alkynyl, wherein each of said $(C_{1-6})$alkyl, $(C_{2-6})$alkenyl, or $(C_{2-6})$alkynyl are optionally substituted with from one to three halogen atoms;

$R^2$ is selected from —$CH_2$—$R^{20}$, —NH—$R^{20}$, —O—$R^{20}$, —S—$R^{20}$, —SO—$R^{20}$, —$SO_2$—$R^{20}$, —$CH_2O$—$R^{20}$, and —O—X—$R^{20}$, wherein X is $(C_{2-3})$alkenyl, $(C_{2-3})$alkynyl, or $(C_{1-3})$alkyl; and $R^{20}$ is $(C_6$ or $C_{10})$aryl or Het, wherein said $(C_6$ or $C_{10})$aryl or Het is optionally substituted with $R^{200}$; wherein $R^{200}$ is one to four substituents each independently selected from H, halogen, cyano, $(C_{1-6})$alkyl, $(C_{3-7})$cycloalkyl, aryl-$(C_{1-16})$alkyl-, aryl, Het, oxo, thioxo, —$OR^{201}$, —$SR^{201}$, —$SOR^{201}$, —$SO_2R^{201}$, —$N(R^{202})R^{201}$, and —$CON(R^{202})R^{201}$; wherein each of said alkyl, cycloalkyl, aryl and Het is optionally further substituted with $R^{2000}$;

$R^{201}$ in each case is independently selected from H, $(C_{1-6})$alkyl, $(C_{2-6})$alkenyl, aryl, —CO—$(C_{1-6})$alkyl and —CO—O—$(C_{1-6})$alkyl, wherein each of said alkyl and aryl is optionally further substituted with $R^{2000}$;

$R^{202}$ in each case is independently selected from H and $(C_{1-6})$alkyl;

$R^{2000}$ in each case is one to three substituents each independently selected from halogen, aryl, Het, —$OR^{2001}$, —$SR^{2001}$, —$SOR^{2001}$, —$SO_2R^{2001}$, cyano, —$N(R^{2002}XR^{2001})$, and $R^{2003}$, wherein said aryl and Het are optionally substituted with one, two or three substituents each independently selected from $(C_{1-6})$alkyl and —O—$(C_{1-6})$alkyl;

$R^{2001}$ in each case is independently selected from aryl, aryl-$(C_{1-6})$alkyl-, —C(O)—$R^{2003}$, —C(O)O—$R^{2003}$, —$CON(R^{2002}XR^{2004})$ and $R^{2004}$;

$R^{2002}$ in each case is independently selected from H and $(C_{1-6})$alkyl;

$R^{2003}$ in each case is independently selected from $(C_{1-8})$alkyl, $(C_{3-7})$cycloalkyl and $(C_{3-7})$cycloalkyl-$(C_{1-4})$alkyl-, wherein said $(C_{3-7})$cycloalkyl and $(C_{3-7})$cycloalkyl-$(C_{1-4})$alkyl- are each optionally substituted with one to three substituents each independently selected from $(C_{1-3})$alkyl; and $R^{2004}$ in each case is independently selected from H and $R^{2003}$;

$R^3$ is $(C_{1-8})$alkyl, $(C_{3-7})$cycloalkyl or $(C_{3-7})$cycloalkyl-$(C_{1-3})$alkyl-, each optionally substituted with one or more substituents each independently selected from $(C_{1-6})$alkyl, $(C_{2-6})$alkenyl, halogen, cyano, —$OR^{30}$, —$SR^{30}$, —C(=O)$OR^{30}$, —C(=O)$NH_2$, —C(=O)NH$(C_{1-6})$alkyl, C(=O)N$((C_{1-6})$alkyl$)_2$, —$NH_2$, —NH$(C_{1-6})$alkyl, —N$((C_{1-6})$alkyl$)_2$, aryl, and aryl$(C_{1-6})$alkyl-, wherein $R^{30}$ is H, $(C_{1-6})$alkyl, aryl, or aryl$(C_{1-6})$alkyl-;

$R^5$ is selected from B, B—C(=O)—, B—O—C(=O)—, B—N$(R^{51})$—C(=O)—; B—N$(R^{51})$—C(=S)—, B—$SO_2$— and B—N$(R^{51})$—$SO_2$—; wherein B is selected from:

(i), $(C_{1-10})$alkyl optionally substituted with one or more substituents each selected independently from —COOH, —COO$(C_{1-6})$alkyl, —OH, halogen, —OC(=O)$(C_{1-6})$alkyl, —O$(C_{1-6})$alkyl, —$NH_2$, —NH$(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;

(ii) $(C_{3-7})$cycloalkyl, or $(C_{3-7})$cycloalkyl-$(C_4)$alkyl-, each optionally substituted with one or more substituents each selected independently from $(C_{1-6})$alkyl, halogen, —COOH, —COO$(C_{1-6})$alkyl, —OH, —O$(C_{1-6})$alkyl, —$NH_2$, —NH$(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;

(iii) aryl or aryl$(C_{1-6})$alkyl-, each optionally substituted with one or more substituents each selected independently from $(C_{1-6})$alkyl, —OH, —$NH_2$, —NH$(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$;

(iv) Het or Het-$(C_{1-6})$alkyl-, each optionally substituted with one or more substituents each selected independently from $(C_{1-6})$alkyl, —OH, —$NH_2$, —NH$(C_{1-6})$alkyl, —N$((C_{1-6})$alkyl$)_2$, —C(=O)$NH_2$, —C(=O)NH$(C_{1-6})$alkyl and —C(=O)N$((C_{1-6})$alkyl$)_2$; and (v) $(C_{2-6})$alkenyl, or $(C_{2-6})$alkynyl, each optionally substituted with 1 to 3 halogens; and wherein $R^{51}$ is selected from H and $(C_{1-6})$alkyl;

Y is H or $(C_{1-6})$alkyl;

$R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl, Het, and aryl-$(C_{1-6})$alkyl-; wherein said $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one or more substituents each independently selected from halogen, $(C_{1-6})$alkyl, hydroxy, cyano, O—$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl; or $R^4$ and $R^6$ are linked, together with the nitrogen to which they are bonded, to form a 3- to 7-membered monocyclic saturated or unsaturated heterocycle optionally fused to at least one other cycle to form a heteropolycycle, each of said heterocycle and heteropolycycle optionally containing from one to three additional heteroatoms each independently selected from N, S and $O_1$ and each of said heterocycle and heteropolycycle being optionally substituted with one or more substituents each independently selected from halogen, $(C_{1-6})$alkyl, hydroxy, cyano, O-$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl;

with the proviso that when:

$R^5$ is B—O—C(=O)— or B—N$(R^{51})$—C(=O)—, wherein $R^{51}$ is H; and

B is selected from (C$_{1-10}$)alkyl, (C$_{3-7}$)cycloalkyl, and (C$_{3-7}$)cycloalkyl-(C$_{1-4}$)alkyl,
a) wherein said alkyl, cycloalkyl, and cycloalkyl-alkyl are optionally mono-, di- or tri-substituted with (C$_{1-3}$)alkyl; and
b) wherein said alkyl, cycloalkyl, and cycloalkyl-alkyl are optionally mono- or di-substituted with substituents selected from hydroxy and O—(C$_{1-4}$)alkyl; and
c) wherein each of said alkyl groups may be mono-, di- or tri-substituted with halogen; and
d) wherein in each of said cycloalkyl groups being 4-, 5-, 6- or 7-membered, one (for the 4-, 5-, 6-, or 7-membered) or two (for the 5-, 6- or 7-membered) —CH$_2$-groups not directly linked to each other may be replaced by —O— to provide a heterocycle, such that the O-atom is linked to the —O—C(=O) or —N(R$^{51}$)—C(=O) group via at least two carbon atoms; and R$^2$ is O—R$^{20}$; then R$^{20}$ cannot be

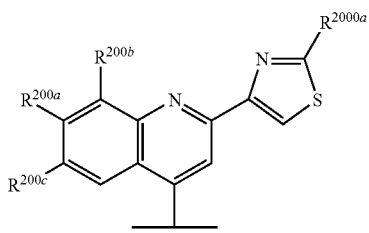

wherein

R$^{200a}$ is H, halogen, (C$_{1-4}$)alkyl, —OH, —O—(C$_{1-4}$)alkyl, —NH$_2$, —NH(C$_{1-4}$)alkyl or —N((C$_{1-4}$)alkyl)$_2$;

R$^{200b}$, R$^{200c}$ are each independently halogen, cyano, (C$_{1-4}$)alkyl, —O—(C$_{1-4}$)alkyl, —S—CC$^{\wedge}$alkyl, —SO—(C$_{1-4}$)alkyl, or —SO$_2$—(C$_{1-4}$)alkyl, wherein each of said alkyl groups is optionally substituted with from one to three halogen atoms; and either R$^{200b}$ or R$^{200c}$ (but not both at the same time) may also be H; or R$^{200a}$ and R$^{200b}$ or R$^{200a}$ and R$^{200c}$ may be covalenty bonded to form, together with the two C-atoms to which they are linked, a 5- or 6-membered carbocyclic ring wherein one or two —CH$_2$-groups not being directly linked to each other may be replaced each independently by —O— or NR$^a$ wherein R$^a$ is H or (C$_{1-4}$)alkyl, and wherein said carbo- or heterocyclic ring is optionally mono- or di-substituted with (C$_{1-4}$)alkyl; and R$^{2000a}$ is R$^{2003}$, —N(R$^{2002}$)COR$^{2003}$, —N(R$^{2002}$)COOR$^{2003}$, —N(R$^{2002}$)(R$^{2004}$), or —N(R$^{2002}$)CON(R$^{2002}$)(R$^{2004}$), wherein R$^{2002}$ is H or methyl;

R$^{2003}$ is (C$_{1-8}$)alkyl, (C$_{3-7}$)cycloalkyl or (C$_{3-7}$)cycloalkyl-(C$_{1-4}$)alkyl-, wherein said (C$_{3-7}$)cycloalkyl and (C$_{3-7}$) cycloalkyl-(C$_{1-4}$)alkyl- are optionally mono-, di-, or tri-substituted with (C$_{1-3}$)alkyl; and R$^{2004}$ is H or R$^{2003}$;

and with the further proviso that when:

R$^5$ is B—O—C(=O)— and B is selected from methyl and 1,1-dimethylethyl; and

R$^3$ is 1,1-dimethylethyl; and

R$^1$ is ethenyl; and the group —N(R$^4$)R$^6$ is selected from:

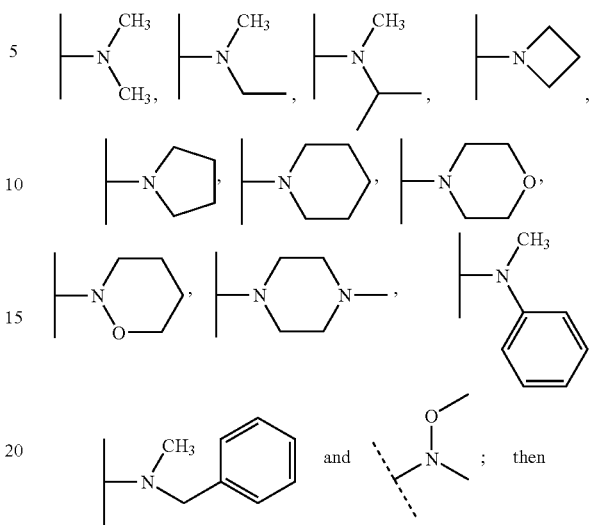

R$^2$ is not selected from:

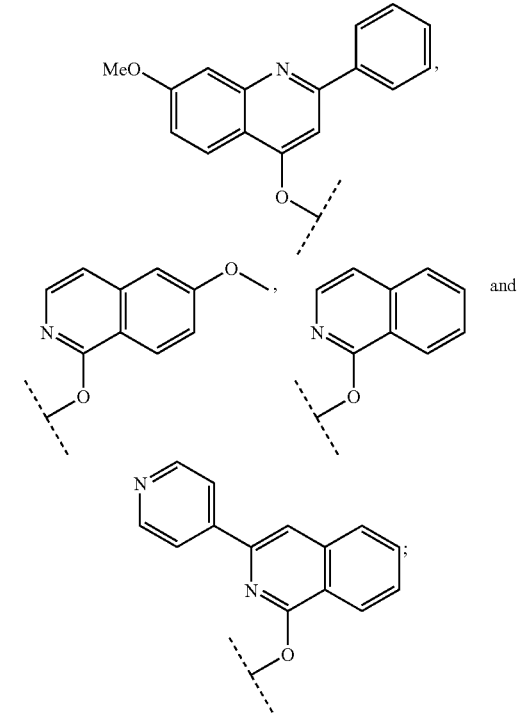

wherein Het as used in the above definitions unless otherwise stated is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a diastereomer thereof or a salt thereof.

R⁵:

Preferably, R⁵ is selected from B—C(═O)—, B—O—C(═O)—, and B—N(R⁵¹)—C(═O)—; wherein B and R⁵¹ are as defined herein.

More preferably, R⁵ is selected from B—C(═O)—, B—O—C(═O)—, and B—NH—C(═O)—; wherein B is selected from:

(i) (C$_{1-10}$)alkyl optionally substituted with one or more substituents each selected independently from —COOH, —COO(Ci$_{-6}$)alkyl, —OH, halogen, —OC(═O)(C$_{1-6}$)alkyl, —O(C$_{1-6}$)alkyl, —NH$_2$, —NH(C$_{1-6}$)alkyl, —N((Ci$_{-6}$)alkyl)$_2$, —C(═O)NH$_2$, —C(═O)NH(C$_{1-6}$)alkyl and —C(═O)N((Ci$_{-6}$)alkyl)$_2$;

(ii) (C$_{3-7}$)cycloalkyl, or (C$_{3-7}$)cycloalkyl-(C$_{1-4}$)alkyl-, each optionally substituted with one or more substituents each selected independently from (Ci$_{-6}$)alkyl, halogen, —COOH, —COO(C$_{1-6}$)alkyl, —OH, —O(Ci$_{-6}$)alkyl, —NH$_2$, —NH(C$_{1-6}$)alkyl, —N((C$_{1-6}$)alkyl)$_2$, —C(═O)NH$_2$, —C(═O)NH(C$_{1-6}$)alkyl and —C(═O)N((C$_{1-6}$)alkyl)$_2$;

(iii) aryl or aryl(C$_{1-6}$)alkyl-, each optionally substituted with one or more substituents each selected independently from (C$_{1-6}$)alkyl, —OH, —NH$_2$, —NH(C$_{1-6}$)alkyl, —N((C$_{1-6}$)alkyl)$_2$, —C(═O)NH$_2$, —C(═O)NH(C$_{1-6}$)alkyl and —C(═O)N((C$_{1-6}$)alkyl)$_2$; and (iv) Het or Het-(C-t$_{-6}$)alkyl-, each optionally substituted with one or more substituents each selected independently from (Ci$_{-6}$)alkyl, —OH, —NH$_2$, —NH(C$_{1-6}$)alkyl, —N((Ci$_{-6}$)alkyl)$_2$, —C(═O)NH$_2$, —C(═O)NH(C$_{1-6}$)alkyl and —C(═O)N((C$_{1-6}$)alkyl)$_2$.

Even more preferably, R⁵ is selected from B—C(═O)—, B—O—C(═O)—, and B—NH—C(═O)—, and B is selected from:

(i) (C$_{1-10}$)alkyl optionally substituted with one or more substituents each selected independently from —COO(Ci$_{-6}$)alkyl, —OH, —O(Ci$_{-6}$)alkyl, and is halogen;

(ii) (C$_{3-7}$)cycloalkyl, or (C$_{3-7}$)cycloalkyl-(Ct$_{-4}$)alkyl-, each optionally substituted with one or more substituents each selected independently from (C$_{1-6}$)alkyl, —OH and —O(C$_{1-6}$)alkyl;

(iii) aryl(C$_{1-6}$)alkyl-; and (iv) Het.

Yet more preferably, R⁵ is selected from B—C(═O)—, B—O—C(═O)—, and B—NH—C(═O)—, and B is selected from:

(i) (C$_{1-7}$)alkyl optionally substituted with one or two or three substituents each independently selected from fluoro, chloro, bromo, hydroxy, methoxy and ethoxy; or optionally substituted with —COOCH$_3$;

(ii) (C$_{3-7}$)cycloalkyl, or (Cs$^{\circ}$cycloalkyl-methyl-, each optionally substituted with one or two substituents each independently selected from methyl, ethyl, hydroxy, methoxy and ethoxy;

(iii) benzyl; and (iv) Het, wherein Het comprises a 3-, A-, 5-, 6, or 7-membered heterocyle having one to four heteroatoms each independently selected from O, N, and S, which may be saturated or unsaturated or aromatic.

Most preferred are compounds wherein R⁵ is selected from B—C(═O)—, B—O—C(═O)—, and B—NH—C(═O)—, and B is selected from 1,1-dimethylethyl optionally substituted with 1, 2, or 3 halogen substituents, cyclopropyl-CH$_2$—, benzyl, 2,2-dimethylpropyl, cyclopentyl, cyclobutyl, tetrahydrofuranyl, 1,1-dimethylpropyl,

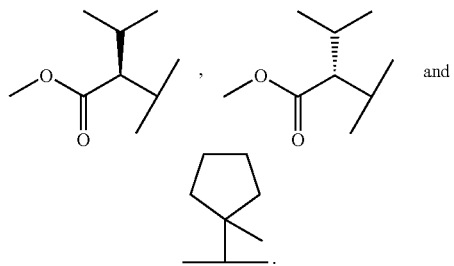

Therefore, a preferred embodiment provides compounds where R⁵ is B—O—C(═O)—, wherein B is selected from 1,1-dimethylethyl, 2,2-dimethylpropyl, 1,1-dimethylpropyl, 2,2,2-trichloro-1,1-dimethylethyl, benzyl, cyclopentyl, cyclobutyl, tetrahydrofuranyl and

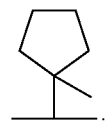

An alternative preferred embodiment provides compounds where R⁵ is B—NH—C(═O)—, wherein B is selected from cyclopentyl, 1,1-dimethylpropyl, 1,1-dimethylethyl, 2,2,2-trifluoro-1,1-dimethylethyl,

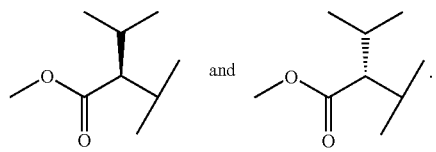

Another alternative preferred embodiment provides compounds where R⁵ is B—C(═O)—, wherein B is selected from cyclopentyl, —(CH$_2$)-cyclopropyl, and 2,2-dimethylpropyl.

Most preferably, R⁵ is B—O—C(═O)—, wherein B is cyclopentyl.

Any and each individual definition of R⁵ as set out herein may be combined with any and each individual definition of R¹, R², R³, R⁴, R⁶, Y, n, and m as set out herein.

Y:

Preferably Y is H.

Any and each individual definition of Y as set out herein may be combined with any and each individual definition of R¹, R², R³, R⁴, R⁵, R⁶, n, and m as set out herein.

R³:

Preferably, R³ is (C$_{1-8}$)alkyl or (C$_{3-7}$)cycloalkyl, each of which are optionally substituted with one or more substituents each independently selected from (C-t$_{-6}$)alkyl, —OR³⁰, and —C(═O)OR³⁰, wherein R³⁰ is H, (C$_{1-6}$)alkyl, or aryl (C$_{1-6}$)alkyk More preferably, R³ is (C$_{1-8}$)alkyl or (C$_{3-7}$)cycloalkyl, the (Ci$_{-8}$)alkyl being optionally substituted with hydroxy, (C$_{1-6}$)alkoxy or —C(═O)OR³⁰, wherein R³⁰ is (C$_{1-s}$)alkyl or aryl (C$_{1-6}$)alkyk Even more preferably, R³ is selected from 1,1-dimethylethyl, 1-methylethyl, 1-methylpropyl, 1-hydroxy-1-methylethyl, 1-methoxyethyl, 1-ifert-butoxyethyl, 1-ethoxyethyl, cyclopentyl,

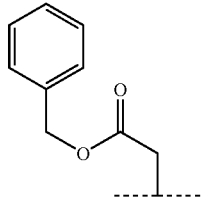 and 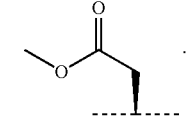

Still more preferably, R³ is 1,1-dimethylethyl or cyclopentyl.

Most preferably, R³ is 1,1-dimethylethyl.

Any and each individual definition of R³ as set out herein may be combined with any and each individual definition of R¹, R², R⁴, R⁵, R⁶, Y, n, and m as set out herein.

R²:

Preferably, R² is selected from —O—R²⁰, —S—R²⁰, and —O—X—R²⁰, wherein each of R²⁰ and X is as defined herein, and with the proviso that when:

R⁵ of formula (I) is B—O—C(=O)— or B—N(R⁵¹)—C(=O)—, wherein
R⁵¹ is H; and
B is selected from (C₁₋₁₀)alkyl, (C₃₋₇)cycloalkyl, and (C₃₋₇)cycloalkyl-(C₁₋₄)alkyl,
a) wherein said alkyl, cycloalkyl, and cycloalkyl-alkyl are optionally mono-, di- or tri-substituted with (C₁₋₃)alkyl; and
b) wherein said alkyl, cycloalkyl, and cycloalkyl-alkyl are optionally mono- or di-substituted with substituents selected from hydroxy and O—(C₁₋₄)alkyl; and
c) wherein each of said alkyl groups may be mono-, di- or tri-substituted with halogen; and
d) wherein in each of said cycloalkyl groups being A-, 5-, 6- or 7-membered, one (for the A-, 5-, 6-, or 7-membered) or two (for the 5-, 6- or 7-membered)—CH₂-groups not directly linked to each other may be replaced by —O— to provide a heterocycle, such that the O-atom is linked to the —O—C(=O) or —N(R⁵¹)—C(=O) group via at least two carbon atoms; and R² is O—R²⁰; then R²⁰ cannot be

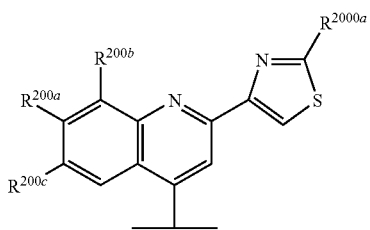

wherein R²⁰⁰ᵃ, R²⁰⁰ᵇ, R²⁰⁰ᶜ and R²⁰⁰ᵈ are as defined herein;

and with the further proviso that when:

R⁵ is B—O—C(=O)— and B is selected from methyl and 1,1-dimethylethyl; and

R³ is 1,1-dimethylethyl; and
R¹ is ethenyl; and the group —N(R⁴)R⁶ is selected from:

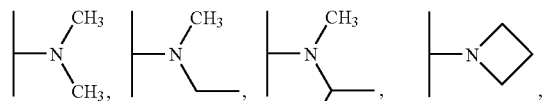

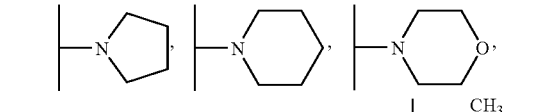

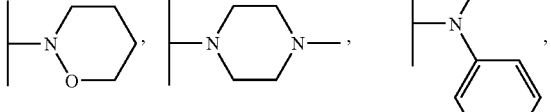

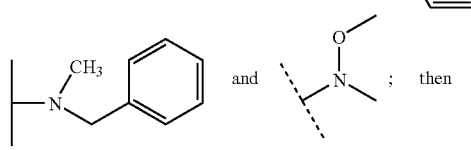

; then

R² is not selected from:

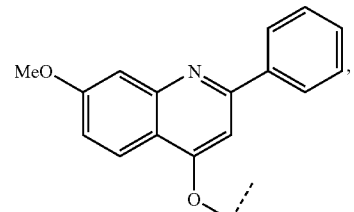

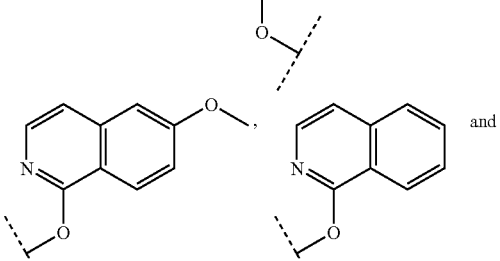

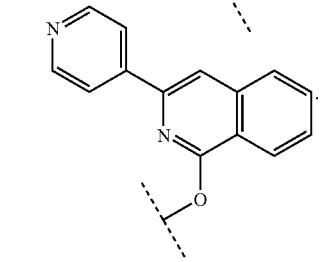

More preferably, R² is selected from —O—R²⁰, —S—R²⁰, and —O—X—R²⁰; wherein X is (C₂₋₃)alkynyl or (d₋₃)alkyl; and R²⁰ is (C₆ or C₁₀)aryl or Het, wherein said (C₆ or C₁₀)aryl or Het are each optionally substituted with R²⁰⁰, wherein R²⁰⁰ is as defined herein; with the proviso that when:

R⁵ of formula (I) is B—O—C(=O)— or B—N(R⁵¹)—C(=O)—, wherein
R⁵¹ is H; and
B is selected from (C₁₋₁₀)alkyl, (C₃₋₇)cycloalkyl, and (C₃₋₇)cycloalkyl-(C₁₋₄)alkyl, a) wherein said alkyl, cycloalkyl, and cycloalkyl-alkyl are optionally mono-, di- or tri-substituted with $(C_{1-3})$alkyl; and
b) wherein said alkyl, cycloalkyl, and cycloalkyl-alkyl are optionally mono- or di-substituted with substituents selected from hydroxy and O—$(C_{1-4})$alkyl; and
c) wherein each of said alkyl groups may be mono-, di- or tri-substituted with halogen; and
d) wherein in each of said cycloalkyl groups being 4-, 5-, 6- or 7-membered, one (for the 4-, 5-, 6-, or 7-membered) or two (for the 5-, 6- or 7-membered) —$CH_2$- groups not directly linked to each other may be replaced by —O— to provide a heterocycle, such that the O-atom is linked to the —O—C(=O) or —N($R^{51}$)—C(=O) group via at least two carbon atoms; and $R^2$ is O—$R^{20}$; then
$R^{20}$ cannot be

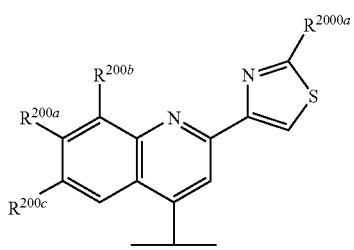

wherein $R^{200a}$, $R^{200b}$, $R^{200c}$ and $R^{2000a}$ are as defined herein;

and with the further proviso that when:
$R^5$ is B—O—C(=O)— and B is selected from methyl and 1,1-dimethylethyl; and
$R^3$ is 1,1-dimethylethyl; and
$R^1$ is ethenyl; and the group —N($R^4$)$R^b$ is selected from:

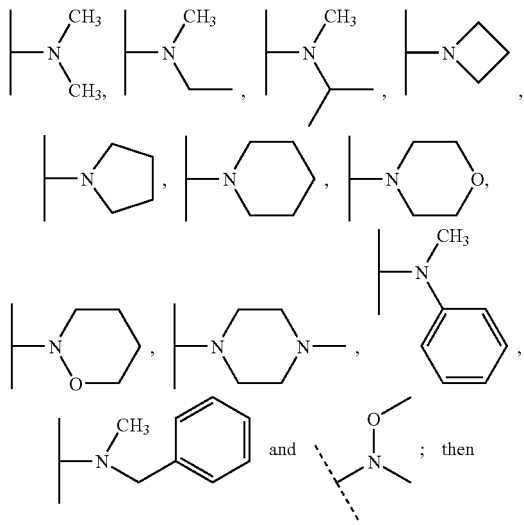

$R^2$ is not selected from:

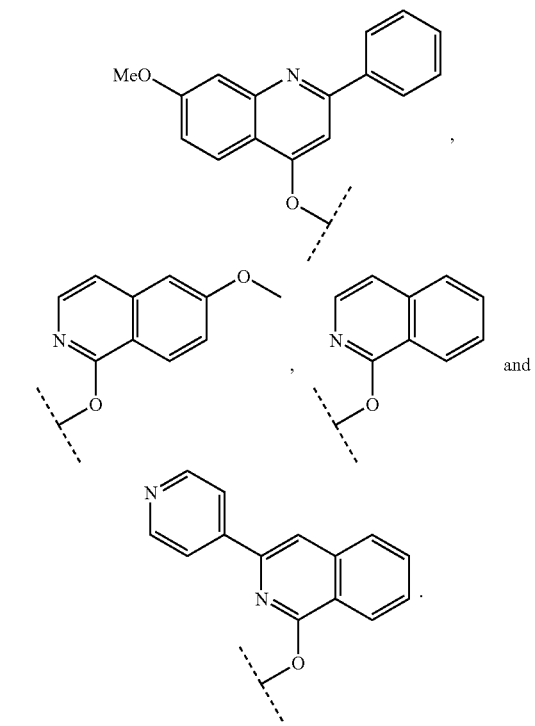

In a preferred embodiment, $R^2$ is —O—X—$R^{20}$, wherein X is $(C_3)$alkynyl or $(d)$alkyl; and $R^{20}$ is $(C_6$ or $C_{10})$aryl, preferably phenyl.

More preferably, $R^2$ is —O—X—$R^{20}$, wherein X is $(C_3)$alkynyl; and $R^{20}$ is $(C_6$ or $C_{10})$aryl, preferably phenyl.

Most preferably when $R^2$ is —O—X—$R^{20}$, X is —$CH_2C\equiv C$—; and $R^{20}$ is phenyl.

In yet another preferred embodiment, $R^2$ is —O—$R^{20}$, wherein $R^{20}$ is Het, optionally substituted with $R^{200}$, wherein $R^{200}$ is as defined herein, and with the proviso that when:
$R^5$ of formula (I) is B—O—C(=O)— or B—N($R^{51}$)—C(=O)—, wherein
$R^{51}$ is H; and
B is selected from (C-t-io)alkyl, $(C_{3-7})$cycloalkyl, and $(C_{3-7})$cycloalkyl-$(C_{1-4})$alkyl,
a) wherein said alkyl, cycloalkyl, and cycloalkyl-alkyl are optionally mono-, di- or tri-substituted with $(C_{1-3})$jallCyl; and
b) wherein said alkyl, cycloalkyl, and cycloalkyl-alkyl are optionally mono- or di-substituted with substituents selected from hydroxy and O—$(Ci_{-4})$alkyl; and
c) wherein each of said alkyl groups may be mono-, di- or tri-substituted with halogen; and
d) wherein in each of said cycloalkyl groups being 4-, 5-, 6- or 7-membered, one (for the A-, 5-, 6-, or 7-membered) or two (for the 5-, 6- or 7-membered)—$CH_2$- groups not directly linked to each other may be replaced by —O— to provide a heterocycle, such that the O-atom is linked to the —O—C(=O) or —N($R^{51}$)—C(=O) group via at least two carbon atoms; then $R^{20}$ cannot be
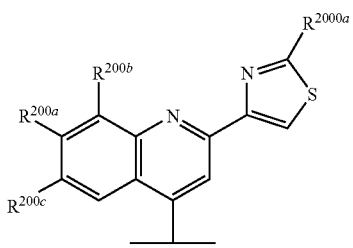
wherein $R^{200a}$, $R^{200b}$, $R^{200c}$ and $R^{2000a}$ are as defined herein;
and with the further proviso that when:
$R^5$ is B—O—C(=O)— and B is selected from methyl and 1,1-dimethylethyl; and
$R^3$ is 1,1-dimethylethyl; and
$R^1$ is ethenyl; and
the group —N($R^4$)$R^6$ is selected from:
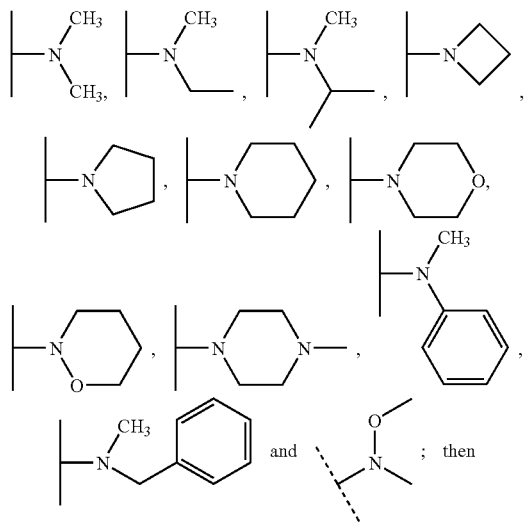
$R^2$ is not selected from:
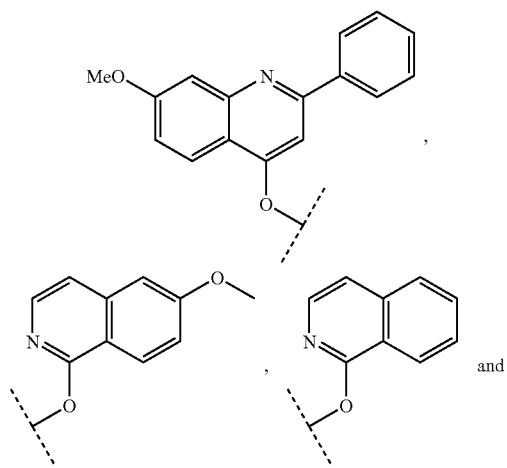
-continued
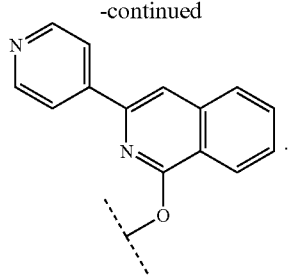
More preferably, $R^2$ is —O—$R^{20}$, wherein $R^{20}$ is Het selected from
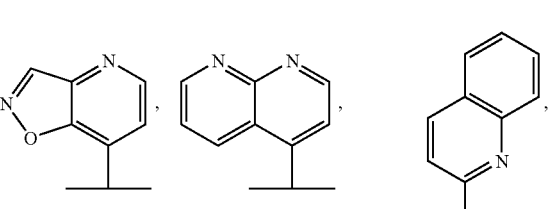
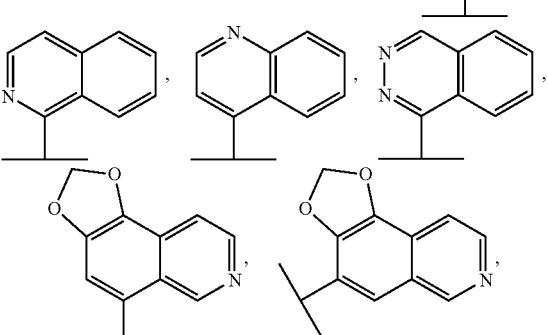
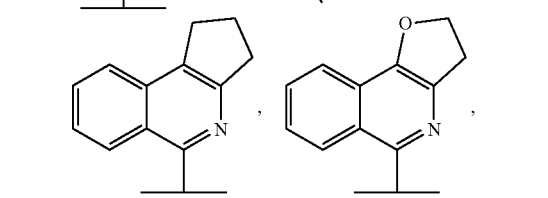
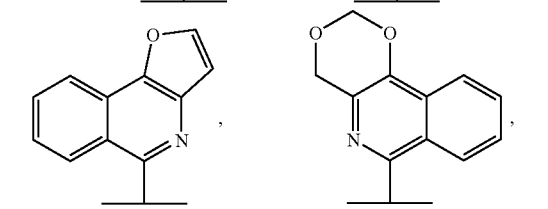
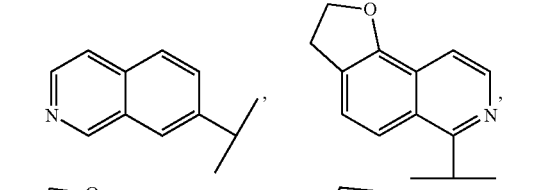
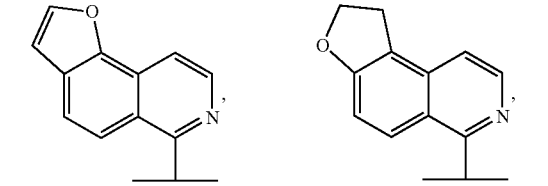

-continued

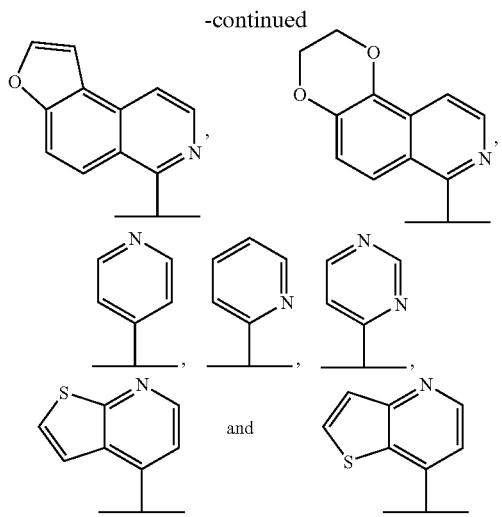

and wherein said Het is optionally substituted with $R^{200}$, wherein $R^{200}$ is as defined herein, and with the proviso that when:

$R^5$ of formula (I) is B—O—C(=O)— or B—N($R^{51}$)—C(=O)—, wherein
$R^{51}$ is H; and
B is selected from $(C_{1-10})$alkyl, $(C_{3-7})$cycloalkyl, and $(C_{3-7})$cycloalkyl-$(C_{1-4})$alkyl,
 a) wherein said alkyl, cycloalkyl, and cycloalkyl-alkyl are optionally mono-, di- or tri-substituted with $(C_{1-3})$alkyl; and
 b) wherein said alkyl, cycloalkyl, and cycloalkyl-alkyl are optionally mono- or di-substituted with substituents selected from hydroxy and O—$(C_{1-4})$alkyl; and
 c) wherein each of said alkyl groups may be mono-, di- or tri-substituted with halogen; and
 d) wherein in each of said cycloalkyl groups being A-, 5-, 6- or 7-membered, one (for the A-, 5-, 6-, or 7-membered) or two (for the 5-, 6- or 7-membered)—CH$_2$-groups not directly linked to each other may be replaced by —O— to provide a heterocycle, such that the O-atom is linked to the —O—C(=O) or —N($R^{51}$)—C(=O) group via at least two carbon atoms; then
$R^{20}$ cannot be

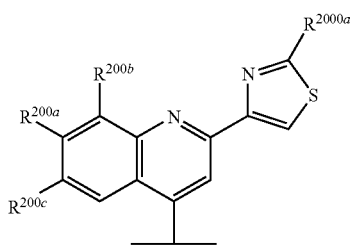

wherein $R^{200a}$, $R^{200b}$, $R^{200c}$ and $R^{2000a}$ are as defined herein;

and with the further proviso that when:
$R^5$ is B—O—C(=O)— and B is selected from methyl and 1,1-dimethylethyl; and $R^3$ is 1,1-dimethylethyl; and
$R^1$ is ethenyl; and the group —N($R^4$)$R^6$ is selected from:

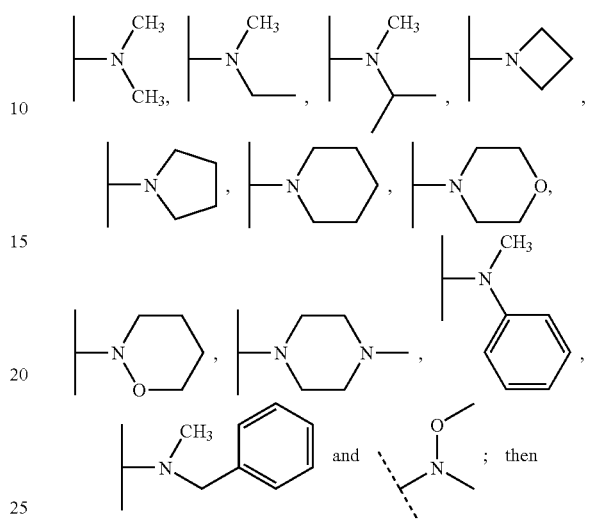

$R^2$ is not selected from:

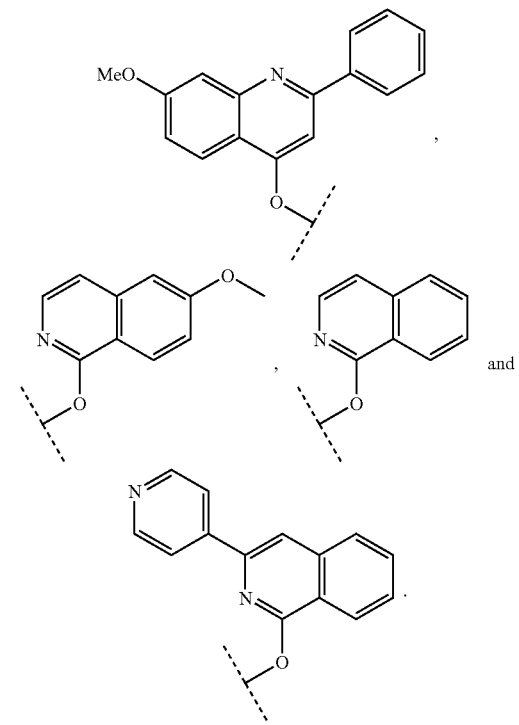

Preferably, $R^{200}$ is one to four substituents each independently selected from H, halogen, cyano, $(C_{1-6})$alkyl; $(C_{3-7})$cycloalkyl; aryl, Het, —OR$^{201}$, —SR$^{201}$, and —SO$_2$R$^{201}$; wherein each said alkyl, cycloalkyl, aryl and Het is optionally further substituted with $R^{2000}$;

$R^{201}$ is in each case independently selected from H, $(C_{1-6})$alkyl and $(C_{2-6})$alkenyl, wherein $(C_{1-6})$alkyl is optionally further substituted with $R^{2000}$.

$R^{2000}$ is in each case one to three substituents each independently selected from halogen, $(C_{3-7})$cycloalkyl, aryl, —$OR^{2001}$, cyano, and —$N(R^{2002})R^{2001}$;

$R^{2001}$ is in each case independently selected from H and $(C_{1-6})$alkyl; and $R^{2002}$ is in each case independently selected from H and $(C_{1-6})$alkyl.

Even more preferably, when $R^2$ is —O—$R^{20}$, $R^{20}$ is

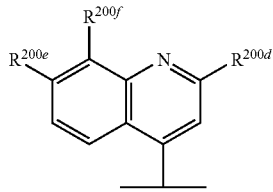

wherein $R^{200d}$ is —$OR^{201}$, wherein $R^{201}$ is $(C_{1-6})$alkyl;

$R^{200e}$ is H or —$OR^{201}$, wherein $R^{201}$ is $(C_{1-6})$alkyl; and $R^{200f}$ is $(C_{1-6})$alkyl, halogen, —$SR^{201}$, —$SO_2R^{201}$, or —$OR^{201}$ wherein $R^{201}$ is $(C_{1-6})$alkyl optionally further substituted with $(C_{3-7})$cycloalkyl or phenyl.

Most preferably, when $R^2$ is —O—$R^{20}$ and $R^{20}$ is

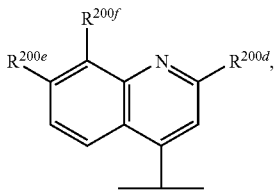

$R^{200d}$ is —$OR^{201}$, wherein $R^{201}$ is ethyl;

$R^{200e}$ is H or —$OR^{201}$, wherein $R^{201}$ is $(C_{1-6})$alkyl; and $R^{200f}$ is $(C_{1-6})$alkyl, halogen, —$SR^{201}$, —$SO_2R^{201}$, or —$OR^{201}$, wherein $R^{201}$ is $(C_{1-6})$alkyl optionally further substituted with $(C_{3-7})$cycloalkyl or phenyl.

Alternatively even more preferably, when $R^2$ is —O—$R^{20}$, $R^{20}$ is

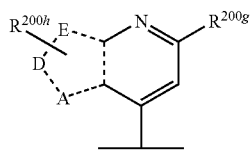

wherein one of A, D, and E represents a S atom and the other two of A, D, and E represent C atoms;

— represents a single bond between a C atom and an S atom, and represents a single bond or a double bond between two C atoms; provided that each C atom is bonded by one double bond;

$R^{200g}$ is H or —$OR^{201}$, wherein $R^{201}$ is $(C_{1-6})$alkyl or $(C_{2-6})$alkenyl; and $R^{200h}$ is one or two substituents each independently selected from H, cyano, $(C_{1-6})$alkyl and —$SO_2$—$(C_{1-6})$alkyl; wherein each $R^{200h}$ is bonded to a C atom which would otherwise bear a hydrogen atom.

Most preferably, when $R^2$ is —O—$R^{20}$, $R^{20}$ is

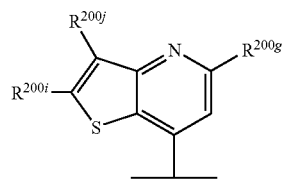

wherein $R^{200g}$ is H or —$OR^{201}$, wherein $R^{201}$ is $(C_{1-6})$alkyl or $(C_{2-6})$alkenyl;

$R^{200j}$ is H, $(C_{1-6})$alkyl or —$SO_2$—$(C_{1-6})$alkyl; and $R^{200i}$ is H or $(C_{1-6})$alkyl.

Alternatively most preferably, when $R^2$ is —O—$R^{20}$, $R^{20}$ is

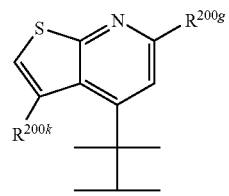

wherein $R^{200g}$ is —$OR^{201}$, wherein $R^{201}$ is $(C_{1-6})$alkyl; and $R^{200k}$ is cyano.

Therefore preferably, $R^2$ is selected from:

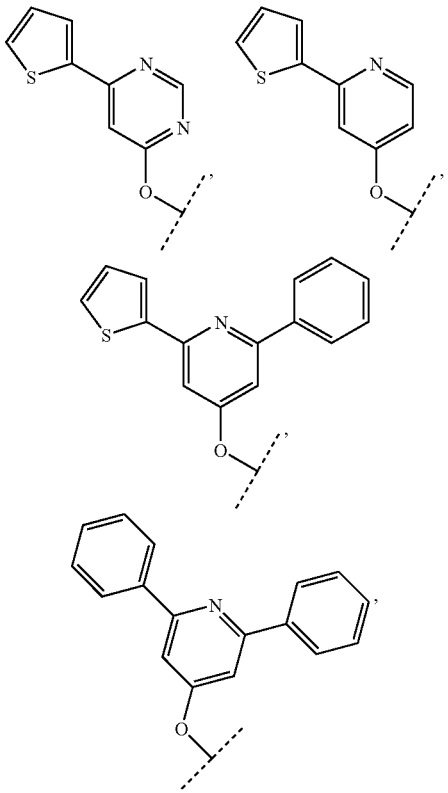

-continued
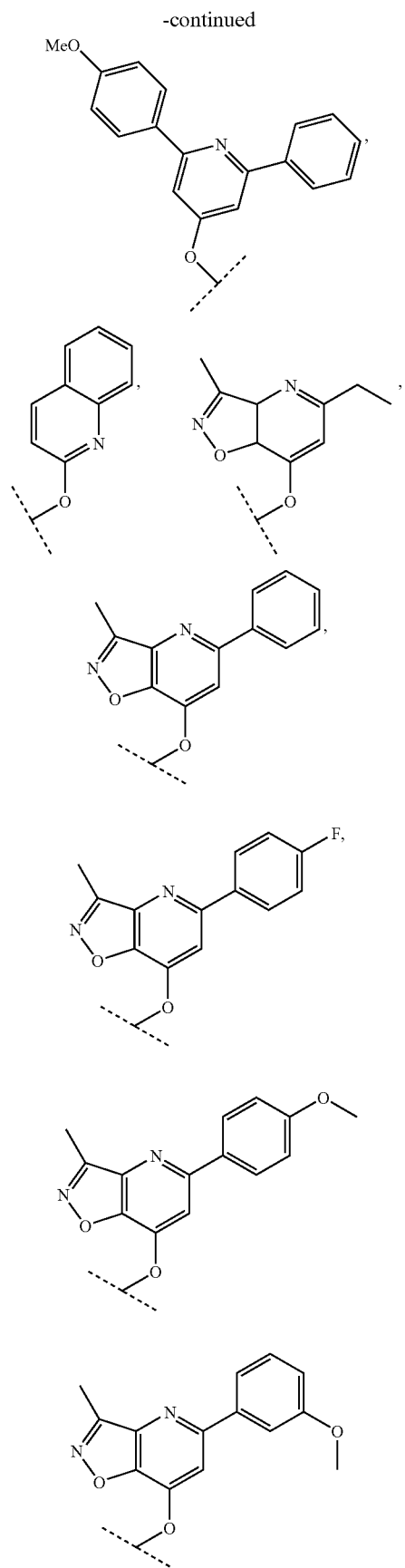
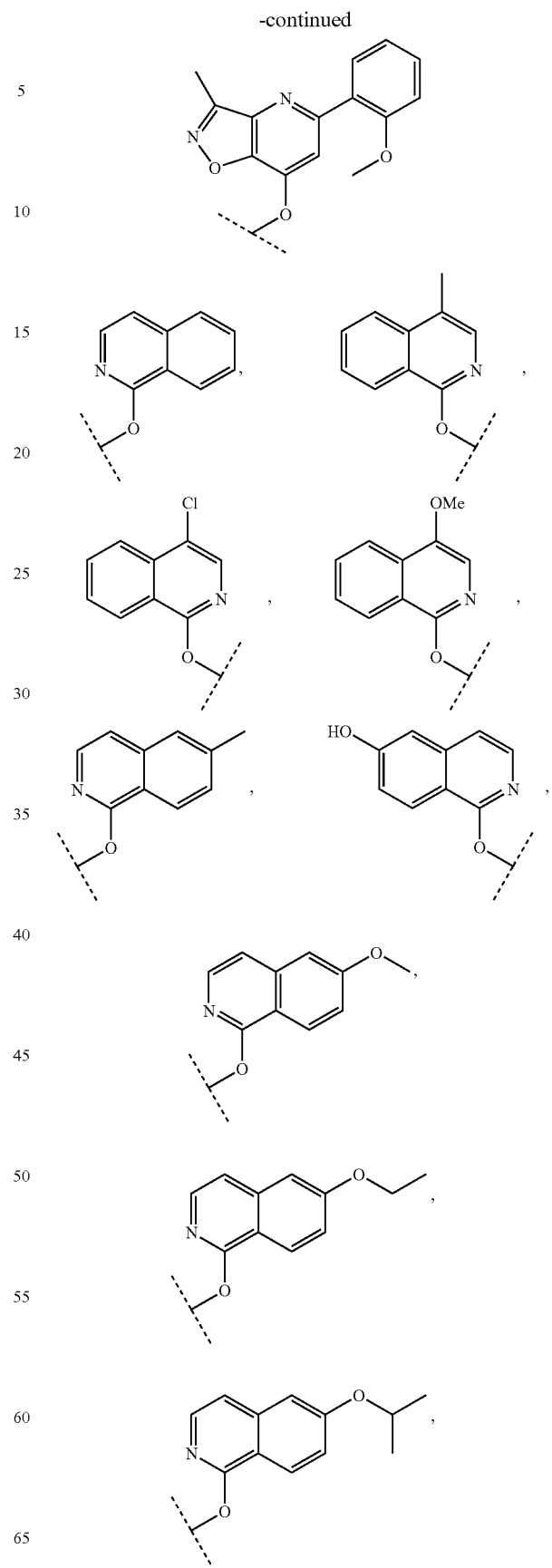

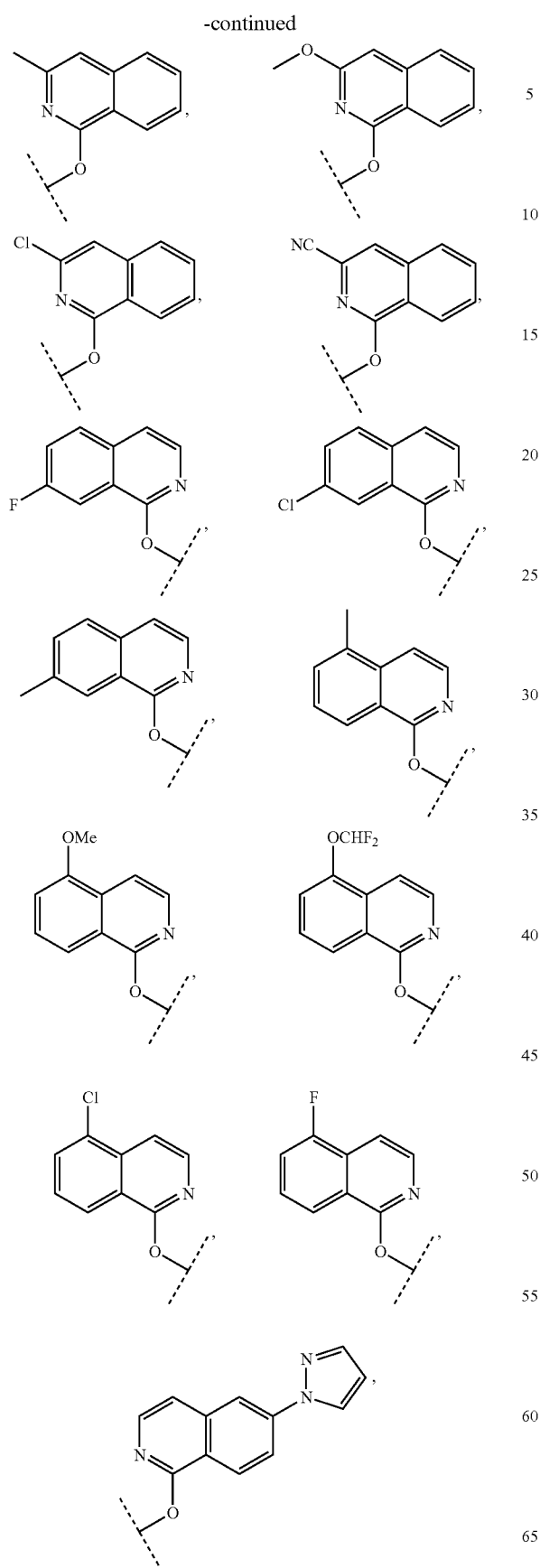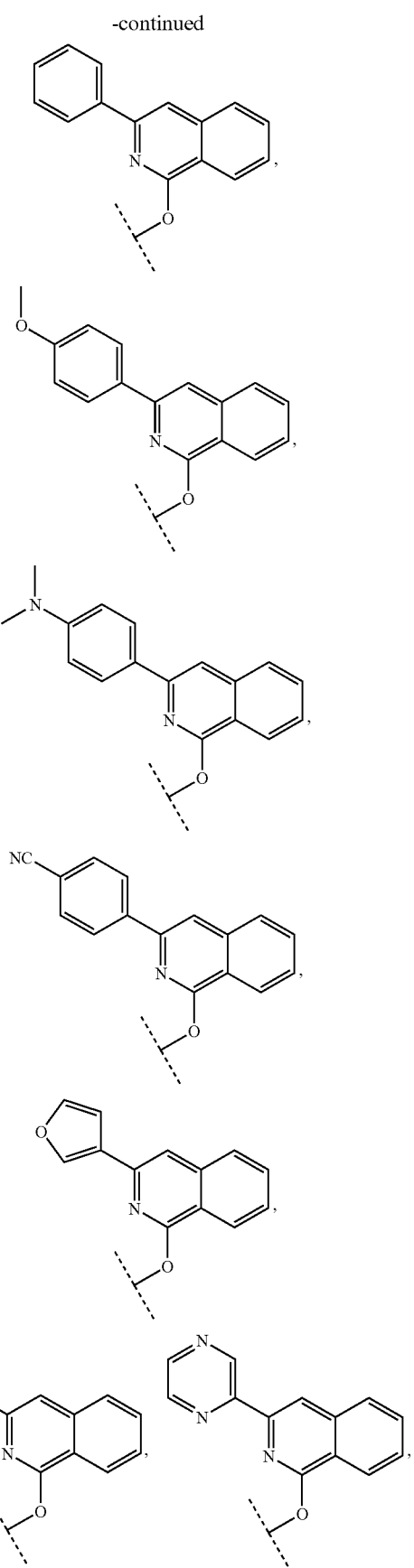

-continued
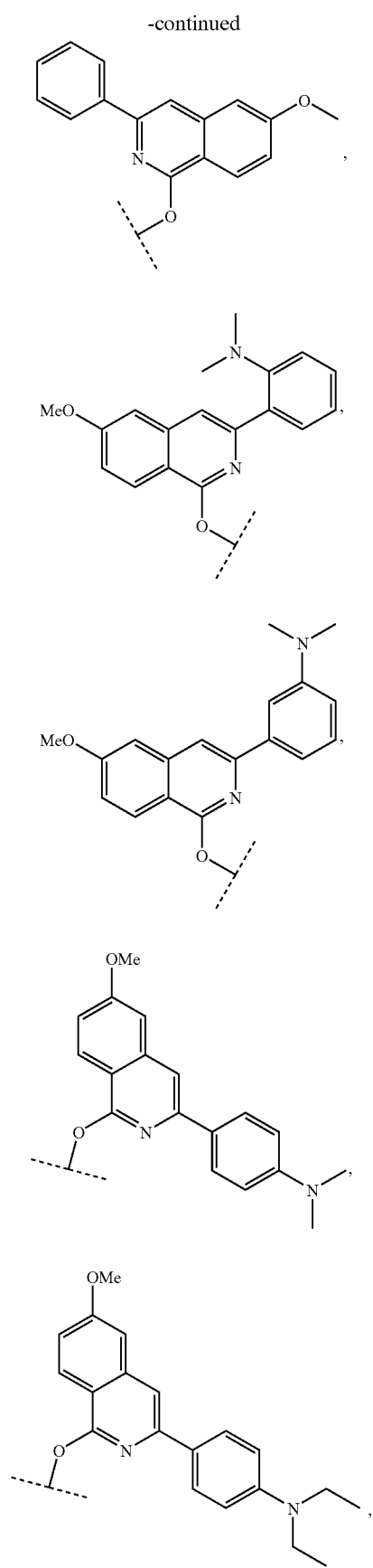
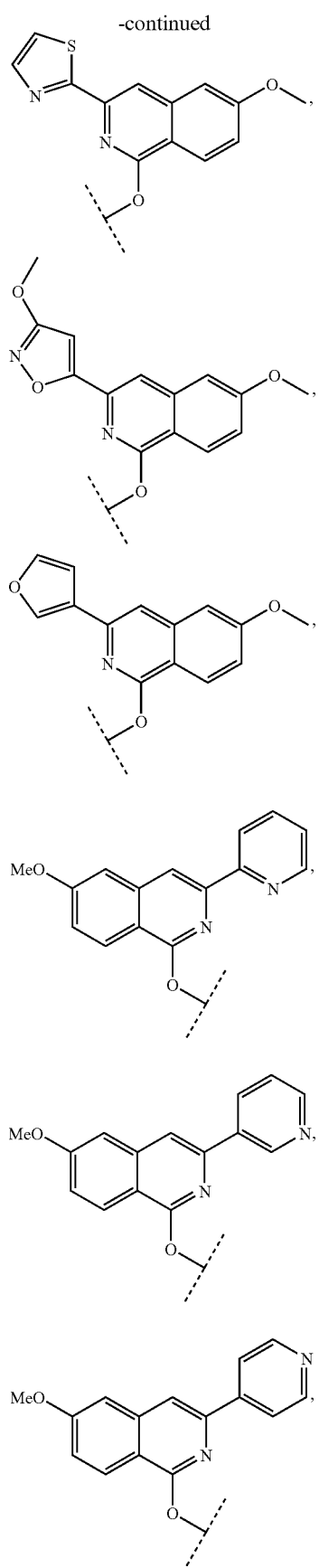

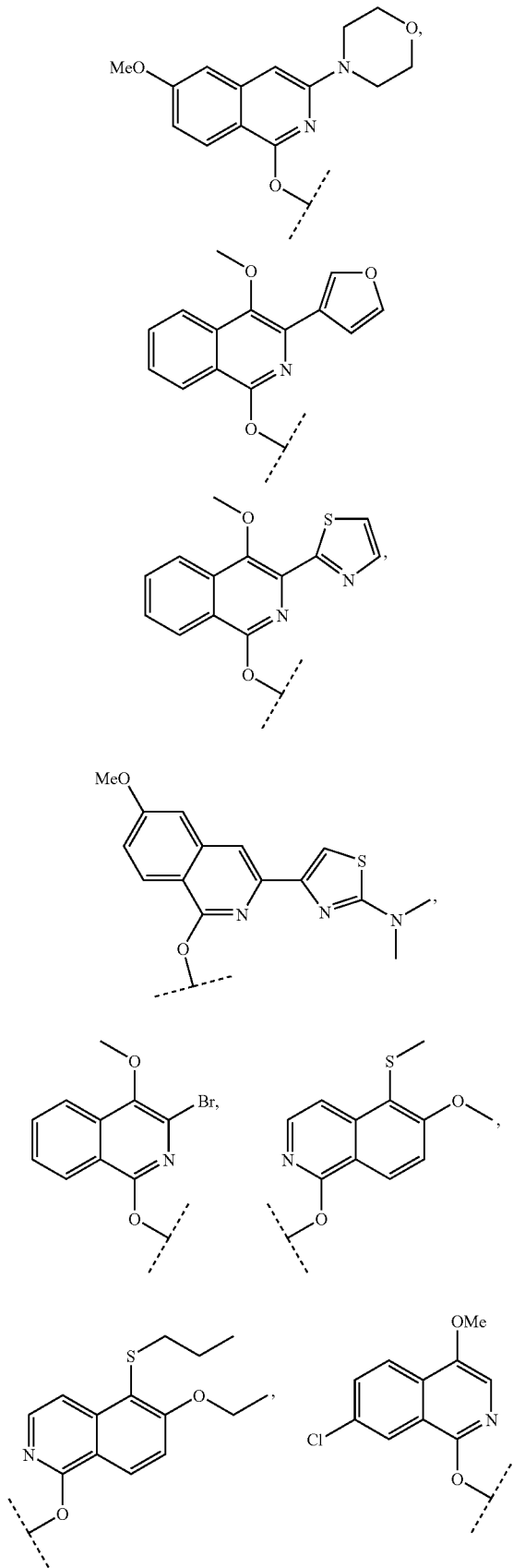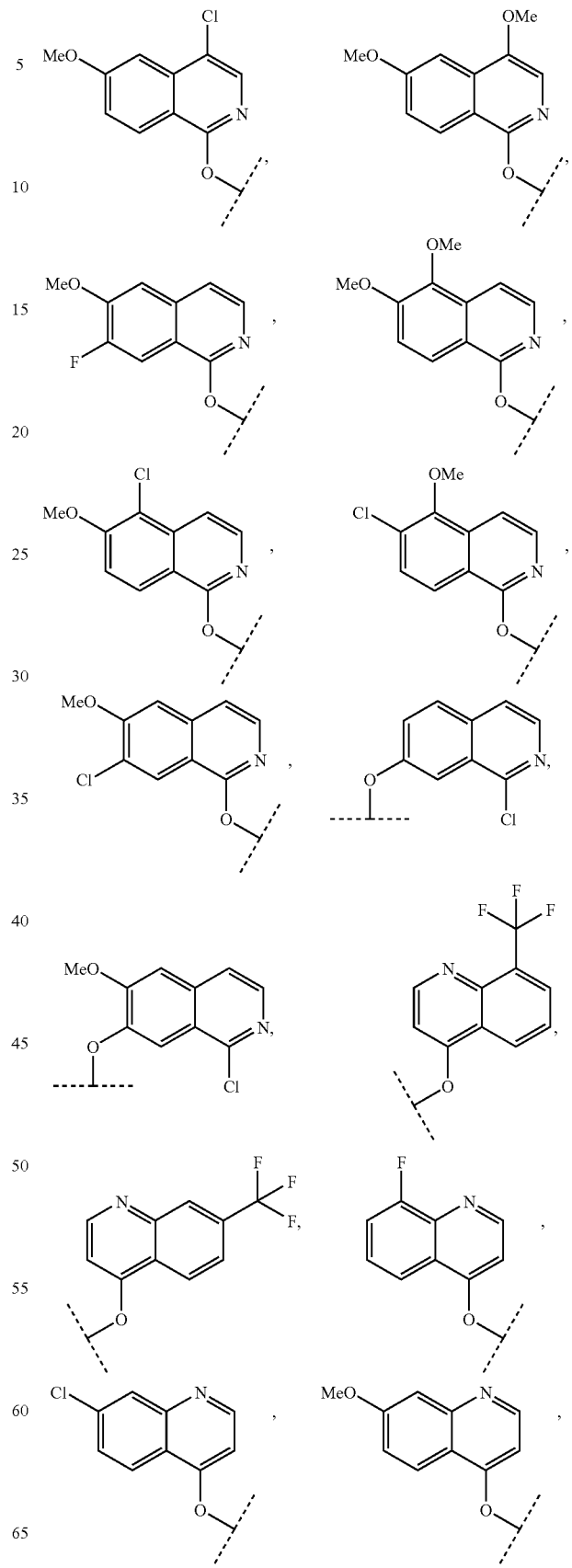

-continued
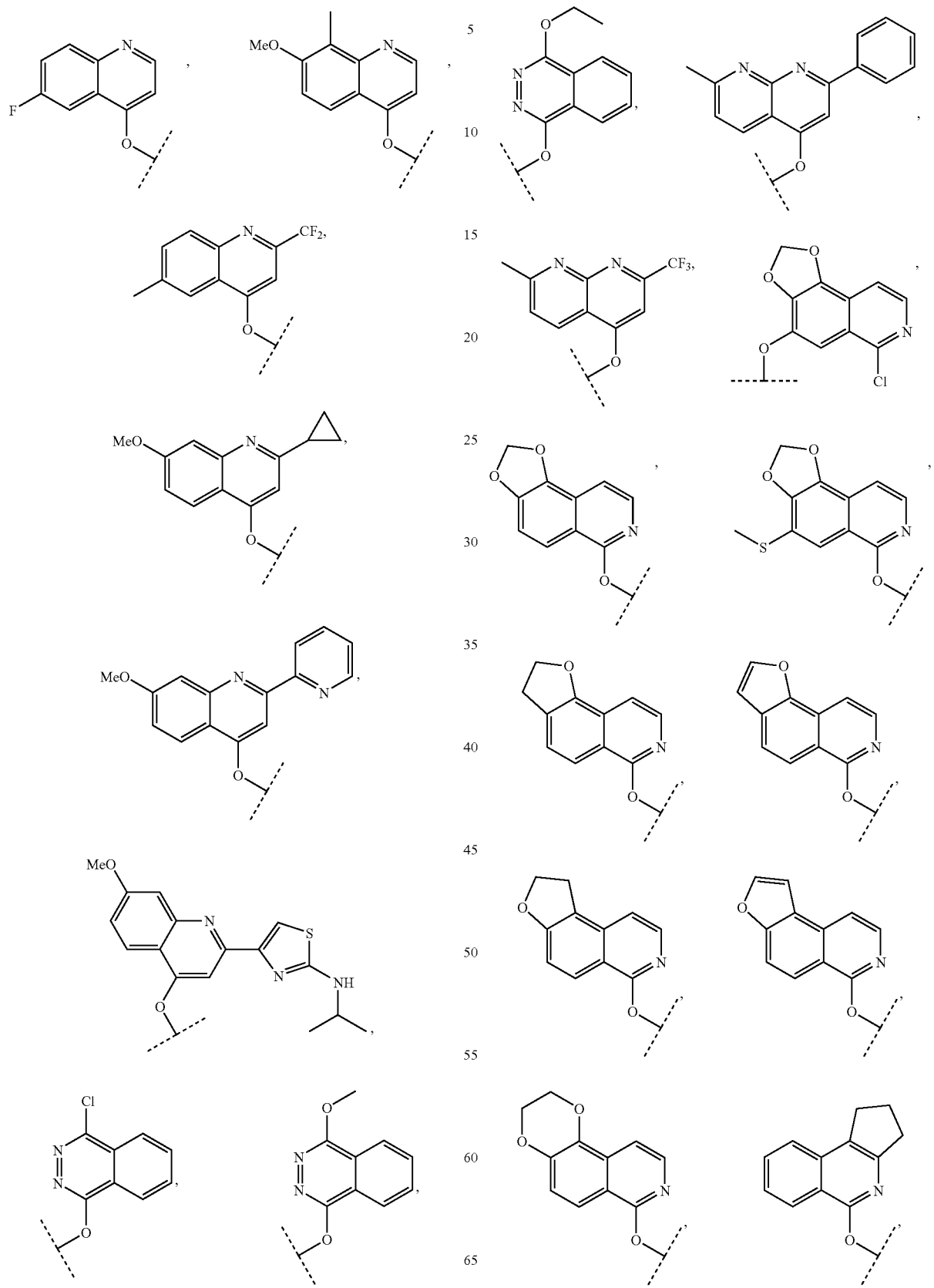

-continued
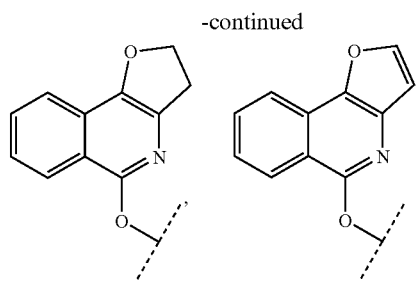
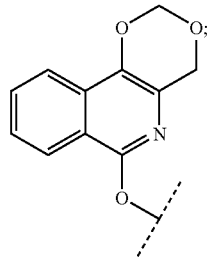
or R² is —O—R²⁰ wherein R²⁰ is selected from:
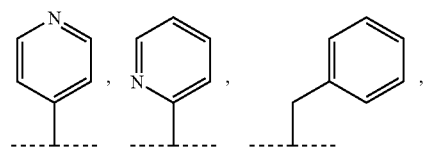
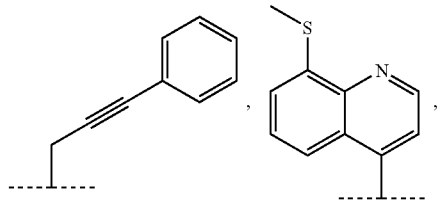
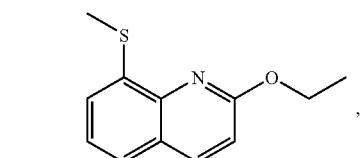
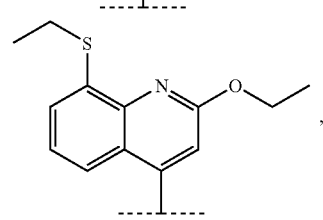
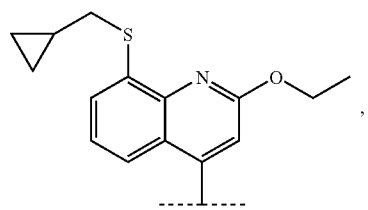
-continued
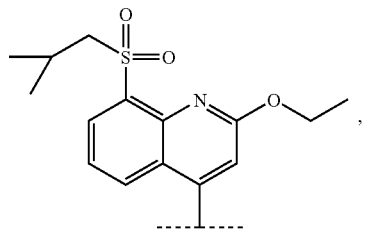
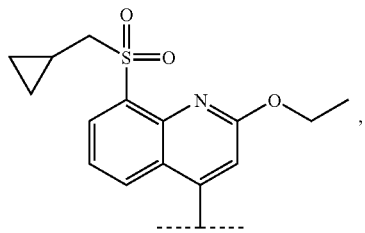
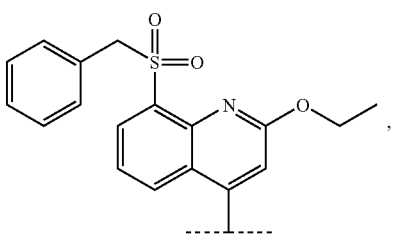
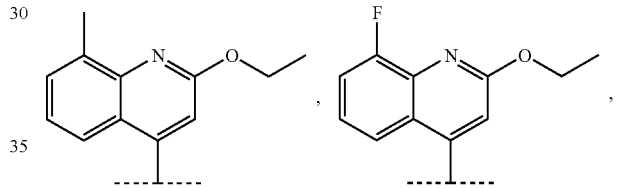
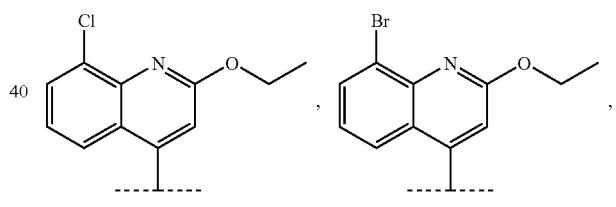
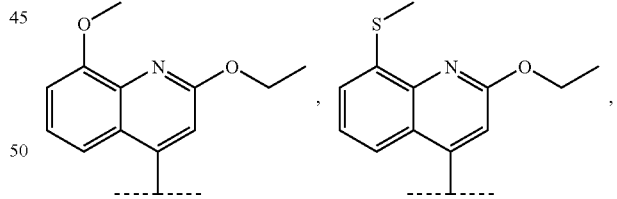
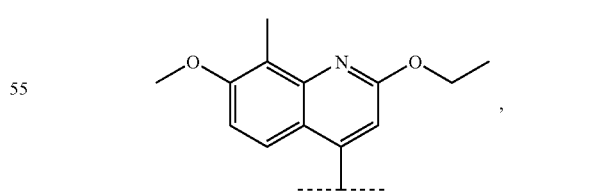
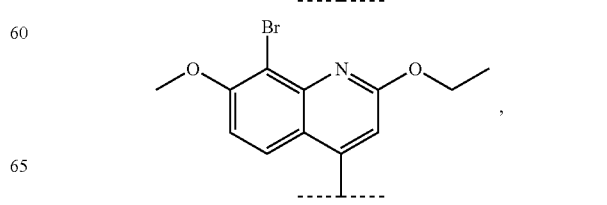

-continued
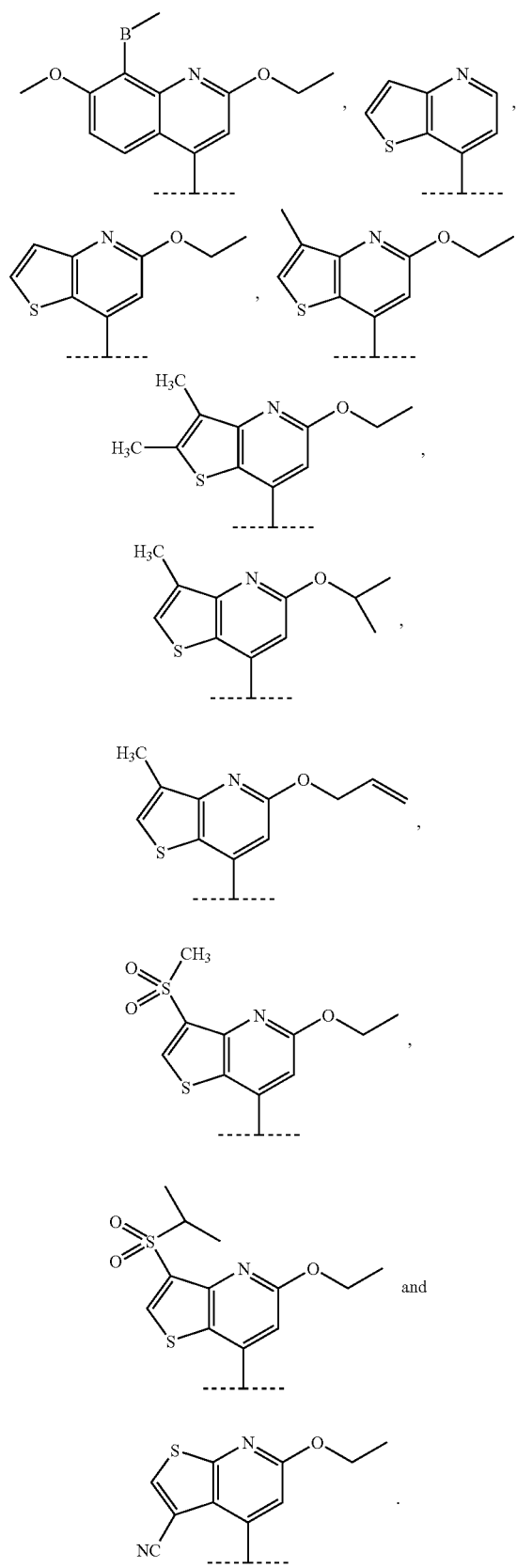
More preferably, $R^2$ is —O—$R^{20}$ wherein $R^{20}$ is selected from:
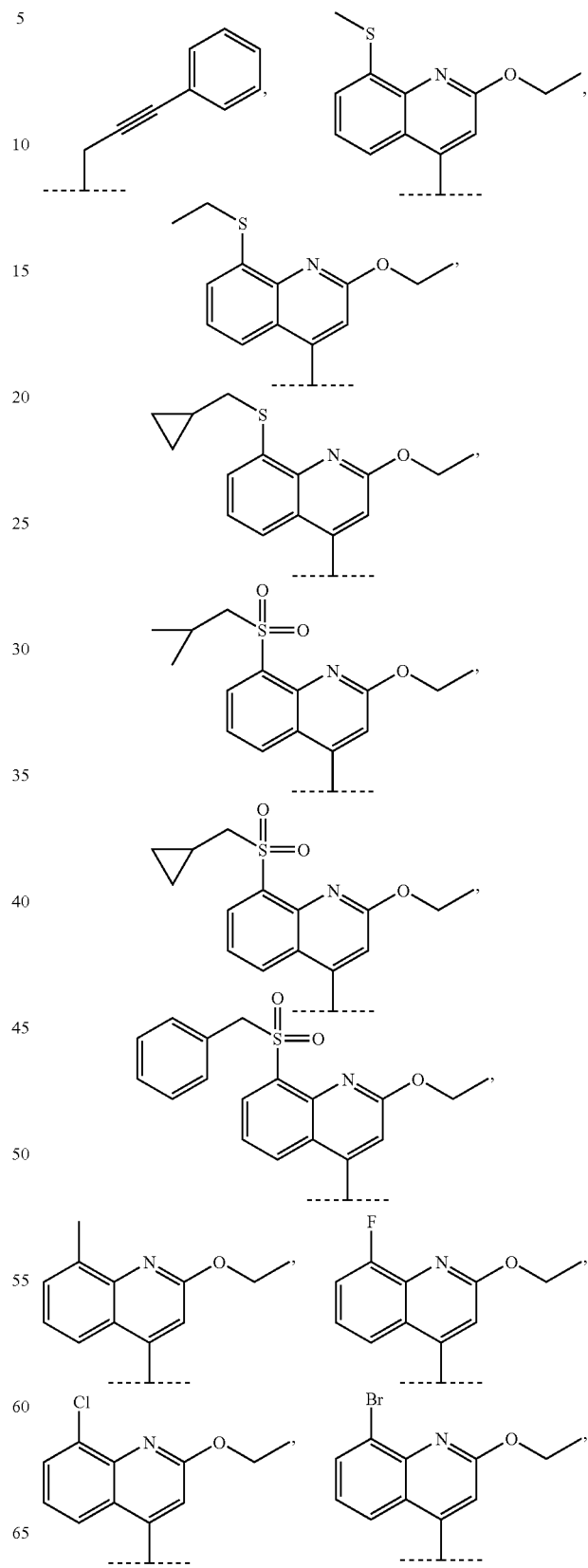

-continued

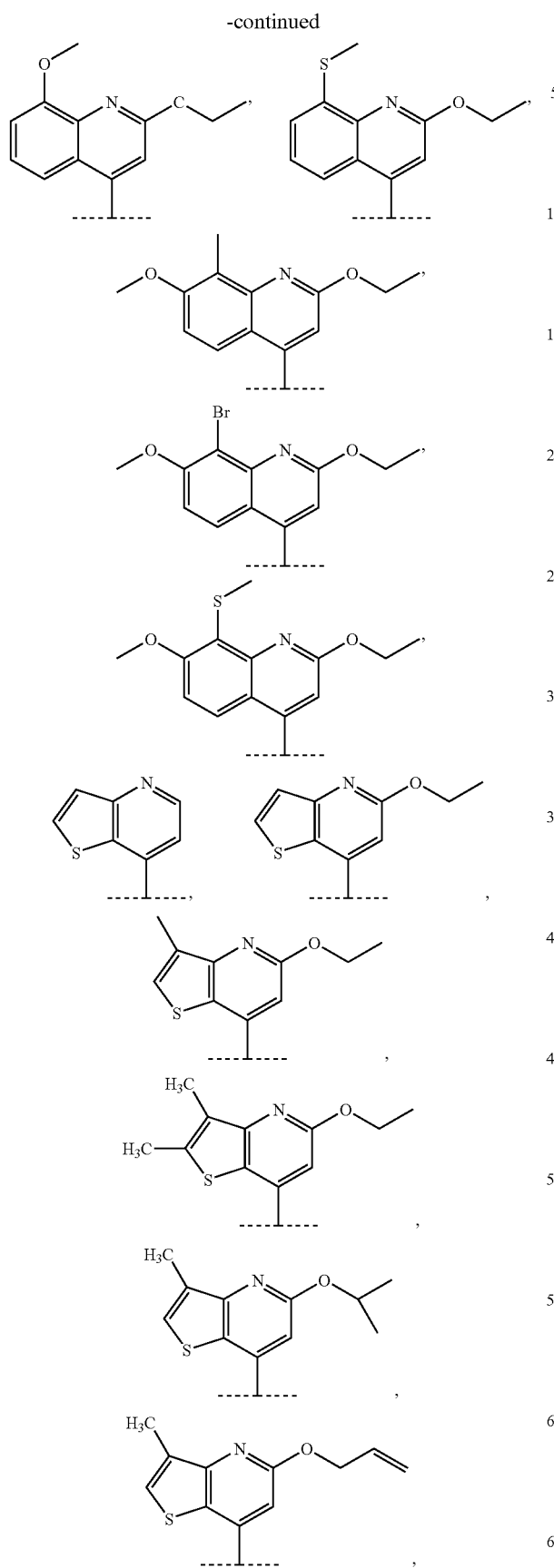

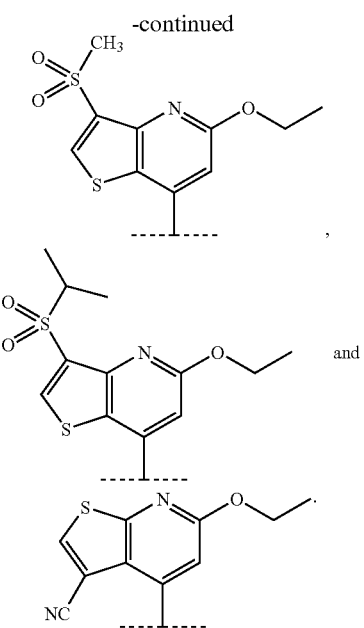

Any and each individual definition of $R^2$ as set out herein may be combined with any and each individual definition of $R^1$, $R^3$, $R^4$, $R^5$, $R^6$, Y, n, and m as set out herein.

n:

Preferably, n is 1.

Any and each individual definition of n as set out herein may be combined with any and each individual definition of $R^1$, $R^2$, $R^3$, $R^4$, $R^5$, $R^6$, Y and m as set out herein.

$R^1$:

Preferably, $R^1$ is $(C_{1-6})$alkyl, $(C_{2-6})$alkenyl, or $(C_{2-6})$alkynyl; each of which are optionally substituted with from one to three halogen atoms.

More preferably, $R^1$ is $(C_{2-6})$alkenyl or $(C_{2-6})$alkyl.

Even more preferably, $R^1$ is ethyl or ethenyl.

In the moiety P1 the substituent $R^1$ and the carbonyl take a syn orientation. Therefore, in embodiments where $R^1$ is ethyl, and n is 1, the asymmetric carbon atoms in the cyclopropyl group take the R,R configuration according to the subformula:

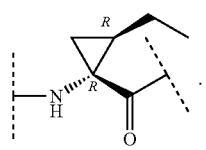

In embodiments where $R^1$ is ethenyl, the asymmetric carbon atoms in the cyclopropyl group take the R, S configuration according to the subformula:

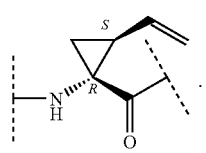

Therefore, in a preferred embodiment, the compounds of the present invention have the formula (Ia):

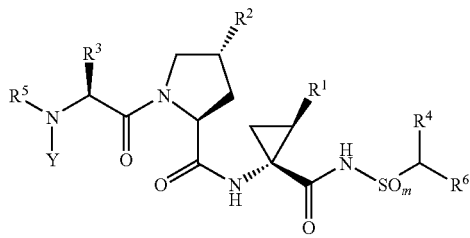

In a preferred embodiment of the present invention, compounds of formula (I) are those wherein n is 1 and $R^1$ is ethenyl.

Any and each individual definition of $R^1$ as set out herein may be combined with any and each individual definition of $R^2$, $R^3$, $R^4$, $R^5$, $R^6$, Y, n, and m as set out herein.

m:

Preferably m is 2. Particularly preferred are compounds of formula (I) wherein n is 1, m is 2 and $R^1$ is ethyl or ethenyl.

Any and each individual definition of m as set out herein may be combined with any and each individual definition of $R^1$, $R^2$, $R^3$, $R^4$, $R^5$, $R^6$, Y and n as set out herein.

$R^4$ and $R^6$:

Preferably:

(i) $R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one to three substituents each independently selected from halogen, $(C_{1-6})$alkyl, hydroxy, cyano, O—$(C_{1-6})$alkyl, —COOH, and —COO$(C_{1-6})$alkyl; or (ii) $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N, S and O, and said 3- to 7-membered monocyclic saturated or unsaturated heterocycle being optionally substituted with one to three substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —COOH, and —COO$(C_{1-6})$alkyl.

Alternatively preferably:

(i) $R^4$ and $R^6$ are each independently selected from H, $(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one to three substituents each independently selected from halogen, $(C_{1-6})$alkyl, hydroxy, cyano, O—$(C_{1-6})$alkyl, —COOH, and —COO$(C_{1-6})$alkyl; or (ii) $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N, S and O, and said 3- to 7-membered monocyclic saturated or unsaturated heterocycle being optionally substituted with one to three substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —COOH, and —COO$(C_{1-6})$alkyl.

More preferably:

(i) $R^4$ and $R^6$ are each independently selected from H, $(C_{1-6})$alkyl, —O—$(C_{1-6})$alkyl, $(C_{3-7})$cycloalkyl, aryl and aryl-$(C_{1-6})$alkyl-; wherein said $(C_{1-6})$alkyl, aryl and aryl-$(C_{1-6})$alkyl- are each optionally substituted with one to three substituents independently selected from halogen, $(C_{1-6})$alkyl, hydroxy, cyano, and —COOH; or (ii) $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N and O, and said 3- to 7-membered monocyclic saturated or unsaturated heterocycle being optionally substituted with one to three substituents each independently selected from $(C_{1-6})$alkyl, hydroxy, —NH$_2$, —NH$(C_{1-4})$alkyl, —N$((C_{1-4})$alkyl$)_2$, and —COOH.

Alternatively more preferably:

(i) $R^4$ and $R^6$ are each independently selected from H, $(C_{1-6})$alkyl: $(C_{3-7})$cycloalkyl, aryl and aryl-$(C_{1-6})$alkyl-; wherein said $(C_{1-6})$alkyl, aryl and aryl-$(C_{1-8})$alkyl- are each optionally substituted with one to three substituents independently selected from halogen, $(C_{1-6})$alkyl, hydroxy, cyano, and —COOH; or (ii) $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N and O, and said 3- to 7-membered monocyclic saturated or unsaturated heterocycle being optionally substituted with one to three substituents each independently selected from $(C_{1-6})$alkyl, hydroxy, —NH$_2$, —NH$(C_{1-4})$alkyl, —N$((C_{1-4})$alkyl$)_2$, and —COOH.

Even more preferably:

(i) $R^4$ and $R^6$ are each independently selected from H, methyl, ethyl, propyl, 1-methylethyl, methoxy, ethoxy, propoxy, cyclopropyl, phenyl, and benzyl, the methyl, ethyl, propyl, 1-methylethyl, phenyl and benzyl each being optionally substituted with chloro, hydroxy, cyano, or —COOH; or (ii) $R^4$ and $R^6$ are linked, together with the nitrogen to which they are bonded, to form a 4-, 5- or 6-membered monocyclic saturated or unsaturated heterocycle, optionally containing from one to three additional heteroatoms each independently selected from N and O, and optionally substituted with from one to three substituents each independently selected from $(C_{1-6})$alkyl, hydroxy, —N$((C_{1-4})$alkyl$)_2$, and —COOH.

Alternatively even more preferably:

(i) $R^4$ and $R^6$ are each independently selected from H, methyl, ethyl, propyl, 1-methylethyl, cyclopropyl, phenyl, and benzyl, the methyl, ethyl, propyl, 1-methylethyl, phenyl and benzyl each being optionally substituted with chloro, hydroxy, cyano, or —COOH; or (ii) $R^4$ and $R^6$ are linked, together with the nitrogen to which they are bonded, to form a 4-, 5- or 6-membered monocyclic saturated or unsaturated heterocycle, optionally containing from one to three additional heteroatoms each independently selected from N and O, and optionally substituted with from one to three substituents each independently selected from $(C_{1-6})$alkyl, hydroxy, —N$((C_{1-4})$alkyl$)_2$, and —COOH.

In a more preferred embodiment, $R^4$ and $R^6$ are each independently selected from methoxy, methyl and ethyl; or $R^4$ and $R^6$ are linked, together with the nitrogen to which they are bonded, to form a 5-membered monocyclic saturated or unsaturated heterocycle.

In an alternative more preferred embodiment, $R^4$ and $R^6$ are each independently selected from methyl and ethyl; or $R^4$ and $R^6$ are linked, together with the nitrogen to which they are bonded, to form a 5-membered monocyclic saturated or unsaturated heterocycle.

In yet another preferred embodiment; the group —$N(R^4)R^6$ is selected from:

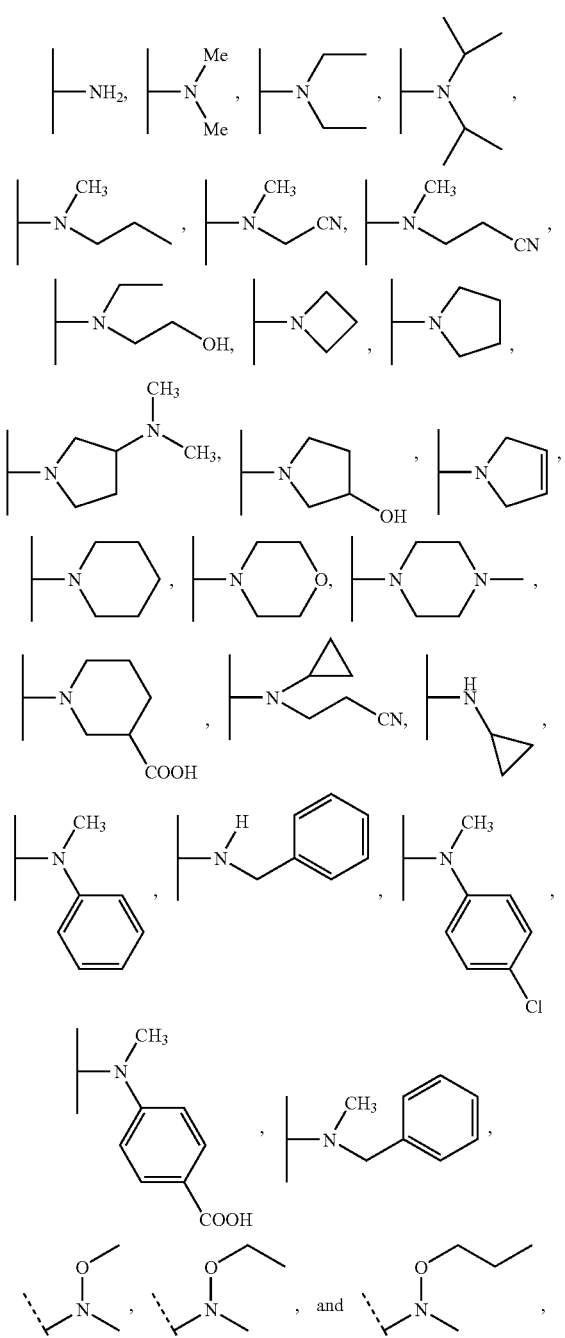

More preferably, the group —$N(R^4)R^6$ is selected from:

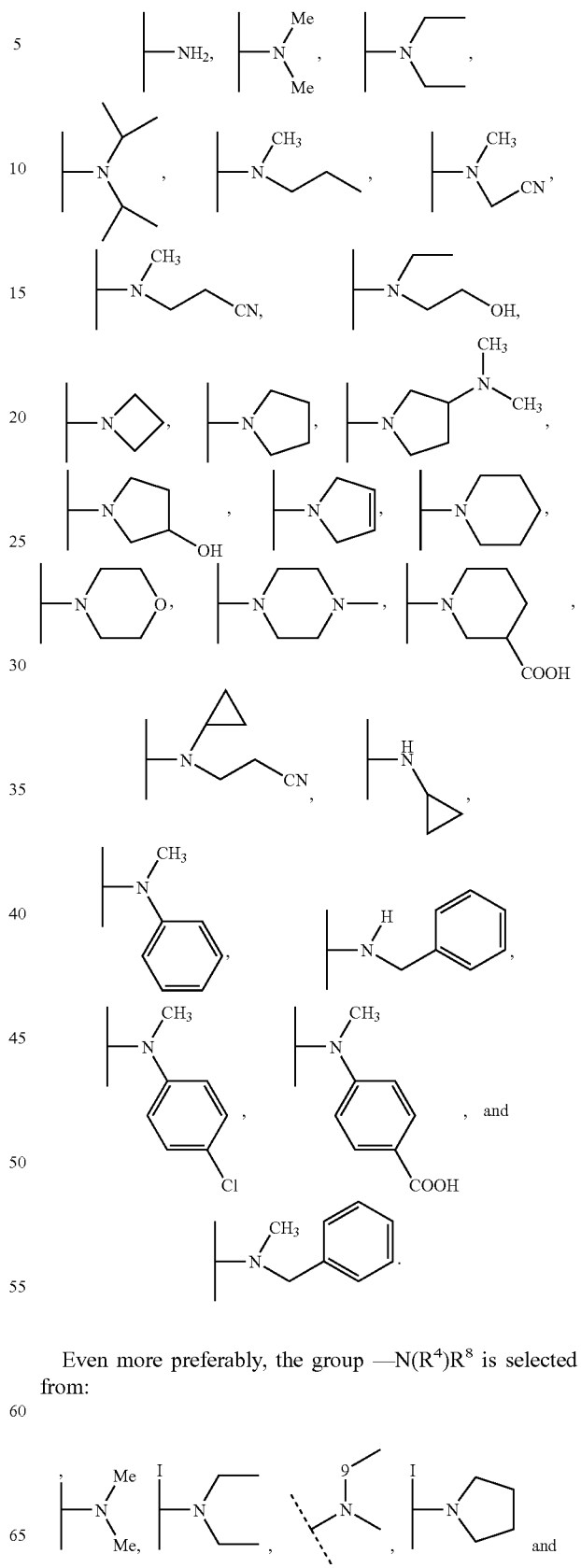

Even more preferably, the group —$N(R^4)R^8$ is selected from:

-continued

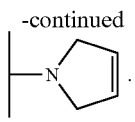

Still more preferably, the group —N(R$^4$)R$^6$ is selected from:

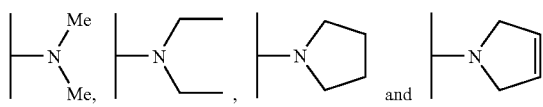

Most preferably, R$^4$ and R$^6$ are both methyl.

Any and each individual definition of R$^4$ and R$^6$ as set out herein may be combined with any and each individual definition of R$^1$, R$^2$, R$^3$, R$^5$, Y, n, and m as set out herein.

Therefore, one embodiment of the present invention provides a compound of formula (I):

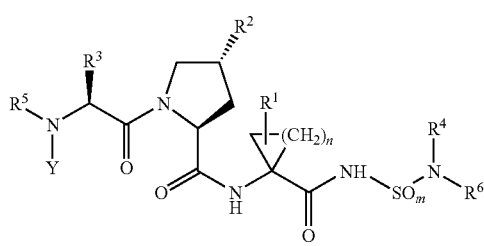

wherein
n is 1 or 2;
m is 1 or 2;
R$^1$ is H, (C$_{1-6}$)alkyl, (C$_{2-6}$)alkenyl, or (C$_{2-6}$)alkynyl, wherein said (C$_{2-6}$)alkyl, (C$_{2-6}$)alkenyl, or (C$_{2-6}$)alkynyl are optionally substituted with from one to three halogen atoms;
R$^2$ is selected from —CH$_2$—R$^{20}$, —NH—R$^{20}$, —O—R$^{20}$, —S—R$^{20}$, —SO—R$^{20}$, —SO$_2$—R$^{20}$, —CH$_2$O—R$^{20}$, and —O—X—R$^{20}$, wherein
X is (C$_{2-3}$)alkenyl, (C$_{2-3}$)alkynyl, or (C$_{1-3}$)alkyl; and
R$^{20}$ is (C$_6$ or C$_{10}$)aryl or Het, wherein said (C$_6$ or C$_{10}$)aryl or Het is optionally mono-, di-, tri- or tetra-substituted with R$^{200}$, wherein each R$^{200}$ is independently selected from H, halogen, cyano, (C$_{1-6}$)alkyl, (C$_{3-7}$)cycloalkyl, aryl-(C$_{1-6}$)alkyl-, aryl, Het, oxo, thioxo, —OR$^{201}$, —SR$^{201}$, —SOR$^{201}$, —SO$_2$R$^{201}$, —N(R$^{202}$)R$^{201}$, and —CON(R$^{202}$)R$^{201}$; wherein each of said alkyl, cycloalkyl, aryl and Het is optionally further substituted with R$^{2000}$;
R$^{201}$ in each case is independently selected from H, (C$_{1-6}$)alkyl, aryl, —CO—(C$_{1-6}$)alkyl and —CO—O—(C$_{1-6}$)alkyl, wherein each of said alkyl and aryl is optionally further substituted with R$^{2000}$;
R$^{202}$ is H or (C$_{1-6}$)alkyl;
R$^{2000}$ is one to three substituents each independently selected from halogen, aryl, Het, —OR$^{2001}$, —SR$^{2001}$, —SOR$^{2001}$, —SO$_2$R$^{2001}$, cyano, —N(R$^{2002}$)(R$^{2001}$), and R$^{2003}$, wherein said aryl and Het are optionally substituted with one, two or three substituents selected from (C$_{1-6}$)alkyl and —O—(C$_{1-6}$)alkyl;
R$^{2001}$ in each case is independently selected from aryl, aryl-(C$_{1-6}$)alkyl-, —C(O)—R$^{2003}$, —C(O)O—R$^{2003}$, —CON(R$^{2002}$XR$^{2004}$) and R$^{2004}$;
R$^{2002}$ is H or (C$_{1-6}$)alkyl;
R$^{2003}$ is (C$_{1-8}$)alkyl, (C$_{3-7}$)cycloalkyl or (C$_{3-7}$)cycloalkyl-(C$_{1-4}$)alkyl-, wherein said (C$_{3-7}$)cycloalkyl and (C$_{3-7}$) cycloalkyl-(C$_{1-4}$)alkyl- are optionally mono-, di-, or tri-substituted with (C$_{1-3}$)alkyl; and
R$^{2004}$ is H or R$^{2003}$;
R$^3$ is (C$_{1-8}$)alkyl, (C$_{3-7}$)cycloalkyl or (C$_{3-7}$)cycloalkyl-(C$_{1-3}$) alkyl-, each optionally substituted with one or more substituents independently selected from (C$_{1-6}$)alkyl, (C$_{2-6}$) alkenyl, halogen, cyano, —OR$^{30}$, —SR$^{30}$, —C(=O) OR$^{30}$, —C(=O)NH$_2$, —C(=O)NH(C$_{1-6}$)alkyl, C(=O)N ((C$_{1-6}$)alkyl)$_2$, —NH$_2$, —NH(C$_{1-6}$)alkyl, —N((C$_{1-6}$) alkyl)$_2$, aryl, and aryl(C$_{1-6}$)alkyl-, wherein R$^{30}$ is H, (C$_{1-6}$) alkyl, aryl, or aryl(C$_{1-6}$)alkyl-;
R$^5$ is selected from B, B—C(=O)—, B—O—C(=O)—, B—N(R$^{51}$)—C(=O)—; B—N(R$^{51}$)—C(=S), B—SO$_2$— and B—N(R$^{51}$)—SO$_2$—; wherein B is selected from:
(i) (C$_{1-10}$)alkyl optionally substituted with one or more substituents each selected independently from —COOH, —COO(C$_{1-6}$)alkyl, —OH, halogen, —OC(=O)(C$_{1-6}$)alkyl, —O(C$_{1-6}$)alkyl, —NH$_2$, —NH(C$_{1-6}$) alkyl, —N((C$_{1-6}$)alkyl)$_2$, —C(=O)NH$_2$, —C(=O)NH (C$_{1-6}$)alkyl and —C(=O)N((C$_{1-6}$)alkyl)$_2$;
(ii) (C$_{3-7}$)cycloalkyl, or (C$_{3-7}$)cycloalkyl-(C$_{1-4}$)alkyl-, each optionally substituted with one or more substituents each selected independently from (C$_{1-6}$)alkyl, halogen, —COOH, —COO(C$_{1-6}$)alkyl, —OH, —O(C$_{1-6}$) alkyl, —NH$_2$, —NH(C$_{1-6}$)alkyl, —N((C$_{1-6}$)alkyl)$_2$, —C(=O)NH$_2$, —C(=O)NH(C$_{1-6}$)alkyl and C(=O)N ((C$_{1-6}$)alkyl)$_2$;
(iii) aryl or aryl(C$_{1-6}$)alkyl-, each optionally substituted with one or more substituents each selected independently from (C$_{1-6}$)alkyl, —OH, —NH$_2$, —NH(C$_{1-6}$) alkyl, —N((C$_{1-6}$)alkyl)$_2$, —C(=O)NH$_2$, —C(=O)NH (C$_{1-6}$)alkyl and C(=O)N((C$_{1-6}$)alkyl)$_2$;
(iv) Het or Het-(C$_{1-6}$)alkyl-, each optionally substituted with one or more substituents each selected independently from (C$_{1-6}$)alkyl, —OH, —NH$_2$, —NH(C$_{1-6}$) alkyl, —N((C$_{1-6}$)alkyl)$_2$, —C(=O)NH$_2$, —C(=O)NH (C$_{1-6}$)alkyl and C(=O)N((C$_{1-6}$)alkyl)$_2$; and
(v) (C$_{2-6}$)alkenyl, or (C$_{2-6}$)alkynyl, each optionally substituted with 1 to 3 halogens; and wherein
R$^{51}$ is selected from H and (C$_{1-6}$)alkyl;
Y is H or (C$_{1-6}$)alkyl;
R$^4$ and R$^6$ are each independently selected from H, (C$_{1-6}$) alkyl, (C$_{3-7}$)cycloalkyl, (C$_{3-7}$)cycloalkyl-(C$_{1-6}$)alkyl-, aryl, Het, and aryl-(C$_{1-6}$)alkyl-; wherein said (C$_{1-6}$)alkyl, (C$_{3-7}$)cycloalkyl, (C$_{3-7}$)cycloalkyl-(C$_{1-6}$)alkyl-, aryl and aryl-(C$_{1-6}$)alkyl- are optionally substituted with one or more substituents independently selected from halogen, (C$_{1-6}$)alkyl, hydroxy, cyano, O—(C$_{1-6}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-6}$)alkyl; or
R$^4$ and R$^6$ are linked, together with the nitrogen to which they are bonded, to form a 3- to 7-membered monocyclic saturated or unsaturated heterocycle optionally fused to at least one other cycle to form a heteropolycycle, said heterocycle and heteropolycycle optionally containing from one to three further heteroatoms independently selected from N, S and O, and said 3 to 7-membered monocyclic saturated or unsaturated heterocycle being optionally substituted with one or more substituents independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —CO—NH$_2$, —CO—NH$(C_{1-4})$alkyl, —CO—N$((C_{1-4})$alkyl$)_2$, —COOH, and —COO$(C_{1-6})$alkyl;

with the proviso that when:

R$^5$ is B—O—C(=O)— or B—N(R$^{51}$)—C(=O)—, wherein R$^{51}$ is H; and

B is selected from $(C_{1-10})$alkyl, $(C_{3-7})$cycloalkyl, and $(C_{3-7})$cycloalkyl-$(C_{1-4})$alkyl, a) wherein said alkyl, cycloalkyl, and cycloalkyl-alkyl are optionally mono-, di- or tri-substituted with $(C_{1-3})$alkyl; and b) wherein said alkyl, cycloalkyl, and cycloalkyl-alkyl are optionally mono- or di-substituted with substituents selected from hydroxy and O—$(C_{1-4})$alkyl; and c) wherein each of said alkyl groups may be mono-, di- or tri-substituted with halogen; and d) wherein in each of said cycloalkyl groups being 4-, 5-, 6- or 7-membered, one (for the 4-, 5-, 6-, or 7-membered) or two (for the 5-, 6- or 7-membered) —CH$_2$-groups not directly linked to each other may be replaced by —O— to provide a heterocycle, such that the O-atom is linked to the —O—C(=O) or —N(R$^{51}$)—C(=O) group via at least two carbon atoms; and R$^2$ is O—R$^{20}$; then
R$^{20}$ cannot be

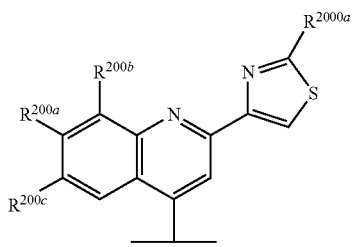

wherein
R$^{200a}$ is H, halogen, $(C_{1-4})$alkyl, —OH, —O—$(C_{1-4})$alkyl, —NH$_2$, —NH$(C_{1-4})$alkyl or —N$((C_{1-4})$alkyl$)_2$;

R$^{200b}$, R$^{200c}$ are each independently halogen, cyano, $(C_{1-4})$alkyl, —O—$(C_{1-4})$alkyl, —S—$(C_1$-OalkVI, —SO—$(C_{1-4})$alkyl, or —SO$_2$—$(C_{1-4})$alkyl, wherein each of said alkyl groups is optionally substituted with from one to three halogen atoms; and either R$^{200b}$ or R$^{200c}$ (but not both at the same time) may also be H; or R$^{200a}$ and R$^{200b}$ or R$^{200a}$ and R$^{200c}$ may be covalently bonded to form, together with the two C-atoms to which they are linked, a 5- or 6-membered carbocyclic ring wherein one or two —CH$_2$-groups not being directly linked to each other may be replaced each independently by —O— or NR$^a$ wherein R$^a$ is H or $(C_{1-4})$alkyl, and wherein said carbo- or heterocyclic ring is optionally mono- or di-substituted with $(C_{1-4})$alkyl; and R$^{2000a}$ is R$^{2003}$, —N(R$^{2002}$)COR$^{2003}$, —N(R$^{2002}$)COOR$^{2003}$, —N(R$^{2002}$)(R$^{2004}$), or —N(R$^{2002}$)CON(R$^{2002}$)(R$^{2004}$), wherein R$^{2002}$ is H or methyl;

R$^{2003}$ is $(C_{1-8})$alkyl, $(C_{3-7})$cycloalkyl or $(C_{3-7})$cycloalkyl-$(C_{1-4})$alkyl-, wherein said $(C_{3-7})$cycloalkyl and $(C_{3-7})$cycloalkyl-$(C_{1-4})$alkyl- are optionally mono-, di-, or tri-substituted with $(C_{1-3})$alkyl; and R$^{2004}$ is H or R$^{2003}$;

wherein Het as used in the above definitions unless otherwise stated is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a diastereomer thereof or a salt thereof.

Preferred compounds of formula (I) are those wherein:

R$^5$ is selected from B—C(=O)—, B—O—C(=O, and B—NH—C(=O)—; wherein B is selected from:

(i) $(C_{1-10})$alkyl optionally substituted with one or more substituents each selected independently from —COOH, —COO$(C_{1-6})$alkyl, —OH, halogen, —OC(=O)$(C_{1-6})$alkyl, —O$(C_{1-6})$alkyl, —NH$_2$, —NH$(C_{1-6})$alkyl, —N$((C_{1-6})$alkyl$)_2$, —C(=O)NH$_2$, —C(=O)NH$(C_{1-6})$alkyl and —C(=O)N$((C_{1-6})$alkyl$)_2$;

(ii) $(C_{3-7})$cycloalkyl, or $(C_{3-7})$cycloalkyl-$(C_{1-4})$alkyl-, each optionally substituted with one or more substituents each selected independently from $(C_{1-6})$alkyl, halogen, —COOH, —COO$(C_{1-6})$alkyl, —OH, —O$(C_{1-6})$alkyl, —NH$_2$, —NH$(C_{1-6})$alkyl, —N$((C_{1-6})$alkyl$)_2$, —C(=O)NH$_2$, —C(=O)NH$(C_{1-6})$alkyl and —C(=O)N$((C_{1-6})$alkyl$)_2$;

(iii) aryl or aryl$(C_{1-6})$alkyl-, each optionally substituted with one or more substituents each selected independently from $(C_{1-6})$alkyl, —OH, —NH$_2$, —NH$(C_{1-6})$alkyl, —N$((C_{1-6})$alkyl$)_2$, —C(=O)NH$_2$, —C(=O)NH$(C_{1-6})$alkyl and —C(=O)N$((C_{1-6})$alkyl$)_2$; and (iv) Het or Het-$(C_{1-6})$alkyl-, each optionally substituted with one or more substituents each selected independently from $(C_{1-6})$alkyl, —OH, —NH$_2$, —NH$(C_{1-6})$alkyl, —N$((C_{1-6})$alkyl$)_2$, —C(=O)NH$_2$, —C(=O)NH$(C_{1-6})$alkyl and —C(=O)N$((C_{1-6})$alkyl$)_2$;

Y is H;

R$^3$ is $(C_{1-8})$alkyl or $(C_{3-7})$cycloalkyl, each of which are optionally substituted with one or more substituents each independently selected from $(C_{1-6})$alkyl, —OR$^{30}$, and —C(=O)OR$^{30}$, wherein R$^{30}$ is H, $(C_{1-6})$alkyl, or aryl $(C_{1-6})$alkyl-;

R$^2$ is —O—X—R$^{20}$, wherein X is $(C_3)$alkynyl and R$^{20}$ is $(C_6$ or $C_{10})$aryl; or R$^2$ is —O—R$^{20}$ wherein R$^{20}$ is

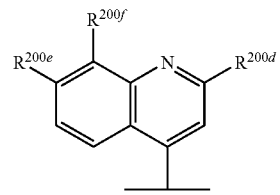

wherein
R$^{200d}$ is —OR$^{201}$, wherein R$^{201}$ is $(C_{1-6})$alkyl;

R$^{200e}$ is H or —OR$^{201}$ wherein R$^{201}$ is $(C_{1-6})$alkyl; and

R$^{200f}$ is $(C_{1-6})$alkyl, halogen, —SR$^{201}$, —SO$_2$R$^{201}$, or —OR$^{201}$, wherein R$^{201}$ is $(C_{1-6})$alkyl optionally further substituted with $(C_{3-7})$cycloalkyl or phenyl;

or $R^{20}$ is

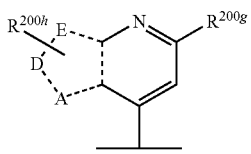

wherein
one of A, D, and E represents a S atom and the other two of A, D, and E represent C atoms;
— represents a single bond between a C atom and an S atom, and represents a single bond or a double bond between two C atoms; provided that each C atom is bonded by one double bond;
$R^{200g}$ is H or —$OR^{201}$, wherein $R^{201}$ is $(C_{1-6})$alkyl or $(C_{2-6})$alkenyl; and
$R^{200h}$ is one or two substituents each independently selected from H, cyano, $(C_{1-6})$alkyl and —$SO_2$-$(C_{1-6})$alkyl; wherein each $R^{200h}$ is bonded to a C atom which would otherwise bear a hydrogen atom;
$R^1$ is $(C_{2-6})$alkenyl or $(C_{2-6})$alkyl;
n is 1;
m is 2; and
$R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are optionally substituted with one to three substituents each independently selected from halogen, $(C_{1-6})$alkyl, hydroxy, cyano, O—$(C_{1-6})$alkyl, —COOH, and —COO$(C_{1-6})$alkyl; or
$R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N, S and O, and said 3- to 7-membered monocyclic saturated or unsaturated heterocycle being optionally substituted with one to three substituents each independently selected from halogen, $(C_{-6})$alkyl, hydroxy, cyano, O—$(C_{1-6})$alkyl, —$NH_2$, —$NH(C_{1-4})$alkyl, —$N((C_{1-4})$alkyl$)_2$, —COOH, and —COO$(C_{1-6})$alkyl;

or a diastereomer thereof or a salt thereof.

Alternatively, preferred compounds of formula (I) are those wherein:
$R^5$ is selected from B—C(═O)—, B—O—C(═O)—, and B—NH—C(═O)—; wherein B is selected from:
(i) $(C_{i-10})$alkyl optionally substituted with one or more substituents each selected independently from —COOH, —COO$(C_{1-6})$alkyl, —OH, halogen, —OC(═O)$(C_{1-6})$alkyl, —O$(C_{1-6})$alkyl, —$NH_2$, —$NH(C_{1-6})$alkyl, —$N((C_{1-6})$alkyl$)_2$, —C(═O)$NH_2$, —C(═O)NH$(C_{1-6})$alkyl and —C(═O)N$((C_{1-6})$alkyl$)_2$;
(ii) $(C_{3-7})$cycloalkyl, or $(C_{3-7})$cycloalkyl-$(C_{i-4})$alkyl-, each optionally substituted with one or more substituents each selected independently from $(C_{i-6})$alkyl, halogen, —$COOH_1$—COO$(C_{1-6})$alkyl, —OH, —O$(d_{-6})$alkyl, —$NH_2$, —$NH(C_{1-6})$alkyl, —$N((d_{-6})$alkyl); —C(═O)$NH_2$, —C(═O)NH$(C_{1-6})$alkyl and —C(═O)N$((C_{1-6})$alkyl$)_2$;
(iii) aryl or aryl$(C_{1-6})$alkyl-, each optionally substituted with one or more substituents each selected independently from $(C_{1-6})$alkyl, —OH, —$NH_2$, —$NH(C_{1-6})$alkyl, —$N((C_{1-6})$alkyl$)_2$, —C(═O)$NH_2$, —C(═O)NH$(C_{1-6})$alkyl and —C(═O)N$((C_{1-6})$alkyl$)_2$; and
(iv) Het or Het-$(C_{1-6})$alkyl-, each optionally substituted with one or more substituents each selected independently from $(C_{1-6})$alkyl, —OH, —$NH_2$, —$NH(C_{1-6})$alkyl, —$N((C_{1-6})$alkyl$)_2$, —C(═O)$NH_2$, —C(═O)NH$(C_{1-6})$alkyl and —C(═O)N$((C_{1-6})$alkyl$)_2$;
Y is H;
$R^3$ is $(C_{i-8})$alkyl or $(C_{3-7})$cycloalkyl, each of which are optionally substituted with one or more substituents each independently selected from $(C_{1-6})$alkyl, —$OR^{30}$, and —C(═O)$OR^{30}$, wherein $R^{30}$ is H, $(C_{1-6})$alkyl, or aryl $(C_{1-6})$alkyl-;
$R^2$ is —O—X—$R^{20}$, wherein X is $(C_3)$alkynyl and $R^{20}$ is $(C_6$ or $C_{10})$aryl; or
$R^2$ is —O—$R^{20}$ wherein $R^{20}$ is

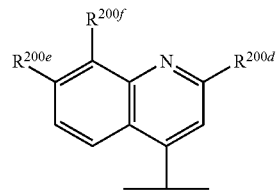

wherein
$R^{200d}$ is —$OR^{201}$, wherein $R^{201}$ is $(C_{1-6})$alkyl;
$R^{200e}$ is H or —$OR^{201}$, wherein $R^{201}$ is $(C_{1-6})$alkyl; and
$R^{200f}$ is $(C_{1-6})$alkyl, halogen, —$SR^{201}$, —$SO_2R^{201}$, or —$OR^{201}$, wherein $R^{201}$ is $(C_{i-6})$alkyl optionally further substituted with $(C_{3-7})$cycloalkyl or phenyl;
or $R^{20}$ is

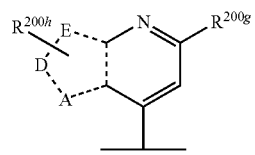

wherein
one of A, D, and E represents a S atom and the other two of A, D, and E represent C atoms;
— represents a single bond between a C atom and an S atom, and represents a single bond or a double bond between two C atoms; provided that each C atom is bonded by one double bond;
$R^{200g}$ is H or —$OR^{201}$, wherein $R^{201}$ is $(C_{1-6})$alkyl or $(C_{2-6})$alkenyl; and
$R^{200h}$ is one or two substituents each independently selected from H, cyano, $(C_{i-6})$alkyl and —$SO_2$—$(C_{1-6})$alkyl; wherein each $R^{200h}$ is bonded to a C atom which would otherwise bear a hydrogen atom;
$R^1$ is $(C_{2-6})$alkenyl or $(C_{2-6})$alkyl;
n is 1;
m is 2; and
$R^4$ and $R^6$ are each independently selected from H, $(C_{1-6})$alkyl, $(C_{3-7})$cycloalkyl, $(C_{3-7})$cycloalkyl-$(C_{i-6})$alkyl-, aryl and aryl-$(C_{i-6})$alkyl-; wherein said $(C_{i-6})$alkyl, $(C_{3-7})$cycloalkyl, $(Cs^{\wedge}$cycloalkyKC^alkyl-, aryl and aryl-$(C_{i-6})$alkyl- are optionally substituted with one to three substituents each independently selected from halogen, $(C_{1-6})$alkyl, hydroxy, cyano, O—$(C_{i-6})$alkyl, —COOH, and —COOCCn-oalkyl; or $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N, S and O, and said 3- to 7-membered monocyclic saturated or unsaturated heterocycle being optionally substituted with one to three substituents each independently selected from halogen, $(C_{1-6})$alkyl, hydroxy, cyano, O—$(C_{1-6})$alkyl, —$NH_2$, —$NH(C_{1-4})$alkyl, —$N((C_{1-4})$alkyl$)_2$, —COOH, and —COO$(C_{1-6})$alkyl;

or a diastereomer thereof or a salt thereof.

More preferred compounds of formula (I) are those wherein:

$R^5$ is selected from B—C(=O), B—O—C(=O), and B—NH—C(=O)—, and B is selected from 1,1-dimethylethyl optionally substituted with 1, 2, or 3 halogen substituents, cyclopropyl-CH$_2$—, benzyl, 2,2-dimethylpropyl, cyclopentyl, cyclobutyl, tetrahydrofuranyl, 1,1,-dimethylpropyl,

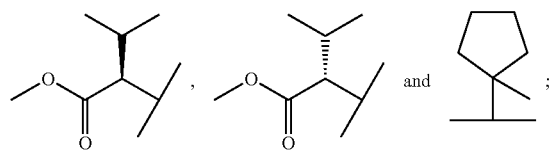

Y is H;

$R^3$ is selected from 1,1-dimethylethyl, 1-methylethyl, 1-methylpropyl, 1-hydroxy-1-methylethyl, 1-methoxyethyl, 1-tert-butoxyethyl, 1-ethoxyethyl, cyclopentyl,

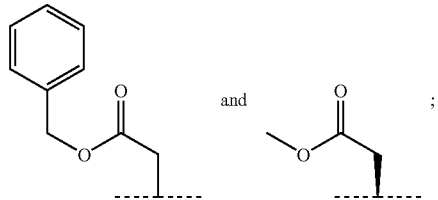

$R^2$ is —O—X—$R^{20}$, wherein X is —$CH_2C\equiv C$—; and $R^{20}$ is phenyl; or $R^2$ is —O—$R^{20}$ wherein $R^{20}$ is

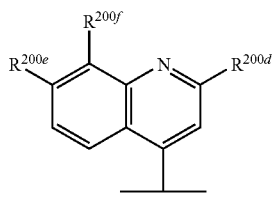

wherein $R^{200d}$ is —$OR^{201}$, wherein $R^{201}$ is ethyl;

$R^{200e}$ is H or —$OR^{201}$, wherein $R^{201}$ is $(C_{1-6})$alkyl; and $R^{200f}$ is $(C_{1-6})$alkyl, halogen, —$SR^{201}$, —$SO_2R^{201}$, or —$OR^{201}$, wherein $R^{201}$ is $(C_{1-6})$alkyl optionally further substituted with $(C_{3-7})$cycloalkyl or phenyl;

or $R^{20}$ is

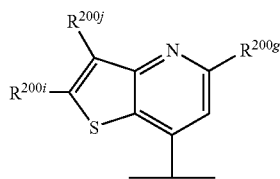

wherein $R^{200g}$ is H or —$OR^{201}$, wherein $R^{201}$ is $(C_{1-6})$alkyl or $(C_{2-6})$alkenyl;

$R^{200j}$ is H, $(C_{1-6})$alkyl or —$SO_2$—$(C_{1-6})$alkyl; and $R^{200i}$ is H or $(C_{1-6})$alkyl;

or $R^{25}$ is

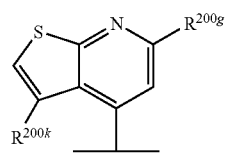

wherein $R^{200g}$ is —$OR^{201}$, wherein $R^{201}$ is $(C_{1-6})$alkyl; and $R^{200k}$ is cyano;

$R^1$ is ethenyl or ethyl;

n is 1;

m is 2; and the group —$N(R^4)R^6$ is selected from:

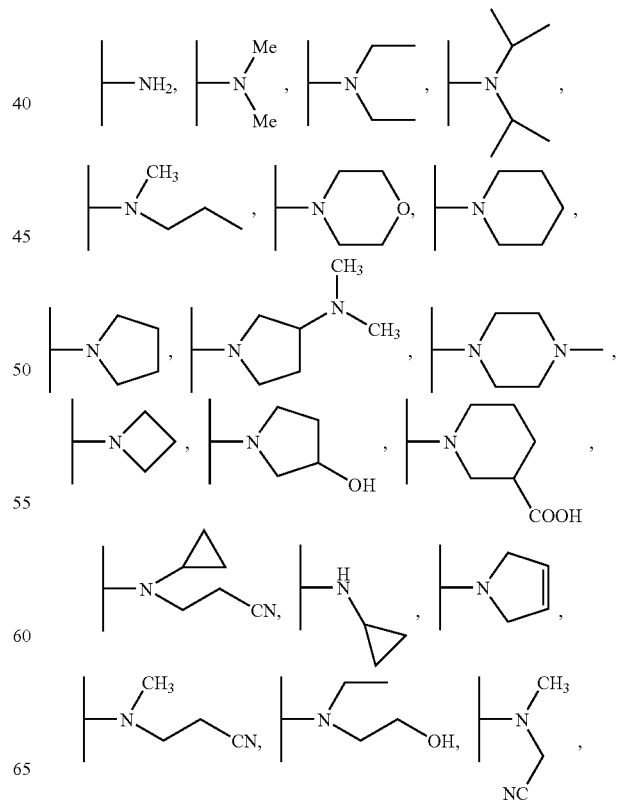

-continued

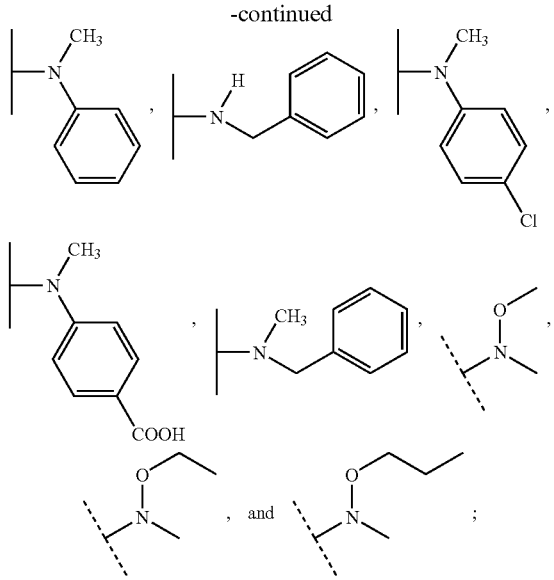

or a diastereomer thereof or a salt thereof.

Alternatively, more preferred compounds of formula (I) are those wherein:

$R^5$ is selected from B—C(=O)—, B—O—C(=O)—, and B—NH—C(=O)—, and B is selected from 1,1-dimethylethyl optionally substituted with 1, 2, or 3 halogen substituents, cyclopropyl-CH$_2$—, benzyl, 2,2-dimethylpropyl, cyclopentyl, cyclobutyl, tetrahydrofuranyl, 1,1,-dimethylpropyl,

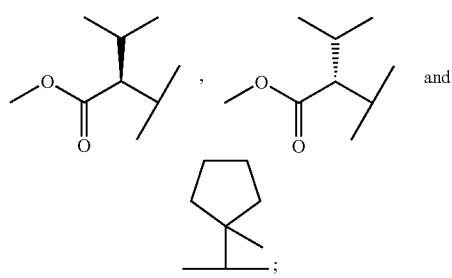

Y is H;

$R^3$ is selected from 1,1-dimethylethyl, 1-methylethyl, 1-methylpropyl, 1-hydroxy-1-methylethyl, 1-methoxyethyl, 1-tert-butoxyethyl, 1-ethoxyethyl, cyclopentyl,

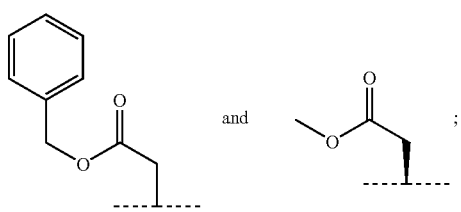

$R^2$ is —O—X—R$^{20}$, wherein X is —CH$_2$C≡C—; and R$^{20}$ is phenyl; or $R^2$ is —O—R$^{20}$ wherein R$^{20}$ is

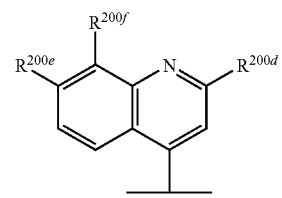

wherein $R^{200d}$ is —OR$^{201}$, wherein R$^{201}$ is ethyl;

$R^{200e}$ is H or —OR$^{201}$, wherein R$^{201}$ is (C$_{1-6}$)alkyl; and $R^{200f}$ is (C$_{1-6}$)alkyl, halogen, —SR$^{201}$, —SO$_2$R$^{201}$, or —OR$^{201}$, wherein R$^{201}$ is (C$_{1-6}$)alkyl optionally further substituted with (C$_{3-7}$)cycloalkyl or phenyl;

or R$^{20}$ is

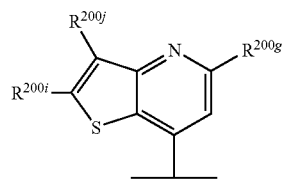

wherein $R^{200g}$ is H or —OR$^{201}$, wherein R$^{201}$ is (C$_{1-6}$)alkyl or (C$_{2-6}$)alkenyl;

$R^{200j}$ is H, (C$_{1-6}$)alkyl or —SO$_2$—(C$_{1-6}$)alkyl; and $R^{200i}$ is H or (C$_{1-6}$)alkyl;

or R$^{20}$ is

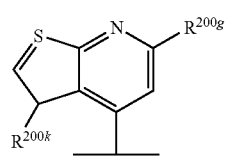

wherein $R^{200g}$ is —OR$^{201}$, wherein R$^{201}$ is (C$_{1-6}$)alkyl; and $R^{200k}$ is cyano;

$R^1$ is ethenyl or ethyl;

n is 1;

m is 2; and the group —N(R$^4$)R$^6$ is selected from:

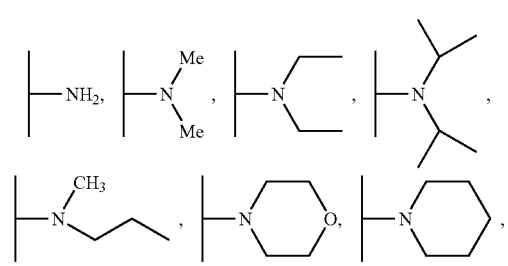

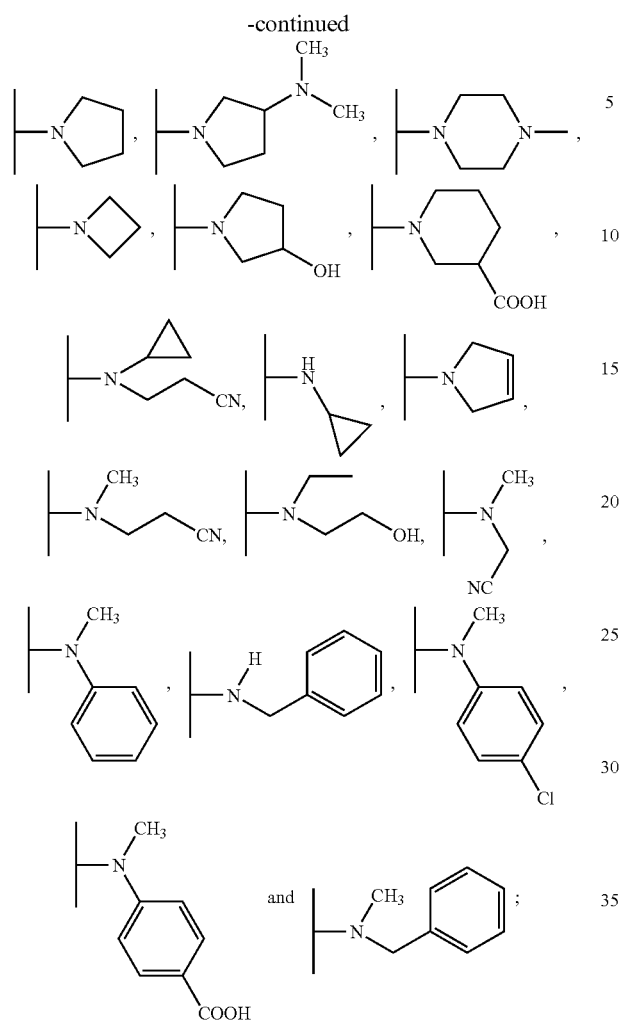
or a diastereomer thereof or a salt thereof.
Most preferably,
$R^5$ is B—O—C(═O)—, wherein B is cyclopentyl;
Y is H;
$R^3$ is 1,1-dimethylethyl;
$R^2$ is —O—$R^{20}$ wherein $R^{20}$ is selected from:
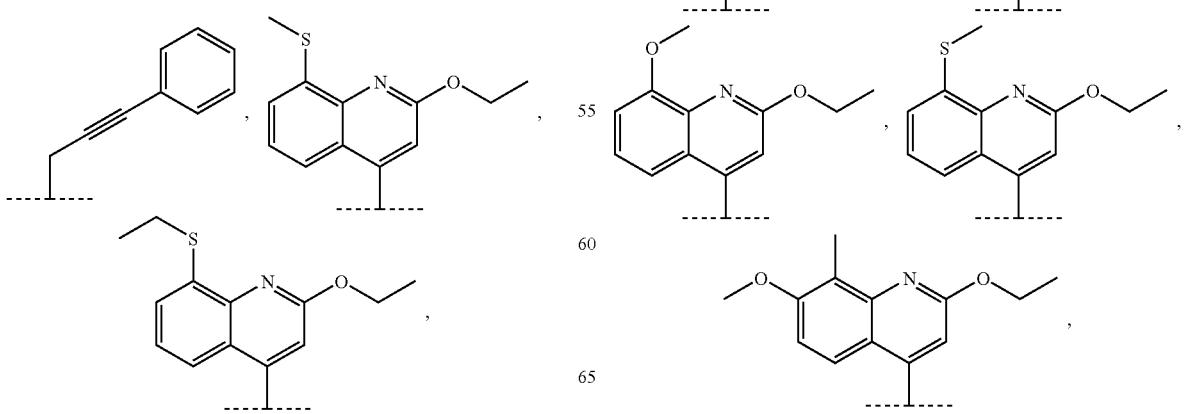

-continued
,
,
,
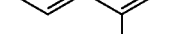,
,
,
,
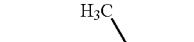,
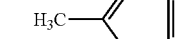,
 and
;
$R^1$ is ethenyl or ethyl;
n is 1;
m is 2; and
the group —N($R^4$)$R^6$ is selected from:
, ,
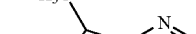,  and hO;
or a diastereomer thereof or a salt thereof.
Alternatively most preferably,
$R^5$ is B—O—C(=O)—, wherein B is cyclopentyl;
Y is H;
$R^3$ is 1,1-dimethylethyl;
$R^2$ is —O—$R^{20}$ wherein $R^{20}$ is selected from:
, ,
,
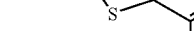,
,
,

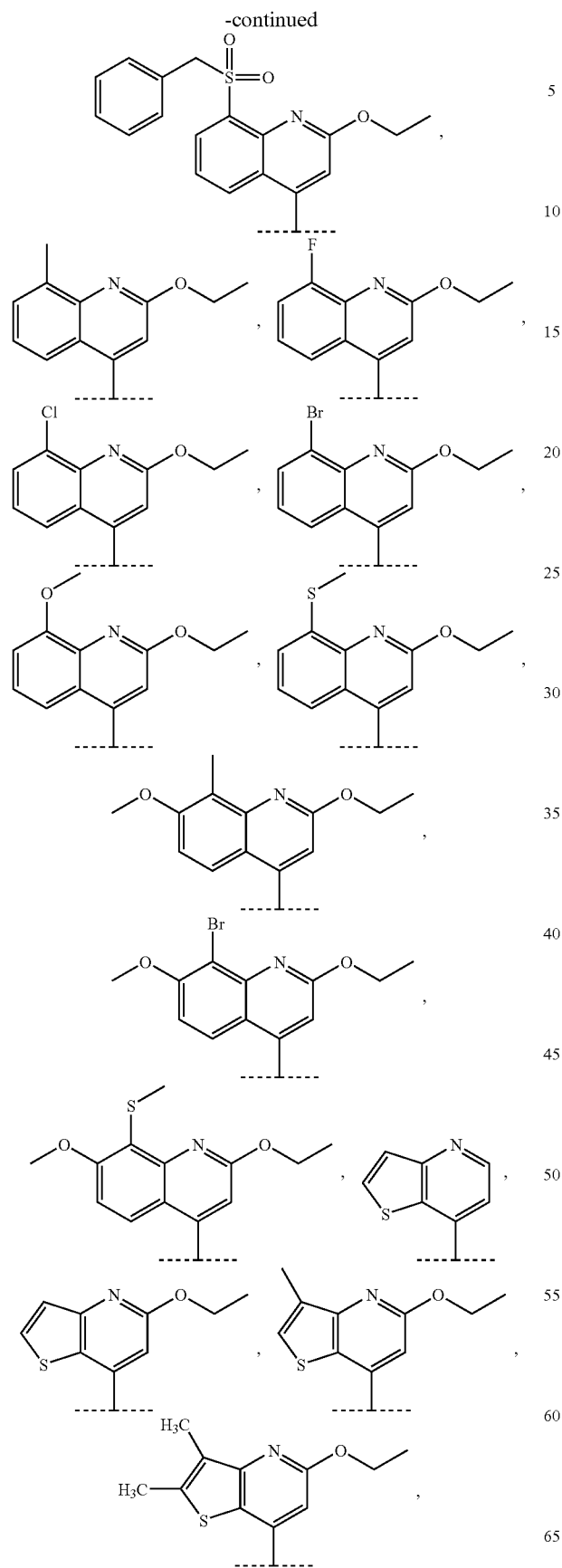

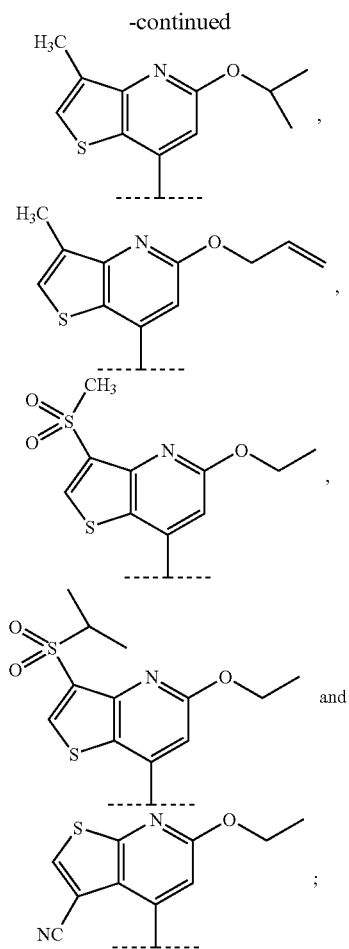

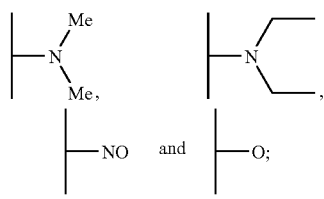

$R^1$ is ethenyl or ethyl;
n is 1;
m is 2; and
the group —N($R^4$)$R^6$ is selected from:

or a diastereomer thereof or a salt thereof.

Alternatively, preferred compounds of formula (I) are those wherein n is 1 or 2;
m is 1 or 2;
$R^1$ is H, ($C_{1-6}$)alkyl, ($C_{2-6}$)alkenyl, or ($C_{2-6}$)alkynyl, wherein said ($C_{1-6}$)alkyl, ($C_{2-6}$)alkenyl, or ($C_{2-6}$)alkynyl are optionally substituted with from one to three halogen atoms;
$R^2$ is selected from —$CH_2$—$R^{20}$, —NH—$R^{20}$, —O—$R^{20}$, —S—$R^{20}$, —SO—$R^{20}$, —$SO_2$—$R^{20}$, —$CH_2$O—$R^{20}$, and —O—X—$R^{20}$, wherein
X is ($C_{2-3}$)alkenyl, ($C_{2-3}$)alkynyl, or ($C_{1-3}$)alkyl; and R²⁰ is (C₆ or C₁₀)aryl or Het, wherein said (C₆ or C₁₀)aryl or Het is optionally substituted with R²⁰⁰, wherein
R²⁰⁰ is from one to four substituents each independently selected from H, halogen, cyano, (C₁₋₆)alkyl, (C₃₋₇)cycloalkyl, aryl-(Ci₋₆)alkyl-, aryl, Het, oxo, thioxo, —OR²⁰¹, —SR²⁰¹, —SOR²⁰¹, —SO₂R²⁰¹, —N(R²⁰²)R²⁰¹, and —CON(R²⁰²)R²⁰¹; wherein each of said alkyl, cycloalkyl, aryl and Het is optionally further substituted with R²⁰⁰⁰;
R²⁰¹ in each case is independently selected from H, (Ci₋₆)alkyl, aryl, —CO—(C₁₋₆)alkyl and —CO—O—(Ci₋₆)alkyl, wherein each said alkyl and aryl is optionally further substituted with R²⁰⁰⁰;
R²⁰² in each case is independently selected from H and (C₁₋₆)alkyl;
R²⁰⁰⁰ in each case is one to three substituents each independently selected from halogen, aryl, Het, —OR²⁰⁰¹, —SR²⁰⁰¹, —SOR²⁰⁰¹, —SO₂R²⁰⁰¹, cyano, —N(R²⁰⁰²XR²⁰⁰¹), and R²⁰⁰³, wherein said aryl and Het are optionally substituted with one, two or three substituents selected from (C₁₋₆)alkyl and —O—(C₁₋₆)alkyl;
R²⁰⁰¹ in each case is independently selected from aryl, aryl-(C₁₋₆)alkyl-, —C(O)—R²⁰⁰³, —C(O)O—R²⁰⁰³, —CON(R²⁰⁰²X R²⁰⁰⁴) and R²⁰⁰⁴;
R²⁰⁰² in each case is independently selected from H and (C₁₋₆)alkyl;
R²⁰⁰³ in each case is independently selected from (d₋₈) alkyl, (C₃₋₇)cycloalkyl and (C₃₋₇)cycloalkyl-(C₁₋₄)alkyl-, wherein said (C₃₋₇)cycloalkyl and (C₃₋₇)cycloalkyl-(C₁₋₄)alkyl- are optionally substituted with one to three substituents each independently selected from (C₁₋₃)alkyl; and
R²⁰⁰⁴ in each case is independently selected from H and R²⁰⁰³;
R³ is (C₁₋₈)alkyl, (C₃₋₇)cycloalkyl or (C₃₋₇)cycloalkyl-(Ci₋₃)alkyl-, each optionally substituted with one or more substituents each independently selected from (C₁₋₆)alkyl, (C₂₋₆)alkenyl, halogen, cyano, —OR³⁰, —SR³⁰, —C(=O)OR³⁰, —C(=O)NH₂, —C(=O)NH(C₁₋₆)alkyl, C(=O)N((C₁₋₆)alkyl)₂, —NH₂, —NH(C₁₋₆)alkyl, —N((Ci₋₆)alkyl)₂ aryl, and aryl(C₁₋₆)alkyl-, wherein R³⁰ is H, (C₁₋₆)alkyl, aryl, or aryl(C₁₋₆)alkyl-;
R⁵ is selected from B, B—C(=O)≠, B—OC(=O)—, B—N(R⁵¹)—C(=O); B—N(R⁵¹)—C(=S)—, B—SO₂— and B—N(R⁵¹)—SO₂—; wherein B is selected from:
(i) (Ci₋ıo)alkyl optionally substituted with one or more substituents each selected independently from —COOH, —COO(C₁₋₆)alkyl, —OH, halogen, —OC(=O)(C₁₋₆)alkyl, —O(C₁₋₆)alkyl, —NH₂, —NH(C₁₋₆)alkyl, —N((C₁₋₆)alkyl)₂, —C(=O)NH₂, —C(=O)NH(C₁₋₆)alkyl and —C(=O)N((C₁₋₆)alkyl)₂;
(ii) (C₃₋₇)CyClOall^l, or (C₃₋₇)cycloalkyl-(C-t₄)alkyl-, each optionally substituted with one or more substituents each selected independently from (C₁₋₆)alkyl, halogen, —COOH, —COO(C₁₋₆)alkyl, —OH, —O(C₁₋₆)alkyl, —NH₂, —NH(C₁₋₆)alkyl, —N((C₁₋₆)alkyl)₂, —C(=O)NH₂, —C(=O)NH(C₁₋₆)alkyl and C(=O)N((C₁₋₆)alkyl)₂;
(iii) aryl or aryl(C₁₋₆)alkyl-, each optionally substituted with one or more substituents each selected independently from (C₁₋₆)alkyl, —OH, —NH₂, —NH(C₁₋₆)alkyl, —N((C₁₋₆)alkyl)₂, —C(=O)NH₂, —C(=O)NH(C₁₋₆)alkyl and C(=O)N((C₁₋₆)alkyl)₂;
(iv) Het or Het-(C₁₋₆)alkyl-, each optionally substituted with one or more substituents each selected independently from (C₁₋₆)alkyl, —OH, —NH₂, —NH(C₁₋₆)alkyl, —N((C₁₋₆)alkyl)₂, —C(=O)NH₂, —C(=O)NH(C₁₋₆)alkyl and C(=O)N((C₁₋₆)alkyl)₂; and
(v) (C₂₋₆)alkenyl, or (C₂₋₆)alkynyl, each of which being optionally substituted with 1 to 3 halogens; and wherein R⁵¹ is selected from H and (Ci₋₆)alkyl;
Y is H or (C₁₋₆)alkyl;
R⁴ and R⁶ are each independently selected from H, (C₁₋₆)alkyl, (C₃₋₇)cycloalkyl, (C₃₋₇)cycloalkyl-(Ci₋₆)alkyl-, aryl and aryl-(C₁₋₆)alkyl-; wherein said (C^alkyl, (C₃₋₇)cycloalkyl, (C₃₋₇)cycloalkyl-(C₁₋₆)alkyl-, aryl and aryl-(C₁₋₆)alkyl- are optionally substituted with one to three substituents each independently selected from halogen, (C₁₋₆)alkyl, hydroxy, cyano, O—(C₁₋₆)alkyl, —NH₂, —NH(C₁₋₄)alkyl, —N((C₁₋₄)alkyl)₂, —CO—NH₂, —CO—NH(C₁₋₄)alkyl, —CO—N((C₁₋₄)alkyl)₂, —COOH, and —COO(C₁₋₆)alkyl; or
R⁴ and R⁶ are linked, together with the nitrogen to which they are bonded, to form a 3- to 7-membered monocyclic saturated or unsaturated heterocycle optionally fused to at least one other cycle to form a heteropolycycle, said heterocycle and heteropolycycle optionally containing from one to three further heteroatoms each independently selected from N, S and O, and said 3- to 7-membered monocyclic saturated or unsaturated heterocycle being optionally substituted with one to three substituents each independently selected from halogen, (C₁₋₆)alkyl, hydroxy, cyano, O—(Ci₋₆)alkyl, —NH₂, —NH(C₁₋₄)alkyl, —N((C₁₋₄)alkyl)₂, —CO—NH₂, —CO—NH(C₁₋₄)alkyl, —CO—N((C₁₋₄)alkyl)₂, —COOH, and —COO(C₁₋₆)alkyl;

with the proviso that when:
R⁵ is B—O—C(=O)— or B—N(R⁵¹)—C(=O)—, wherein R⁵¹ is H; and
B is selected from (Ci.-ıo)alkyl, (C₃₋₇)cycloalkyl, and (C₃₋₇)cycloalkyl-(C₁₋₄)alkyl,
a) wherein said alkyl, cycloalkyl, and cycloalkyl-alkyl are optionally mono-, di- or tri-substituted with (Ci₋₃)alkyl; and
b) wherein said alkyl, cycloalkyl, and cycloalkyl-alkyl are optionally mono- or di-substituted with substituents selected from hydroxy and O—(C₁₋₄)alkyl; and
c) wherein each of said alkyl groups may be mono-, di- or tri-substituted with halogen; and
d) wherein in each of said cycloalkyl groups being A-, 5-, 6- or 7-membered, one (for the 4-, 5-, 6-, or 7-membered) or two (for the 5-, 6- or 7-membered)—CH₂-groups not directly linked to each other may be replaced by —O— to provide a heterocycle, such that the O-atom is linked to the —O—C(=O) or —N(R⁵¹)C(=O) group via at least two carbon atoms; and
R² is O—R²⁰; then
R²⁰ cannot be

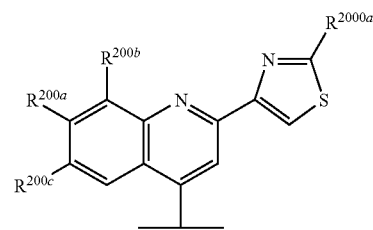

wherein
R²⁰⁰ᵃ is H, halogen, (C₁₋₄)alkyl, —OH, —O—(C₁₋₄)alkyl, —NH₂, —NH(Ci₋₄)alkyl or —N((C₁₋₄)alkyl)₂;

$R^{200b}$, $R^{200c}$ are each independently halogen, cyano, $(C_{1-4})$alkyl, —O—$(C_{1-4})$alkyl, —S—$(C_{1-4})$alkyl, —SO—$(C_{1-4})$alkyl, or —$SO_2$—$(C_{1-4})$alkyl, wherein each of said alkyl groups is optionally substituted with from one to three halogen atoms; and either $R^{200b}$ or $R^{200c}$ (but not both at the same time) may also be H; or $R^{200a}$ and $R^{200b}$ or $R^{200a}$ and $R^{200c}$ may be covalently bonded to form, together with the two C-atoms to which they are linked, a 5- or 6-membered carbocyclic ring wherein one or two —$CH_2$- groups not being directly linked to each other may be replaced each independently by —O— or $NR^a$ wherein $R^a$ is H or $(C_{1-4})$alkyl, and wherein said carbo- or heterocyclic ring is optionally mono- or di-substituted with $(C_{1-4})$alkyl; and $R^{2000a}$ is $R^{2003}$, —$N(R^{2002})COR^{2003}$, —$N(R^{2002})COOR^{2003}$, —$N(R^{2002})(R^{2004})$, or —$N(R^{2002})CON(R^{2002})(R^{2004})$, wherein $R^{2002}$ is H or methyl;

$R^{2003}$ is $(C_{1-8})$alkyl, $(C_{3-7})$cycloalkyl or $(C_{3-7})$cycloalkyl-$(C_{1-4})$alkyl-, wherein said $(C_{3-7})$cycloalkyl and $(C_{3-7})$cycloalkyl-$(C_{1-4})$alkyl- are optionally mono-, di-, or tri-substituted with $(d_{-3})$alkyl; and $R^{2004}$ is H or $R^{2003}$;

and with the further proviso that when $R^4$ and $R^6$ are linked, together with the nitrogen to which they are bonded, to form a 3- to 7-membered monocyclic saturated or unsaturated heterocycle optionally fused to at least one other cycle to form a heteropolycycle, said heterocycle and heteropolycycle optionally containing from one to three further heteroatoms each independently selected from N, S and O, and said 3- to 7-membered monocyclic saturated or unsaturated heterocycle being optionally substituted with one or more substituents each independently selected from halogen, $(C_{1-6})$alkyl, cyano, O—$(C_{-6})$alkyl, —$NH_2$, —$NH(C_{1-4})$alkyl, —$N((C_{1-4})$alkyl$)_2$, —CO—$NH_2$, —CO—$NH(C_{1-4})$alkyl, or —CO—$N((C_{1-4})$alkyl$)_2$;

then $R^2$ cannot be O—$R^{20}$, wherein $R^{20}$ is

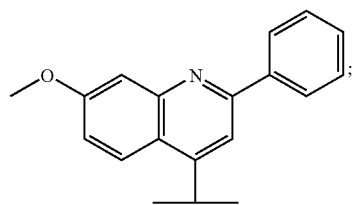

or a pharmaceutically-acceptable salt thereof.

Examples of preferred compounds according to this invention are each single compound listed in Tables 1 to 6.

According to an alternate embodiment, the pharmaceutical composition of this invention may additionally comprise at least one other anti-HCV agent. Examples of anti-HCV agents include, but are not limited to, α-(alpha), β-(beta), δ-(delta), γ-(gamma), ω-(omega) and tau-interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, an agent that inhibits a target selected from a helicase, an NS2/3 protease and an internal ribosome entry site (IRES) and an agent that interferes with the function of an NS5A protein.

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.001 and about 100 mg/kg body weight per day, preferably between about 0.01 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula (I); including a pharmaceutically acceptable salt thereof, and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-, β-, δ-, ω-, γ- and tau-interferon, ribavirin, amantadine; other inhibitors of HCV NS3 protease; inhibitors of HCV polymerase; inhibitors of other targets in the HCV life cycle, which include but are not limited to, agents that inhibit a target selected from a helicase, an NS2/3 protease and an internal ribosome entry site (IRES) and agents that interfere with the function of an NS5A protein; or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula (I), including a pharmaceutically acceptable salt thereof.

In a preferred embodiment, this method is useful in decreasing the NS3 protease activity of the hepatitis C virus infecting a mammal.

As discussed above, combination therapy is contemplated wherein a compound of formula (I), or a pharmaceutically acceptable salt thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

A compound of formula (I), or a pharmaceutically acceptable salt thereof, set forth herein may also be used as a laboratory reagent. Furthermore a compound of this invention, including a pharmaceutically acceptable salt thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt thereof, set forth herein may also be used as a research reagent. A compound of formula (I), including a pharmaceutically acceptable salt thereof, may also be used as positive control to validate surrogate cell-based assays or in vitro or in vivo viral replication assays.

In a further aspect of this invention is provided a process for the preparation of compounds of formula (I) comprising:

a) reacting a compound of formula II

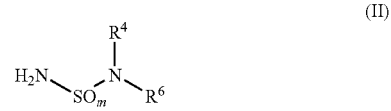

wherein $R^4$ and $R^6$ and m are defined as herein, with a strong base so as to form the corresponding amide anion of formula (IIa)

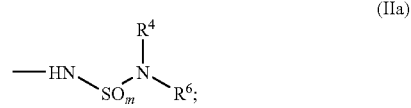

and b) reacting an azalactone of formula (III):

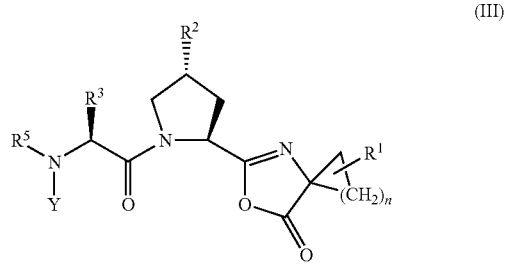

wherein $R^1$, $R^2$, $R^3$, $R^5$, Y and n are as defined herein, with the amide anion of formula IIa. The strong base referred to in step a) is well known to one skilled in the art and includes, but is not limited to, an alkyllithium reagent (including, but not limited to, butyllithium, tert-butyllithium and the like) and the alkali metal salt of a secondary amine or silyl analog thereof (including, but not limited to, lithium hexamethyldisilazide, sodium hexamethyldisilazide, potassium hexamethyldisilazide, lithium diisopropylamide, lithium N-isopropylcyclohexylamide, lithium tetramethylpiperidide, potassium diusopropylamide, and the like).

In yet a further aspect of this invention is provided an intermediate azalactone of formula (111):

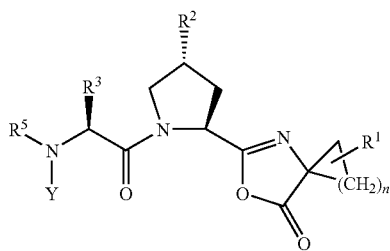

(III)

wherein $R^1$, $R^2$, $R^3$, $R^5$, Y and n are as defined herein.

A further aspect of this invention is the use of the intermediate azalactone of formula (111) as described hereinbefore in the preparation of an HCV NS3 protease inhibitor peptide analog.

Methodology

The compounds of the present invention are synthesized according to a general process wherein the P3, P2, P1, and P1' fragments can be linked by well known peptide coupling techniques. The P3, P2, P1, and PV fragments may be linked together in any order as long as the final compound corresponds to compounds of formula (I), wherein Y, $R^1$, $R^2$, $R^3$, $R^4$, $R^5$, $R^6$, m and n are as defined herein.

For example, P3 can be linked to P2-P1-P1$^1$, or P1-P1' linked to P3-P2. This process is illustrated in Scheme I (wherein CPG is a carboxyl protecting group and APG is an amino protecting group).

fragment or when it has already been coupled to P3 and/or P1 or P1-P1'. In cases where the $R^2$ moiety is to be added at an intermediate stage after coupling to the P3 and/or P1 or P1-P1' fragments, the P2 fragment shown above is replaced with a suitable precursor fragment for the purposes of this scheme.

Generally, peptides are elongated by deprotecting the α-amino group of the N-terminal residue and coupling the unprotected carboxyl group of the next suitably N-protected amino acid through a peptide linkage using well known methods. This deprotection and coupling procedure is repeated until the desired sequence is obtained. This coupling can be performed with the constituent amino acid fragments in stepwise fashion or by solid phase peptide synthesis according to the method originally described in Merrifield, J. Am. Chem. Soc, (1963), 85, 2149-2154.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino

SCHEME I

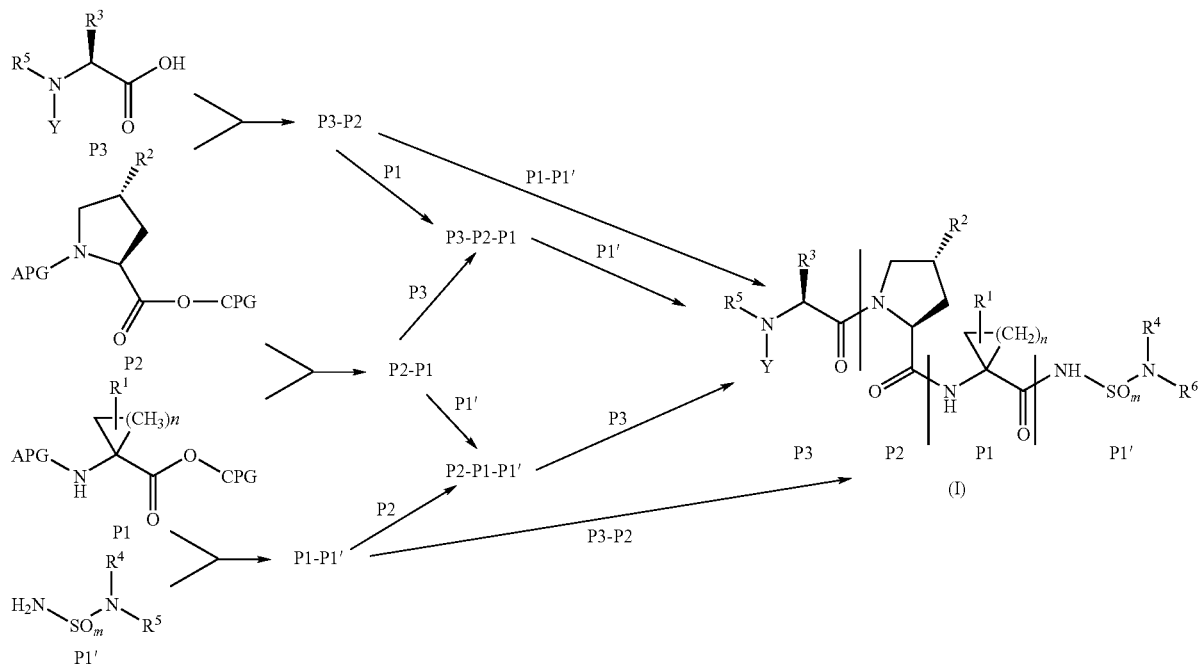

The P2 fragment is generally formed by attaching the $R^2$ moiety to the proline fragment using methodology described in the examples below. This attachment may take place at any stage in this synthetic scheme, i.e., when P2 is an isolated group of the other reactant in the presence of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)-phosphonium hexafluorophosphate, either by itself or in the presence of 1-hydroxybenzotriazole. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, trityl resin and 2-methoxy-4-alkoxybenzylalcohol resin.

Many of these resins are commercially available with the desired C-terminal amino acid already incorporated. Alternatively, the amino acid can be incorporated on the solid support by known methods (Wang, S.-S., J. Am. Chem. Soc, (1973), 95, 1328; Atherton, E.; Shepard, R. C. "Solid-phase peptide synthesis; a practical approach" IRL Press: Oxford, (1989); 131-148). In addition to the foregoing, other methods of peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980-1987); Bodansky et al., "The Practice of Peptide Synthesis" Springer-Verlag, New-York (1984) in the literature.

In general, methods for the preparation of P1, P2 and P3 moieties and methods for coupling between P1, P2 and P3 moieties are also described in greater detail in WO 2000/09543 (Boehringer Ingelheim), WO 2003/064456 (Boehringer Ingelheim), and WO 2003/064416 (Boehringer Ingelheim).

EXAMPLES

The present invention is illustrated in further detail by the following non-limiting examples.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923). Analytical HPLC was carried out under standard conditions using a Combiscreen ODS-AQ C18 reverse phase column, YMC, 50×4.6 mm i.d., 5 μM, 120 A at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations used in the examples include:

AcOH: acetic acid;

Bn: benzyl;

Boc: te/f-butyloxycarbonyl {$Me_3C$—O—C(O)};

brosyl: p-bromobenzenesulfonyl;

CDI: N,N'-Carbonyldiimidazole;

DBU: 1,8-diazabicyclo[5.4.0]undec-7-ene;

DCC: 1.S-dicyclohexylcarbodiimide;

DCM: dichloromethane;

DIAD: diisopropylazodicarboxylate;

DIEA: diisopropylethylamine;

DIPEA: diisopropylethyl amine;

DMAP: 4-dimethylaminopyridine;

DME: 1,2-dimethoxyethane;

DMF: dimethylformamide;

DMSO: dimethylsulfoxide;

ECF: ethyl chloroformate;

EDTA: ethylenediaminetetraacetic acid;

Et: ethyl;

EtOH: ethanol;

EtOAc: ethyl acetate;

$Et_2O$: diethyl ether;

HATU: [0-7-azabenzotriazol-1-yl)-1,1,3,3-tetramethyluronium hexafluorophosphate];

HPLC: high performance liquid chromatography;

IBCF: iso-butyl chloroformate;

LAH: lithium aluminum hydride;

LHMDS: lithium hexamethyldisilazide;

Me: methyl;

MeOH: methanol;

MS: mass spectrometry;

NaHMDS: sodium hexamethyldisilazide;

NMO: N-methylmorpholine-N-oxide;

NMP: N-methylpyrrolidone;

Ph: Phenyl

Pr: propyl;

$t_R$: retention time;

TBAF: tetra-n-butylammonium fluoride;

TBDMSCl: te/f-butyldimethylsilyl chloride;

TBTU: 2-(1H-benzotriazole-1-yl)-1,1,3,3-tetramethyluronium tetrafluoroborate;

TEA: triethylamine;

TFA: trifluoroacetic acid;

THF: tetrahydrofuran;

TPAP: tetra-n-propylammonium perruthenate;

Tris/HCl: tris(hydroxymethyl)aminomethane hydrochloride;

Ts: tosyl (p-methylbenzenesulfonyl)

RT: room temperature.

Synthesis of P3 Fragments

Example 1A

SYNTHESIS OF P3 CARBAMATE 1A

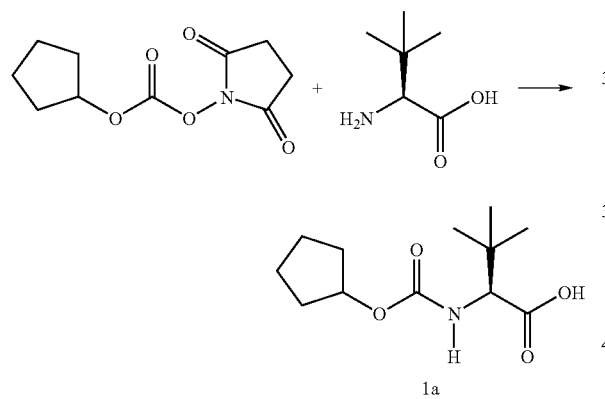

1a

The P3 carbamate fragment 1a was prepared as described in WO 03/064416. THF (350 mL) was added to a flask containing carbonic acid cyclopentyl ester 2,5-dioxo-pyrrolidin-1-yl ester (9.00 g; 39.6 mmol) and tert-butyl glycine (6.24 g; 47.5 mmol) resulting in a suspension. Distilled water (100 mL) was added with vigorous stirring. A small amount of solid remained undissolved. Triethylamine (16.6 mL; 119 mmol) was then added resulting in a homogenous solution which was stirred at RT. After 2.5 h, the THF was evaporated and the aqueous residue diluted with water (100 mL). The reaction was rendered basic by the addition of 1 N NaOH (25 mL—final pH>10). The solution was washed with EtOAc (2×200 mL) and the aqueous phase acidified with 1 N HCl (ca. 70 mL; final pH<2). The turbid solution was extracted with EtOAc (200+150 mL). The extract was dried (MgSO$_4$) and evaporated to give carbamate 1a as a white solid (8.68 g).

It will be apparent to one skilled in the art that analogous P3 carbamate fragments in which the cyclopentyloxycarbonyl group has been replaced by another $R^5$ substituent as defined herein and/or the te/f-butyl group has been replaced by another $R^3$ substituent as defined herein may be prepared using an analogous procedure.

Example 1B

SYNTHESIS OF P3 UREA FRAGMENT 1B

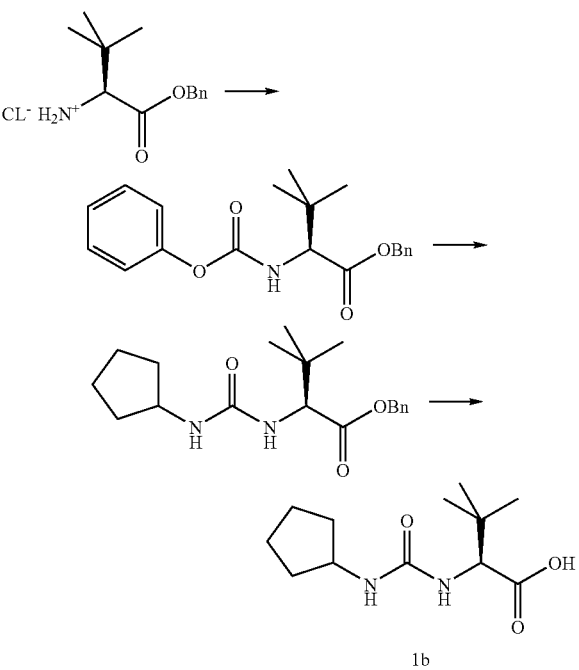

1b

A solution of te/f-butyl glycine benzyl ester hydrochloride salt (2.55 g; 9.89 mmol) in THF (20 mL) and pyridine (2.0 mL; 24.73 mmol) was cooled to 0° C. Phenyl chloroformate (1.30 mL; 10.19 mmol) was added dropwise to the cooled solution. The resulting suspension was stirred for 5 min at 0° C., then at RT. for 1.5 h. The reaction mixture was diluted with EtOAc, washed with 10% citric acid (2×) water (2×) saturated NaHCO$_3$ (2×), water (2×) and brine (1×), dried (MgSO$_4$), filtered and evaporated to obtain the crude compound as a nearly colorless oil (3.73 g; >100%; assume 9.89 mmol). The crude product (1.01 g; 2.97 mmol) was dissolved in DMSO (6.5 mL) and cyclopentylamine was added dropwise. The reaction mixture was stirred at RT. for 45 min and then diluted with EtOAc. The organic phase was washed with 10% citric acid (2×) water (2×) saturated NaHCO$_3$ (2×), water (2×) and brine (1×), dried (MgSO$_4$), filtered and evaporated to give the crude cyclopentyl urea-Tbg-OBn product as a nearly colorless oil. The crude material was purified by flash column chromatography with silica using hexane:EtOAc 9:1 to remove the less polar impurities and 7:3 to elute the purified product as a thick colorless oil (936 mg; 95%). The ester benzyl ester product (936 mg; 2.82 mmol) was deprotected under a hydrogen filled balloon at RT. in absolute ethanol (15 mL) solution by stirring the solution with 10% Pd/C (93.6 mg) for 5.5 h. The reaction mixture was filtered through a 0.45 micron filter and evaporated to dryness to provide urea 1b as a white solid (669 mg; 98%). $^1$H NMR (400 MHz$_1$ DMSOd$_6$): δ 12.39 (s, 1H), 6.09 (d, J=7.4 Hz, 1H), 5.93 (d, J=9.4 Hz, 1H), 3.90 (d, J=9.4 Hz, 1H), 3.87-3.77 (m, 1H), 1.84-1.72 (m, 2H), 1.63-1.42 (m, 4H), 1.30-1.19 (m, 2H), 0.89 (s, 9H). M.S. (electrospray): 241.0 (M−H)−243.0 (M+H)+. Reverse Phase HPLC Homogeneity (0.06% TFA; CH$_3$CN:H$_2$O): 99%.

The preparation of analogous P3 fragments is described in greater detail in WO 2000/09543 (Boehringer Ingelheim), and WO 2003/064456 (Boehringer Ingelheim). Such fragments may be readily substituted for the P3 fragments in the examples below to provide compounds of formula (I).

Synthesis of P2 Fragments

Generally, P2 moieties of compounds of Formula (I) can be prepared using the protocols outlined in WO 00/59929, WO 00/09543, WO 03/064456 and WO 03/064416.

$R^2$ moieties of compounds of formula 1 are either commercially available or have been described previously in the literature. General methods for the synthesis of some of these fragments are described in WO 00/59929, WO 00/09543, WO 03/064456 and WO 03/064416 and more specific and pertinent examples are provided below.

General methods for the introduction of the $R^2$ substituent on the proline to produce the required 4-substituted proline where $R^{20}$ is attached to the proline ring via a O—X-group, wherein X is $(C_{2-3})$alkenyl, $(C_{2-3})$alkynyl or $(C_{1-3})$alkyl, can be carried out as described in WO 00/09543. Likewise, when $R^{20}$ is attached to the proline ring via an oxygen (—O—) or a sulfur (—S—), the synthesis is carried out as described in WO 00/59929, WO 00/09543, WO 03/064456 and WO 03/064416. Other analogs can also be synthesized using this methodology.

Methods for the synthesis of various P2 fragments are also included in the examples below.

Preparation of P2 Aniline Moieties

The corresponding anilines in the P2 fragments are commercially available or may require some well known chemical transformation. For example it can be that the nitro is commercially available and is then converted to the corresponding amine by using a reducing agent. Also when the carboxylic acid is commercially available, it can be transformed into the corresponding amine via a Curtius rearrangement.

Example 2A

SYNTHESIS OF P2 BUILDING block 2-METHYL-3-METHOXYANILINE (2A2)

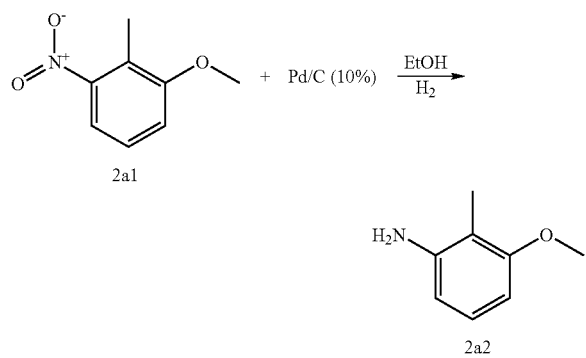

To a solution of 2-methyl-3-nitro anisole which is commercially available (2a1) (5.1 g 30.33 mmol; requires ~30 min. to dissolve) in absolute ethanol (85 mL) was added 10% Pd/C catalyst (500 mg). The solution was hydrogenated under a hydrogen filled balloon at atmospheric pressure and room temperature for 19 hrs. The reaction mixture was filtered through a Celite pad, rinsed and evaporated to dryness to obtain the compound 2a2 as a deep mauve oil (4.1 g; 29.81 mmol; 98% yield). MS 137 (MH)+. Reverse Phase HPLC Homogeneity @ 220 nm (0.06% TFA; $CH_3CN$; $H_2O$): 99%.

Example 2B

SYNTHESIS OF P2 BUILDING BLOCK 2-BROMO-3-METHOXY ANILINE (2B4)

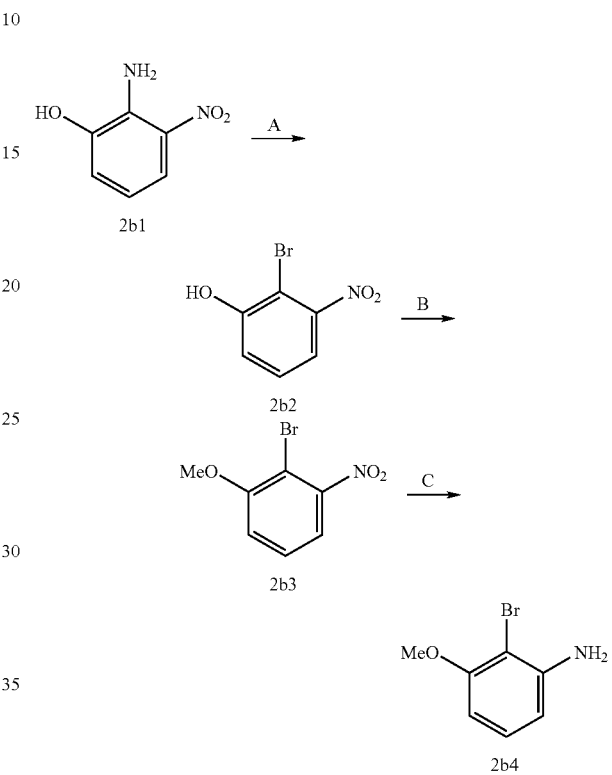

Step A: 2-Amino-3-nitrophenol 2b1 (5 g; 32.4 mmol) was dissolved in $H_2O$ (29.5 mL) and 1,4-dioxane (14.7 mL). The mixture was heated to reflux and hydrobromic acid (48%; 16.7 mL; 147 mmol) was added dropwise over a period of 20 min. Upon completion of the addition, the reflux was maintained an additional 15 min. The reaction was cooled to 0° C. (ice bath), and sodium nitrite (2.23 g; 32.3 mmol) in $H_2O$ (20 mL) was added over a period of 30 min. The stirring was continued for 15 min. at 0° C., the mixture transferred to a jacketed dropping funnel (0° C.) and added dropwise to a stirred mixture of Cu(I)Br (5.34 g; 37.2 mmol) in $H_2O$ (29.5 mL) and HBr (48%; 16.7 mL; 147 mmol) at 0° C. The reaction was stirred for 15 min. at 0° C., warmed to 60° C., stirred for an additional 15 min., cooled to room temperature, and left to stir overnight. The reaction mixture was transferred to a separatory funnel and extracted with ether (3×150 mL). The organic layers were combined, washed with brine (1×), dried ($Na_2SO_4$), filtered and concentrated to afford the crude product (7.99 g) as a red-brown oil. The crude material was purified by flash column chromatography (1:25 ultra pure silica gel, 230-400 mesh, 40-60 mm, 60 angstroms; $CH_2Cl_2$ as the solvent) to afford pure 2-bromo-3-nitrophenol 2b2 (45%; 3.16 g) as an orange-brown solid. MS 217.8 (MHz. Homogeneity by HPLC (TFA) @ 220 nm: 97%.

Step B: The nitrophenol starting material 2b2 (3.1 g; 14.2 mmol) was dissolved in DMF (20 mL) and to the solution was added ground cesium carbonate (5.58 g; 17.1 mmol) followed by MeI (2.6 mL; 42.5 mmol). The mixture was stirred at room temperature overnight. The DMF was evaporated, the residue taken up in ether (1×200 mL), washed with water (1×200 mL), brine (4×100 mL), dried (MgSO$_4$), filtered and evaporated to afford the crude 2-bromo-3-nitroanisole 2b3 (94%; 3.1 g) as an orange solid. MS 234 (M+2H)$^+$; Homogeneity by HPLC (TFA) @ 220 nm: 98%

Step C: 2-Bromo-3-nitroanisole 2b3 (1.00 g; 4.31 mmol) was dissolved in glacial acetic acid (11.0 mL)/ethanol (11.0 mL) and to the solution was added iron powder (0.98 g; 17.5 mmol). The mixture was stirred at reflux for 3.5 hr and worked up. The reaction mixture was diluted with water (35 mL), neutralized with solid Na$_2$CO$_3$ and the product extracted with CH$_2$Cl$_2$(3×50 m L). The extracts were dried (Na$_2$SO$_4$), filtered and concentrated in vacuo to afford the crude product, 2-bromo-3 methoxyaniline 2b4 (91%; 0.79 g) as a pale yellow oil. MS 201.8 (MH)$^+$; Homogeneity by HPLC (TFA) @ 220 nm: 95%

Example 2C

SYNTHESIS OF P2 BUILDING BLOCK 2-CHLORO-3-METHOXY ANILINE (2C3)

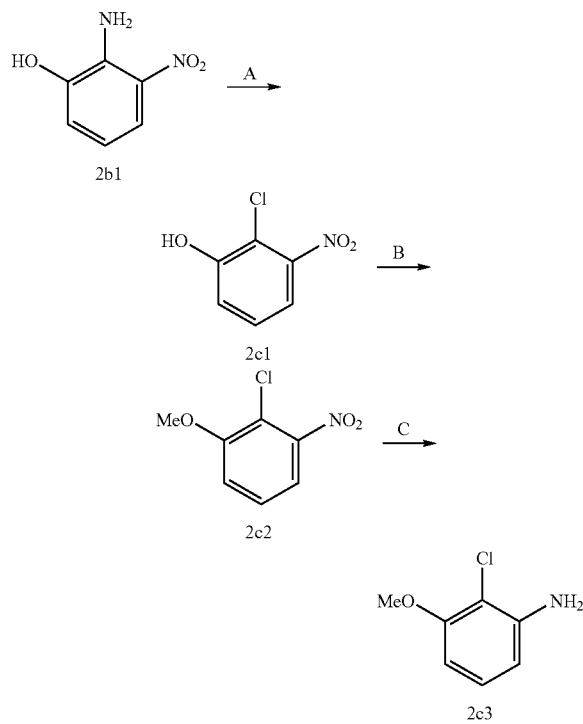

Step A: 2-Amino-3-nitrophenol 2b1 (5 g; 32.4 mmol) was dissolved in concentrated HCl (75 ml_) and 1,4-dioxane (14.7 ml_). The mixture was heated to 70° C. until most of the solids were in solution. The reaction mixture was cooled to 0° C. (ice bath), and sodium nitrite (2.23 g; 32.3 mmol) in H$_2$O (5.4 mL) was added over a period of 3 hours to the brown solution. The temperature was maintained below 10° C. during the addition and the stirring was continued for an additional 15 min. at 0° C. This diazonium intermediate was poured into a solution of Cu(I)Cl(3.8 g; 38.9 mmol) in H$_2$O (18.5 mL) and conc. HCl (18.5 mL) at 0° C. The reaction was stirred for 15 min. at 0° C., warmed to 60° C., and stirred for an additional 15 min. The reaction mixture was then brought to room temperature, and left to stir overnight. The reaction mixture was transferred to a separatory funnel and extracted with ether (3×150 mL). The organic layers were combined, washed with brine (1×), dried (Na$_2$SO$_4$), filtered and concentrated to afford the crude product (5.83 g) as a red-brown oil. The crude material was purified by flash column chromatography (1:25 ultra pure silica gel, 230-400 mesh, 40-60 mm, 60 angstroms; 3:1 hexane/EtOAc as the solvent) to afford pure 2-chloro-3-nitrophenol 2c1 (48%; 2.7 g) as an orange solid. MS 171.8 (MH)$^+$: Homogeneity by HPLC (TFA) @ 220 nm: 96%.

Relevant literature for the Sandmeyer Reaction: *J. Med. Chem*, 1982, 25(4), 446-451.

Step B: The nitrophenol starting material 2c1 (1.3 g; 7.49 mmol) was dissolved in DMF (10 mL) and to this solution was added ground cesium carbonate (2.92 g; 8.96 mmol), followed by MeI (1.4 mL; 22.5 mmol). The mixture was stirred at room temperature overnight. The DMF was evaporated in vacuo and the residue taken up in ether (150 mL), washed with water (150 mL), brine (4×100 mL), and then dried over (MgSO$_4$). The organic phase was filtered and evaporated to afford the crude 2-chloro-3-nitroanisole 2c2 (98%; 1.38 g) as an orange solid.

Homogeneity by HPLC (TFA) @ 220 nm: 93%.

Step C: 2-Chloro-3-nitroanisole 2c2 (1.38 g; 7.36 mmol) was dissolved in a mixture of glacial acetic acid (19 ml_)/ethanol (19 ml_). To this solution was added iron powder (1.64 g; 29.4 mmol). The mixture was stirred at reflux for 3.5 hr and worked up. The reaction mixture was diluted with water (70 ml_), neutralized with solid Na$_2$CO$_3$ and the product extracted with CH$_2$Cl(3×150 mL). The extracts were combined and washed with sat. brine and then dried over (Na$_2$SO$_4$), filtered and concentrated in vacuo to afford the crude product, 2-chloro-3-methoxyaniline 2c3 (100%; 1.2 g) as a yellow oil. This material was used as such in the following steps. MS 157.9 (MH)$^+$; Homogeneity by HPLC (TFA) @ 220 nm: 86%.

Preparation of P2 Quinoline Moieties

Example 2D

GENERAL PROTOCOL FOR THE PREPARATION OF 2-ALKOXY SUBSTITUTED 4-HYDROXYQUINOLINES (2D)

P2 Quinoline moieties wherein $R^{200g}$ and $R^{200h}$ are each independently selected from $R^{200}$ as defined herein and $R^{201}$ is an alkyl group can be prepared according to the following scheme:

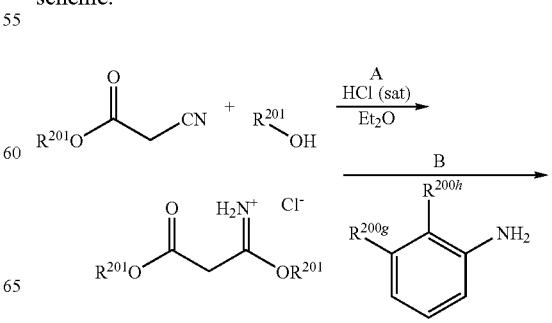

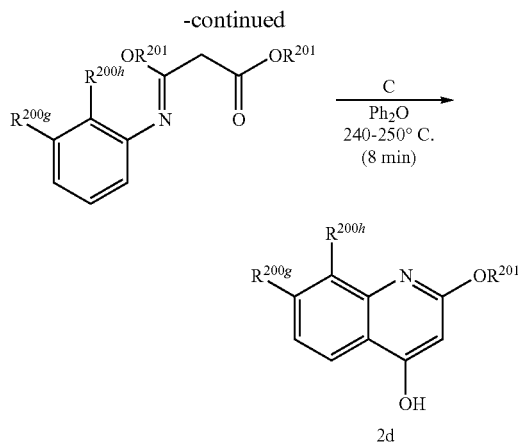

Briefly, following the known Pinner synthesis, a suitably functionalized cyanoester is condensed with the corresponding alcohol using a fully saturated HCl/Et$_2$O solution [Neilson, in Patai, "The Chemistry of Amidines and Imidates." pp. 385-489, Wiley, NY, 1975.]. The resulting imidate salt is then subsequently condensed with an appropriately substituted aniline to form the aniline derived imidate. Thermal cyclization affords the corresponding 2-alkoxy substituted 4-hydroxyquinolines 2d.

For example, when $R^{201}$ is Et in the above scheme, ethyl cyanoacetate and ethanol are used as reagents. When $R^{201}$ is Me in the above scheme, methyl cyanoacetate and methanol are used as reagents.

Example 2E

GENERAL PROTOCOL FOR THE PREPARATION OF 2-ALKYL SUBSTITUTED 4-HYDROXYQUINOLINES (2E)

P2 Quinoline moieties wherein $R^{200g}$ and $R^{200h}$ are each independently selected from $R^{200}$ as defined herein and $R^{200i}$ of the β-ketoester moiety is an alkyl group can be prepared according to the following scheme:

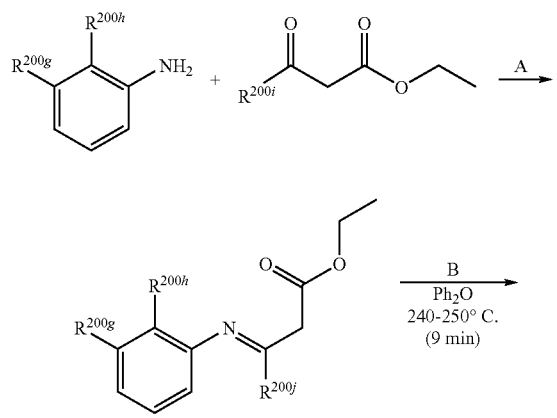

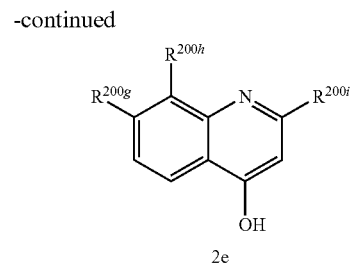

Briefly, appropriately substituted β-ketoesters are condensed with substituted anilines and subsequently thermally cyclized to afford the corresponding 2-alkyl substituted hydroxyquinolines. For example, when the initial condensation reaction with the aniline (step A) is performed with the corresponding methyl ketone, a methyl group is incorporated in the 2-position of the resulting hydroxyquinoline.

Example 2F

GENERAL PROTOCOL FOR THE PREPARATION OF 2-THIOALKYL SUBSTITUTED 4-HYDROXYQUINOLINES (2F)

In general, the various 2-thioalkyl P2 quinoline moieties wherein $R^{200g}$ and $R^{200h}$ are each independently selected from $R^{200}$ as defined herein and $R^{201}$ is an alkyl group were prepared as shown in the following scheme:

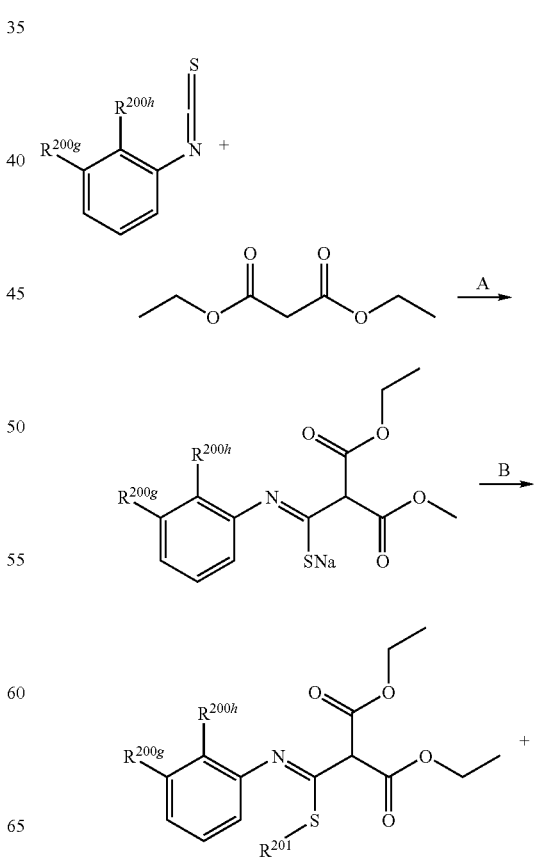

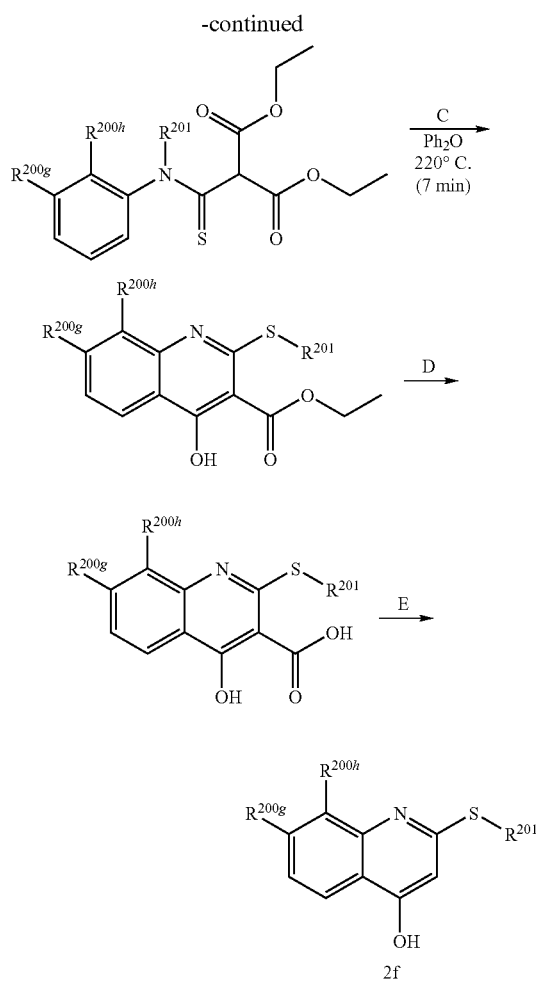

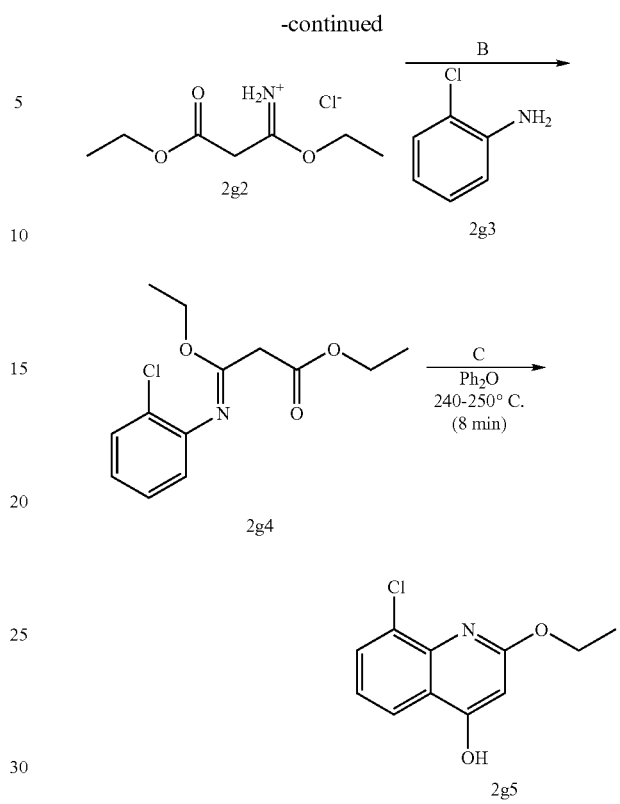

Briefly, condensation of diethyl malonate under basic conditions with a suitably functionalized isothiocyanate produces the malonate adduct as a salt. Treatment of the salt with an alkylating reagent (e.g. EtI) produces a mixture of S- and N-alkylated products. Thermal cyclization of this mixture gives the 3-ethyl carboxylate which is saponified and decarboxylated to produce the desired 2-thioalkyl substituted hydroxyquinolines. For example, utilization of EtI in the alkylation step results in the formation of the 2-thioethyl analog.

Example 2G

SYNTHESIS OF P2 BUILDING BLOCK 2-ETHOXY-4-HYDROXY-8-CHLOROQUINOLINE (2G5)

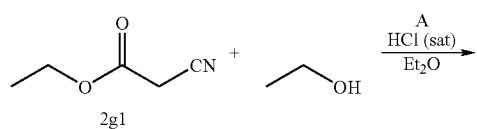

Step A: To ethyl cyanoacetate 2g1 (23 g, 0.203 mol) was added absolute ethanol (10 g, 12.7 mL, 0.22 mol) in diethyl ether (20 mL). The solution was cooled to CC in an ice bath before being treated with HCl gas (bubbled through solution for 12 minutes resulted in an increase in weight of 12 g (~0.33 mol)). This solution was stirred at 0° C. for 6 hrs and then allowed to warm to RT. and was stirred for 16 hrs. The resultant solid was broken up and washed several times with ether and then placed in vacuo for several hours. The imidate salt 2g2 was obtained as a white solid (36.4 g, 92%) and was stored under a nitrogen atmosphere. The $^1$H NMR was consistent with the desired product.

Step B: The imidate salt 2g2 (1.47 g, 7.5 mmol, 1 eq.) was combined with 2-chloroaniline 2g3 (0.96 g, 7.50 mmol, 1 eq.) in ethanol (15 mL) under an $N_2$ atmosphere. The reaction mixture was stirred at RT. (16 hrs) and monitored by HPLC. The reaction mixture was concentrated and then purified directly over silica gel (eluent: 10% EtOAc/Hexanes) to afford the condensation product 2g4 as a clear oil (1.73 g, 86%). MS electrospray: (MH)+; 270 and (M–H)–; 268. TLC (UV) Rf=0.50 (10% EtOAc/hexane).

Step C: The condensation product 2g4(1.73 g, 6.41 mmol) was dissolved in diphenyl ether (10 mL) and placed in a sand bath (300° C.). The internal temperature was monitored and allowed to stay between 240-250° C. for 8 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 2g5 as a beige crystalline solid (0.76 g, 53%). MS electrospray: (M+H)+; 224 and (M−H)−; 222.

Example 2H

SYNTHESIS OF P2 BUILDING BLOCK 4-HYDROXY-8-CHLOROQUINOLINE 2H3

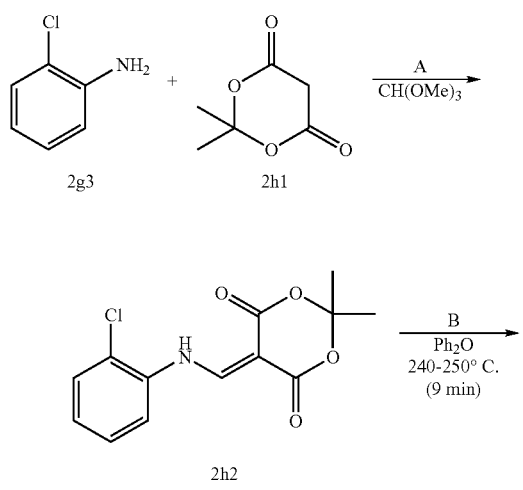

Upon cooling, the product crashed out of solution and was filtered and washed with diethyl ether. After drying in vacuo (16 h), product 2h3 was obtained as a beige solid (417 mg, 67%). MS: (M+H)+; 180.

Example 2I

SYNTHESIS OF P2 BUILDING BLOCK 8-CHLORO-4-HYDROXY-2-METHYLQUINOLINE 2I3

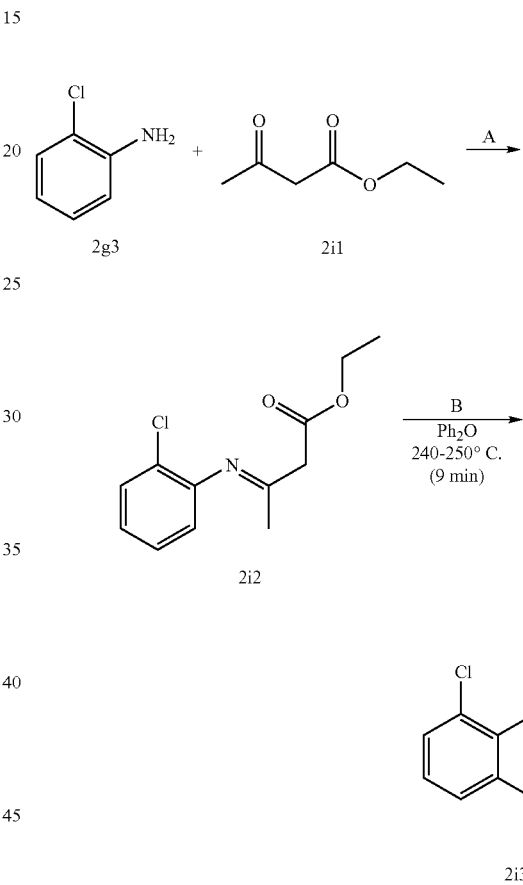

Step A: To 2-chloroaniline 2g3 (1.6 mL, 15.2 mmol, 1 eq) dissolved in anhydrous acetonitrile (50 mL) at RT. was added Meldrum's acid 2h1 (2.41 g, 16.73 mmol, 1.1 eq), followed by trimethyl orthoformate (2.0 mL, 18.25 mmol, 1.2 eq). The resulting mixture was heated to reflux (95° C.) for 2 hrs and monitoring by analytical HPLC until complete. The resulting solution was cooled to RT. and evaporated to dryness to afford a beige solid that was recrystallized from boiling MeOH. After drying in vacuo adduct 2h2 was obtained as a bright yellow solid (2.29 g, 53%).

Step B: In a pre-heated sand bath (300-350° C.), diphenyl ether (6 mL) was heated until the internal temperature reached 220° C. Adduct 2h2 (981 mg, 3.48 mmol) was added portionwise over ca. 4 min period (gas evolution) to the heated solvent. The temperature (220° C.) was maintained for another 5 min. after which the solution was allowed to cool.

Step A: To a solution of ethyl 2-butynoate 2i1 (1.21 mL, 9.51 mmol; 1 eq) in benzene (20 mL) was added 2-chloroaniline 2g3 (1.0 mL; 9.51 mmol; 1 eq) followed by catalytic PTSA (13 mg). The reaction flask was equipped with a Dean-Stark apparatus and heated to reflux for 2 hours. The solvent was removed and the residue purified by column chromatography using silica gel (eluent: 10% EtOAc/Hexanes; $R_f$=0.48) to give compound 2i2 (1.46 g, 64%) as a clear oil. MS: (M+H)+; 240, HPLC homogeneity=99.5%.

Step B: In a pre-heated sand bath (300-350° C.), compound 2i2 (730 mg, 3.0 mmol) in diphenyl ether (8 mL) was heated until the internal temperature reached 220° C. and that temperature was maintained for 7 minutes after which the solution was allowed to cool. Upon cooling, a beige solid crashed out and was filtered and washed with diethyl ether. After drying, the desired quinoline 2i3 was obtained as a beige solid (452 mg, 77%). MS: (M+H)+; 194, HPLC homogeneity=99%.

Example 2J

SYNTHESIS OF P2 BUILDING BLOCK 2-THIOETHYL-8-CHLORO-4-HYDROXYQUINOLINE (2J7)

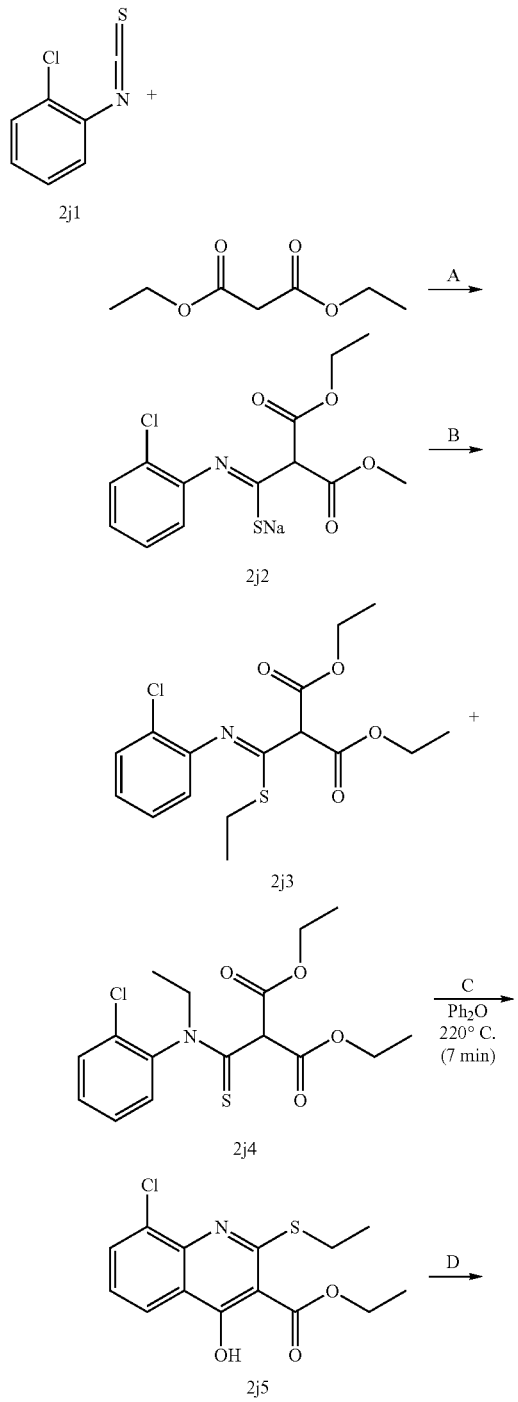

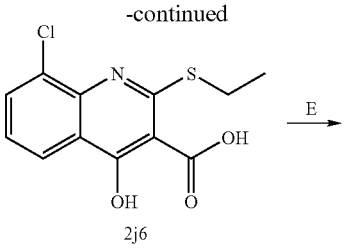

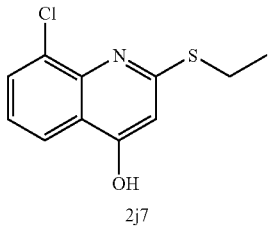

Step A: To THF (30 mL) was added sodium hydride (60% in oil, 920 mg, 23 mmol, 1.2 eq) before being cooled to CPC. Diethyl malonate (2.91 ml_, 19.15 mmol, 1.0 eq) was then added dropwise (gas evolution) and this solution was allowed to warm to RT. and was stirred for 1 hr. This mixture was cooled down to CC before the addition of 2-chlorophenyl isothiocyanate 2j1 (2.5 ml_, 19.15 mmol, 1.0 eq). The resulting mixture was again allowed to warm to RT. for 3 hrs until the SM was consumed. The orange solution was concentrated down and dried in vacuo to afford the sodium salt adduct 2j2 (6.73 g, 100%) as an orange crystalline solid. This material was used as is for subsequent steps.

Step B: A solution of adduct 2j2 (6.0 g, 17.06 mmol, 1 eq) in DMF (50 mL) was cooled down to −45° C. Ethyl iodide (1.64 mL, 20.5 mmol, 1.2 eq) was then slowly added and the solution was stirred at −45° C. for 2 hrs and then at RT. (16 hrs). Water was added and the mixture was extracted twice with a mixture of ether/hexanes (1:1, 3×150 ml_). The combined organic fractions were washed with water (2×), dried over MgSO$_4$, filtered and concentrated to afford approximately a 1:1 mixture of 2j3 and 2j4 (S versus N alkylation) (6.1 g, 100%) as a yellow oil. This mixture can be used in the following step since only the S-alkylated analog will cyclize.

Step C: In a pre-heated sand bath (350° C.) a solution of compounds 2j3 and 2j4 (6.1 g, 17.05 mmol, 1 eq.) in diphenyl ether (60 ml_) was heated until the internal temperature reached 220° C., which was maintained for 7 minutes. The solution was cooled to R.T. and the mixture loaded directly on a silica gel column, being eluted first with hexanes (1-L) to remove the diphenyl ether, and then 3% EtOAc/hexanes to afford the desired quinoline 2j5 (2.76 g, 52%) as a pale yellow solid.

Step D: To a solution of quinoline 2j5 (2.76 g crude; 8.85 mmol; 1 eq) in THF (10 ml_) and methanol (10 ml.) at R.T. was added 1N NaOH (45 ml_; 45 mmol; 5.1 eq). The reaction was allowed to stir at reflux (85° C.) for 24 hrs (monitored by HPLC). The mixture was acidified using 4N HCl and extracted using methylene chloride (3×). The organic fractions were dried over MgSO$_4$, filtered and concentrated to afford the quinoline acid 2j6 (2.43 g, 97%) as a pale yellow solid. MS: (M+H)+; 284. This material was used as is for the following reaction.

Step E: Compound 2j6 (2.43 g, 8.56 mmol) was added to diphenyl ether (20 mL) and the heterogeneous mixture was heated to 250° C. for 12 minutes before being cooled. The mixture was directly transferred to a silica gel column and eluted first with hexanes (to remove diphenyl ether), and then with 30% and 50% EtOAc/hexanes (Rf=0.48 in EtOAc/hexanes (1:1)). Evaporation of the solvent afforded the desired 2-thioethyl-8-chloro-4-hydroxyquinoline 2j7 (1.25 g, 61%) as a pale yellow solid. MS: (M+H)+; 240, HPLC homogeneity=99%.

Example 2K

SYNTHESIS OF P2 BUILDING BLOCK 8-CHLORO-2-ETHOXY-4-HYDROXY-1,7-NAPHTHYRIDINE (2K4)

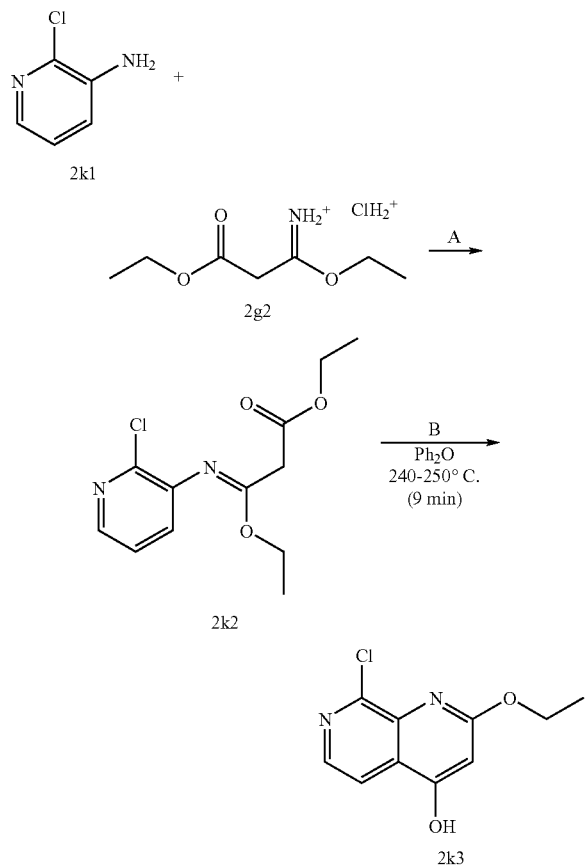

Step A: To 3-amino-2-chloro-pyridine 2k1 (964 mg, 7.5 mmol, 1 eq) was added imidate 2g2 (1.47 g, 7.5 mmol, 1 eq) in ethanol (15 ml_) under a $N_2$ atmosphere. The mixture was stirred at RT. for 24 hrs at which point the reaction was concentrated and purified directly on a silica gel column (eluent: EtOAc/Hexanes (1:9)) to afford adduct 2k2 (1.54 g, 76%) as a clear oil.

Step B: Adduct 2k2 (200 mg, 0.74 mmol) was dissolved in diphenyl ether (5 mL) and placed in a pre-heated sand bath (300° C.). The internal temperature was monitored and allowed to stay between 210° C.-225° C. for 7 minutes. The mixture was directly loaded on a silica gel column and eluted with hexanes to remove diphenyl ether, followed by a gradient of 30% to 50% EtOAc/hexanes: ($R_f$=0.48 in 1:1 EtOAc/hexanes). Concentration and drying in vacuo afforded the desired napthyridine 2k3 (32 mg, 19%) as a white solid. MS: 225 (M+H)+.

Example 2L

SYNTHESIS OF P2 BUILDING BLOCK 2-ETHOXY-8-THIOMETHYL-4-HYDROXYQUINOLINE (2L3)

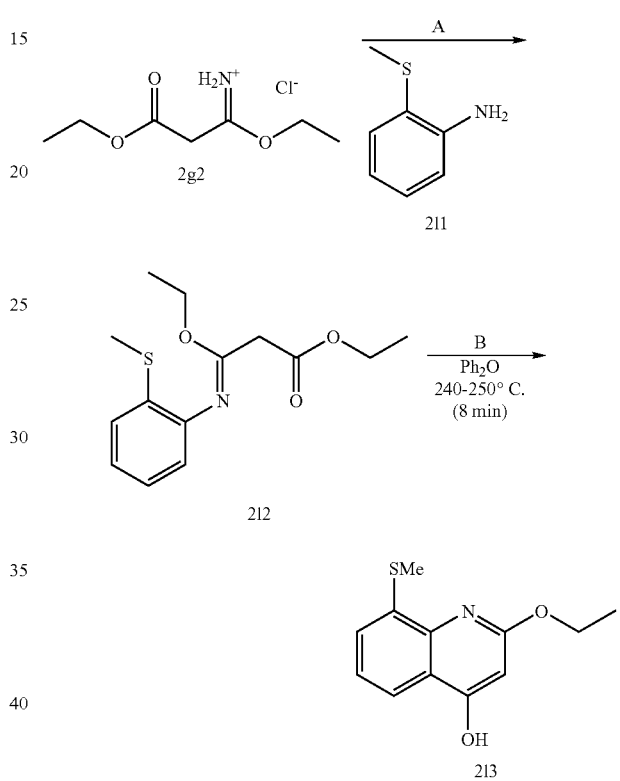

Step A: The imidate salt 2g2(1.4 g, 7.2 mmol, 1 eq.) was combined with 2-(methylthio)-aniline 211 (0.96 g, 7.50 mmol, 1 eq.) in ethanol (15 mL) under an $N_2$ atmosphere. The reaction mixture was stirred at RT. (1 h) and monitored by HPLC. The reaction mixture was concentrated and then ether was added and the mixture filtered. The solids were washed with ether and the combined ether washes concentrated in vacuo. The resulting adduct 212 was obtained as a yellow oil (1.66 g, 82%) and used as is in the next step. MS electrospray: (M+H)+; 282 and (M–H)–; 280.

Step B: The condensation product 212 (1.66 g, 5.90 mmol) was dissolved in diphenyl ether (10 mL) and placed in a sand bath (300° C.). The internal temperature was monitored and allowed to stay between 240-250° C. for 10 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 213 as a yellow solid (0.735 g, 53%). MS electrospray: (M+H)+; 236 and (M–H)–; 234.

Example 2M

SYNTHESIS OF P2 BUILDING BLOCK 2-ETHOXY-7-METHOXY-8-METHYL-4-HYDROXYQUINOLINE (2M3)

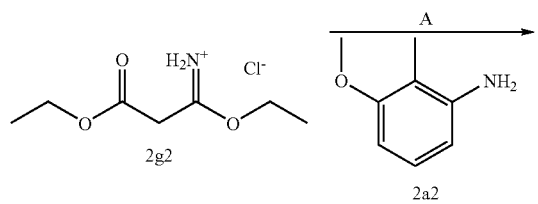

Step A: The imidate salt 2g2 (1.5 g, 7.65 mmol) was combined with 2-methyl-3-aminoanisole 2a2 (1.05 g, 7.65 mmol, 1 eq.) in ethanol (15 mL) under an $N_2$ atmosphere. The reaction mixture was stirred at RT. (24 h) and monitored by HPLC. The reaction mixture was concentrated and then ether was added and the mixture filtered. The solids were washed with ether and the combined ether washes concentrated in vacuo. The resulting adduct 2 ml was purified by chromatography ($SiO_2$, 15% EtOAc/hexanes) to obtain as a yellow oil (2.11 g, 99%). MS electrospray: (M+H)+; 280 and (M–H)–; 278.

Step B: The condensation product 2 ml (2.1 g, 7.52 mmol) was dissolved in diphenyl ether (10 mL) and placed in a sand bath (300° C.). The internal temperature was monitored and allowed to stay between 240-250° C. for 10 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 2 m2 as a yellow oil which solidified upon standing to a yellow solid (1.09 g, 62%). MS electrospray: (M+H)+; 233.4 and (M–H)–; 231.9.

Example 2N

SYNTHESIS OF P2 BUILDING BLOCK 2-ETHOXY-8-METHOXY-4-HYDROXYQUINOLINE (2N3)

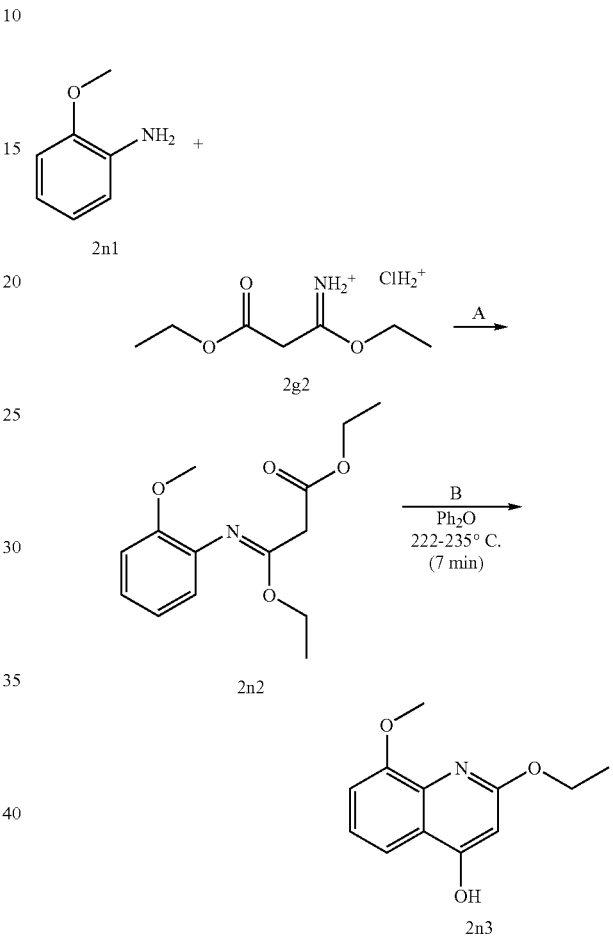

Step A and B: Beginning with ortho-anisidine 2n1 and following the same protocol as outlined in previous examples, the desired 8-methoxyquinoline derivative 2n3 was obtained in 38% overall yield as a pale yellow solid. MS: 220 (M+H)+.

Example 2O

SYNTHESIS OF P2 BUILDING BLOCK 2-ETHOXY-8-BROMO-7-METHOXY-4-HYDROXYQUINOLINE (2O2)

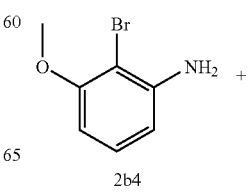

-continued

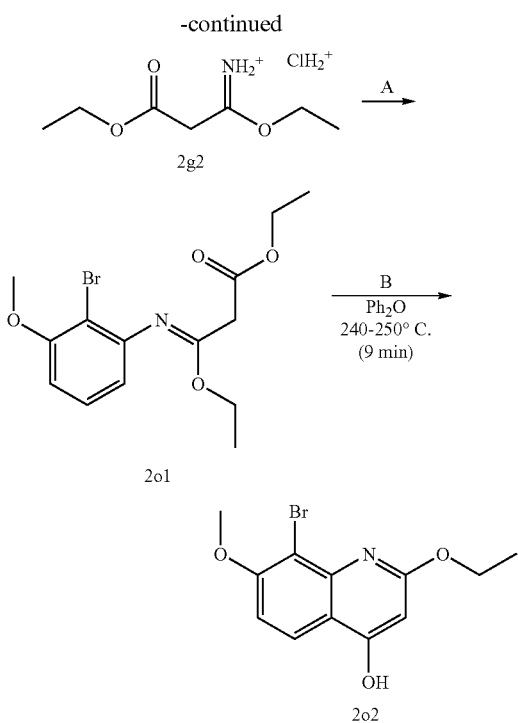

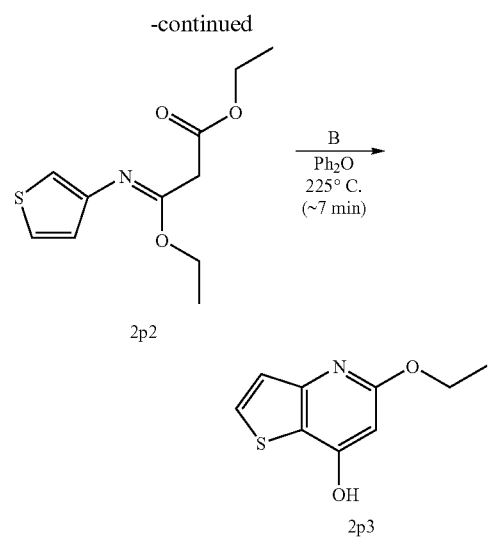

Step A: To 2-bromo-3-aminoanisole 2b4 (750 mg, 3.7 mmol, 1 eq) was added imidate 2g2 (0.73 g, 3.7 mmol, 1 eq) in ethanol (7 mL) under a $N_2$ atmosphere. The mixture was stirred at RT. for 24 hrs at which point the reaction was concentrated and purified directly on a silica gel column (eluent: EtOAc/Hexanes (1:9)) to afford adduct 2o1 (1.12 g, 88%) as a pale yellow oil. MS: 344 (M+H)+ and 346 (MH+2)+.

Step B Adduct 2o1 (1.12 g, 3.25 mmol) was dissolved in diphenyl ether (10 mL) and placed in a pre-heated sand bath (300° C.). The internal temperature was monitored and allowed to stay between 240° C.-250° C. for 8 minutes. The mixture was directly loaded on a silica gel column and eluted with hexanes to remove diphenyl ether, followed by a gradient of 30% to 50% EtOAc/hexanes: (Rf=0.25 in 1:1 EtOAc/hexanes). Concentration and drying in vacuo afforded the desired quinoline 2o2 (734 mg, 76%) as a white solid. MS: 298 (M+H)+ and 300 (MH+2)+.

Example 2P

SYNTHESIS OF P2 BUILDING BLOCK
5-ETHOXY-THIENO[3,2-B]PYRIDIN-7-OL (2P3)

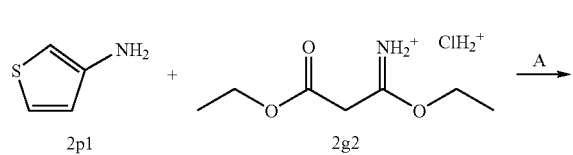

Step A: To available thiophen-3-ylamine 2 µl (0.50 g, 5.04 mmol) was added imidate 292 (1.08 g, 5.5 mmol) in ethanol (10 mL) under a $N_2$ atmosphere. The mixture was stirred at RT. for 3 h at which point the reaction was concentrated. To the residue was added ether, and the suspension filtered and washed with ether to afford adduct 2p2(1.0 g, 82%). This material was sufficiently clean to be used in the subsequent step. MS: 242.1 (MH)+.

Step B: Adduct 2p2 (1.0 g, 4.14 mmol) was dissolved in diphenyl ether (5 mL) and placed in a pre-heated sand bath (300° C.). The internal temperature was monitored and allowed to stay between 210° C.-225° C. for 7 minutes. The mixture was directly loaded on a silica gel column and eluted with hexanes to remove diphenyl ether, followed by a gradient of 30% EtOAc/hexane to neat EtOAc. Concentration and drying in vacuo afforded the desired thieno[3.2-b]pyridinol 2p3 (200 mg, 25%) as a brown solid. MS: 196 (MH)+.

Example 2Q

GENERAL SYNTHESIS OF P2 BUILDING BLOCK
6-SUBSTITUTED-2H-ISOQUINOLINE-1-ONE
(2Q3)

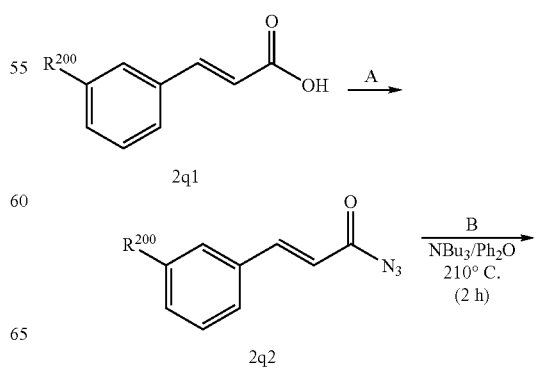

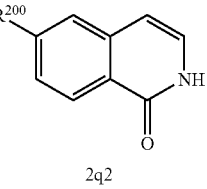

Briefly, 6-substituted isoquinolones can be made from 3-substituted cinnamic acid derivatives by first activation with a chloroformate in base followed by treatment with an azide source. The resulting acyl azide can undergo a Curtius rearrangement followed by thermal cyclization to afford the appropriately substituted isoquinolones. As described here, the cinnamic acid can be differentially substituted.

Example 2R

PREPARATION OF 6-METHOXY-2H-ISOQUINOLINE-1-ONE (2R3)

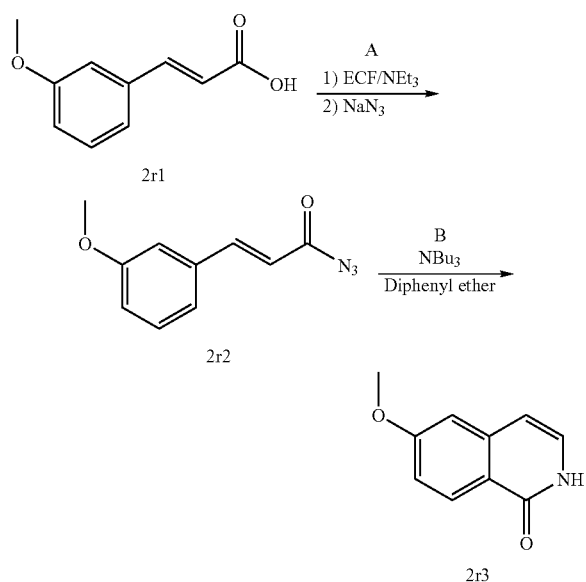

In general, the isoquinolines were prepared according to the following reference; Tetrahedron, 2002, 58, 5761-5766.

Step A: The 3-methoxycinnamic acid 2r1 (2.5 g, 14.03 mmol) was dissolved in acetone (40 mL) and treated with triethylamine (3.94 mL, 28.06 mmol). The solution was cooled to 0° C. and then treated dropwise with ethyl chloroformate (2.0 mL, 21 mmol). A white precipitate immediately formed upon addition of each drop. The solution was stirred for 1 h (with a suspension) before being treated with sodium azide (0.91 g, 14.03 mmol) in 10 mL of H$_2$O dropwise over 30 min. The mixture was allowed to stir at rt 16 h before being diluted with water (20 mL) and the volatiles removed in vacuo. The aqueous phase was extracted with toluene (2×60 mL), dried over MgSO$_4$, and then filtered and concentrated to give a yellow oil (2.23 g) which solidified to a yellow solid 2r2 upon standing.

Step B: The diphenyl ether (10 mL) and tributylamine (7 mL) were heated in a sand bath to 190° C. before the dropwise addition of the acyl azide 2r2 (behind an explosion shield) in toluene (5 mL) over several minutes. The toluene distilled off and the temperature was raised to 210° C. for 2 h. After cooling, the precipitated product was collected by filtration and washed with hexanes to give the desired isoquinoline 2r3 (0.47 g, 19%). MS (electrospray); (M+H)$^+$; 176 and (M−H)$^−$; 174. $^1$H NMR (400 MHz, DMSO-d$_6$) δ 11.05 (bs, 1H), 8.07 (d, J=8.8 Hz, 1H), 7.16-7.09 (m, 2H), 7.04 (dd, J=9, 2.4 Hz, 1H), 6.47 (d, J=7.0 Hz, 1H), 3.86 (s, 3H).

Example 2S

PREPARATION OF P2 ALKYNE MOIETY (2S2)

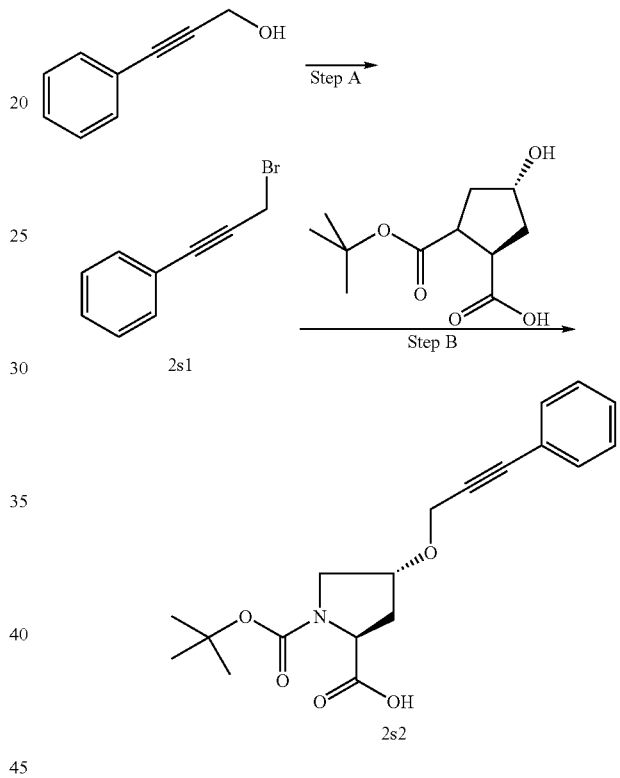

Step A: Pyridine was added (0.18 mL, 2.27 mmol) to a solution of the alcohol (1.50 g, 11.35 mmol) in diethyl ether (19 mL) at 0° C. followed by the addition of PBr$_3$ (0.44 mL, 4.54 mmol). This solution was stirred at 0° C. for 4 h. and the reaction was quenched with NaHCO$_3$ and extracted with EtOAc. The combined organic layers were washed with brine, dried, filtered and concentrated followed by purification by flash column chromatography (15% EtOAc/hex) to yield the desired product 2s1 as a yellow oil (913 mg, 41%).

Step B: NaH was added (96 mg, 3.79 mmol) to commercially available Boc-4R-hydroxy-proline (350 mg, 1.51 mmol) at r.t. and stirred for 1 h followed by the addition of the bromide 2s1 (325 mg, 1.67 mmol). The resulting solution was heated at reflux for 16 h, cooled to r.t., diluted with EtOAc and washed successively with 1M HCl, water and brine to yield the desired product 2s3 (520 mg, 99%).

Synthesis of P1 Fragments

The preparation, separation and identification of the stereoisomers of the P1 moieties of compounds of Formula (I) were prepared using the protocols outlined in WO 00/59929, published Oct. 12, 2000, and WO 00/09543, published on Feb. 24, 2000. In particular, reference is made to pages 33-35, Example 1 of WO00/59929 and Pages 56-69, Example 9-20 of WO0/09543 for the preparation of 1-aminocyclopropyl-carboxylic acid P1 moieties.

Synthesis of PT Fragments

P1' sulfamide fragments are commercially available (for example, $N_1N$-dimethylsulfamide [available from TCI America]) or may be prepared by methods similar to those described in Examples 3A, 3B or 3C below.

Example 3A

SYNTHESIS OF P1' FRAGMENT SULFAMIDE 3A3

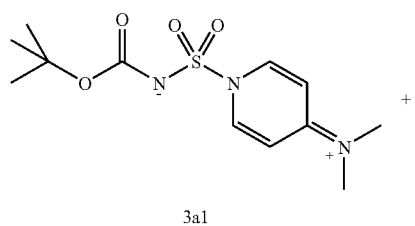

3a1

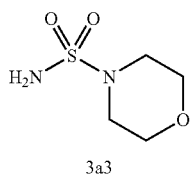

Step A

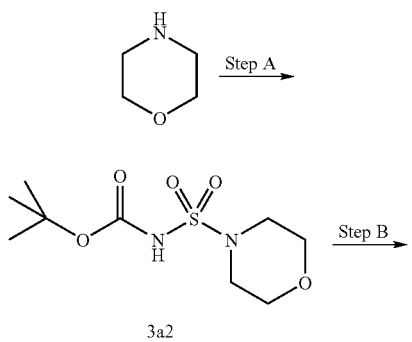

3a2

Step B $H_2N$—S—N morpholine

3a3

Step 1: Reagent 3a1 (0.3 g, 0.99 mmol) [prepared according to Winum, J-Y; Toupet, L; Barragan, V; Dewynter, G; Montero, J.-L., Org. Lett., 14(3), 2241-2243 (2001)] was suspended in $CH_2Cl_2$ before morpholine (0.086 mL, 0.99 mmol) was added and stirred for 5 h. The reaction was followed by TLC. On completion the reaction mixture was directly adsorbed on the silica gel and eluted the product with 6% MeOH in $CHCl_3$ to afford 0.258 g (98%) of compound 3a2 as a white solid.

Step 2: Compound 3a2 (0.150 g, 0.56 mmol) was dissolved in $CH_2Cl_2$ (5 mL) and treated with TFA (1 mL). The reaction was stirred for 4 h and monitored by TLC. Upon completion, the solvent was evaporated and the residue directly adsorbed on the silica gel and eluted with 5% MeOH in $CHCl_3$ to afford 0.075 g (80.2%) of compound 3a3 as a white solid.

Example 3B

SYNTHESIS OF PV FRAGMENT SULFAMIDE 3B2

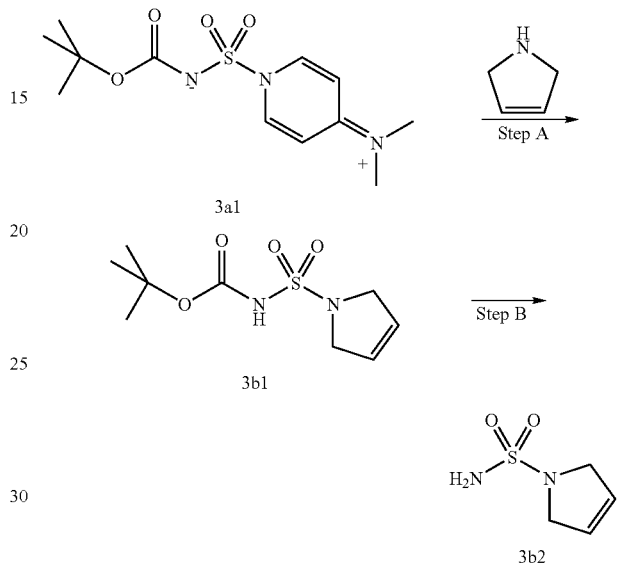

Step A: Reagent 3a1 (1.5 g, 4.98 mmol) was suspended in 12 mL of $CH_2Cl_2$ before the pyrroline (0.40 mL, 5.22 mmol, 1.05 equiv.) was added and stirred overnight. On completion, the reaction mixture was directly adsorbed on the silica gel and eluted the product with 1% AcOEt in $CH_2Cl_2$ to afford 0.919 g (74%) of compound 3b1 as a white solid.

Step B: Compound 3b1 (0.919 g, 3.70 mmol) was dissolved in 10 ml_of $CH_2Cl_2$ and treated with TFA (2 ml_). The reaction was stirred at room temperature for 4 h. The solvent was then evaporated in vacuo, the residue was dried under vacuum to afford 0.5659 (quantitative) of compound 3b2 as a beige solid.

Example 3C

SYNTHESIS OF PV FRAGMENT SULFAMIDE 3C2

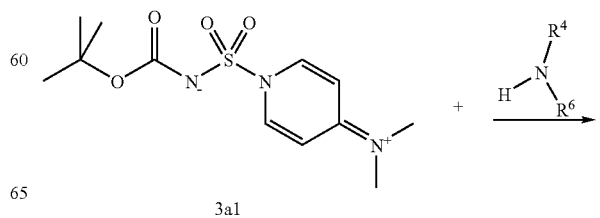

3a1

-continued

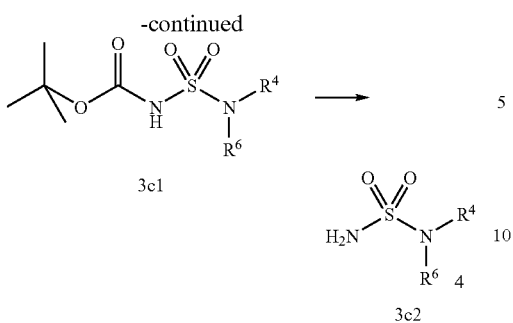

3c1

$$H_2N-\underset{\underset{O}{\overset{O}{\|}}}{\overset{\overset{O}{\|}}{S}}-\underset{R^6}{N}-R^4$$

3c2 4

Step A: Note: the reaction was performed on a solid phase synthesizer (Advanced Chemtech ACT 396), using the 96 wells block. The starting material 3a1 (45.2 mg, 0.15 mmol) was weighed in 96 Eppendorf vials and 96 different amines (0.18 mmol, 1.2 equiv.) were weighed and placed in separate Eppendorf vials. Each well of the reaction block were filled with 1.2 ml of 1,2-dichloroethane and the starting material 3a1 and the various amines were added. The reaction mixtures were shaken for 12 h in the case of aliphatic amines and for 36 h in the case of anilines derivatives. After the required stirring time, PS-trisamine resin was added to each well (Argonaut Technologies, 3.42 mmol/g loading, 0.63 mmol, 0.184 g, 4.2 equiv.). After shaking for 3 h, the solvent was drained and the resins were washed successively with $CH_2Cl_2$ (3×1 mL), MeOH (3×1 mL) and $CH_2Cl_2$ (3×1 mL). In each well was then added $CH_2Cl_2$ (1.2 mL) and AcOH (100 W) and the shaking was maintained for 30 minutes. The solutions were drained in pre-tarred 2 dram vials to recover the filtrate and each resins were washed once with $CH_2Cl_2$ (1.2 mL) and MeOH (1.2 mL). The filtrates were recovered in the same 2-dram vials as before. The vials were finally placed on a vacuum centrifuge to remove the solvent and the desired products 3d were obtained in 41-54% yields (18-27 mg of product). Those compounds were used as is in the next step.

Step B: The products 3d in 2-dram vials were dissolved in 1,2-dichloroethane (0.5 mL) and TFA (0.5 mL) and the vials were shaken on an orbital shaker for 1.5 h. The volatiles were removed on a vacuum centrifuge to afford the desired products 3c2 in yields ranging from 71% to quantitative (12-20 mg of product). Those compounds were used as is in the next step of synthesis of compounds of formula (I).

Synthesis of P1-P2 Fragment

P1-P2 dipeptide intermediates were synthesized according to the general methods described in WO 00/09543, and via methods in the following examples which are understood to be non-limiting with respect to the appended claims.

Example 5A

SYNTHESIS OF DIPEPTIDE (5A1)

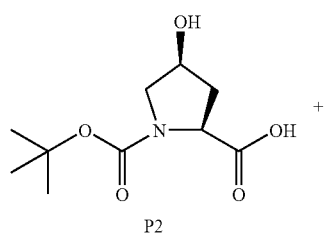

P2

-continued

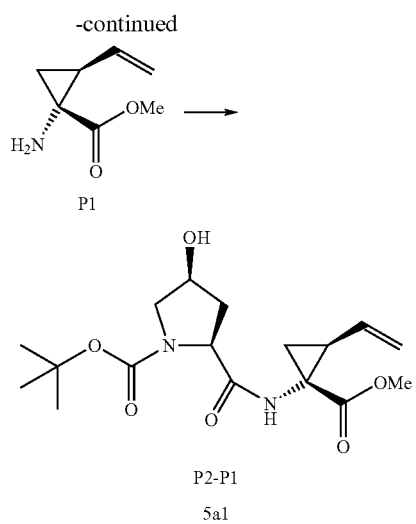

P1

P2-P1
5a1

A mixture of Boc-hydroxyproline P2 (50.0 g, 216 mmol), vinyl-ACCA methyl ester P1 (42.25 g, 238 mmol, Hequiv.), TBTU (76.36 g, 238 mmol, 1.1 equiv.) and DIPEA (113 ml_, 649 mmol, 3 equiv.) in DMF (800 mL) was stirred at R.T. under a nitrogen atmosphere. After 3.5 h, the solvent was evaporated and the residue extracted with EtOAc. The extract was washed with hydrochloric acid (10%), saturated sodium bicarbonate and brine. The organic phase was then dried over magnesium sulfate, filtered and evaporated to afford an oil. After drying overnight under high vacuum, dipeptide 5a1 was obtained as a yellow foam (72.0 g, 94%, purity>95% by HPLC).

Example 5B

PREPARATION OF DIPEPTIDE S23

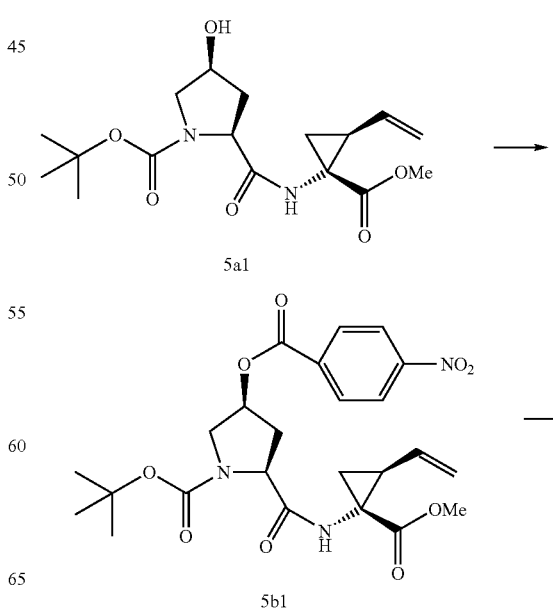

5a1

5b1

-continued

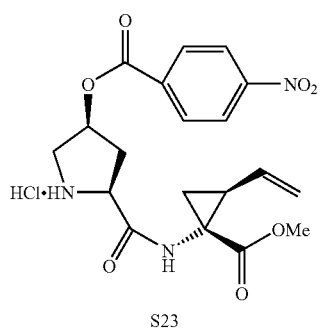

S23

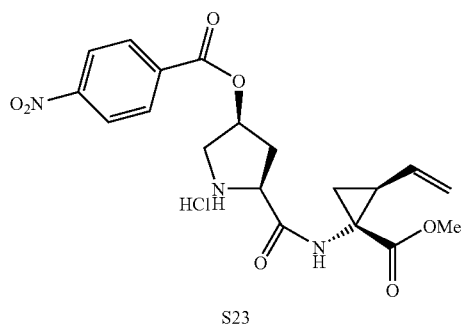

S23

Dipeptide 5a1 (72.0 g, 203 mmol), triphenylphosphine (63.94 g, 243.8 mmol, 1.2 equiv.) and 4-nitrobenzoic acid (41.08 g, 245.8 mmol, 1.2 equiv) were dissolved in dry THF (1.4 L) The stirred solution was cooled to 0° C. under a nitrogen atmosphere. Diethyl azodicarboxylate (38.4 mL, 244 mmol, 1.2 equiv.) was then added dropwise over 45 min and the reaction allowed to warm to R.T. After 4 h, the solvent was evaporated. The residue was divided into four portions. Each of these was purified by chromatography over fine silica gel (10-40 µm mesh, column diameter 12 cm, column length 16 cm) using a gradient of 2:1 hexane/EtOAc to 1:1 hexane/EtOAc to pure EtOAc. In this manner, the Boc-dipeptide ester 5b1 was obtained as an amorphous white solid after evaporation of the solvents and drying of the residues under high vacuum at 70° C. % for 1 h (108.1 g, quantitative). A solution of 4N hydrogen chloride in dioxane was added to the Boc-dipeptide ester 5b1 (108 g, 243 mmol) resulting in a colorless solution. The solution was stirred at R.T. for 1 h. The solvent was evaporated and the residue placed under high vacuum for 3 h affording the hydrochloride salt of compound S23 as an amorphous solid. The solid was used as such.

Preparation of Tripeptides

Methodology:

The following schemes illustrate convenient processes using known methods for preparing the compounds of formula (I) when $R^1$ is ethenyl.

Example 6A

GENERAL SYNTHESIS OF TRIPEPTIDE S29

Scheme 2

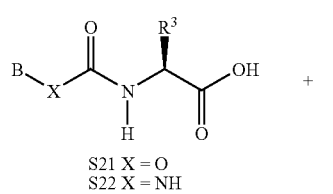

S21 X = O
S22 X = NH

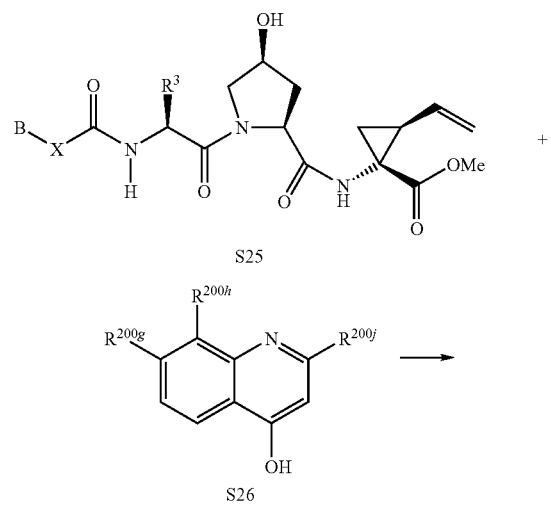

S24

S25

S26

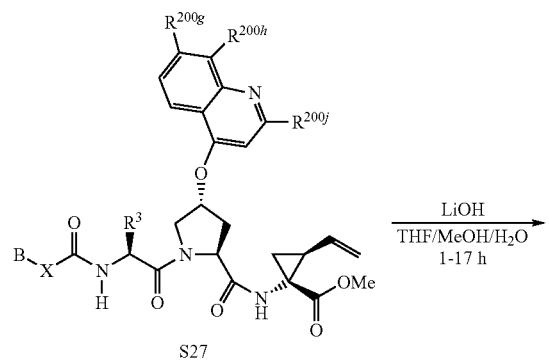

S27

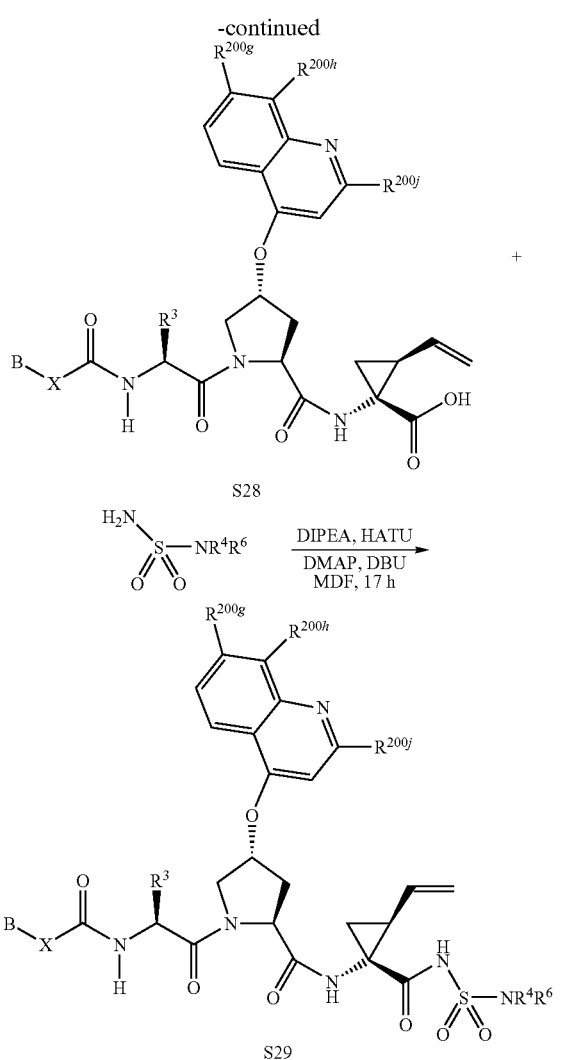

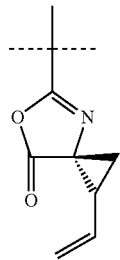

conditions as described previously. The stereochemistry of the hydroxyl group is inverted by the well known Mitsunobu reaction using para-nitrobenzoic acid. Coupling of dipeptide S23 with the P3 moiety (prepared using standard methodology and exemplified in the examples section) yielded tripeptide S24. Introduction of the quinoline moiety to the hydroxyl group of the tripeptide S25 with inversion of configuration can be carried out using either a Mitsunobu reaction or by converting the free hydroxyl group into a good leaving group (such as a brosylate) and displacing it with the hydroxylquinoline derivative S26 wherein $R^{200g}$, $R^{200h}$ and $R^{200j}$ are each independently selected from $R^{200}$ defined herein. Basic hydrolysis of the corresponding ester S27 followed by coupling the free acid with the corresponding sulfamide wherein $R^4$ and $R^6$ are as defined herein afforded the desired compounds as shown on scheme 2. Although several commonly used coupling agents can be employed, TBTU and HATU have been found to be practical. Alternatively, the acid can be activated by the formation of an anhydride and undergo an internal cyclization to afford an azalactone as depicted below. This azalactone can be isolated and purified by column chromatography. Treatment of the azalactone with lithiated sulfamide provides the desired compounds.

Briefly, the synthesis of dipeptide S23, wherein B and X are as defined herein is carried out by coupling the P1 residue to the properly protected trans-hydroxy praline under standard Alternatively, compounds of formula I can be prepared according to the following schemes 3 and 4.

Example 6B

GENERAL SYNTHESIS OF TRIPEPTIDE S29

Scheme 3

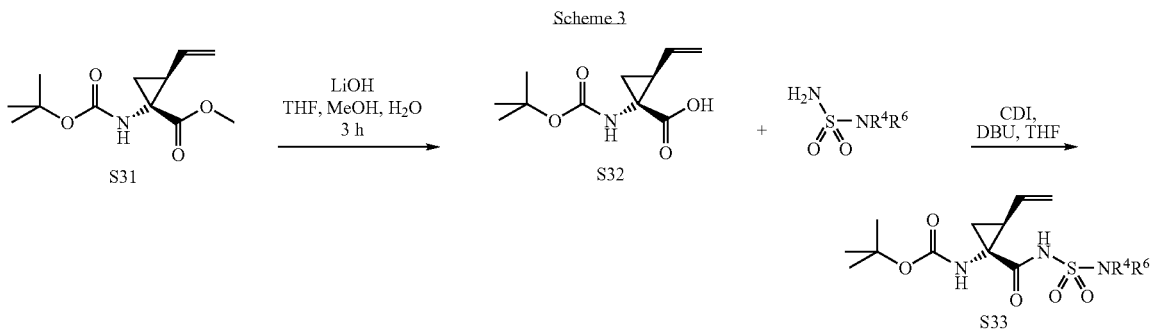

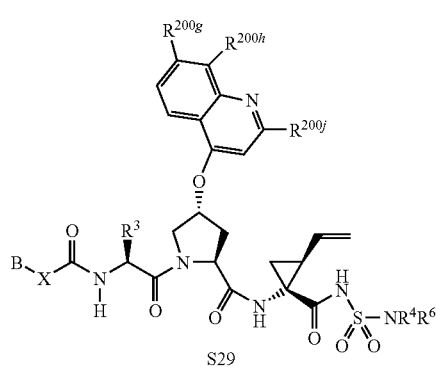
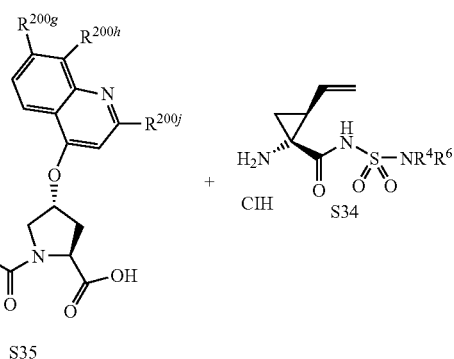
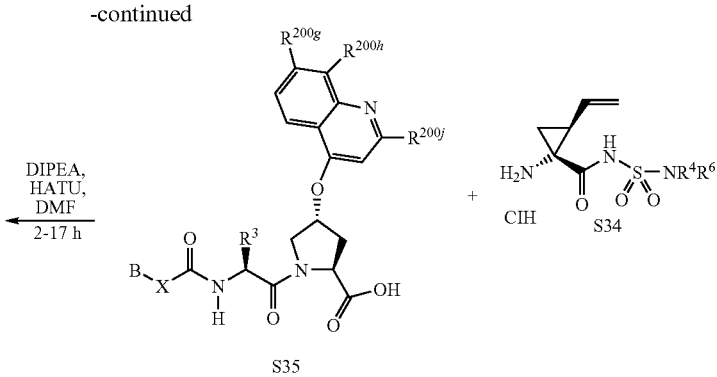

Briefly, the desired sulfamide wherein $R^4$ and $R^6$ are as defined herein can be coupled with the properly protected P1 residue S32. The adduct S33 can then be coupled to a preformed P3-P2 residue S35 wherein B, X, $R^{200g}$, $R^{200h}$ and $R^{200j}$ are each independently selected from $R^{200}$ as defined herein to yield the desired S29.

Alternatively, compounds of formula S29 can also be prepared according to Scheme 4 of Example 6c.

Example 6C

GENERAL SYNTHESIS OF TRIPEPTIDE S29

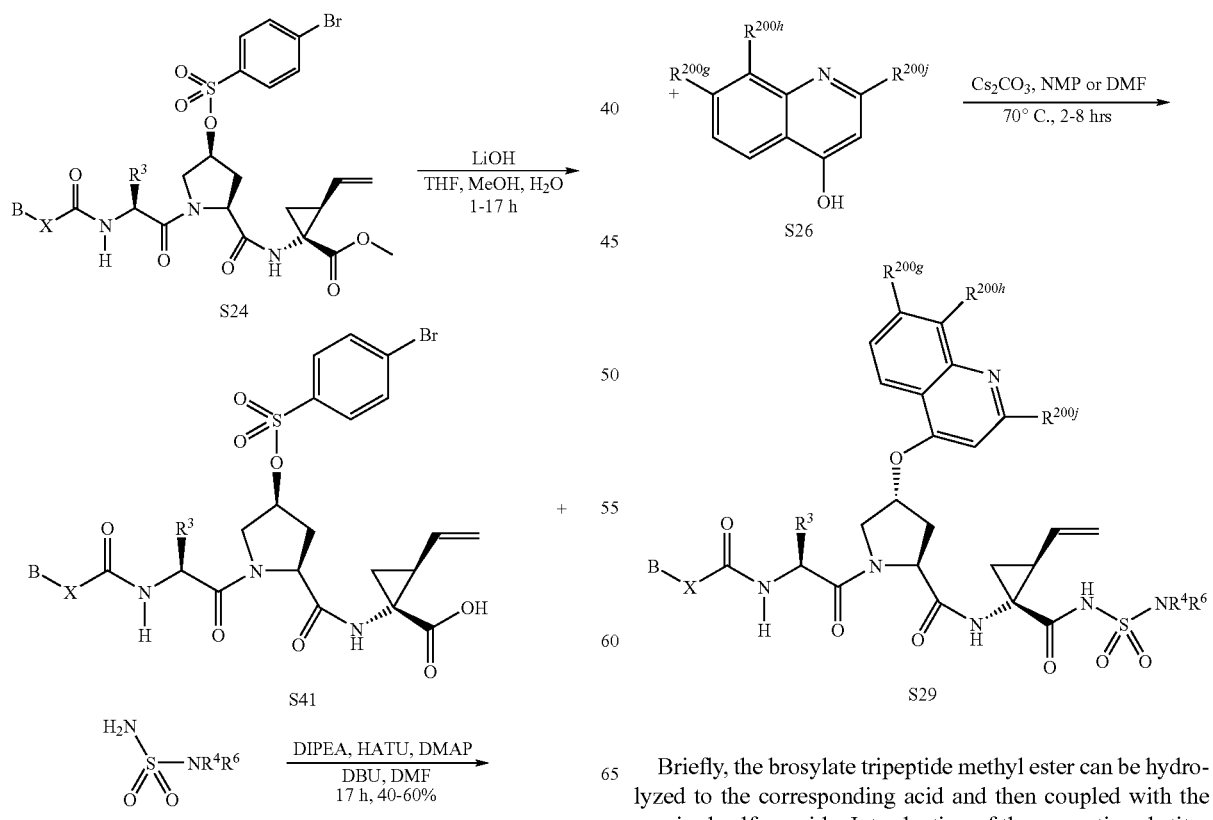

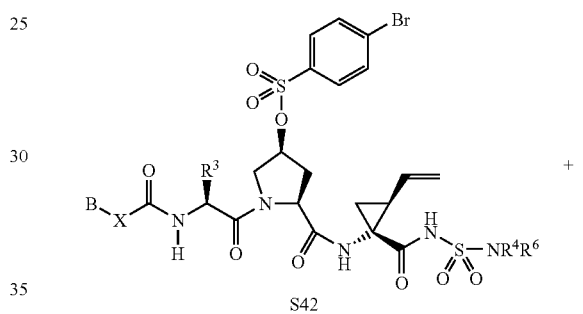

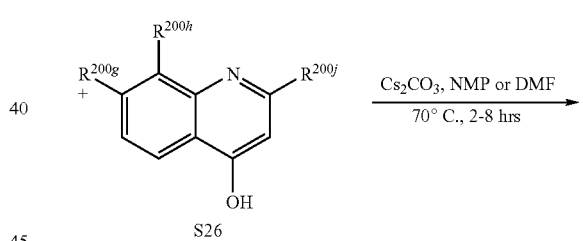

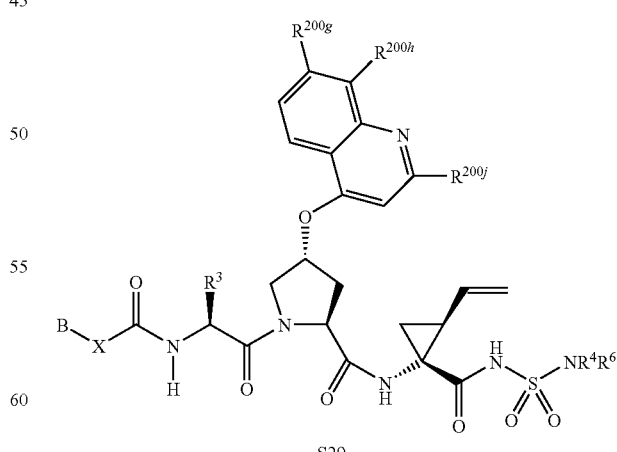

Briefly, the brosylate tripeptide methyl ester can be hydrolyzed to the corresponding acid and then coupled with the required sulfonamide. Introduction of the aromatic substituent on P2 can then be achieved by displacing the brosylate moiety with the desired hydroxyl aryl or heteroaryl derivative.

Example 6D

SYNTHESIS OF TRIPEPTIDE (6D1)

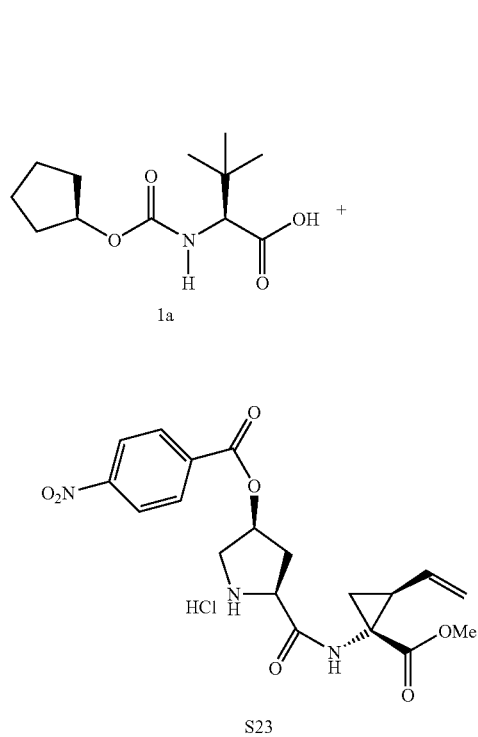

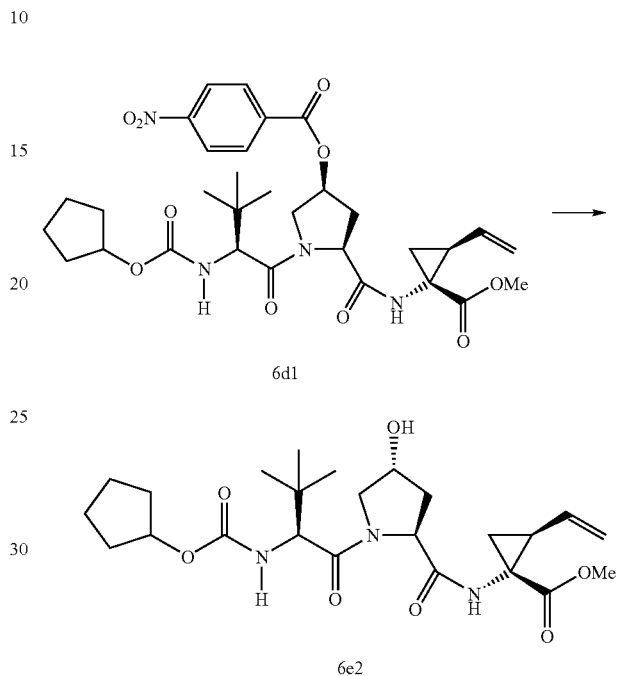

Carbamate 1a (6.15 g, 22.5 mmol) and TBTU (7.72 g, 24.7 mmol) were suspended in DCM and the suspension was stirred rapidly. DIPEA (3.92 mL, 22.5 mmol) was added at RT. and after 10 min, the reaction was nearly homogeneous. A solution of dipeptide S23 (10.39 g, 23.6 mmol) in anhydrous DCM (100 ml.) containing DIPEA (4.11 ml_, 23.62 mmol) was then poured into the reaction. The resulting yellow solution was allowed to stir for 14 h. The solvent was then evaporated yielding a yellow syrup which was extracted with EtOAc (300+150 mL) and washed with 0.05N HCl (2×200 mL), saturated $Na_2CO_3$ (300 mL) and brine (150 mL). The combined extracts were dried over $MgSO_4$ and evaporated to yield the tripeptide 6d1 as a pale yellow foam (15.68 g, quantitative).

Example 6E

SYNTHESIS OF TRIPEPTIDE (6E2)

The tripeptide 6d1 (15.68 g) was dissolved in THF (200 mL) and water (30 mL) was added. The resulting solution was cooled to 0° C. and a solution of lithium hydroxide monohydrate (1.18 g, 28.12 mmol) was added over 3 min. with vigorous stirring. After 3 h at 0° C., the excess base was neutralized with 1N HCl (final pH ca. 6) and the THF evaporated, resulting in an aqueous suspension (yellow gum). The mixture was extracted with EtOAc (2×200 mL) and washed with saturated $NaHCO_3$ (2×300 mL). The combined extracts were dried over $MgSO_4$ and evaporated to yield a pale yellow foam. Flash chromatography of the foam over silica gel using EtOAc as eluent afforded 6e2 as a white amorphous solid (9.77 g, 91%).

Example 6F

SYNTHESIS OF TRIPEPTIDE (6F2)

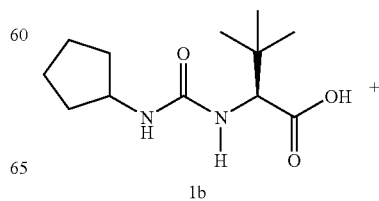

-continued

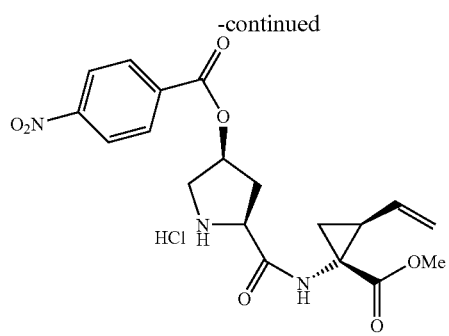
S23

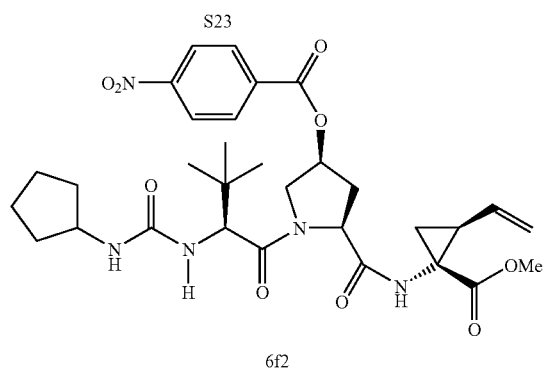
6f2

The cyclopentylurea-Tbg 1b (2.21 g, 9.10 mmol) and TBTU (3.12 g, 10.0 mmol) were dissolved/suspended in anhydrous dichloromethane (40 mL) and DIPEA (1 equiv.) added. The reaction was stirred at ambient temperature under a nitrogen atmosphere until the solution became nearly homogeneous (ca. 10 min). A solution of P1-P2 dipeptide S23 (4.20 g, 9.56 mmol) in anhydrous dichloromethane (35 mL containing 1 equiv. DIPEA) was then added to the reaction and the resulting yellow solution allowed to stir for 14 h after the reaction was rendered basic by the addition of DIPEA (ca. 1.5 mL). The solvent was evaporated yielding a yellow syrup which was extracted with ethyl acetate (150+50 mL) and washed with 0.1 N HCl (150 mL), water (100 mL, emulsion broken with brine), saturated $Na_2CO_3$ (150 mL) and brine (100 mL). The combined extracts were then dried over $MgSO_4$ and evaporated to a pale yellow solid 6f2 (6.21 g, HPLC purity 95%).

Example 6G

SYNTHESIS OF TRIPEPTIDE (6G1)

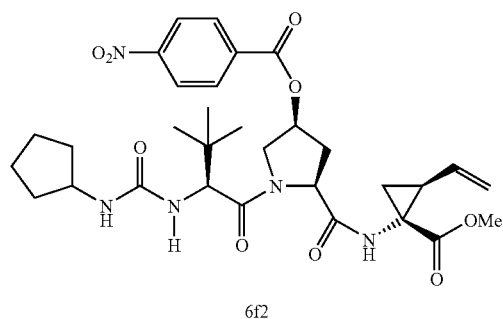
6f2

-continued

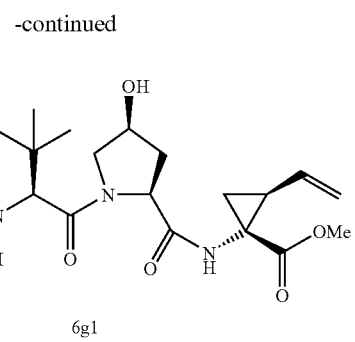
6g1

The crude pNBz ester 6f2 prepared above was dissolved in THF (90 mL) and methanol (40 mL) added. 1.0 N sodium hydroxide solution (12.0 mL; 12.0 mmol) was then added with vigorous stirring over 10 min (dropping funnel) and the hydrolysis allowed to proceed at ambient temperature. After 2 h, the excess base was neutralized by the careful addition of 1 N HCl (ca. 1.5 mL, added dropwise until the yellow color faded; final pH ca. 6). The organic solvents were evaporated and the aqueous residue was extracted with ethyl acetate (150+50 mL) and washed with saturated sodium bicarbonate (3×150 mL) and brine (100 mL). The combined extracts were dried over $MgSO_4$ and evaporated to a pale yellow, amorphous solid which was dried under high vacuum 6g1 (4.11 g, 87% from the P3-urea, HPLC purity 93%).

Example 6H

SYNTHESIS OF BROSYLATE DERIVATIVE (6H1)

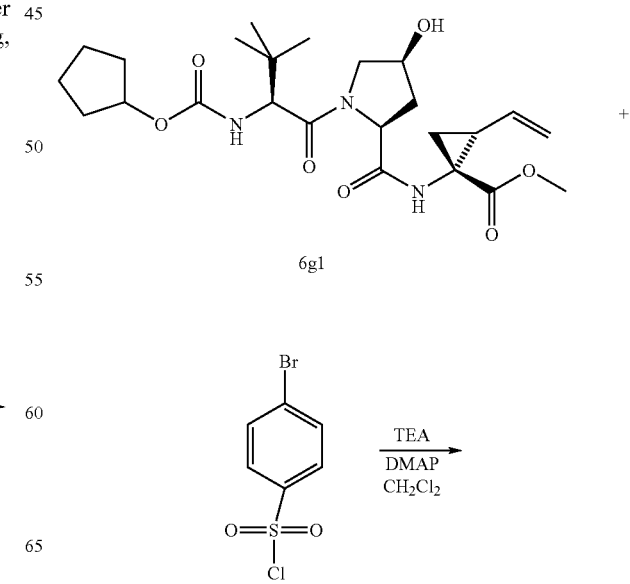

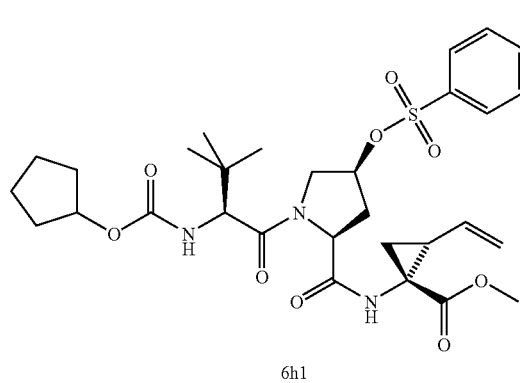

6h1

To a cooled solution (0° C.) of tripeptide 6g1 (10 g; 20.85 mmol) brosyl chloride (11.19 g; 43.79 mmol) and dimethylaminopyridine (254 mg; 2.09 mmol) dissolved in dichloromethane (75 mL) was added dropwise triethylamine (10.2 mL; 72.98 mmol). The yellow solution was stirred 1 hour at 0° C. before slowly allowed to warm to room temperature and stirred 60 hours at room temperature. The reaction mixture was concentrated to dryness, diluted with EtOAc, washed with saturated sodium bicarbonate solution, water and brine, dried (MgSO$_4$), filtered and evaporated to dryness to obtain the crude product The crude material was purified by flash column chromatography with hexane: EtOAc; 60:40 to 50:50 to provide the pure product 6h1 as a white foam (11.66 g; 80%). M.S. 698 (M+H)$^+$; 700.2 (MH+2)$^+$. Homogeneity by HPLC(TFA) @ 220 nm: 99%.

Example 6I

SYNTHESIS OF BROSYLATE DERIVATIVE (6I1)

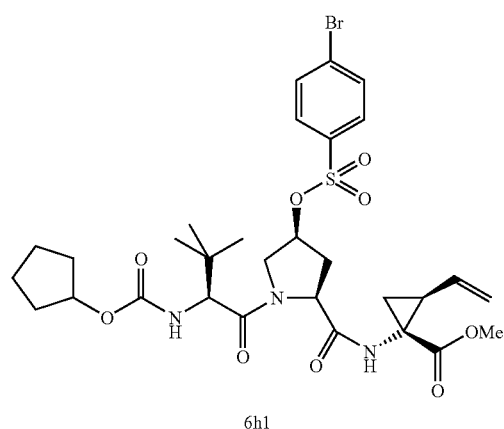

6h1

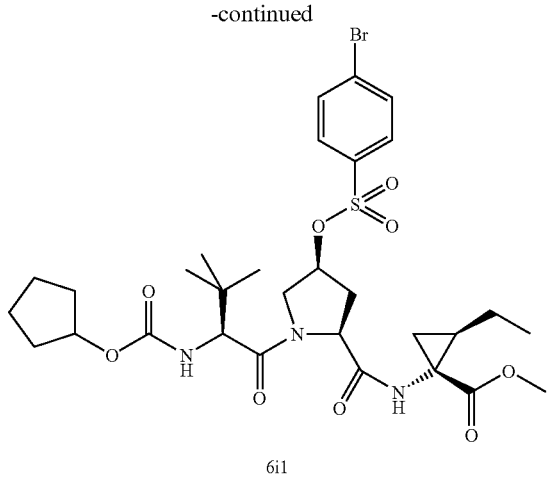

6i1

To a solution of the unsaturated tripeptide 6h1 (1.0 g, 1.43 mmol), in 12 ml of EtOAc, was added 200 mg of rhodium 5% on alumina. The resulting suspension was stirred at room temperature under H$_2$ atmosphere for 7h30. The reaction mixture was filtered on a Millex and the solvent removed in vacuo to yield 0.975 g (97%) of the crude material. M.S. 700.1 (M+H)$^+$; 702.1 (MH+2)$^+$. Homogeneity by HPLC(TFA) @ 220 nm: 98%.

Example 6J

SYNTHESIS OF COMPOUND 4015, TABLE 4

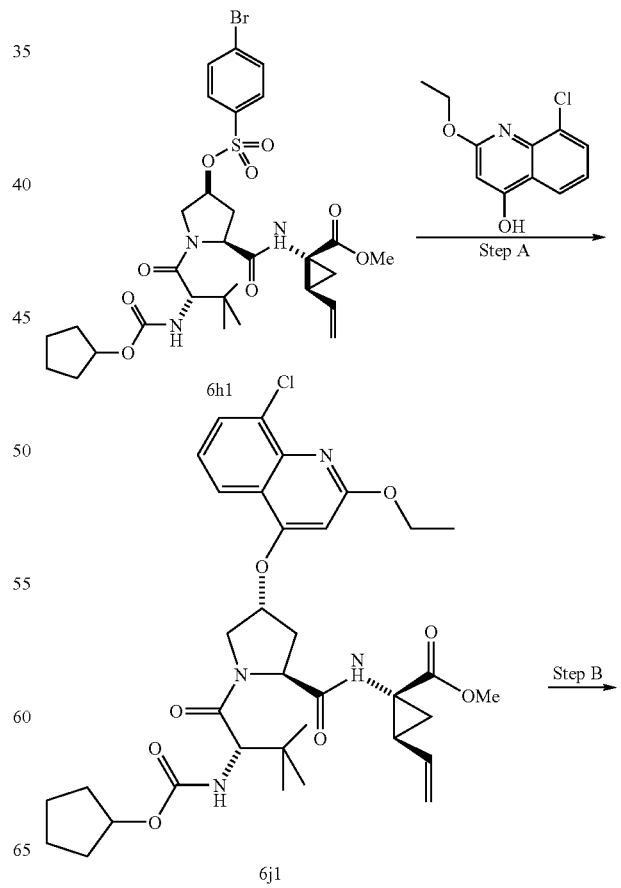

-continued

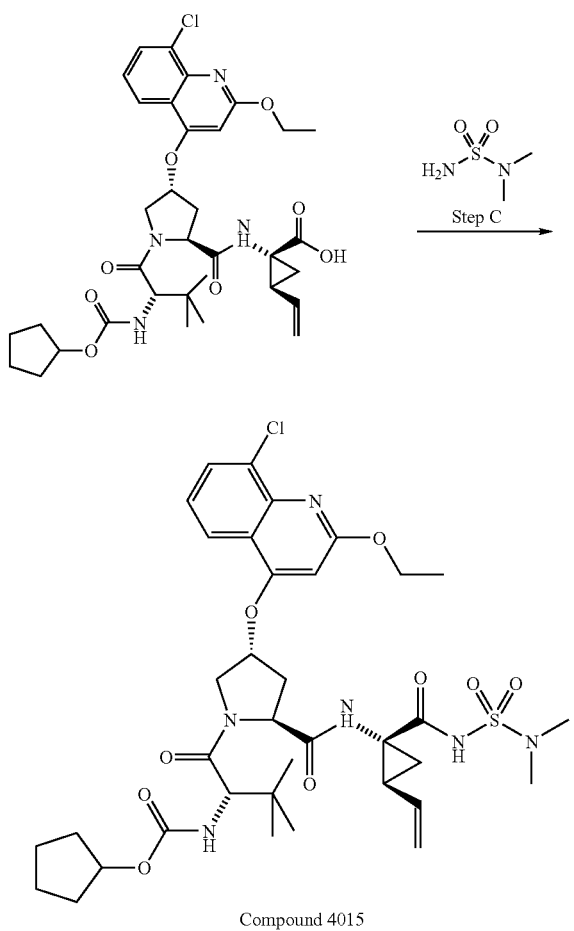

Compound 4015

Step A. To a solution of the brosylate intermediate 6h1 (50 mg, 0.072 mmol, 1.0 eq.), dissolved in NMP (3 mL) was added the hydroxyquinoline (16.1 mg, 0.072 mmol, 1.0 eq.) and cesium carbonate (25.7 mg, 0.079 mmol, 1.1 eq.). The mixture was heated at 70° C. for 7 hours. After the complete conversion of starting material to products, the reaction mixture was diluted with EtOAc and washed with $H_2O$ (2×), saturated aq. $NaHCO_3$(2×), and brine (1×). The organic layer was dried over anhydrous $MgSO_4$, filtered and evaporated to dryness. Product 6j1 (49.3 mg, 100%) was sufficiently clean to be used directly in the following step.

Step B. The methyl ester 6j1 (49.3 mg, L0mmol) was dissolved in a solution of $THF/MeOH/H_2O$ (2:1:1, 1.2 mL) and saponified with 1N NaOH (0.58 ml_, 0.58 mmol, 8 eq.)—The hydrolysis reaction was carried out over 5 h at RT. Thereafter, the solution was evaporated to dryness to give an off-white solid. This material was dissolved in acetic acid and purified by preparative HPLC ($ACCN/H_2O/TFA$). Pure fractions were combined, frozen, and lyophilized to afford the tripeptide intermediate as a white solid (29.5 mg; 61% yield), 99.8% homogeneity by analytical HPLC.

Step C: The intermediate acid (50 mg, 0.074 mmol), N,N-dimethylsulfamide (36.7 mg, 0.296 mmol), DIPEA (0.065 mL, 0.37 mmol) and DMAP (36.1 mg, 0.296 mmol), were dissolved in DMF (2.5 mL) and to it was added DBU (0.047 mL, 0.33 mmol). Stirred for 5 min, then added HATU (31 mg, 0.081 mmol). The reaction mixture was stirred for 12 h. The reaction mixture was concentrated and the residue was dissolved in AcOH, purified by preparatory HPLC (YMC Combiscreen ODS-AQ, 50×20 mm ID S-5 micron, 120 A; 220 nm) using a linear gradient and 0.06% TFA CH3CN/H2O. The pure fractions were combined, concentrated and lyophilized to provide the product, compound 4015, as the TF salt (4 mg, 7%). 1H NMR(400 MHz, DMSO-$d_6$): δ 10.31 (s, 1H), 8.69 (s, 1H), 7.99 (d, J=8 Hz, 1H), 7.81 (t, J=8 Hz, 1H), 7.26 (d, J=8 Hz, 1H), 7.0 ((d, J=8 Hz, 1H), 6.62 (s, 1H), 5.70-5.45 (m, 1H), 5.42 (brs, 1H), 5.20 (d, J=17 Hz, 1H), 5.10 (d, J=10 Hz, 1H), 4.58 (brs, 2H), 4.51 (q, J=7 Hz, 2H), 4.45-4.25 (m, 2H), 4.06 (d, J=8 Hz, 1H), 3.95-3.80 (m, 1H), 2.76 (s, 6H), 2.60-2.40 (m, 1H, along with the DMSO peak), 2.16-2.05 (m, 2H), 1.72-1.42 (m, 8H), 1.40 (t, J=7 Hz, 3H), 1.33-1.19 (m, 1H), 0.95 (s, 9H). EIMS: (M+H)=777.3, (M−H)=775.3

Example 6K

SYNTHESIS OF COMPOUND 4023, TABLE 4

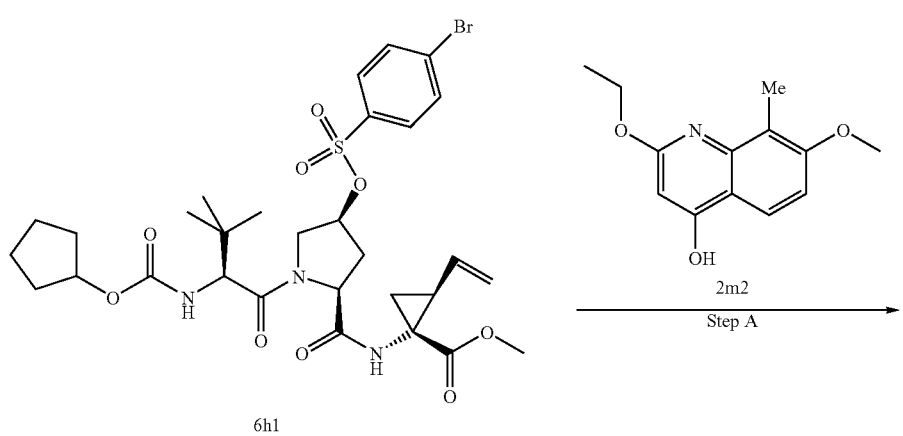

6h1

-continued
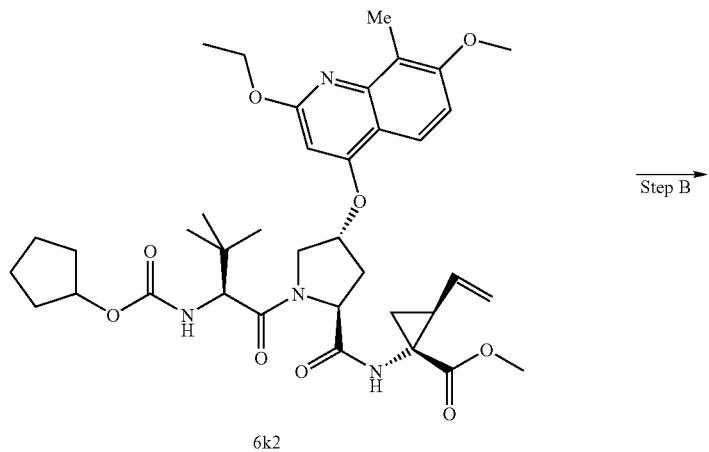
6k2
Step B →
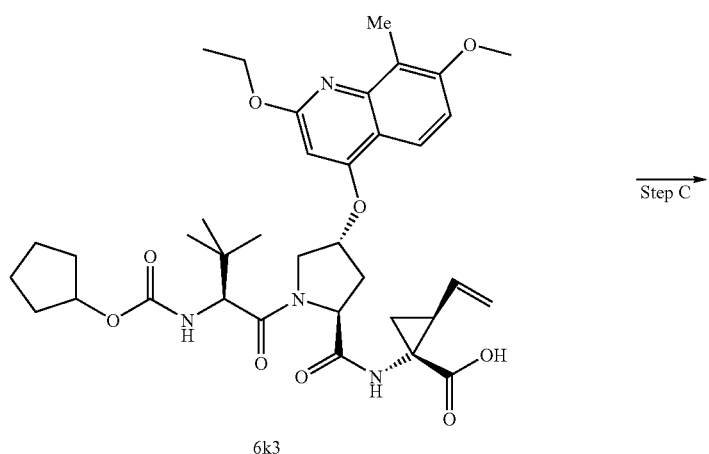
6k3
Step C →
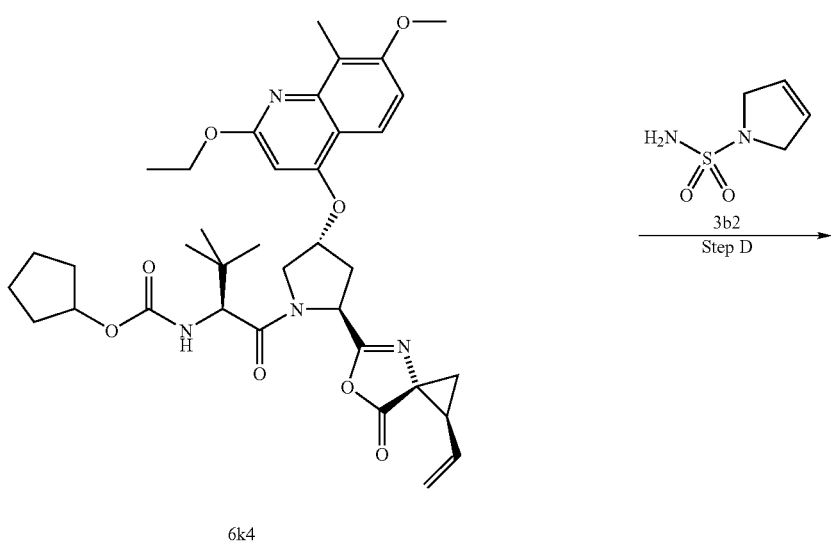
6k4
3b2
Step D →

-continued

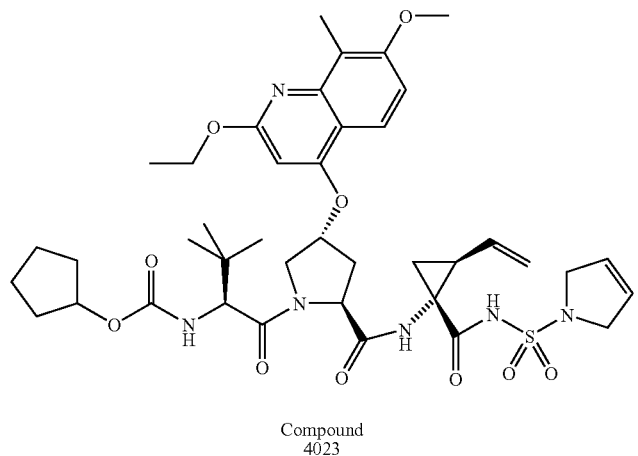

Compound
4023

Step A. To a solution of the brosylate intermediate 6h1 (50 mg, 0.072 mmol, 1 eq.), dissolved in NMP (2 ml_) was added the hydroxyquinoline 2 m2 (20 mg, 0.086 mmol, 1.2 eq.) and cesium carbonate (33 mg, 0.10 mmol, 1.4 eq.). The mixture was heated at 70° C. for 8 hours. After the complete conversion of starting material to products, the reaction mixture was diluted with EtOAc and washed with $H_2O$ (2×), saturated aq. $NaHCO_3$ (2×), and brine (1×). The organic layer was dried over anhydrous $MgSO_4$, filtered and evaporated to dryness. The material was purified by chromatography ($SiO_2$, 20% to 40% EtOAc/hexane) to give product 6k2 (36 mg, 72%) as an off white solid. Homogeneity by analytical HPLC (97%). MS: (M+H)+; 695.3 and (M+Na)+; 717.

Step B. The methyl ester 6k2 (36 mg, 0.052 mmol) was dissolved in a solution of THF/MeOH/H 20(2:1:1, 1.5 ml_) and saponified with 1N NaOH (0.42 mL, 0.42 mmol, 8 eq.). The hydrolysis reaction was carried out over 16 h at RT. Thereafter, the solution was evaporated to dryness to give an off-white solid. This material was dissolved in acetic acid and purified by preparative HPLC ($AcCN/H_2O$/TFA). Pure fractions were combined, frozen, and lyophilized to afford 6k3 (compound 4023) as a white solid (16.5 mg; 47% yield). Homogeneity by analytical HPLC (100%). MS: (M+H)+; 681.3. $^1$H NMR (400 MHz, DMSO-$d_6$): major rotamer: δ 12.41 (bs, 1H), 8.54 (s, 1H), 7.83 (d, J=8.5 Hz, 1H), 7.08 (d, J=9 Hz, 1H), 6.96 (d, J=9 Hz, 1H), 6.33 (s, 1H), 5.77-5.65 (m, 1H), 5.33 (bs, 1H), 5.19 (d, J=18 Hz, 1H), 5.06 (d, J=11 Hz, 1H), 4.70-4.58 (m, 1H), 4.47 (q, J=7 Hz, 1H), 4.52-4.33 (m, 1H), 4.26 (d, J=12 Hz, 1H), 4.11 (d, J=9 Hz, 1H), 4.05-3.9 (m, 1H), 3.88 (s, 3H), 2.43 (s, 3H), 2.24-2.14 (m, 1H), 2.07-1.98 (m, 1H), 1.82-1.63 (m, 1H), 1.63-1.43 (m, 8H), 1.39 (t, J=7 Hz, 3H), 1.34-1.20 (m, 2H), 0.95 (s, 9H).

Step C: To a solution of the acid 6k3 (140 mg, 0.206 mmol), in 5 mL of $CH_2Cl_2$, was added 0.086 mL of $Et_3N$ (0.617 mmol, 3.01 equiv.). The resulting solution was cooled to 0° C. for the addition of the isobutyl chloroformate (0.040 mL, 0.308 mmol, 1.50 equiv.). The ice bath was removed one hour later and the reaction stirred at room temperature for an extra 4 hours. The reaction mixture was concentrated to dryness. The crude material was purified by flash column chromatography with Hexanes/EtOAc; 70:30 to provide 84 mg of the desired compound 6k4 (620% o yield).

Step D: A solution of the sulfamide 3b2, in 1.5 mL of THF, was cooled down to −15° C. for the addition of LiHMDS 1M sln/THF (0.080 mL, 0.080 mmol, 1.26 equiv.). The resulting solution was stirred 5 minutes at this temperature and 20 minutes at room temperature. The reaction was then cooled back to −15° C. and a solution of the azalactone 6k4 (42 mg, 0.063 mmol, 1 equiv.), in 1.5 mL of THF, was added drop by drop. The resulting solution was stirred 30 minutes at −15, −10° C. then overnight at room temperature. The reaction mixture, diluted with AcOH, was purified by preparatory HPLC (YMC Combiscreen ODS-AQ, 50×20 mm ID S-5 micron, 120 A 220 nm) using a linear gradient and 0.06% TFA $CH_3CN/H_2O$. The pure fractions were combined, concentrated and lyophilized to provide the product, compound 4015, as the TF salt (28 mg, 54%). $^1$H NMR (400 MHz, DMSO-$d_6$): ca, 85:15 mixture of rotamers, major isomer description; 510.33 (s, 1H), 8.75 (s, 1H), 7.85 (d, J=9.0 Hz, 1H), 7.07 (d, J=9.0 Hz, 1H), 7.01-6.91 (m, 1H), 6.34 (s, 1H), 5.81-5.74 (m, 2H), 5.50-5.34 (m, 2H), 5.24-5.15 (m, 1H), 5.10-5.02 (m, 1H), 4.72-4.61 (m, 1H), 4.46 (q, J=6.9 Hz, 2H), 4.38-4.28 (m, 2H), 4.21-4.04 (m, 5H), 3.95-3.89 (m, 1H),₁3.88 (s, 3H), 2.42 (s, 3H), 2.17-2.05 (m, 2H), 1.80-1.20 (m, 11H), 1.38 (t, J=7.0 Hz, 3H), 0.96 (s, 9H). M.S. (electrospray): 809.4 (M−H)-811.5 (M+H)+. Reverse Phase HPLC Homogeneity (0.06% TFA; $CH_3CN:H_2O$): 99%

Example 6L
SYNTHESIS OF COMPOUND 4035, TABLE 4
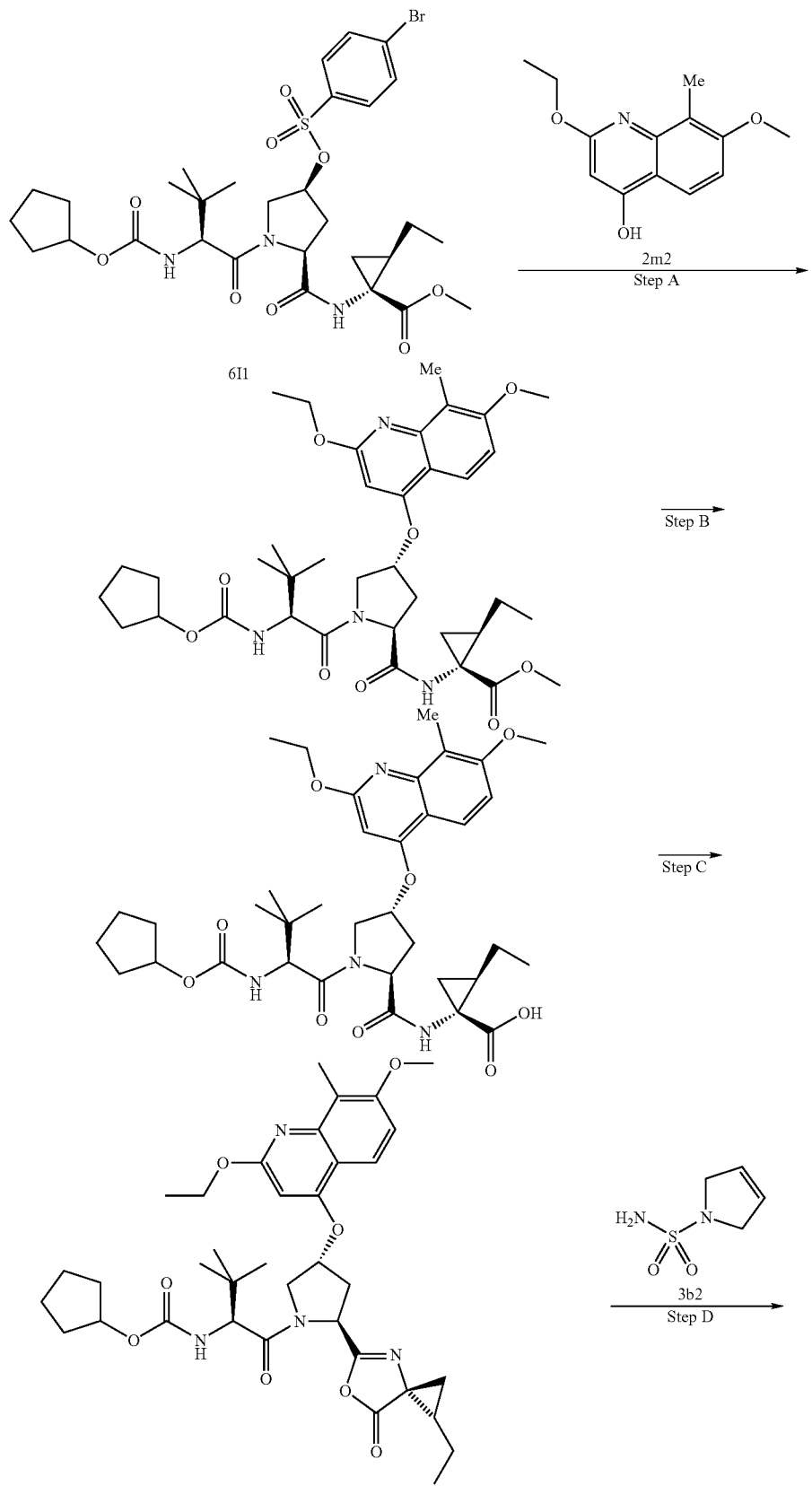

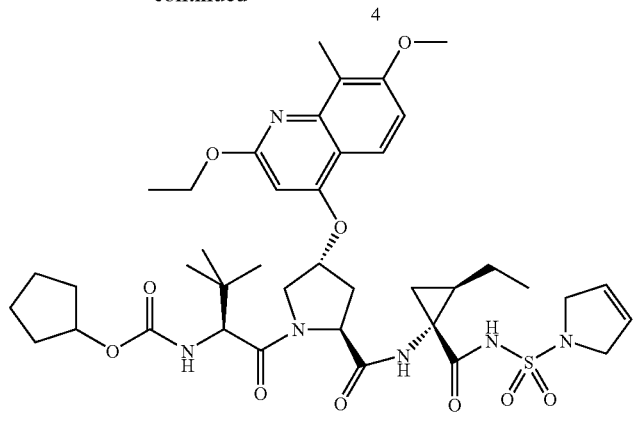

Compound 4035

Using the same procedure as described in Example 6K but using brosylate tripeptide 6l1 instead of 6h1 gave the title compound 4035: $^1$H NMR (400 MHz, DMSO-d$_6$): ca. 80:20 mixture of rotamers, major isomer description; δ 10.23 (s, 1H), 8.64 (s, 1H), 7.85 (d, J=9.0 Hz, 1H), 7.07 (d, J=9.2 Hz, 1H), 6.94 (d, J=8.2 Hz, 1H), 6.34 (s, 1H), 5.79-5.74 (m, 2H), 5.39-5.33 (m, 1H), 4.69-4.60 (m, 1H), 4.46 (q, J=7.0 Hz, 2H), 4.38-4.28 (m, 2H), 4.23-4.06 (m, 5H), 3.97-3.87 (m, 1H), 3.88 (s, 3H), 3.37-3.27 (m, 1H), 2.42 (s, 3H), 2.13-2.03 (m, 1H), 1.79-1.19 (m, 13H), 1.38 (t, J=7.0 Hz, 3H), 0.96 (s, 9H), 0.85 (t, J=7.0 Hz, 3H). M.S. (electrospray): 811.3 (M−H)−813.4 (M+H)+. Reverse Phase HPLC Homogeneity (0.06% TFA; CH$_3$CN: H$_2$O): 99%

Example 6M

SYNTHESIS OF COMPOUND 4012, TABLE 4

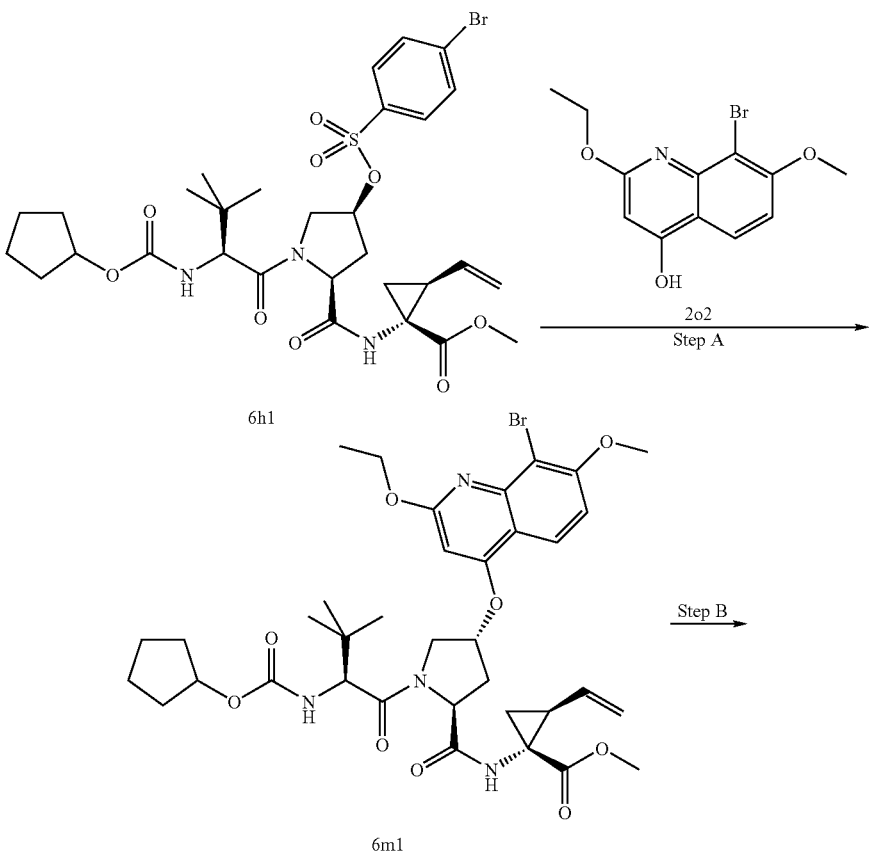

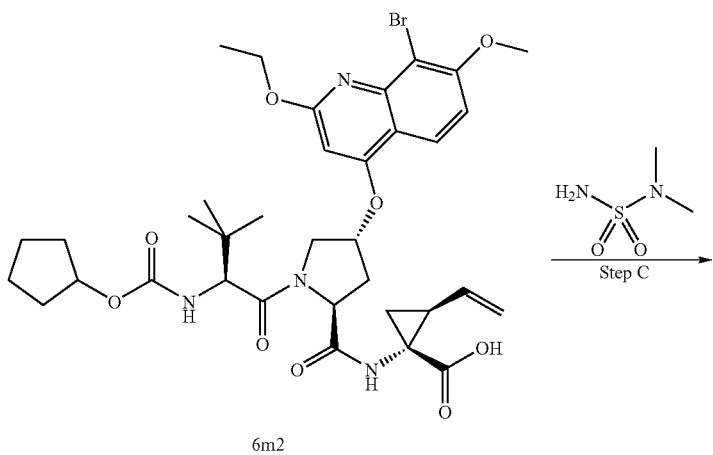

6m2

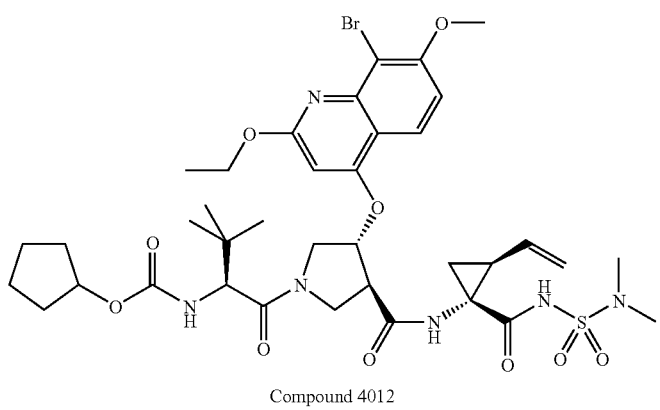

Compound 4012

Steps A and B were carried out as described above in Example 6K but using the 8-bromo-2-ethoxy-7-methoxy-4-quinolinol 2o2 instead of 8-methyl-2-ethoxy-7-methoxy-4-quinolinol 2 m2 in step A.

Step C: To a mixture of the acid 6 m2 (50 mg, 0.067 mmol), N,N-dimethylsulfamide (33.3 mg, 0.268 mmol), DIPEA (0.06 ml_, 0.335 mmol) and DMAP (33 mg, 0.268 mmol) in DMF (2.5 mL) was added DBU (0.04 ml. 0.301 mmol). The mixture was stirred for 5 min, then HATU (28 mg, 0.074 mmol) was added and the reaction mixture was stirred for 12 h. The reaction mixture was concentrated and the residue was dissolved in AcOH, purified by preparatory HPLC (YMC Combiscreen ODS-AQ, 50×20 mm ID S-5 micron, 120A; 220 nm) using a linear gradient and 0.06% TFA CH3CN/H$_2$O. The pure fractions were combined, concentrated and lyophilized to provide the product compound 4012 as the TF salt (22 mg, 38%). $^1$H NMR (400 MHz, DMSO-d$_6$) δ 10.31 (s, 1H), 8.69 (s, 1H), 8.0 (d, J=9 Hz, 1H), 7.16 (d, J=9 Hz, 1H), 6.97 (d, J=8 Hz, 1H), 6.45 (s, 1H), 5.58-5.49 (m, 1H), 5.40 (brs, 1H), 5.21 (d, J=17 Hz, 1H), 5.09 (d, J=10 Hz, 1H), 4.60-4.46 (m, 3H), 4.40-4.30 (m, 2H), 4.05 (d, J=8 Hz, 2H), 3.95 (s, 3H), 3.91-3.83 (m, 1H), 2.76 (s, 6H), 2.17-2.05 (m, 2H), 1.71-1.42 (m, 9H), 1.39 (t, J=7 Hz, 3H), 1.31-1.19 (m, 1H), 0.94 (s, 9H). EIMS: (M+)=851.3, (M+2)=853.3

Example 6N

SYNTHESIS OF COMPOUND 2001, TABLE 2

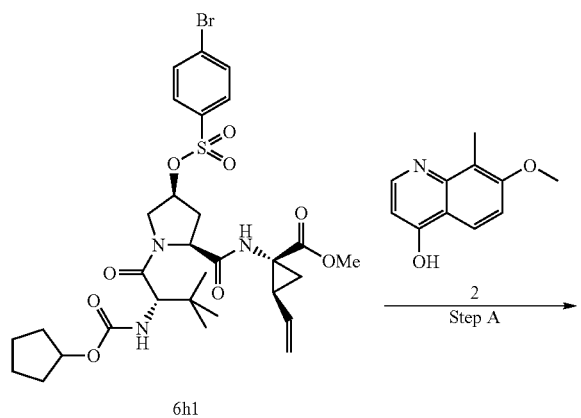

6h1

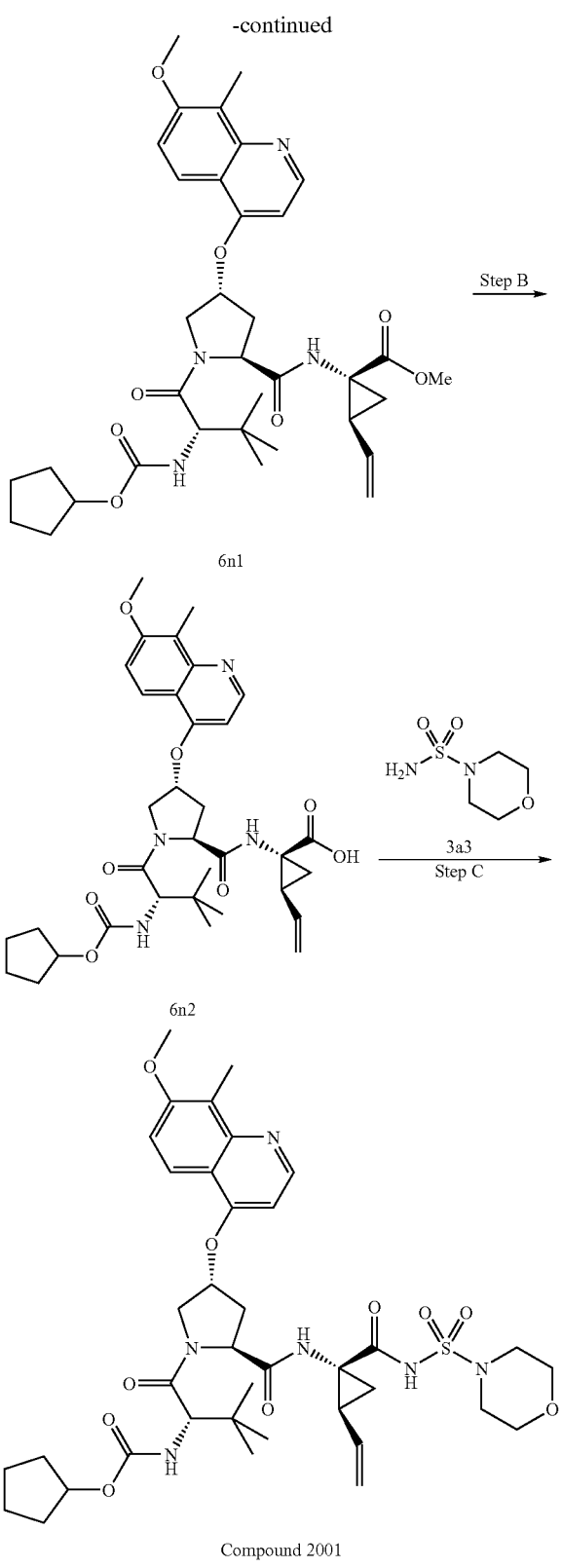

Step C: Acid 6n2 (100 mg, 0.157 mmol), HATU (71 mg, 0.187 mmol), DIPEA (0.07 ml-0.40 mmol) were dissolved in DMF (2 mL) and stirred for 1 h. In another flask, a solution of sulfamide 3a3 (55 mg, 0.331 mmol), DBU (0.1 mL, 0.71 mmol), DMAP (77 mg, 0.63 mmol) and DIPEA (0.07 mL, 0.40 mmol) in DMF (2 mL) was made and added to it. Stirred the reaction mixture for 16 h. The DMF was evaporated and the residue was taken up in EtOAc (100 mL) and washed with 1N HCl (2×50 mL) and water (2×50 mL) followed by brine. Concentrated and the residue was dissolved in DMSO (2.5 mL) and purified by preparatory HPLC (YMC Combiscreen ODS-AQ, 50×20 mm ID S-5 micron, 120 A; 220 nm) using a linear gradient and 0.06% TFA CH$_3$CN/H$_2$O. The pure fractions were combined, concentrated and lyophilized to provide the product compound 2001 as the TF salt (38.2 mg, 31%). $^1$H NMR(400 MHz, DMSO-d$_\beta$): δ 10.43 (s, 1H), 8.92 (brd, J=5 Hz, 1H), 8.69 (s, 1H), 8.21 (brd, J=9 Hz, 1H), 7.53 (brd, J=9 Hz, 1H), 7.33 (brs, 1H), 6.98 (d, J=8 Hz, 1H), 5.68 (brs, 1H), 5.21 (d, J=17 Hz, 1H), 5.10 (d, J=10 Hz, 1H), 4.5-4.40 (m, 2H), 4.35-4.25 (m, 1H), 4.20-3.85 (m, 6H), 3.75-3.25 (m, 4H, under the H$_2$O peak), 3.25-3.05 (m, 5H), 2.70-2.55 (m, 1H), 2.35-2.0 (m, 2H), 1.75-1.65 (m, 1H), 1.60-1.10 (m, 11H), 0.93 (s, 9H). EIMS: (M+H)=785.4, (M−H)=783.4

Example 6O

SYNTHESIS OF COMPOUND 2002, TABLE 2

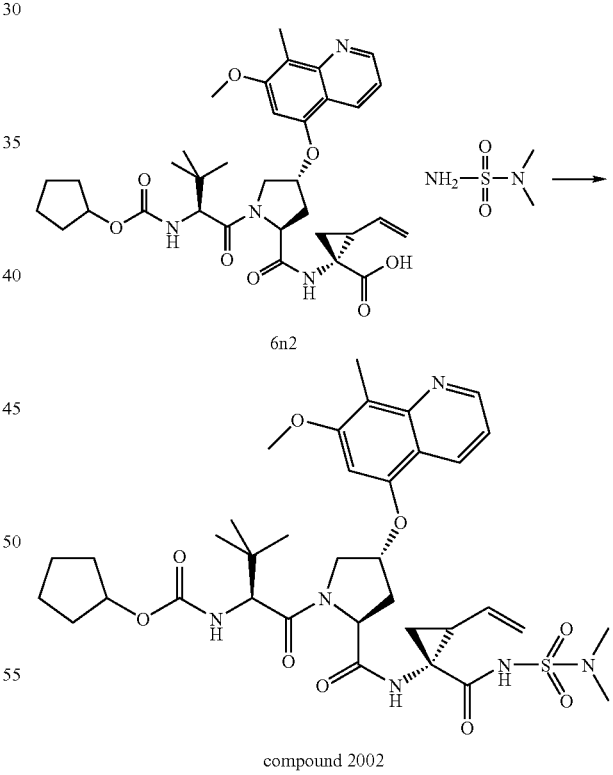

compound 2002

Steps A and B were carried out as described above in example 6K but using 8-methyl-7-methoxy-4-quinolinol instead of 8-methyl-2-ethoxy-7-methoxy-4-quinolinol 2 m2 in step A.

This synthesis uses the intermediate 6n2 from Example 6N as starting material. The acid 6n2 (50 mg, 0.074 mmol), N,N-dimethyl sulfamide (39.2 mg, 0.316 mmol), DIPEA (0.07 mL, 0.395 mmol) and DMAP (40 mg, 0.316 mmol), were dissolved in DMF (2 mL) and to it was added DBU (0.05 mL, 0.356 mmol). Stirred for 5 min, then added HATU (33 mg, 0.087 mmol). The reaction mixture was stirred for 12 h.

The reaction mixture was concentrated and the residue was dissolved in AcOH, purified by preparatory HPLC (YMC Combiscreen ODS-AQ, 50×20 mm ID S-5 micron, 120A 220 nm) using a linear gradient and 0.06% TFA CH$_3$CN/H$_2$O. The pure fractions were combined, concentrated and lyophilized to provide the product compound 2002 as the TF salt (16.2 mg, 28%). $^1$H NMR (400 MHz, DMSO-d$_6$): δ 10.31 (s, 1H), 8.93 (brs, 1H), 8.73 (s, 1H) 8.24 (brd, J=8 Hz, 1H), 7.55 (brs, 1H), 7.34 (brs, 1H), 7.00 (d, J=8 Hz, 1H), 5.69 (brs, 1H), 5.58-5.49 (m, 1H), 5.22 (d, J=17 Hz, 1H), 5.11 (d, J=10 Hz, 1H), 4.55-4.40 (m, 2H), 4.40-4.25 (brs, 1H), 4.10-3.90 (m, 5H), 2.77 (s, 6H), 2.65-2.55 (m, 3H), 2.35-2.20 (m, 1H), 2.10 (q, J=9 Hz, 1H), 1.75-1.65 (m, 1H), 1.60-1.15 (m, 10H), 0.95 (s, 9H). EIMS: (M+H)=743.3, (M−H)=741.3

Example 6P

SYNTHESIS OF COMPOUND 3001, TABLE 3

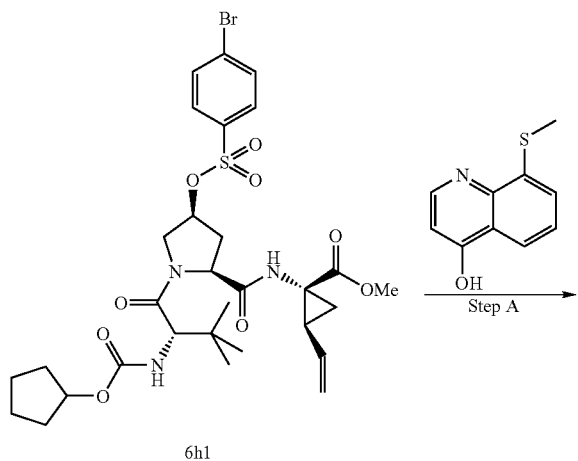

6h1

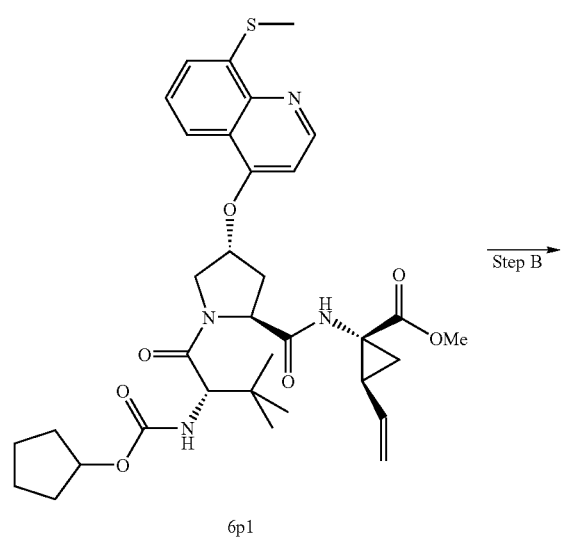

6p1

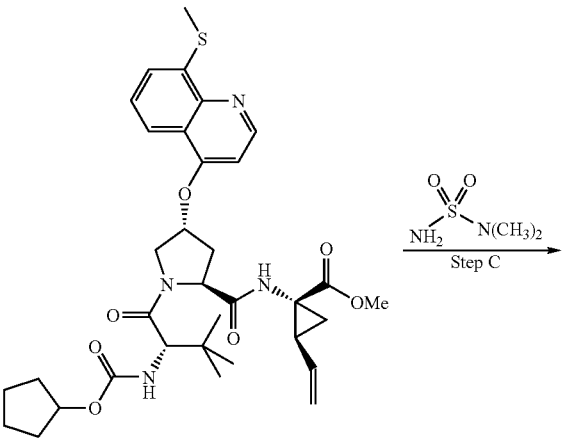

6p2

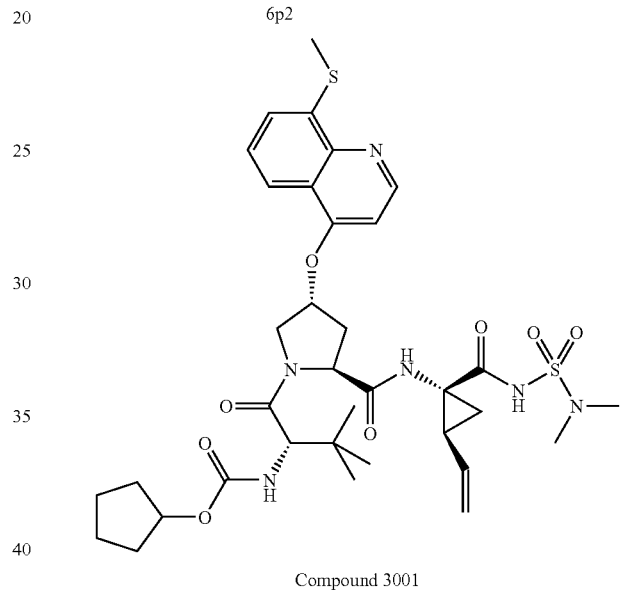

Compound 3001

Steps A and B were done as described above in example 6K but using the 8-thiomethoxy-4-quinolinol instead of 8-methyl-2-ethoxy-7-methoxy-4-quinolinol 2 m2 in step A.

Step C: The acid 6p2 (72 mg, 0.113 mmol), N,N-dimethyl sulfamide (56 mg, 0.452 mmol), DIPEA (0.1 mL, 0.565 mmol) and DMAP (55 mg, 0.452 mmol), were dissolved in DMF (5 mL) and to it was added DBU (0.07 mL, 0.508 mmol). Stirred for 5 min, then added HATU (47 mg, 0.124 mmol). The reaction mixture was stirred for 12 h. The reaction mixture was concentrated and the residue was dissolved in AcOH, purified by preparatory HPLC (YMC Combiscreen ODS-AQ, 50×20 mm ID S-5 micron, 120 A; 220 nm) using a linear gradient and 0.06% TFA CH$_3$CN/H$_2$O. The pure fractions were combined, concentrated and lyophilized to provide compound 3001 as the TF salt (42 mg, 50%). $^1$H NMR (400 MHz, DMSO-d$_6$): 610.31 (s, 1H), 8.76 (d, J=5 Hz), 1H), 8.72 (s, 1H), 7.94 (d, J=8 Hz, 1H), 7.51-7.40 (m, 2H), 7.18 (d, J=5 Hz, 1H), 7.00 (d, J=8 Hz, 1H), 5.60-5.43 (m, 2H), 5.20 (d, J=17 Hz, 1H), 5.10 (d, J=11 Hz, 1H), 4.59 (brs, 1H), 4.49-4.31 (m, 2H), 4.07 (d, J=8.2 Hz, 1H), 3.93 (brd, J~9.4 Hz, 1H), 2.76 (s, 6H), 2.60-2.41 (m, 4H), 2.24-2.02 (m, 2H), 1.17-1.72 (m, 10H), 0.96 (s, 9H). EIMS: (M+H)=745.1, (M−H)=743.1

Example 6Q

SYNTHESIS OF COMPOUND 6002, TABLE 6

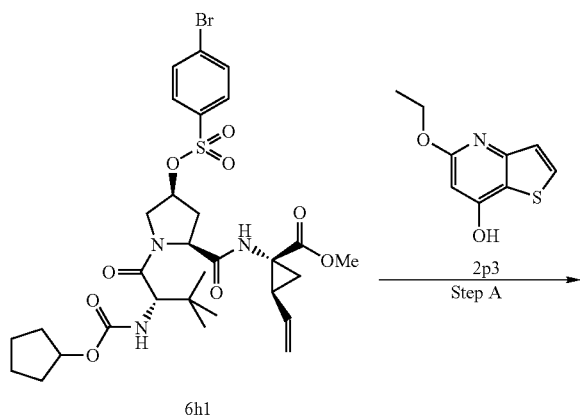

6h1

Step A →

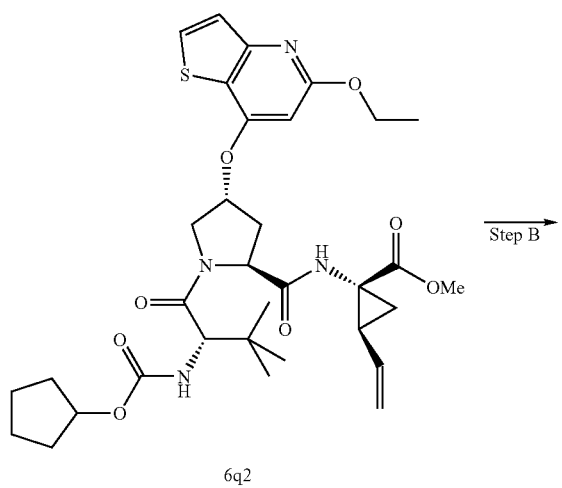

6q2

Step B →

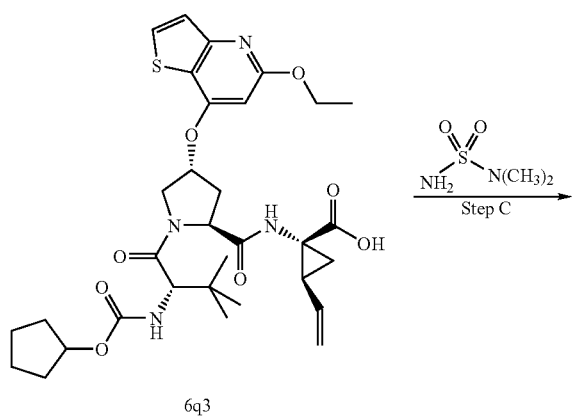

6q3

Step C →

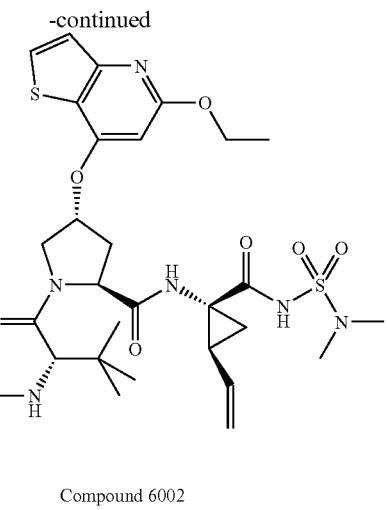

Compound 6002

Step A: Thienopyridine 2p3, (35 mg, 0.18 mmol) was added to a solution of the tripeptide (6h1, 133 mg, 0.19 mmol) in NMP (2 mL) and cesium carbonate (62 mg, 0.19 mmol) at 23° C. The reaction was heated to 70° C. (internal temperature) and stirred for 2h at 70° C. and then cooled to 23° C. The reaction mixture was extracted with EtOAc (3×) and then washed with NaHCO$_3$ (1×) followed by brine (3×). The organic layer was dried, filtered and concentrated to obtain an off-white solid (6q2, 100 mg, 85%) which was employed in subsequent reaction without purification. MS ES+=657.3.

Step B: 1 M NaOH solution (0.8 mL, 0.8 mmol) was added to starting ester (6q2, 50 mg, 0.076 mmol) in a THF/MeOH/water solvent mixture (2:1:1 ratio, 4 mL total volume) and allowed to stir overnight at rt. The reaction mixture was concentrated, diluted with DMSO and purified by prep-HPLC (H$_2$O/CH$_3$CN/0.06% TFA). The pure fractions were combined and the solvents removed by lyophilization to obtain a white solid (6q3, 38 mg, 78%). MS ES+=643.3.

Step C: HATU (25 mg, 0.066 mmol) was added to a solution of the acid (6q3, 25 mg, 0.039 mmol) and DIPEA (0.035 mL, 0.198 mmol) in DMF (1.4 mL) at rt. The solution immediately changed color from colourless to yellow. Then a solution of N$_1$N-dimethylsulfamide (11 mg, 0.090 mmol) and DMAP (19 mg, 0.16 mmol) in DMF (0.5 ml.) was added and the reaction was stirred for an additional hour followed by the addition of DBU (0.03 ml_, 0.18 mmol) in DMF (0.5 mL). The reaction was then stirred for 16 h at 23° C. The solvent was removed and dissolved in DMSO (2.5 mL) and purified by prep HPLC (H$_2$O/CH$_3$CN+0.06% TFA) to yield compound 6002 as a white lyophilized solid (10 mg, 34%). MS ES+=749.1, ES−=747.1. $^1$H NMR, 400 MHz, DMSO-d$_6$: 10.28 (s, 1H); 8.78, (s, 1H); 7.95 (d, J=5.1 Hz, 1H), 7.35 (d, J=5.1 Hz, 1H); 6.88 (d, J=8.8 Hz, 1H); 6.47 (s, 1H); 5.53-5.62 (m, 1H); 5.41 (s, 1H); 5.22 (d, J=17.3 Hz, 1H); 5.11 (d, J=10.9 Hz, 1H); 4.65 (s, br, 1H); 4.34-4.39 (m, 4H); 4.20-4.22 (m, 1H); 4.07 (d, J=9.8 Hz, 1H); 3.96-3.98 (m, 1H); 2.77 (s, 6H); 2.13-2.19 (m, 2H); 1.65-1.71 (m, 2H); 1.25-1.63 (m, 11H); 0.95 (s, 9H).

Example 6R

SYNTHESIS OF AZA-LACTONE INTERMEDIATE

Compound 6r1 was synthesized by sequential coupling as described, for example, in Example 6D, but using commercially available 4-R-benzyloxy proline instead of 4-hydroxyproline. The methyl ester was hydrolyzed under basic conditions as described in example 6K.

Example 6S

OPENING OF THE AZA-LACTONE 6R2

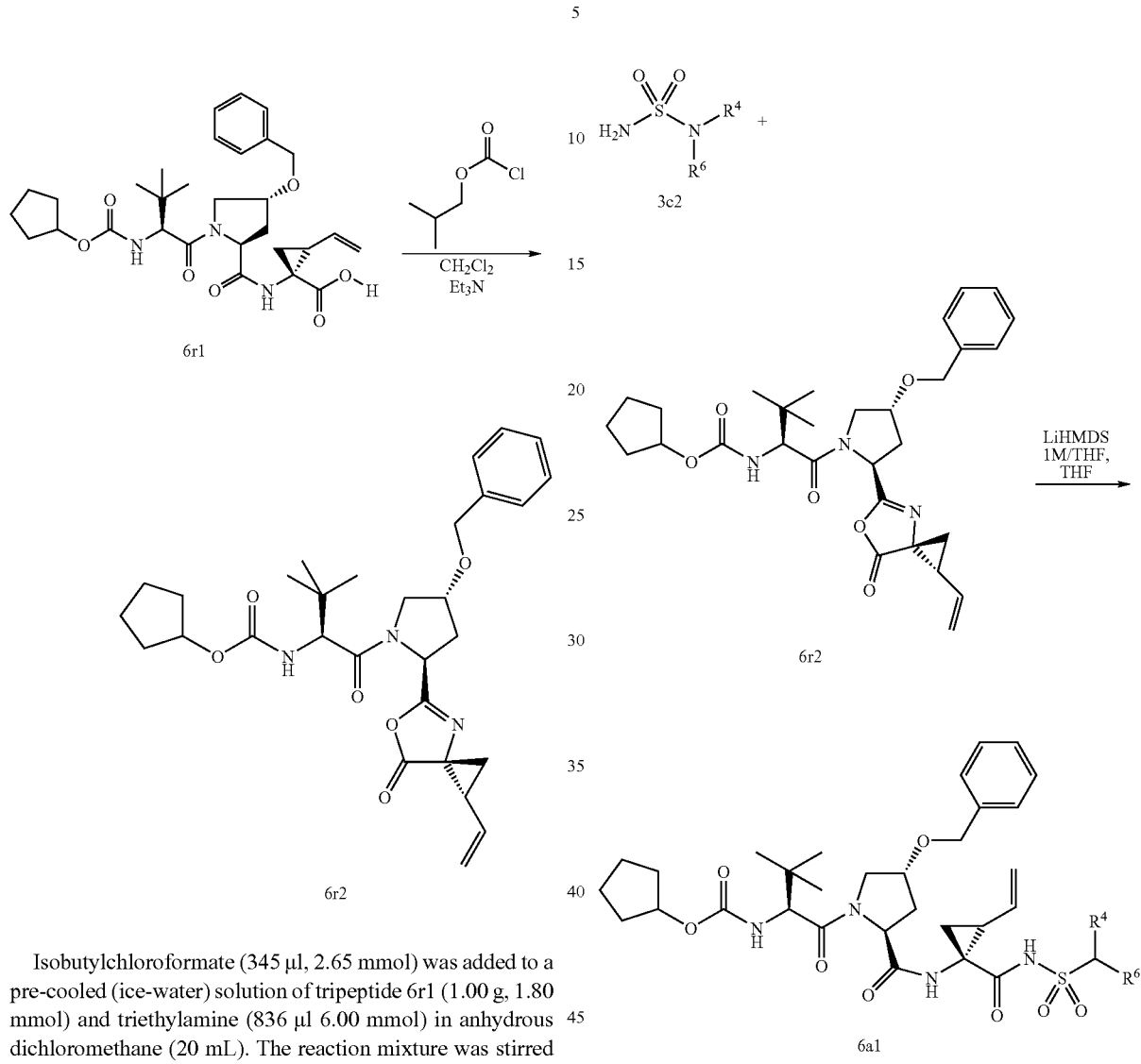

Isobutylchloroformate (345 µl, 2.65 mmol) was added to a pre-cooled (ice-water) solution of tripeptide 6r1 (1.00 g, 1.80 mmol) and triethylamine (836 µl 6.00 mmol) in anhydrous dichloromethane (20 mL). The reaction mixture was stirred for 1 h at 0° C. and 1 h at room temperature. The mixed anhydride and lactone formation were monitored by HPLC. The mixture was then transferred to a column containing 20 g of dry silica gel and the compound was eluted with a 3:7 v/v EtOAc-hexane to afford a white solid. Residual isobutanol was removed by co-evaporation with carbon tetrachloride to give the desired pure aza-lactone 6r2 (943 mg, 97% yield). HPLC ($CH_3CN/H_2O$, 0.06% TFA): 96.5%; LC-MS 538.1 ($MH^+$); $^1H$ NMR (DMSO-$d_6$) Mixture of rotamers δ 7.34-7.28 (m, 5H), 7.07 (d, J=9.0 Hz, major rotamer, 0.8H), 6.62 (d, J=9.0 Hz, minor rotamer, 0.2H), 5.79-5.70 (m, 1H), 5.37 (d, J=17.0 Hz, 1H), 5.17 (d, J=10.3 Hz, 1H), 4.91 (broad, 1H), 4.65 (t, J=8.3 Hz, 1H), 4.54 (d, J=11.1 Hz, 1H), 4.45 (d, J=11.5 $Hz_1$ 1H), 4.28 (broad, 1H), 4.21 (d, J=9 Hz, 1H), 4.15 (d, J=11.3 Hz, 1H), 3.68 (dd, $J_1$=3.3 Hz, $J_2$=11.3 Hz, 1H), 2.81 (q, J=9.0 Hz, 1H), 2.40-2.37 (m, 1H), 2.23-2.15 (m, 1H), 2.02 (dd, $J_1$=5.2 Hz, $J_2$=9.2 Hz, 1H), 1.82-1.40 (m, 9H) and 0.91 (s, 9H).

The sulfamide 3c2 in a 2-dram vial was dried under house vacuum in a dessicator containing $P_2O_5$ for a few days. The vial was fitted with a screw cap and septum. Anhydrous THF (0.5 ml_) was added to the vial and 3 vacuum-argon cycles were performed. LiHMDS (1.0 M in THF, 1.2 equiv. based on the amount of sulfamide present in each vial) was added with a gastight syringe and the reaction mixture were stirred at room temperature using an orbital shaker. After 15 minutes, the solution was cooled to −10° C. and the aza-lactone 6r2 (0.1 M stock solution in THF, 1 equiv. based on the amount of sulfamide present) was added to the vial. The vial was placed on an orbital shaker and stirred at −10° C. for 1 hour and at room temperature for another hour. The reactions was quenched with a few drop of acetic acid and the product was purified on reversed-phase HPLC (Waters Symmetry C18 column, $CH_3CN/H_2O$ 0.06% TFA gradient) to give the desired product 6s1 after lyophilization with yields that vary from 31% to 41% (12-20 mg).

Example 6T

SYNTHESIS OF COMPOUND 5012, TABLE 5

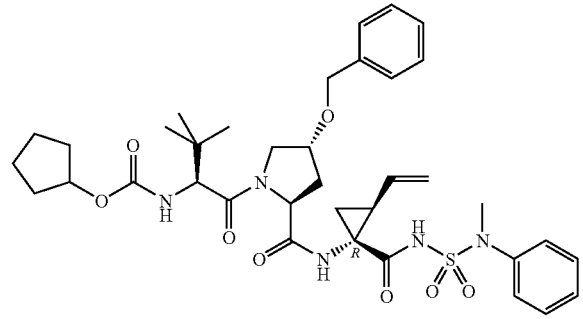

Compound 5012 of Table 5 was prepared following the procedures as set out in Example 6R and 6S above. $^1$H NMR (DMSO-d$_6$) δ 10.45 (s, 1H), 8.74 (s, 1H), 7.38-7.27 (m. 11H). 6.83 (d. J=8.8 Hz. 1H), 5.64-5.54 (m, 1H), 5.22 (d, J=17.2 Hz, 1H), 5.12 (d, J=10.7 Hz, 1H), 4.89 (broad s, 1H), 4.40 (d, part of a AB system, J=11.3 Hz, 1H), 4.32 (d, part of a AB system, J=11.5 Hz, 1H), 4.24-4.07 (m, 4H), 3.63 (d, J=13.5 Hz, 1H), 2.19-2.05 (m, 2H), 1.87-1.41 (m, 11H), 1.29-1.22 (m, 1H), 0.92 (s, 10H).

Example 6U

SYNTHESIS OF COMPOUND 5005, OF TABLE 5

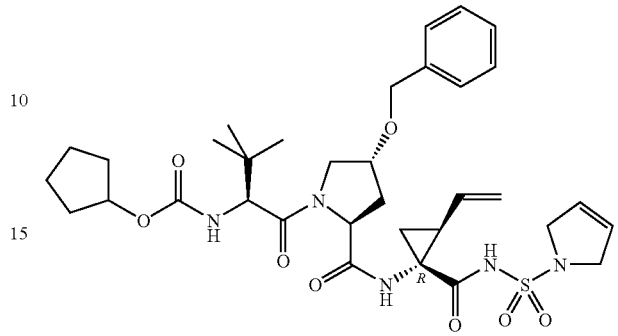

Compound 5005 of Table 5 was prepared following the procedures as set out in Example 6R and 6S above. $^1$H NMR (DMSO-d$_6$) δ 10.27 (s, 1H), 8.82 (s, 1H), 7.36-7.27 (m, 5H), 6.88 (d, J=8.4 Hz, 1H), 5.77 (s, 2H), 5.49-5.39 (m, 1H)$_1$ 5.21 (d, J=17.0 Hz, 1H), 5.06 (d, J=11.7 Hz, 1H), 4.91 (broad s, 1H), 4.52 (d, part of a AB system, J=11.2 Hz, 1H), 4.42 (d, part of a AB system, J=11.5 Hz, 1H), 4.24-4.11 (m, 6H), 3.65 (d, J=10.9 Hz, 1H), 2.23-2.19 (m, 1H), 2.11 (q, J=8.6 Hz, 1H), 1.91-1.48 (m, 10H), 1.26-1.22 (m, 1H), 0.95 (s, 9H).

Example 6V

SYNTHESIS OF COMPOUND 6003, OF TABLE 6

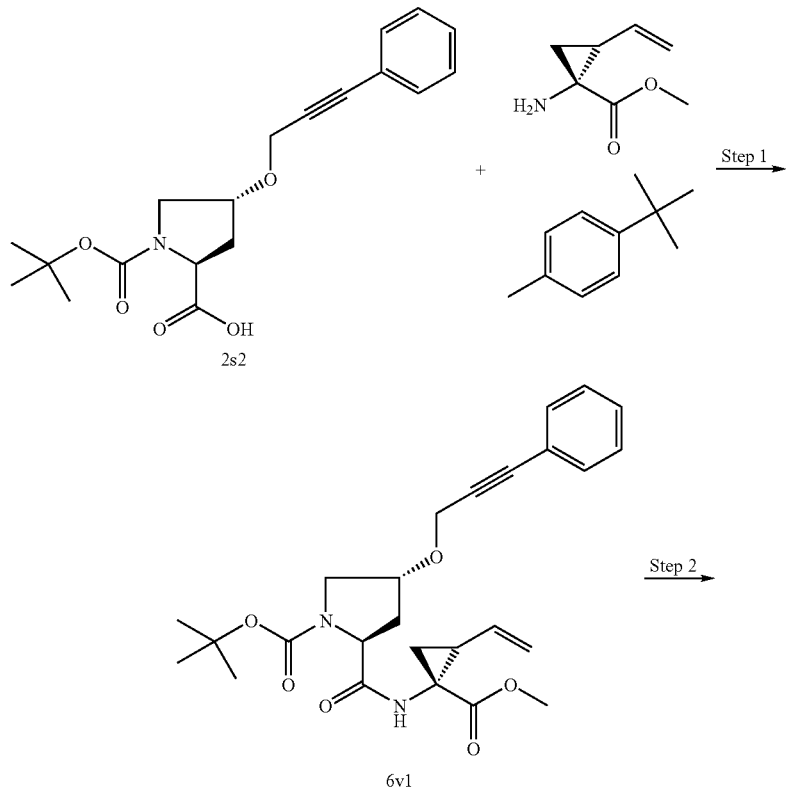

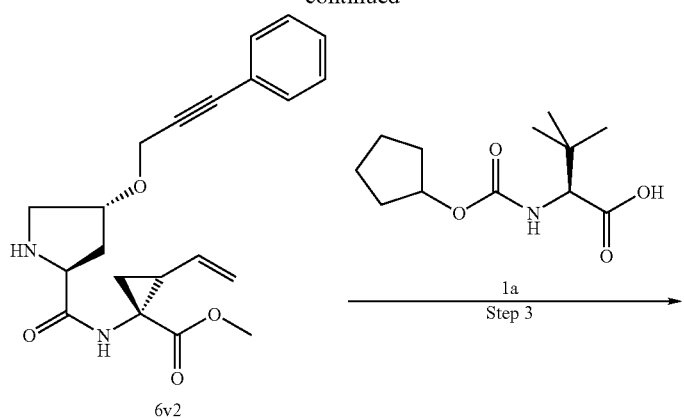
6v2
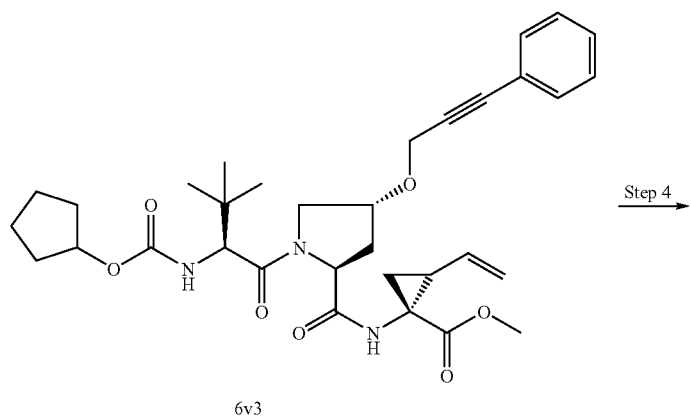
6v3
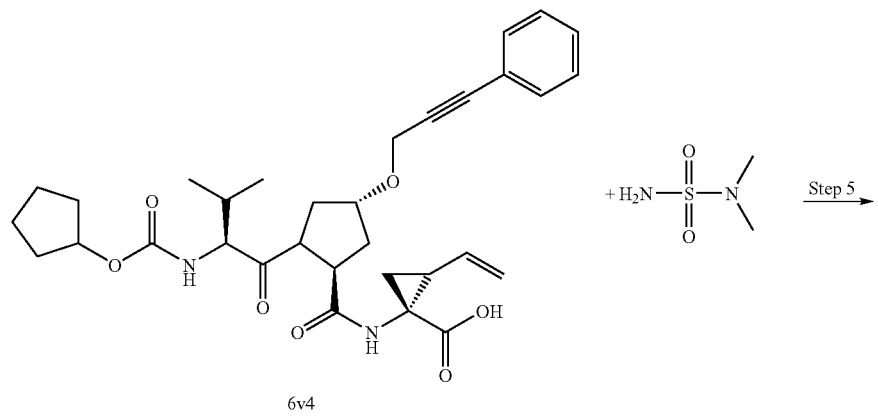
6v4
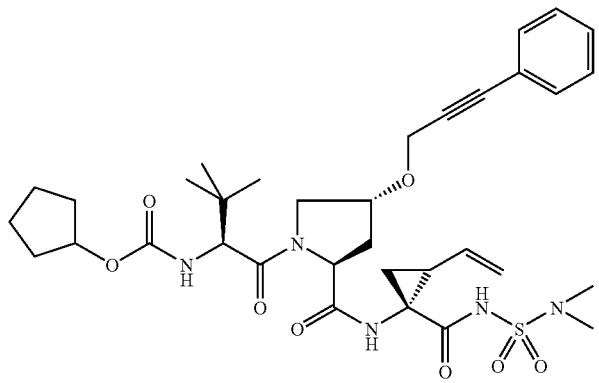
Compound 6003

Step 1: To a solution of the starting amine (452 mg, 1.44 mmol) in DMF (7 mL) was added the acid 2s2 (453 mg, 1.31 mmol) followed by DIPEA (0.73 mL, 4.20 mmol) followed by TBTU (463 mg, 1.44 mmol). The solution was stirred at rt for 16 h, diluted with EtOAc and washed successively with 1N HCl, NaHCO$_3$ (saturated aq. solution) and brine (3×). The organic phase was dried, filtered and concentrated to give the desired product 6v1 as a yellow gum (469 mg, 89%). MS ES+=469.3.

Step 2: 4M HCl/dioxane (10 mL) was added to 6v1 (530 mg, 1.13 mmol) and stirred 1 h at r.t. followed by concentration to yield the desired product 6v2 (450 mg, 99%). MS ES+=369.1.

Step 3: To a solution of the starting amine 6v2 (545 mg, 1.35 mmol) in DCM (12 mL) was added the acid 1a (360 mg, 1.48 mmol) followed by DIPEA (0.59 mL, 3.37 mmol) followed by TBTU (432 mg, 1.35 mmol). The solution was stirred at t for 48 h, diluted with EtOAc and washed successively with 1N HCl, NaHCO$_3$ (saturated aq. solution) and brine (3×). The organic phase was dried, filtered and concentrated to give the desired product 6v3 as a yellow foam (688 mg, 86%). MS ES+=594.3.

Step 4: To a solution of the starting ester 6v3 (350 mg, 0.59 mmol) in THF/MeOH/water (2:1:1, 6 mL total volume) was added LiOH (247 mg, 5.89 mmol) and allowed to stir 16 h at it The reaction was then concentrated, diluted in DMSO and purified by semi-prep RP-HPLC. The pure fraction were combined and lyophilized to yield the desired product 6v4 (135 mg, 40%). MS ES+=580.3.

Step 5: The acid 6v4 (50 mg, 0.09 mmol) was combined with HATU (65 mg, 0.17 mmol) and DIPEA (0.05 mL, 0.30 mmol) in DMF (0.8 mL) before being stirred at RT for 1 h. Next, a solution of DBU (0.025 mL, 0.17 mmol), DMAP (21 mg, 0.17 mmol) and N,N-dimethylsulfamide (20 mg, 0.16 mmol) in DMF (1 mL) was added to the preactivated acid. The reaction mixture was stirred at RT for 48 h. The reaction was diluted with DMSO and purified by preparative HPLC to give compound 6003 (9.3 mg, 16%) as a white solid. MS: 686.2 (M+H)+. Homogeneity by HPLC (TFA) @ 220 nm: 99%. $^1$H NMR (400 MHz, DMSO-d$_6$) δ 10.22 (s, 1H), 8.77 (bs, 1H), 7.45-7.47 (m, 2H), 7.37-7.39 (m, 3H), 6.84 (d, J=8.8 Hz, 1H), 5.50-5.58 (m, 1H), 5.23 (d, J=17.4 Hz, 1H), 5.11 (d, J=10.2 Hz, 1H), 4.90-4.96 (m, 1H), 4.37-4.44 (m, 3H)$_1$4.22 (t, J=4.4 Hz, 1H), 4.14 (d, 5.3 Hz, 1H), 3.98-4.03 (m, 1H), 3.69-3.73 (m, 1H), 2.76 (s, 6H), 2.31-2.33 (m, 1H), 2.19-2.29 (m, 1H), 1.86-1.95 (m, 1H), 1.40-1.79 (m, 9H), 1.26 (q, J=5.5H, 1H), 0.94 (s, 9H).

Example 6W

SYNTHESIS OF COMPOUND 4038 OF TABLE 4

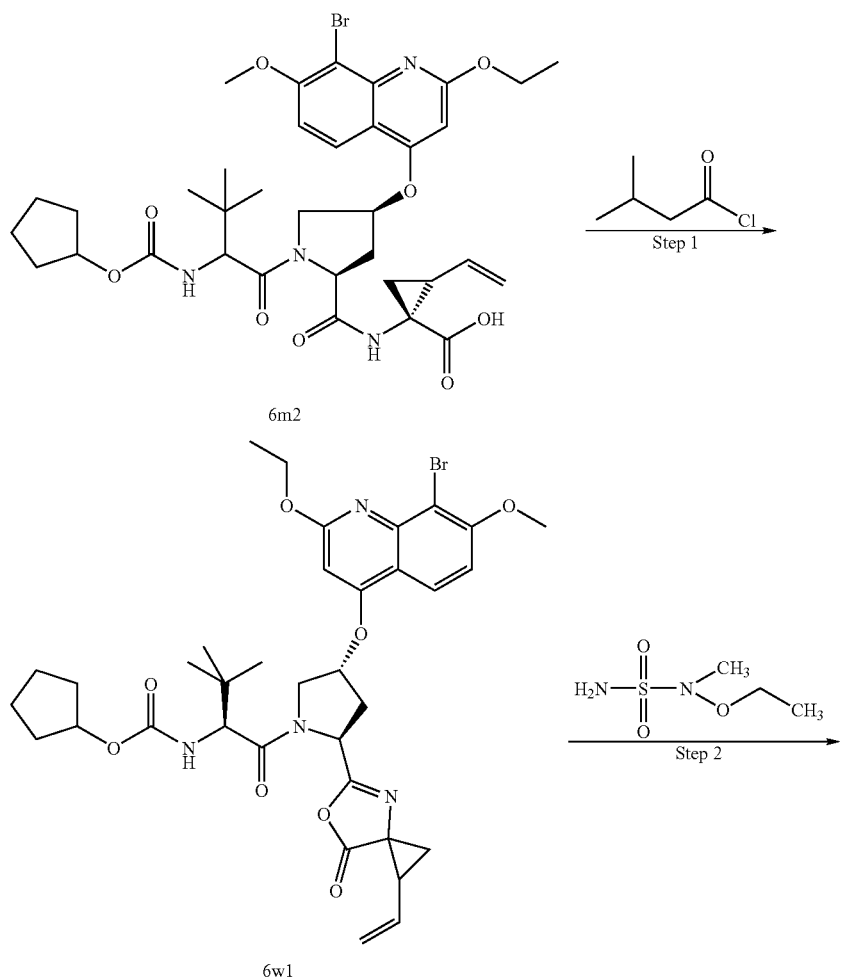

-continued

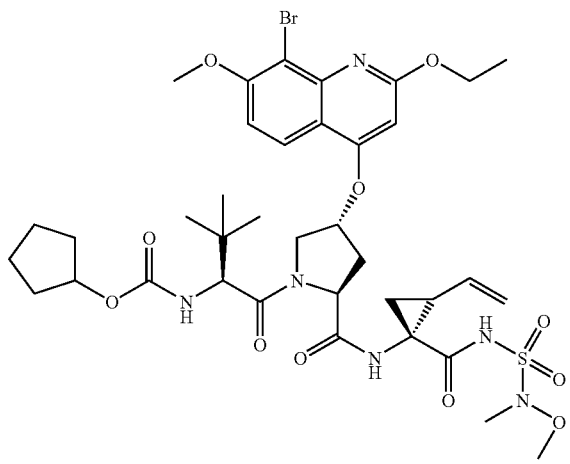

Compound 4038

Step 1: To a solution of compound 6 m2 (143 mg, 0.192 mmol) in CH$_2$Cl$_2$(5 mL) at 0° C. was added TEA (80.3 µL, 0.57 mmol) followed by the dropwise addition of isobutyl chloroformate (33 mL, 0.29 mmol). The reaction mixture was stirred at 0° C. for 30 min, then the ice bath was removed and stirring was continued at rt for 16 h. On completion of the reaction as indicated by TLC, the mixture was concentrated to give a brown residue which was purified by flash chromatography (silica gel 40-60 g) 1:1 Hex/EtOAc) to give 104 mg of compound 6w1 as a yellow oil (yield 74%). EIMS: (MH$^+$)=727.4, (MH+2)$^+$=729.4

Step 2: In an oven dried reaction flask was dissolved N-methyl-N-methoxysulfamide (14.4 mg, 0.1 mmol) in anhydrous THF (1.5 mL) and cooled to −20° C. To the cold solution was added a solution (1M in THF) of LiHMDS (103 mL, 0.1 mmol), in one portion. The reaction mixture was allowed to stir at bath temperature for 5 min, then at RT. for 20 min. The reaction mixture was then cooled to a bath temp of −10 to −15° C., then a solution of azalactone 6w1 from Step 1 in THF was added dropwise. The reaction mixture was warmed slowly to rt and allowed to stir at that temperature for 12 h, then was concentrated to dryness. The residue was dissolved in AcOH and purified by prep HPLC (Combiprep ODS-AQ, 20×50 mm) to give 29 mg of compound 4038 as a white amorphous solid (48%).

$^1$H NMR (DMSO-de, 400 MHz)-δ 10.83 (s, 1H), 8.63 (s, 1H), 7.98 (d, J=9 Hz, 1H), 7.17 (d, J=9 Hz, 1H), 7.01 (d, J=8 Hz, 1H), 6.47 (s, 1H), 5.38-5.56 (m, 2H), 5.26-5.16 (m, 1H), 5.15-5.08 (m, 1H), 4.65-4.46 (m, 3H), 4.40-4.28 (m, 2H), 4.13-4.00 (m, 1H), 3.94-3.82 (m, 4H), 3.64 (s, 3H), 2.94 (s, 3H), 2.57-2.50 (m, 1H, partially under DMSO-de signal), 2.25-2.05 (m, 2H), 1.72-1.16 (m, 13H), 1.0-0.89 (m, 9H) EIMS: (MH+)=867.5, (MH+2)=869.4, HPLC=retention time=6.8 min, purity=100%

Example 7

NS3-NS4A PROTEASE ASSAY

The enzymatic assay used to evaluate the present compounds is described in WO 00/09543 and WO 00/59929.

Example 8

CELL-BASED LUCIFERASE REPORTER HCV RNA REPLICATION ASSAY

The assay used to evaluate the activity of the present compounds in cells expressing a stable subgenomic HCV replicon is described in WO 2005/028501.

Representative compounds according to this invention were found to be active when evaluated in the preceding enzymatic and cell based assays.

Example 9

SPECIFICITY ASSAYS

The specificity assays used to evaluate the selectivity of compounds according to this invention were performed as described in WO 00/09543 except that the assay buffer for the Elastase assay was comprised of 50 mM Tris-HCl pH 8, 0.25 M NaCitrate, 0.01% n-dodecyl β-d-maltoside, and 5.25% DMSO.

Representative compounds according to this invention were found to be selective in that they do not show significant inhibition (no measurable activity at concentrations up to 30 µM) in the Human Leukocyte Elastase assay or Human Liver Cathepsin B assays.

Tables Of Compounds

The following tables list compounds representative of the invention. Many of the compounds listed in the Tables were found to have IC$_5$0values below 1 µM in the NS3-NS4A protease assay of Example 7. In addition, many of the compounds listed in the Tables have EC$_{50}$ values below 1 μM in the cell-based luciferase reporter HCV RNA replication assay of Example 8. Retention times (t$_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

[Structure shown with substituents B, W, R$^1$, R$^2$, R$^3$ and NHSO$_2$N(Me)$_2$ group]

| Cpd | B | W | R$^3$ | R$^2$ | R$^1$ |
|---|---|---|---|---|---|
| 1001 | t-Bu | O | t-Bu | 3-methyl-5-phenyl-isoxazolo[4,5-b]pyridin-7-yloxy | vinyl |
| 1002 | t-Bu | O | t-Bu | 2-methyl-7-phenyl-1,8-naphthyridin-4-yloxy | vinyl |
| 1003 | t-Bu | O | t-Bu | 3-methyl-5-(4-methoxyphenyl)-isoxazolo[4,5-b]pyridin-7-yloxy | vinyl |
| 1004 | t-Bu | O | t-Bu | 3-methyl-5-(4-fluorophenyl)-isoxazolo[4,5-b]pyridin-7-yloxy | vinyl |

TABLE 1-continued

| Cpd | B | W | R³ | R² | R¹ |
|---|---|---|---|---|---|
| 1005 | tert-butyl-CH₂- | O | tert-butyl | 3-methyl-5-(3-methoxyphenyl)isoxazolo[4,5-b]pyridin-7-yloxy | vinyl |
| 1006 | tert-butyl-CH₂- | O | tert-butyl | 3-methyl-5-(2-methoxyphenyl)isoxazolo[4,5-b]pyridin-7-yloxy | vinyl |
| 1007 | tert-butyl-CH₂- | O | tert-butyl | quinolin-2-yloxy | vinyl |
| 1008 | tert-butyl-CH₂- | O | tert-butyl | 2-methyl-7-(trifluoromethyl)-1,8-naphthyridin-4-yloxy | vinyl |
| 1009 | tert-butyl-CH₂- | O | tert-butyl | 3-methyl-5-ethylisoxazolo[4,5-b]pyridin-7-yloxy | vinyl |

TABLE 1-continued

| Cpd | B | W | R³ | R² | R¹ |
|---|---|---|---|---|---|
| 1010 | neopentyl | O | tert-butyl | 3-methyl-5-phenyl-isoxazolo[4,5-b]pyridin-7-yloxy | vinyl |
| 1011 | neopentyl | O | isopropyl | 6-methoxy-isoquinolin-1-yloxy | vinyl |
| 1012 | neopentyl | O | sec-butyl | 6-methoxy-isoquinolin-1-yloxy | vinyl |
| 1013 | isobutyl | O | tert-butyl | 6-methoxy-isoquinolin-1-yloxy | vinyl |
| 1014 | neohexyl | O | tert-butyl | 6-methoxy-isoquinolin-1-yloxy | vinyl |
| 1015 | (S)-tetrahydrofuran-3-yl | O | tert-butyl | 6-methoxy-isoquinolin-1-yloxy | vinyl |

TABLE 1-continued
| Cpd | B | W | R³ | R² | R¹ |
|---|---|---|---|---|---|
| 1016 |  | O |  | 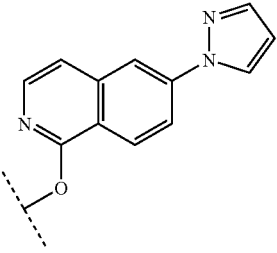 |  |
| 1017 | 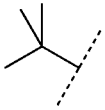 | O |  |  | 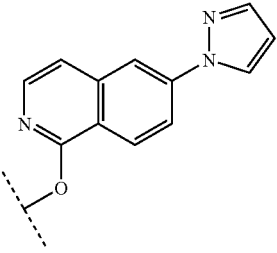 |
| 1018 |  | O | 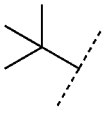 |  |  |
| 1019 | 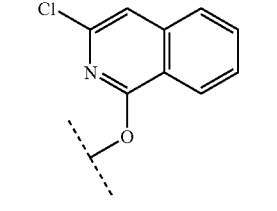 | O |  | 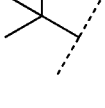 |  |

TABLE 1-continued

| Cpd | B | W | R³ | R² | R¹ |
|---|---|---|---|---|---|
| 1020 | *tert-butyl* | O | *tert-butyl* | 4-(dimethylamino)phenyl-substituted isoquinoline-O- | vinyl |
| 1021 | *tert-butyl* | O | *tert-butyl* | 4-cyanophenyl-substituted isoquinoline-O- | vinyl |
| 1022 | *tert-butyl* | O | *tert-butyl* | furan-3-yl-substituted isoquinoline-O- | vinyl |
| 1023 | *tert-butyl* | O | *tert-butyl* | pyrazin-2-yl-substituted isoquinoline-O- | vinyl |
| 1024 | *tert-butyl* | O | *tert-butyl* | 3-cyano-isoquinoline-O- | vinyl |

TABLE 1-continued

| Cpd | B | W | R³ | R² | R¹ |
|---|---|---|---|---|---|
| 1025 | t-Bu-CH₂- | O | t-Bu | 3-methyl-isoquinolin-1-yloxy | vinyl |
| 1026 | t-Bu-CH₂- | O | t-Bu | 3-methoxy-isoquinolin-1-yloxy | vinyl |
| 1027 | t-Bu-CH₂- | O | t-Bu | 6-methoxy-3-phenyl-isoquinolin-1-yloxy | vinyl |
| 1028 | t-Bu-CH₂- | O | t-Bu | 6-methoxy-3-(thiazol-2-yl)-isoquinolin-1-yloxy | vinyl |
| 1029 | t-Bu-CH₂- | O | t-Bu | 6-methoxy-3-(3-methoxy-isoxazol-5-yl)-isoquinolin-1-yloxy | vinyl |

TABLE 1-continued

| Cpd | B | W | R³ | R² | R¹ |
|---|---|---|---|---|---|
| 1030 | tert-pentyl | O | tert-butyl | 3-(furan-3-yl)-6-methoxyisoquinolin-1-yloxy | vinyl |
| 1031 | tert-butyl | O | tert-butyl | 6-ethoxyisoquinolin-1-yloxy | vinyl |
| 1032 | cyclopentyl | — | tert-butyl | 6-methoxyisoquinolin-1-yloxy | vinyl |
| 1033 | cyclopropylmethyl | — | tert-butyl | 6-methoxyisoquinolin-1-yloxy | vinyl |
| 1034 | benzyl | O | tert-butyl | 6-methoxyisoquinolin-1-yloxy | vinyl |
| 1035 | 2,2-dimethylbutyl | O | tert-butyl | 6-methoxyisoquinolin-1-yloxy | vinyl |

TABLE 1-continued

| Cpd | B | W | R³ | R² | R¹ |
|---|---|---|---|---|---|
| 1036 | CCl₃C(CH₃)₂- | O | t-Bu | 6-methoxy-isoquinolin-1-yloxy | vinyl |
| 1037 | cyclopentyl (1,1-disub) | O | t-Bu | 6-methoxy-isoquinolin-1-yloxy | vinyl |
| 1038 | cyclopentylmethyl | O | t-Bu | 6-methoxy-isoquinolin-1-yloxy | vinyl |
| 1039 | cyclobutylmethyl | O | t-Bu | 6-methoxy-isoquinolin-1-yloxy | vinyl |
| 1040 | cyclopentylmethyl | NH | t-Bu | 6-methoxy-isoquinolin-1-yloxy | vinyl |
| 1041 | (CH₃CH₂)C(CH₃)₂- | NH | t-Bu | 6-methoxy-isoquinolin-1-yloxy | vinyl |

TABLE 1-continued

| Cpd | B | W | R³ | R² | R¹ |
|---|---|---|---|---|---|
| 1042 | neopentyl | O | 2-hydroxypropan-2-yl (HO-C(CH₃)₂-CH-) | 6-methoxyisoquinolin-1-yloxy | vinyl |
| 1043 | neopentyl | O | (S)-1-methoxyethyl | 6-methoxyisoquinolin-1-yloxy | vinyl |
| 1044 | neopentyl | O | (R)-1-methoxyethyl | 6-methoxyisoquinolin-1-yloxy | vinyl |
| 1045 | neopentyl | O | 1-tert-butoxyethyl | 6-methoxyisoquinolin-1-yloxy | vinyl |
| 1046 | neopentyl | NH | 1-methoxyethyl | 6-methoxyisoquinolin-1-yloxy | vinyl |
| 1047 | 2,2-dimethylbutyl | NH | 1-methoxyethyl | 6-methoxyisoquinolin-1-yloxy | vinyl |

TABLE 1-continued

| Cpd | B | W | R³ | R² | R¹ |
|---|---|---|---|---|---|
| 1048 | cyclopentylmethyl | NH | OMe (isopropoxy) | 6-methoxyisoquinolin-1-yloxy | vinyl |
| 1049 | cyclopentylmethyl | O | methoxy | 6-methoxyisoquinolin-1-yloxy | vinyl |
| 1050 | 2,2-dimethylbutyl | O | methoxy | 6-methoxyisoquinolin-1-yloxy | vinyl |
| 1051 | CF₃-tBu-CH₂ | NH | methoxy | 6-methoxyisoquinolin-1-yloxy | vinyl |
| 1052 | tBu-CH(Me) | O | methoxy | 3-phenylisoquinolin-1-yloxy | vinyl |

TABLE 1-continued

| Cpd | B | W | R³ | R² | R¹ |
|---|---|---|---|---|---|
| 1053 | *t*-Bu-C(CH₃)₂– | O | (S)-CH(CH₃)OEt | 3-phenyl-isoquinolin-1-yloxy | vinyl |
| 1054 | *t*-Bu-C(CH₃)₂– | CH₂ | *t*-Bu | isoquinolin-1-yloxy | vinyl |
| 1055 | *t*-Bu-C(CH₃)₂– | O | CH₂C(O)OCH₂Ph | 6-methoxy-isoquinolin-1-yloxy | vinyl |
| 1056 | *t*-Bu-C(CH₃)₂– | O | CH₂C(O)OMe | 6-methoxy-isoquinolin-1-yloxy | vinyl |
| 1057 | MeO₂C-CH(iPr)– | NH | *t*-Bu | 6-methoxy-isoquinolin-1-yloxy | vinyl |
| 1058 | MeO₂C-CH(iPr)– | NH | *t*-Bu | 6-methoxy-isoquinolin-1-yloxy | vinyl |

TABLE 1-continued

| Cpd | B | W | R³ | R² | R¹ |
|---|---|---|---|---|---|
| 1059 | methyl 2,3-dimethylbutanoate | NH | tert-butyl | 6-methoxyisoquinolin-1-yloxy | vinyl |
| 1060 | tert-butyl | O | cyclopentyl | 6-methoxyisoquinolin-1-yloxy | vinyl |
| 1061 | tert-butyl | O | tert-butyl | 7-(trifluoromethyl)quinolin-4-yloxy | vinyl |
| 1062 | tert-butyl | O | tert-butyl | 8-(trifluoromethyl)quinolin-4-yloxy | vinyl |
| 1063 | tert-butyl | O | tert-butyl | 6-isopropoxyisoquinolin-1-yloxy | vinyl |

TABLE 1-continued

| Cpd | B | W | R³ | R² | R¹ |
|---|---|---|---|---|---|
| 1064 | *t-Bu* | O | *t-Bu* | 1-chloro-4-oxyphthalazine | vinyl |
| 1065 | *t-Bu* | O | *t-Bu* | 1-ethoxy-4-oxyphthalazine | vinyl |
| 1066 | *t-Bu* | O | *t-Bu* | 1-methoxy-4-oxyphthalazine | vinyl |
| 1067 | *t-Bu* | O | *t-Bu* | 5-(propylthio)-6-ethoxy-1-oxyisoquinoline | vinyl |
| 1068 | *t-Bu* | O | *t-Bu* | 5-(methylthio)-6-methoxy-1-oxyphthalazine | vinyl |

TABLE 1-continued

| Cpd | B | W | R³ | R² | R¹ |
|---|---|---|---|---|---|
| 1069 | *t-Bu-CH₂-C(Me)₂-* | O | *t-Bu* | 7-methyl-isoquinolin-1-yloxy | vinyl |
| 1070 | *t-Bu* | O | *t-Bu* | [1,3]dioxolo-isoquinolin-yloxy | vinyl |
| 1071 | *t-Bu* | O | *t-Bu* | 6-chloro-[1,3]dioxolo-isoquinolin-yloxy | vinyl |
| 1072 | *t-Bu* | O | *t-Bu* | methylthio-[1,3]dioxolo-isoquinolin-yloxy | vinyl |
| 1073 | *t-Bu* | O | *t-Bu* | 2,3-dihydro-1H-cyclopenta[c]isoquinolin-5-yloxy | vinyl |

TABLE 1-continued
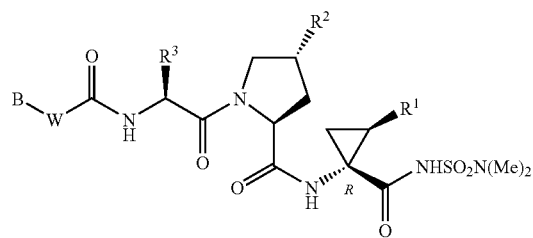
| Cpd | B | W | R³ | R² | R¹ |
|---|---|---|---|---|---|
| 1074 | *t*-Bu | O | *t*-Bu | 2,3-dihydrofuro[3,2-c]isoquinolin-5-yloxy | vinyl |
| 1075 | *t*-Bu | O | *t*-Bu | furo[3,2-c]isoquinolin-5-yloxy | vinyl |
| 1076 | *t*-Bu | O | *t*-Bu | 3-bromo-4-methoxyisoquinolin-1-yloxy | vinyl |
| 1077 | *t*-Bu | O | *t*-Bu | 4H-[1,3]dioxino[5,4-c]isoquinolin-6-yloxy | vinyl |
| 1078 | *t*-Bu | O | *t*-Bu | 3-(furan-3-yl)-4-methoxyisoquinolin-1-yloxy | vinyl |

TABLE 1-continued

| Cpd | B | W | R³ | R² | R¹ |
|---|---|---|---|---|---|
| 1079 | t-Bu | O | t-Bu | 4-methoxy-3-(thiazol-2-yl)isoquinolin-1-yloxy | vinyl |
| 1080 | t-Bu | O | t-Bu | 6-fluoroquinolin-4-yloxy | vinyl |
| 1081 | t-Bu | O | t-Bu | 1-chloroisoquinolin-7-yloxy | vinyl |
| 1082 | t-Bu | O | t-Bu | 8-fluoroquinolin-4-yloxy | vinyl |
| 1083 | t-Bu | O | t-Bu | 4-methylisoquinolin-1-yloxy | vinyl |

TABLE 1-continued
| Cpd | B | W | R³ | R² | R¹ |
|---|---|---|---|---|---|
| 1084 |  | O | 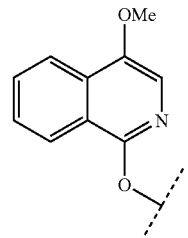 |  |  |
| 1085 |  | O | 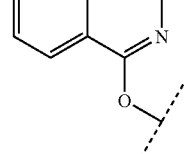 |  |  |
| 1086 |  | O | 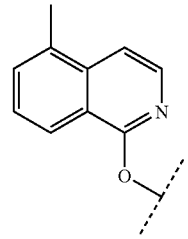 |  |  |
| 1087 |  | O | 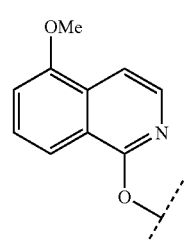 |  |  |
| 1088 |  | O | 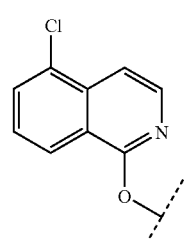 |  |  |

TABLE 1-continued

| Cpd | B | W | R³ | R² | R¹ |
|---|---|---|---|---|---|
| 1089 | t-Bu | O | t-Bu | 7-fluoro-isoquinolin-1-yloxy | vinyl |
| 1090 | t-Bu | O | t-Bu | 7-chloro-isoquinolin-1-yloxy | vinyl |
| 1091 | t-Bu | O | t-Bu | 7-methyl-isoquinolin-1-yloxy | vinyl |
| 1092 | t-Bu | O | t-Bu | 6-methoxy-7-fluoro-isoquinolin-1-yloxy | vinyl |
| 1093 | t-Bu | O | t-Bu | 6-methoxy-1-chloro-isoquinolin-7-yloxy | vinyl |
| 1094 | t-Bu | O | t-Bu | 2,3-dihydrofuro[3,2-h]isoquinolin-6-yloxy | vinyl |

TABLE 1-continued
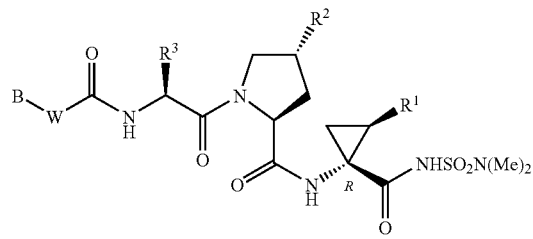
| Cpd | B | W | R³ | R² | R¹ |
|---|---|---|---|---|---|
| 1095 | *t*-Bu | O | *t*-Bu | furo[3,2-h]isoquinolin-4-yloxy | vinyl |
| 1096 | *t*-Bu | O | *t*-Bu | 2,3-dihydrofuro[3,2-h]isoquinolin-4-yloxy | vinyl |
| 1097 | *t*-Bu | O | *t*-Bu | furo[2,3-h]isoquinolin-6-yloxy | vinyl |
| 1098 | *t*-Bu | O | *t*-Bu | 5,6-dimethoxyisoquinolin-1-yloxy | vinyl |
| 1099 | *t*-Bu | O | *t*-Bu | 7-chloro-6-methoxyisoquinolin-1-yloxy | vinyl |

TABLE 1-continued

| Cpd | B | W | R³ | R² | R¹ |
|---|---|---|---|---|---|
| 1100 | t-Bu | O | t-Bu | 5-Cl, 6-OMe isoquinolin-1-yloxy | vinyl |
| 1101 | t-Bu | O | t-Bu | 7-Cl, 4-OMe isoquinolin-1-yloxy | vinyl |
| 1102 | t-Bu | O | t-Bu | 6-Cl, 5-OMe isoquinolin-1-yloxy | vinyl |
| 1103 | t-Bu | O | t-Bu | 4-Cl, 6-OMe isoquinolin-1-yloxy | vinyl |
| 1104 | t-Bu | O | t-Bu | 6,7-di-OMe, 4-OMe isoquinolin-1-yloxy | vinyl |

TABLE 1-continued
| Cpd | B | W | R³ | R² | R¹ |
|---|---|---|---|---|---|
| 1105 |  | O | 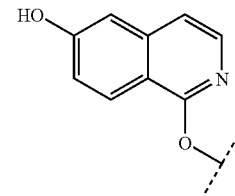 |  |  |
| 1106 |  | O | 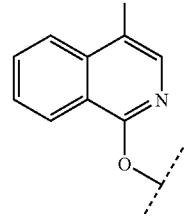 |  |  |
| 1107 |  | O | 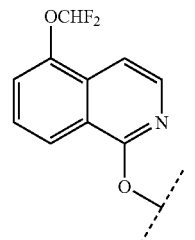 |  |  |
| 1108 |  | O | 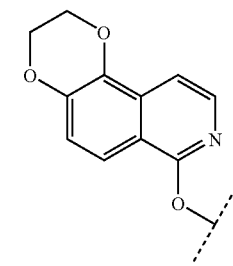 |  |  |
| 1109 |  | O | 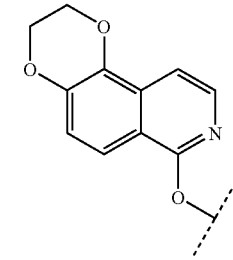 |  | |

TABLE 1-continued
| Cpd | B | W | R³ | R² | R¹ |
|---|---|---|---|---|---|
| 1110 | 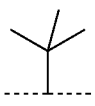 | O |  | 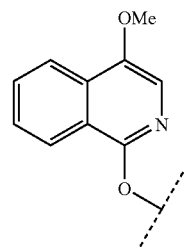 | 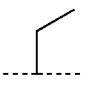 |
| 1111 | 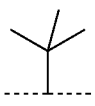 | O |  | 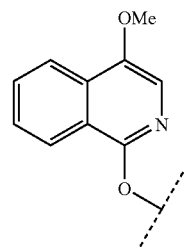 | 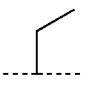 |
| 1112 | 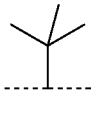 | O | 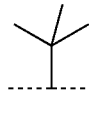 | 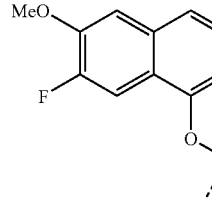 | 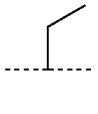 |
| 1113 | 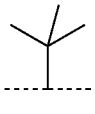 | O | 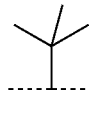 | 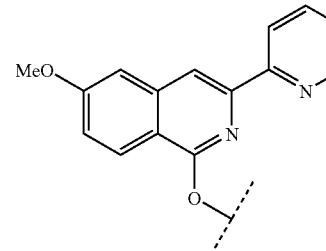 | 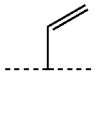 |
| 1114 |  | O |  | 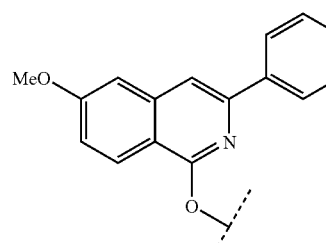 | 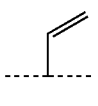 |

TABLE 1-continued
| Cpd | B | W | R³ | R² | R¹ |
|---|---|---|---|---|---|
| 1115 |  | O | 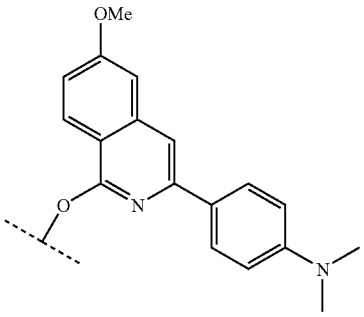 | 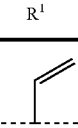 |  |
| 1116 |  | O | 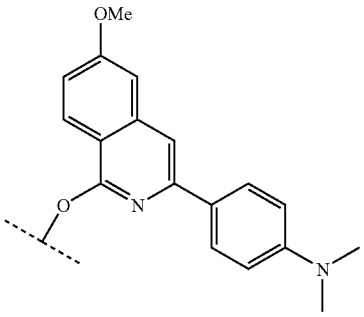 | 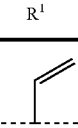 |  |
| 1117 |  | O | 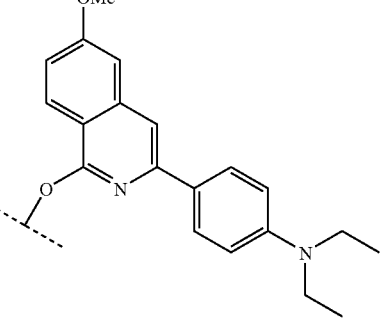 |  |  |
| 1118 |  | O | 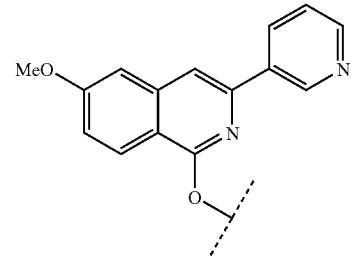 |  |  |

TABLE 1-continued

| Cpd | B | W | R³ | R² | R¹ |
|---|---|---|---|---|---|
| 1119 | t-Bu | O | t-Bu | 3-(3-(dimethylamino)phenyl)-6-methoxyisoquinolin-1-yloxy | vinyl |
| 1120 | t-Bu | O | t-Bu | 2-(2-(isopropylamino)thiazol-4-yl)-7-methoxyquinolin-4-yloxy | vinyl |
| 1121 | t-Bu | O | t-Bu | 7-chloroquinolin-4-yloxy | vinyl |
| 1122 | cyclopentyl | O | t-Bu | 7-chloroquinolin-4-yloxy | vinyl |
| 1123 | t-Bu | O | t-Bu | 2-cyclopropyl-7-methoxyquinolin-4-yloxy | vinyl |

TABLE 1-continued

| Cpd | B | W | R³ | R² | R¹ |
|---|---|---|---|---|---|
| 1124 | tert-butyl | O | tert-butyl | 7-MeO-quinolin-4-yloxy | vinyl |
| 1125 | tert-butyl | O | isopropyl | 7-MeO-quinolin-4-yloxy | vinyl |
| 1126 | tert-butyl | O | tert-butyl | 7-MeO-2-(pyridin-2-yl)quinolin-4-yloxy | vinyl |
| 1127 | tert-butyl | NH | tert-butyl | 6-MeO-isoquinolin-1-yloxy | vinyl |
| 1128 | 1-methylcyclopentyl | O | tert-butyl | 6-MeO-isoquinolin-1-yloxy | vinyl |

TABLE 1-continued

| Cpd | B | W | R³ | R² | R¹ |
|---|---|---|---|---|---|
| 1129 | t-Bu | O | t-Bu | 6-MeO-3-morpholino-isoquinolin-1-yloxymethyl | vinyl |
| 1130 | t-Bu | O | t-Bu | 6-methyl-2-(trifluoromethyl)quinolin-4-yloxymethyl | vinyl |
| 1131 | t-Bu | O | t-Bu | 6-(thiophen-2-yl)pyrimidin-4-yloxymethyl | vinyl |
| 1132 | t-Bu | O | t-Bu | 2-phenyl-6-(thiophen-2-yl)pyridin-4-yloxymethyl | vinyl |
| 1133 | t-Bu | O | t-Bu | 2-(4-methoxyphenyl)-6-phenylpyridin-4-yloxymethyl | vinyl |

TABLE 1-continued

| Cpd | B | W | R³ | R² | R¹ |
|---|---|---|---|---|---|
| 1134 | *t-Bu* | O | *t-Bu* | 2,6-diphenylpyridin-4-yloxy | vinyl |
| 1135 | *t-Bu* | O | *t-Bu* | 2-(thiophen-2-yl)pyridin-4-yloxy | vinyl |

TABLE 2

| Cpd | N(R⁴)R⁶ | (MH)⁺ | $t_R$ (min) |
|---|---|---|---|
| 2001 | morpholino | 785.4 | 5.62 |

TABLE 2-continued

| Cpd | N(R⁴)R⁶ | (MH)⁺ | $t_R$ (min) |
|---|---|---|---|
| 2002 | N(Me)₂ | 743.3 | 5.18 |

TABLE 2-continued
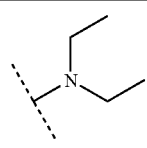
| Cpd | N(R⁴)R⁶ | (MH)⁺ | $t_R$ (min) |
|---|---|---|---|
| 2003 | 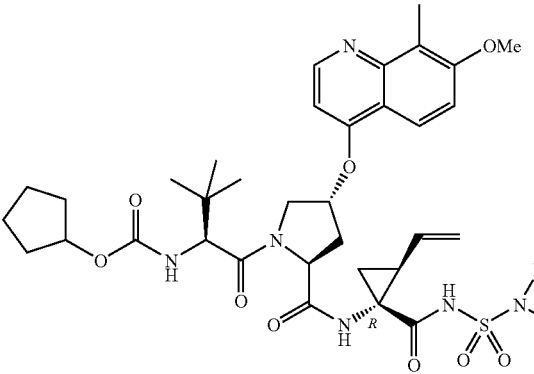 | 771.4 | 5.86 |
| 2004 | 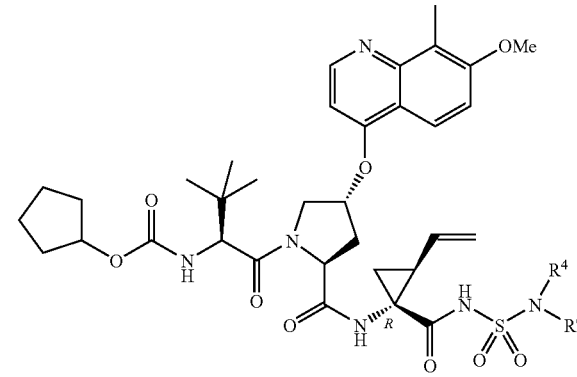 | 799.4 | 6.31 |
| 2005 | 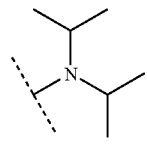 | 783.3 | 5.82 |
| 2006 | 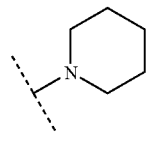 | 769.4 | 5.54 |
| 2007 | 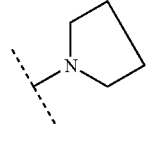 | 812.3 | 4.21 |
| 2008 | 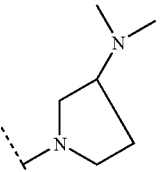 | 798.3 | 4.18 |
| 2009 | 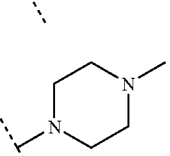 | 755.3 | 5.68 |
TABLE 2-continued
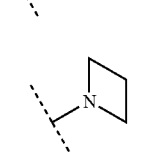
| Cpd | N(R⁴)R⁶ | (MH)⁺ | $t_R$ (min) |
|---|---|---|---|
| 2010 | 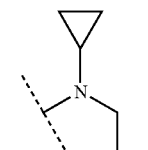 | 808.3 | 5.83 |
| 2011 | 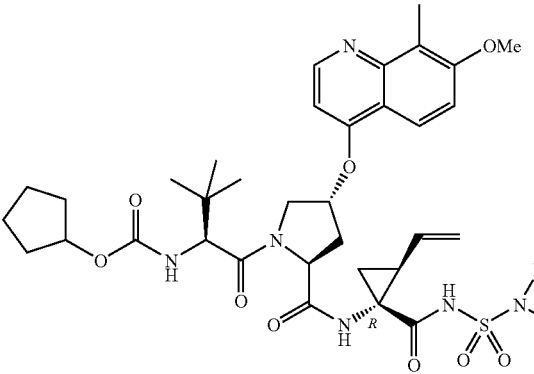 | 782.3 | 4.98 |
| 2012 | 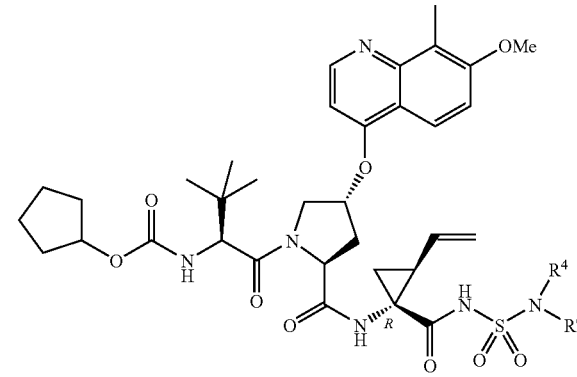 | 715.3 | 5.30 |
TABLE 3
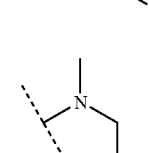
| Cpd | R²⁰ | N(R⁴)R⁶ | R¹ | (MH)⁺ | $t_R$ (min) |
|---|---|---|---|---|---|
| 3001 | 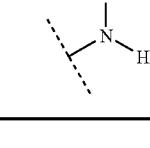 | 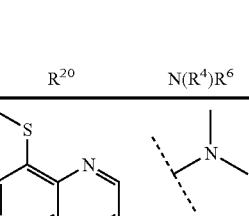 | —CH=CH₂ | 745.1 | 5.12 |

TABLE 3-continued
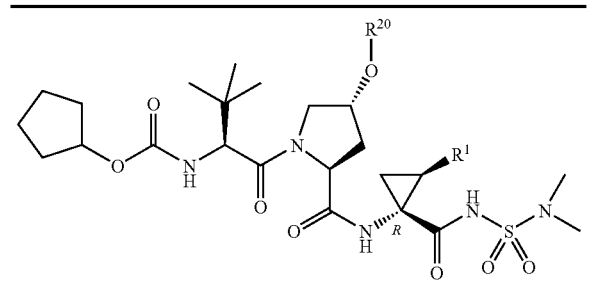
| Cpd | R[20] | N(R[4])R[6] | R[1] | (MH)+ | t_R (min) |
|---|---|---|---|---|---|
| 3002 | 4-pyridyl | N(CH3)2 | —CH=CH2 | 649.3 | 4.34 |
| 3003 | 4-pyridyl | N(cyclopropyl)(CH2CH2CN) | —CH=CH2 | 714.3 | 4.49 |
| 3004 | 2-pyridyl | N(CH3)2 | —CH=CH2 | 636.3 | 6.14 |
TABLE 3-continued
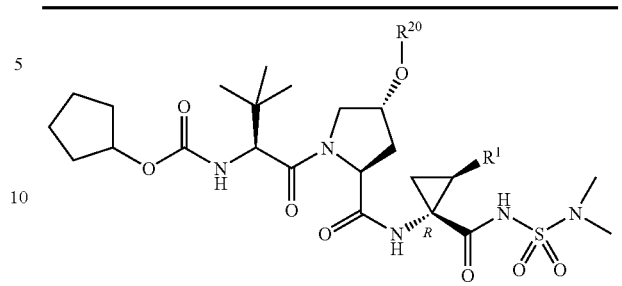
| Cpd | R[20] | N(R[4])R[6] | R[1] | (MH)+ | t_R (min) |
|---|---|---|---|---|---|
| 3005 | 4-pyridyl | pyrrolidinyl | —CH=CH2 | 675.3 | 4.39 |
| 3006 | 4-pyridyl | 2,5-dihydropyrrolyl | —CH=CH2 | 673.3 | 4.40 |
| 3007 | 4-pyridyl | N(CH3)(Ph) | —CH=CH2 | 711.3 | 5.06 |
TABLE 4
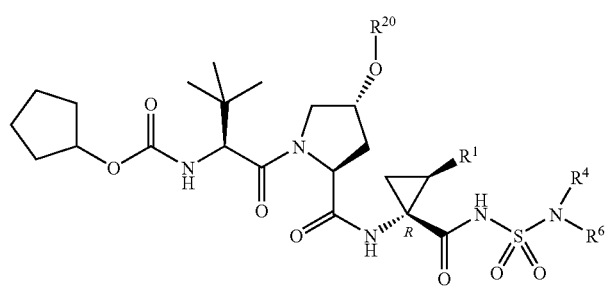
| Cpd | R[20] | N(R[4])R[6] | R[1] | (MH)+ | t_R (min) |
|---|---|---|---|---|---|
| 4001 | 8-(methylthio)-2-ethoxyquinolin-4-yl | N(CH3)2 | —CH=CH2 | 789.3 | 7.54 |

TABLE 4-continued

| Cpd | R20 | N(R4)R6 | R1 | (MH)+ | tR (min) |
|---|---|---|---|---|---|
| 4002 | 8-(methylthio)-2-ethoxyquinolin-4-yl | N(CH3)2 | —CH2—CH3 | 791.3 | 7.57 |
| 4003 | 8-(ethylthio)-2-ethoxyquinolin-4-yl | N(CH3)2 | —CH=CH2 | 803.3 | 7.67 |
| 4004 | 8-(cyclopropylmethylthio)-2-ethoxyquinolin-4-yl | N(CH3)2 | —CH=CH2 | 829.4 | 7.86 |
| 4005 | 8-(isobutylsulfonyl)-2-ethoxyquinolin-4-yl | N(CH3)2 | —CH=CH2 | 863.4 | 7.26 |
| 4006 | 8-(cyclopropylmethylsulfonyl)-2-ethoxyquinolin-4-yl | N(CH3)2 | —CH=CH2 | 861.4 | 6.98 |

TABLE 4-continued

| Cpd | R20 | N(R4)R6 | R1 | (MH)+ | tR (min) |
|---|---|---|---|---|---|
| 4007 | benzylsulfonyl-2-ethoxyquinolin-4-yl | N(CH3)2 | —CH=CH2 | 897.4 | 7.22 |
| 4008 | 8-(methylthio)-2-ethoxyquinolin-4-yl | pyrrolidinyl | —CH=CH2 | 815.3 | 7.49 |
| 4009 | 8-methyl-2-ethoxyquinolin-4-yl | N(CH3)2 | —CH=CH2 | 757.3 | 6.48 |
| 4010 | 8-methyl-2-ethoxyquinolin-4-yl | N(CH2CH3)2 | —CH=CH2 | 785.4 | 6.95 |
| 4011 | 8-methyl-2-ethoxyquinolin-4-yl | pyrrolidinyl | —CH=CH2 | 783.4 | 6.77 |
| 4012 | 8-bromo-7-methoxy-2-ethoxyquinolin-4-yl | N(CH3)2 | —CH=CH2 | 851.3, 853.3 | 7.21 |

TABLE 4-continued

| Cpd | R[20] | N(R[4])R[6] | R[1] | (MH)+ | t_R (min) |
|---|---|---|---|---|---|
| 4013 | 8-Br, 7-OMe, 2-OEt quinolin-4-yl | N(Et)₂ | —CH=CH₂ | 879.3 881.3 | 7.54 |
| 4014 | 8-Br, 7-OMe, 2-OEt quinolin-4-yl | pyrrolidin-1-yl | —CH=CH₂ | 877.3 879.3 | 7.39 |
| 4015 | 8-Cl, 2-OEt quinolin-4-yl | N(Me)₂ | —CH=CH₂ | 777.3 779.3 | 7.42 |
| 4016 | 8-Cl, 2-OEt quinolin-4-yl | N(Et)₂ | —CH=CH₂ | 805.3 807.3 | 7.74 |
| 4017 | 8-Cl, 2-OEt quinolin-4-yl | pyrrolidin-1-yl | —CH=CH₂ | 803.3 805.3 | 7.62 |
| 4018 | 8-SMe, 2-OEt quinolin-4-yl | N(Et)₂ | —CH=CH₂ | 817.4 | 7.65 |

TABLE 4-continued

| Cpd | R²⁰ | N(R⁴)R⁶ | R¹ | (MH)⁺ | t_R (min) |
|---|---|---|---|---|---|
| 4019 | 8-methoxy-2-ethoxyquinolin-4-yl | dimethylamino | —CH=CH₂ | 773.4 | 4.99 |
| 4020 | 8-methoxy-2-ethoxyquinolin-4-yl | 2,5-dihydropyrrol-1-yl | —CH=CH₂ | 797.4 | 5.24 |
| 4021 | 8-methylthio-7-methoxy-2-ethoxyquinolin-4-yl | 2,5-dihydropyrrol-1-yl | —CH=CH₂ | 813.4 | 7.18 |
| 4022 | 7-methoxy-8-methyl-2-ethoxyquinolin-4-yl | dimethylamino | —CH=CH₂ | 787.5 | 5.74 |
| 4023 | 7-methoxy-8-methyl-2-ethoxyquinolin-4-yl | 2,5-dihydropyrrol-1-yl | —CH=CH₂ | 811.5 | 5.98 |
| 4024 | 8-bromo-2-ethoxyquinolin-4-yl | dimethylamino | —CH=CH₂ | 821.3, 823.3 | 7.29 |

TABLE 4-continued

| Cpd | R20 | N(R4)R6 | R1 | (MH)+ | tR (min) |
|---|---|---|---|---|---|
| 4025 | 8-Br, 2-ethoxy-quinolin-4-yl | 2,5-dihydro-1H-pyrrol-1-yl | —CH=CH2 | 845.4, 847.4 | 7.43 |
| 4026 | 8-Br, 2-ethoxy-quinolin-4-yl | N,N-dimethylamino | —CH2—CH3 | 823.4, 825.4 | 7.35 |
| 4027 | 8-Br, 2-ethoxy-quinolin-4-yl | 2,5-dihydro-1H-pyrrol-1-yl | —CH2—CH3 | 847.4, 849.4 | 7.48 |
| 4028 | 8-Br, 2-ethoxy-quinolin-4-yl | pyrrolidin-1-yl | —CH2—CH3 | 849.4, 851.4 | 7.53 |
| 4029 | 8-SMe, 2-ethoxy-quinolin-4-yl | 2,5-dihydro-1H-pyrrol-1-yl | —CH2—CH3 | 815.4 | 7.24 |
| 4030 | 8-SMe, 2-ethoxy-quinolin-4-yl | pyrrolidin-1-yl | —CH2—CH3 | 817.4 | 7.25 |

TABLE 4-continued

| Cpd | R20 | N(R4)R6 | R1 | (MH)+ | $t_R$ (min) |
|---|---|---|---|---|---|
| 4031 | 8-methoxy-2-ethoxyquinolin-4-yl | N(CH3)2 | —CH2—CH3 | 775.4 | 4.99 |
| 4032 | 8-methoxy-2-ethoxyquinolin-4-yl | 2,5-dihydro-1H-pyrrol-1-yl | —CH2—CH3 | 799.4 | 5.26 |
| 4033 | 8-methoxy-2-ethoxyquinolin-4-yl | pyrrolidin-1-yl | —CH2—CH3 | 801.4 | 5.25 |
| 4034 | 7-methoxy-8-methyl-2-ethoxyquinolin-4-yl | N(CH3)2 | —CH2—CH3 | 789.4 | 5.74 |
| 4035 | 7-methoxy-8-methyl-2-ethoxyquinolin-4-yl | 2,5-dihydro-1H-pyrrol-1-yl | —CH2—CH3 | 813.4 | 5.97 |
| 4036 | 7-methoxy-8-methyl-2-ethoxyquinolin-4-yl | pyrrolidin-1-yl | —CH2—CH3 | 815.4 | 6.00 |

TABLE 4-continued

| Cpd | R20 | N(R4)R6 | R1 | (MH)+ | tR (min) |
|---|---|---|---|---|---|
| 4037 | MeO-, CH3, quinoline, OEt | N(OMe)(Me) | —CH=CH2 | 803.5 | 5.96 |
| 4038 | MeO-, Br, quinoline, OEt | N(OMe)(Me) | —CH=CH2 | 867, 869 | 6.82 |
| 4039 | Cl, quinoline, OEt | N(OMe)(Me) | —CH=CH2 | 793.4, 795.4 | 7.04 |
| 4040 | SMe, quinoline, OEt | N(OMe)(Me) | —CH=CH2 | 805.2 | 6.96 |
| 4041 | CH3, quinoline, OEt | N(OMe)(Me) | —CH=CH2 | 773.2 | 6.03 |
| 4042 | OMe, quinoline, OEt | N(OMe)(Me) | —CH=CH2 | 789.2 | 4.96 |

TABLE 4-continued
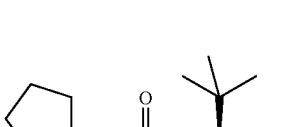
| Cpd | R[20] | N(R[4])R[6] | R[1] | (MH)+ | t_R (min) |
|---|---|---|---|---|---|
| 4043 | 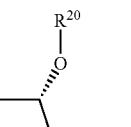 | 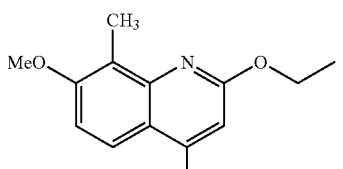 | —CH=CH₂ | 817.4 | 5.87 |
| 4044 | 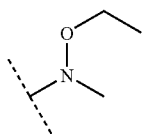 | 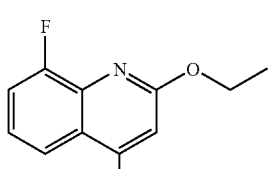 | —CH=CH₂ | 831.5 | 6.21 |
| 4045 | 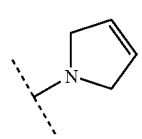 | 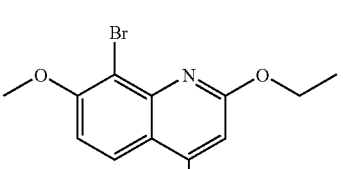 | —CH=CH₂ | | |
| 4046 | 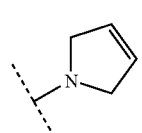 | 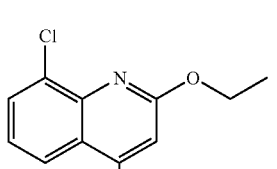 | —CH=CH₂ | | |
| 4047 | 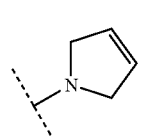 | 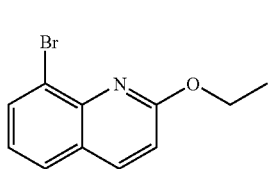 | —CH=CH₂ | | |
| 4048 | 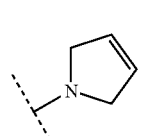 | | —CH=CH₂ | | |

TABLE 4-continued

| Cpd | R20 | N(R4)R6 | R1 | (MH)+ | tR (min) |
|---|---|---|---|---|---|
| 4049 | 8-Cl, 2-ethoxy-quinolin-4-yl | N(CH3)2 | —CH=CH2 | | |
| 4050 | 8-Br, 7-methoxy, 2-ethoxy-quinolin-4-yl | N(CH3)2 | —CH2—CH3 | | |
| 4051 | 8-methyl, 2-ethoxy-quinolin-4-yl | N(CH3)2 | —CH=CH2 | | |
| 4052 | 8-methyl, 2-ethoxy-quinolin-4-yl | N(CH3)2 | —CH2—CH3 | | |

TABLE 5

| Cpd | N(R⁴)R⁶ | (MH)⁺ | $t_R$ (min) |
|---|---|---|---|
| 5001 | N(CH₃)₂ | 662.3 | 6.69 |
| 5002 | NHCH₂Ph | 724.3 | 7.60 |
| 5003 | 4-methylpiperazin-1-yl | 717.4 | 5.30 |
| 5004 | NH-cyclopropyl | 674.4 | 7.06 |
| 5005 | 2,5-dihydro-1H-pyrrol-1-yl | 686.3 | 7.24 |
| 5006 | N(CH₃)CH₂CN | 687.3 | 7.13 |
| 5007 | N(CH₃)(n-propyl) | 690.4 | 7.48 |
| 5008 | 3-hydroxypyrrolidin-1-yl | 704.4 | 6.45 |
| 5009 | N(Et)(CH₂CH₂OH) | 706.4 | 6.67 |

TABLE 5-continued

| Cpd | N(R⁴)R⁶ | (MH)⁺ | $t_R$ (min) |
|---|---|---|---|
| 5010 | N(CH₃)CH₂Ph | 738 | 7.69 |
| 5011 | 3-carboxypiperidin-1-yl | 746.4 | 6.80 |
| 5012 | N(CH₃)Ph | 724.4 | 7.61 |
| 5013 | N(CH₃)(4-chlorophenyl) | 758.3 | 7.85 |
| 5014 | N(CH₃)(4-carboxyphenyl) | 768.4 | 6.72 |
| 5015 | pyrrolidin-1-yl | 688.4 | 6.36 |

TABLE 6
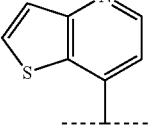
| Cpd | R<sup>20</sup> | N(R$^4$)R$^6$ | R$^1$ | (MH)$^+$ | $t_R$ (min) |
|---|---|---|---|---|---|
| 6001 |  | 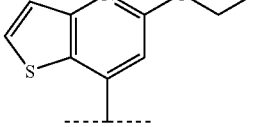 | —CH=CH$_2$ | 705.2 | 5.10 |
| 6002 |  | 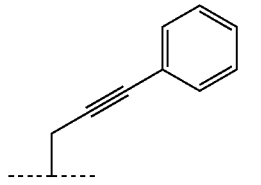 | —CH=CH$_2$ | 749.1 | 6.62 |
| 6003 |  | 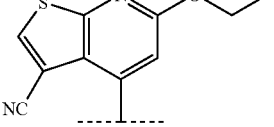 | —CH=CH$_2$ | 686.2 | 7.41 |
| 6004 |  | 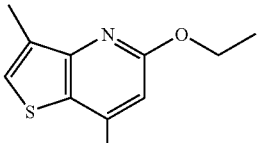 | —CH=CH$_2$ | 773.3 | 7.37 |
| 6005 |  | 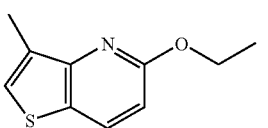 | —CH=CH$_2$ | 763.3 | 7.21 |
| 6006 | 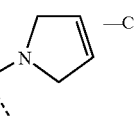 | 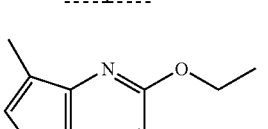 | —CH=CH$_2$ | 787.3 | 7.21 |
| 6007 | 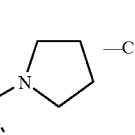 | | —CH=CH$_2$ | 789.3 | 7.23 |

TABLE 6-continued

| Cpd | R[20] | N(R[4])R[6] | R[1] | (MH)+ | t_R (min) |
|---|---|---|---|---|---|
| 6008 | | | —CH=CH₂ | 855.3 | 6.96 |
| 6009 | | | —CH=CH₂ | 777.3 | 7.24 |
| 6010 | | | —CH=CH₂ | 775.4 | 7.39 |
| 6011 | | | —CH=CH₂ | 827.4 | 6.48 |
| 6012 | | | —CH=CH₂ | 793.3 | 7.8 |

What is claimed is:
1. A compound of formula I:

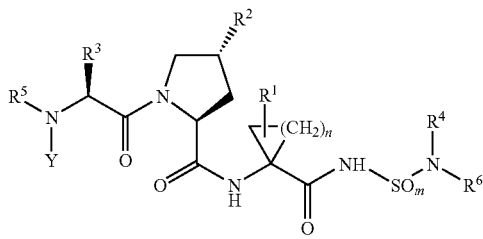

wherein
n is 1;
m is 2;
$R^1$ is ethyl or vinyl;
$R^2$ is selected from $—CH_2—R^{20}$, $—NH—R^{20}$, $—O—R^{20}$, and $—O—X—R^{20}$, wherein
X is $(C_{2-3})$alkenyl, $(C_{2-3})$alkynyl, or $(C_{1-3})$alkyl; and
$R^{20}$ is ($C_6$ or $C_{10}$)aryl or Het, wherein said ($C_6$ or $C_{10}$) aryl or Het is optionally substituted with $R^{200}$; wherein
$R^{200}$ is one to four substituents each independently selected from H, halogen, cyano, $(C_{1-6})$alkyl, $(C_{3-7})$cycloalkyl, aryl-$(C_{1-6})$alkyl-, aryl, oxo, thioxo, $—OR^{201}$, $—SR^{201}$, $—SOR^{201}$, $—SO_2R^{201}$, $—N(R^{202})R^{201}$, and $—CON(R^{202})R^{201}$; wherein each of said alkyl, cycloalkyl, and aryl is optionally further substituted with $R^{2000}$;
$R^{201}$ in each case is independently selected from H, $(C_{1-6})$alkyl, $(C_{2-6})$alkenyl, and aryl, wherein each of said alkyl and aryl is optionally further substituted with $R^{2000}$;
$R^{202}$ in each case is independently selected from H and $(C_{1-6})$alkyl;
$R^{2000}$ in each case is one to three substituents each independently selected from halogen, aryl, Het, $—OR^{2001}$, cyano, $—N(R^{2002})(R^{2001})$, and $R^{2003}$, wherein said aryl and Het are optionally substituted with one, two or three substituents each independently selected from $(C_{1-6})$alkyl and $—O—(C_{1-6})$alkyl;
$R^{2001}$ in each case is independently selected from aryl, aryl-$(C_{1-6})$alkyl-, $—C(O)—R^{2003}$, $—C(O)O—R^{2003}$;
$R^{2002}$ in each case is independently selected from H and $(C_{1-6})$alkyl;
$R^{2003}$ in each case is independently selected from $(C_{1-8})$alkyl, and $(C_{3-7})$cycloalkyl;
$R^3$ is $(C_{1-8})$alkyl or $(C_{3-7})$cycloalkyl, each optionally substituted with one substituent selected from, $—OR^{30}$, $—C(=O)OR^{30}$, wherein $R^{30}$ is H, $(C_{1-6})$alkyl, aryl, or aryl$(C_{1-6})$alkyl-;
$R^5$ is selected from $B—C(=O)—$, $B—O—C(=O)—$, and $B—N(R^{51})—C(=O)—$; wherein B is selected from:
(i) $(C_{1-10})$alkyl optionally substituted with one or more substituents each selected independently from $—COOH$, $—COO(C_{1-6})$alkyl, $—OH$, halogen, $—OC(=O)(C_{1-6})$alkyl, $—O(C_{1-6})$alkyl, $—NH_2$, $—NH(C_{1-6})$alkyl, $—N((C_{1-6})$alkyl$)_2$, $—C(=O)NH_2$, $—C(=O)NH(C_{1-6})$alkyl and $—C(=O)N((C_{1-6})$alkyl$)_2$;
(ii) $(C_{3-7})$cycloalkyl, or $(C_{3-7})$cycloalkyl-$(C_{1-4}$alkyl-, each optionally substituted with one or more substituents each selected independently from $(C_{1-6})$alkyl, halogen, $—COOH$, $—COO(C_{1-6})$alkyl, $—OH$, $—O(C_{1-6})$alkyl, $—NH_2$, $—NH(C_{1-6})$alkyl, $—N((C_{1-6})$alkyl$)_2$, $—C(=O)NH_2$, $—C(=O)NH(C_{1-6})$alkyl and $—C(=O)N((C_{1-6})$alkyl$)_2$;
$R^{51}$ is selected from H and $(C_{1-6})$alkyl;
provided that B is not $(C_{1-10})$alkyl unsubstituted or $(C_{1-10})$alkyl substituted with halogen when $R^5$ is $B—O—C(=O)—$;
Y is H;
$R^4$ and $R^6$ are each independently selected from H, $(C_{1-6})$alkyl, $—O—(C_{1-6})$alkyl, $(C_{3-7})$cycloalkyl, $(C_{3-7})$cycloalkyl-$(C_{1-6})$alkyl-, aryl, Het, and aryl-$(C_{1-6})$alkyl-; wherein said $(C_{1-6})$alkyl, $—O—(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one or more substituents each independently selected from halogen, $(C_{1-6})$alkyl, hydroxy, cyano, $O—(C_{1-6})$alkyl, $—NH_2$, $—NH(C_{1-4}$alkyl), $—N((C_{1-4}$alkyl$)_2$, $—COOH$, and $—COO(C_{1-6})$alkyl; or
$R^4$ and $R^6$ are linked, together with the nitrogen to which they are bonded, to form a 3- to 7-membered monocyclic saturated or unsaturated heterocycle optionally fused to at least one other cycle to form a heteropolycycle, each of said heterocycle and heteropolycycle optionally containing from one to three additional heteroatoms each independently selected from N, S and O, and each of said heterocycle and heteropolycycle being optionally substituted with one or more substituents each independently selected from halogen, $(C_{1-6})$alkyl, hydroxy, cyano, $O—(C_{1-6})$alkyl, $—NH_2$, $—NH(C_{1-4}$alkyl), $—N((C_{1-4}$alkyl$)_2$, $—CO—NH_2$, $—CO—NH(C_{1-4})$alkyl, $—CO—N((C_{1-4}$alkyl$)_2$, $—COOH$, and $—COO(C_{1-6})$alkyl;
wherein Het is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;
or a diastereomer thereof or a salt thereof.

2. The compound according to claim 1 wherein
n is 1;
m is 2;
$R^1$ is ethyl or vinyl;
$R^2$ is selected from $—CH_2—R^{20}$, $—NH—R^{20}$, $—O—R^{20}$, and $—O—X—R^{20}$, wherein
X is $(C_{2-3})$alkynyl, or $(C_{1-3})$alkyl; and
$R^{20}$ is ($C_6$ or $C_{10}$)aryl or Het, wherein said ($C_6$ or $C_{10}$) aryl or Het is optionally substituted with $R^{200}$; wherein
$R^{200}$ is one to four substituents each independently selected from H, halogen, cyano, $(C_{1-6})$alkyl, $(C_{3-7})$cycloalkyl, aryl-$(C_{1-6})$alkyl-, aryl, oxo, thioxo, $—OR^{201}$, $—SR^{201}$, $—SOR^{201}$, $—SO_2R^{201}$, $—N(R^{202})R^{201}$, and $—CON(R^{202})R^{201}$; wherein each of said alkyl, cycloalkyl, and aryl is optionally further substituted with $R^{2000}$;
$R^{201}$ in each case is independently selected from H, $(C_{1-6})$alkyl, $(C_{2-6})$alkenyl, and aryl, wherein each of said alkyl and aryl is optionally further substituted with $R^{2000}$;
$R^{202}$ in each case is independently selected from H and $(C_{1-6})$alkyl;
$R^{2000}$ in each case is one to three substituents each independently selected from halogen, aryl, Het, —OR$^{2001}$, cyano, —N(R$^{2002}$)(R$^{2001}$), and R$^{2003}$, wherein said aryl and Het are optionally substituted with one, two or three substituents each independently selected from (C$_{1-6}$)alkyl and —O—(C$_{1-6}$) alkyl;

R$^{2001}$ in each case is independently selected from aryl, aryl-(C$_{1-6}$)alkyl-, —C(O)—R$^{2003}$;

R$^{2002}$ in each case is independently selected from H and (C$_{1-6}$)alkyl;

R$^{2003}$ in each case is independently selected from (C$_{1-8}$)alkyl and (C$_{3-7}$)cycloalkyl;

R$^3$ is (C$_{1-8}$)alkyl, or (C$_{3-7}$)cycloalkyl

R$^5$ is selected from B—C(=O)—, B—O—C(=O)—, and B—N(R$^{51}$)—C(=O)— wherein B is selected from:
(i) (C$_{1-10}$)alkyl optionally substituted with one or more substituents each selected independently from —COOH, —COO(C$_{1-6}$)alkyl, —OH, halogen, —OC(=O)(C$_{1-6}$)alkyl, —O(C$_{1-6}$)alkyl, —NH$_2$, —NH(C$_{1-6}$)alkyl, —N((C$_{1-6}$)alkyl)$_2$, —C(=O)NH$_2$, —C(=O)NH(C$_{1-6}$)alkyl and —C(=O)N((C$_{1-6}$)alkyl)$_2$;
(ii) (C$_{3-7}$)cycloalkyl, or (C$_{3-7}$)cycloalkyl-(C$_{1-4}$alkyl-, each optionally substituted with one or more substituents each selected independently from (C$_{1-6}$)alkyl, halogen, —COOH, —COO(C$_{1-6}$)alkyl, —OH, —O(C$_{1-6}$)alkyl, —NH$_2$, —NH(C$_{1-6}$alkyl, —N((C$_{1-6}$alkyl)$_2$, —C(=O)NH$_2$, —C(=O)NH(C$_{1-6}$)alkyl and —C(=O)N((C$_{1-6}$)alkyl)$_2$;

R$^{51}$ is H;

provided that B is not (C$_{1-10}$)alkyl unsubstituted or (C$_{1-10}$) alkyl substituted with halogen when R$^5$ is B—O—C(=O)—;

Y is H;

R$^4$ and R$^6$ are each independently selected from H, (C$_{1-6}$) alkyl, —O—(C$_{1-6}$)alkyl, (C$_{3-7}$)cycloalkyl, (C$_{3-7}$)cycloalkyl-(C$_{1-6}$)alkyl-, aryl, Het, and aryl-(C$_{1-6}$)alkyl-; wherein said (C$_{1-6}$)alkyl, —O—(C$_{1-6}$)alkyl, (C$_{3-7}$)cycloalkyl, (C$_{3-7}$)cycloalkyl-(C$_{1-6}$)alkyl-, aryl and aryl-(C$_{1-6}$)alkyl- are each optionally substituted with one or more substituents each independently selected from halogen, (C$_{1-6}$)alkyl, hydroxy, cyano, O—(C$_{1-6}$)alkyl, —NH$_2$, —NH(C$_{1-4}$alkyl, —N((C$_{1-4}$alkyl)$_2$ and —COOH, or R$^4$ and R$^6$ are linked, together with the nitrogen to which they are bonded, to form a 3- to 7-membered monocyclic saturated or unsaturated heterocycle optionally fused to at least one other cycle to form a heteropolycycle, each of said heterocycle and heteropolycycle optionally containing from one to three additional heteroatoms each independently selected from N, S and O, and each of said heterocycle and heteropolycycle being optionally substituted with one or more substituents each independently selected from halogen, (C$_{1-6}$)alkyl, hydroxy, cyano, O—(C$_{1-6}$)alkyl, —NH$_2$, —NH(C$_{1-4}$alkyl, —N((C$_{1-4}$alkyl)$_2$, —CO—NH$_2$, —CO—NH(C$_{1-4}$) alkyl, —CO—N((C$_{1-4}$alkyl)$_2$, —COOH, and —COO(C$_{1-6}$)alkyl;

wherein Het is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;

or a diastereomer thereof or a salt thereof.

3. The compound according to claim 1 wherein R$^5$ is selected from B—O—C(=O)—, and B—N(R$^{51}$)—C(=O)—; wherein B and R$^{51}$ are defined as in claim 1, provided that B is not (C$_{1-10}$)alkyl unsubstituted or (C$_{1-10}$)alkyl substituted with halogen when R$^5$ is B—O—C(=O)—.

4. The compound according to claim 3 wherein R$^{51}$ is H and B is selected from:
(i) (C$_{1-7}$)alkyl optionally substituted with one or two or three substituents each independently selected from fluoro, chloro, bromo, hydroxy, methoxy and ethoxy; or optionally substituted with —COOCH$_3$;
(ii) (C$_{3-7}$)cycloalkyl, or (C$_{3-7}$)cycloalkyl-methyl-, each optionally substituted with one or two substituents each independently selected from methyl, ethyl, hydroxy, methoxy and ethoxy;

provided that B is not (C$_{1-7}$)alkyl unsubstituted or (C$_{1-7}$) alkyl substituted with halogen when R$^5$ is B—O—C(=O)—.

5. The compound according to claim 1 wherein Y is H.

6. The compound according to claim 1 wherein R$^3$ is tert-butyl.

7. The compound according to claim 1 wherein R$^2$ is selected from —O—R$^{20}$ and —O—X—R$^{20}$, wherein R$^{20}$ and X are defined as in claim 1.

8. The compound according to claim 7 wherein R$^2$ is —O—X—R$^{20}$, wherein X is (C$_3$)alkynyl and R$^{20}$ is (C$_6$ or C$_{10}$)aryl.

9. The compound according to claim 7 wherein R$^2$ is —O—R$^{20}$, wherein R$^{20}$ is

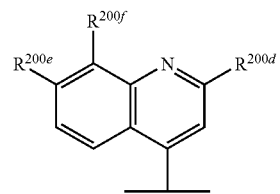

wherein
R$^{200d}$ is —OR$^{201}$, wherein R$^{201}$ is (C$_{1-6}$)alkyl;
R$^{200e}$ is H or —OR$^{201}$, wherein R$^{201}$ is (C$_{1-6}$)alkyl; and
R$^{200f}$ is (C$_{1-6}$)alkyl, halogen, —SR$^{201}$, —SO$_2$R$^{201}$, or —OR$^{201}$, wherein R$^{201}$ is (C$_{1-6}$)alkyl optionally further substituted with (C$_{3-7}$)cycloalkyl or phenyl.

10. The compound according to claim 9 wherein R$^{200d}$ is —OR$^{201}$ wherein R$^{201}$ is ethyl.

11. The compound according to claim 7 wherein R$^2$ is —O—R$^{20}$, wherein R$^{20}$ is

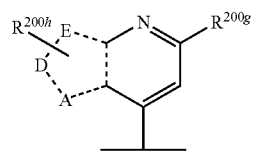

wherein
one of A, D, and E represents a S atom and the other two of A, D, and E represent C atoms;
— represents a single bond between a C atom and an S atom, and represents a single bond or a double bond between two C atoms; provided that each C atom is bonded by one double bond;

$R^{200g}$ is H or —$OR^{201}$, wherein $R^{201}$ is $(C_{1-6})$alkyl or $(C_{2-6})$alkenyl; and $R^{200h}$ is one or two substituents each independently selected from H, cyano, $(C_{1-6})$alkyl and —$SO_2$—$(C_{1-6})$alkyl; wherein each $R^{200h}$ is bonded to a C atom which would otherwise bear a hydrogen atom.

12. The compound according to claim 1 wherein n is 1.

13. The compound according to claim 1 wherein $R^1$ is vinyl.

14. The compound according to claim 1 wherein:
(i) $R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one to three substituents each independently selected from halogen, $(C_{1-6})$alkyl, hydroxy, cyano, O—$(C_{1-6})$alkyl, and —COOH; or
(ii) $R^4$ and $R^6$ are linked, together with the nitrogen to which they are bonded, to form a 3- to 7-membered monocyclic saturated or unsaturated heterocycle, said heterocycle optionally containing from one to three additional heteroatoms each independently selected from N, S and O, and said 3- to 7-membered monocyclic saturated or unsaturated heterocycle being optionally substituted with one to three substituents each independently selected from halogen, $(C_{1-6})$alkyl, hydroxy, cyano, O—$(C_{1-6})$alkyl, —$NH_2$, —$NH(C_{1-4}$alkyl), —$N((C_{1-4}$alkyl$)_2)$, —COOH, and COO$(C_{1-6})$alkyl.

15. The compound according to claim 1 wherein:
n is 1;
m is 2;
$R^1$ is ethyl or vinyl;
$R^2$ is selected from —O—$R^{20}$ and —O—X—$R^{20}$, wherein X is $(C_{2-3})$alkenyl, $(C_{2-3})$alkynyl, or $(C_{1-3})$alkyl; and
$R^{20}$ is $(C_6$ or $C_{10})$aryl or Het, wherein said $(C_6$ or $C_{10})$aryl or Het is optionally mono-, di-, tri- or tetra-substituted with $R^{200}$, wherein each $R^{200}$ is independently selected from H, halogen, cyano, $(C_{1-6})$alkyl, $(C_{3-7})$cycloalkyl, aryl-$(C_{1-6})$alkyl-, aryl, oxo, thioxo, —$OR^{201}$, —$SR^{201}$, —$SOR^{201}$, —$SO_2R^{201}$, —$N(R^{202})R^{201}$, and —$CON(R^{202})R^{201}$; wherein each of said alkyl, cycloalkyl, and aryl is optionally further substituted with $R^{2000}$;
$R^{201}$ in each case is independently selected from H, $(C_{1-6})$alkyl and aryl, wherein each of said alkyl and aryl is optionally further substituted with $R^{2000}$;
$R^{202}$ is H or $(C_{1-6})$alkyl;
$R^{2000}$ is one to three substituents each independently selected from halogen, aryl, Het, —$OR^{2001}$, cyano, —$N(R^{2002})(R^{2001})$, and $R^{2003}$, wherein said aryl and Het are optionally substituted with one, two or three substituents selected from $(C_{1-6})$alkyl and —O—$(C_{1-6})$alkyl;
$R^{2001}$ in each case is independently selected from aryl, aryl-$(C_{1-6})$alkyl-, —C(O)—$R^{2003}$,
$R^{2002}$ is H or $(C_{1-6})$alkyl;
$R^{2003}$ is $(C_{1-8})$alkyl and $(C_{3-7})$cycloalkyl;
$R^3$ is $(C_{1-8})$alkyl;
$R^5$ is selected from B—O—C(=O)—; and B—N($R^{51}$)—C(=O)—; wherein B is selected from:
(i) $(C_{1-10})$alkyl optionally substituted with one or more substituents each selected independently from —COOH, —OH, halogen, —$NH_2$, —$NH(C_{1-6})$alkyl, —$N((C_{1-6})$alkyl$)_2$, (ii) $(C_{3-7})$cycloalkyl, optionally substituted with one or more substituents each selected independently from $(C_{1-6})$alkyl, halogen, —COOH, —COO$(C_{1-6})$alkyl, —OH, —O$(C_{1-6})$alkyl, —$NH_2$, —$NH(C_{1-6})$alkyl, —$N((C_{1-6})$alkyl$)_2$, $R^{51}$ is selected from H and $(C_{1-6})$alkyl;
provided that B is not $(C_{1-10})$alkyl unsubstituted or $(C_{1-10})$alkyl substituted with halogen,
when $R^5$ is B—O—C(=O)—;
Y is H;
$R^4$ and $R^6$ are each independently selected from H, $(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are optionally substituted with one or more substituents independently selected from halogen, $(C_{1-6})$alkyl, hydroxy, cyano, O—$(C_{1-6})$alkyl, —$NH_2$, —$NH(C_{1-4}$alkyl), —$N((C_{1-4}$alkyl$)_2)$, —COOH, and —COO$(C_{1-6})$alkyl; or $R^4$ and $R^6$ are linked, together with the nitrogen to which they are bonded, to form a 3- to 7-membered monocyclic saturated or unsaturated heterocycle optionally fused to at least one other cycle to form a heteropolycycle, said heterocycle and heteropolycycle optionally containing from one to three further heteroatoms independently selected from N, S and O, and said 3- to 7-membered monocyclic saturated or unsaturated heterocycle being optionally substituted with one or more substituents independently selected from halogen, $(C_{1-6})$alkyl, hydroxy, cyano, O—$(C_{1-6})$alkyl, —$NH_2$, —$NH(C_{1-4}$alkyl), —$N((C_{1-4}$alkyl$)_2)$, —CO—$NH_2$, —CO—$NH(C_{1-4})$alkyl, —CO—$N((C_{1-4}$alkyl$)_2)$, —COOH, and —COO$(C_{1-6})$alkyl;

wherein Het is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, said heteropolycycle being saturated, unsaturated or aromatic;
or a diastereomer thereof or a salt thereof.

16. The compound according to claim 1 wherein:
$R^5$ is B—O—C(=O)—; wherein B is selected from:
(i) $(C_{1-10})$alkyl optionally substituted with one or more substituents each selected independently from —COOH, —COO$(C_{1-6})$alkyl, —OH, halogen, —OC(=O)$(C_{1-6})$alkyl, —O$(C_{1-6})$alkyl, —$NH_2$, —$NH(C_{1-6})$alkyl, —$N((C_{1-6})$alkyl$)_2$,
(ii) $(C_{3-7})$cycloalkyl, or $(C_{3-7})$cycloalkyl-$(C_{1-4}$alkyl-,
provided that B is not $(C_{1-10})$alkyl unsubstituted or $(C_{1-10})$alkyl substituted with halogen,
when $R^5$ is B—O—C(=O)—;
Y is H;
$R^3$ is tert-butyl;
$R^2$ is —O—X—$R^{20}$, wherein X is $(C_3)$alkynyl and $R^{20}$ is $(C_6$ or $C_{10})$aryl; or $R^2$ is —O—$R^{20}$ wherein $R^{20}$ is

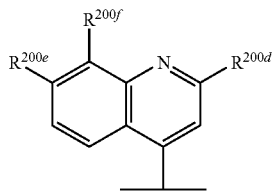

wherein
$R^{200d}$ is —$OR^{201}$, wherein $R^{201}$ is $(C_{1-6})$alkyl;
$R^{200e}$ is H or —$OR^{201}$, wherein $R^{201}$ is $(C_{1-6})$alkyl; and
$R^{200f}$ is $(C_{1-6})$alkyl, halogen, —$SR^{201}$, —$SO_2R^{201}$, or —$OR^{201}$, wherein $R^{201}$ is $(C_{1-6})$alkyl optionally further substituted with $(C_{3-7})$cycloalkyl or phenyl;
or $R^{20}$ is

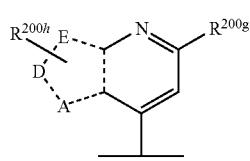

wherein
one of A, D, and E represents a S atom and the other two of A, D, and E represent C atoms;
— represents a single bond between a C atom and an S atom, and represents a single bond or a double bond between two C atoms; provided that each C atom is bonded by one double bond;
$R^{200g}$ is H or —$OR^{201}$, wherein $R^{201}$ is $(C_{1-6})$alkyl or $(C_{2-6})$alkenyl; and
$R^{200h}$ is one or two substituents each independently selected from H, cyano, $(C_{1-6})$alkyl and —$SO_2$—$(C_{1-6})$alkyl; wherein each $R^{200h}$ is bonded to a C atom which would otherwise bear a hydrogen atom;
$R^1$ is ethyl or vinyl;
n is 1;
m is 2; and
$R^4$ and $R^6$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein said $(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are optionally substituted with one to three substituents independently selected from halogen, $(C_{1-6})$alkyl, hydroxy, cyano, O—$(C_{1-6})$alkyl, —COOH, and —COO$(C_{1-6})$alkyl; or $R^4$ and $R^6$ are linked, together with the nitrogen to which they are bonded, to form a 3- to 7-membered monocyclic saturated or unsaturated heterocycle, said heterocycle optionally containing from one to three further heteroatoms each independently selected from N, S and O, and said 3- to 7-membered monocyclic saturated or unsaturated heterocycle being optionally substituted with one to three substituents each independently selected from halogen, $(C_{1-6})$alkyl, hydroxy, cyano, O—$(C_{1-6})$alkyl, —$NH_2$, —$NH(C_{1-4}$alkyl), —$N((C_{1-4}$alkyl)$_2$), —COOH, and —COO$(C_{1-6})$alkyl;
or a diastereomer thereof or a salt thereof.

17. A pharmaceutical composition comprising an anti-hepatitis C virally effective amount of a compound according to claim 1, or a pharmaceutically acceptable salt thereof; and a pharmaceutically acceptable carrier medium or auxiliary agent.

18. The pharmaceutical composition according to claim 17 additionally comprising a therapeutically effective amount of at least one other antiviral agent.

19. A method of treating a hepatitis C viral infection in a mammal comprising administering to the mammal an anti-hepatitis C virally effective amount of a compound according to claim 1, or a pharmaceutically acceptable salt thereof, or a pharmaceutical composition comprising said compound or pharmaceutically acceptable salt thereof; and a pharmaceutically acceptable carrier medium or auxiliary agent.

20. A method of inhibiting the replication of hepatitis C virus by exposing the virus to a hepatitis C viral NS3 protease inhibiting amount of the compound according to claim 1, or a pharmaceutically acceptable salt thereof.

21. An article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound according to claim 1 or a pharmaceutically acceptable salt thereof, and a pharmaceutically acceptable carrier medium or auxiliary agent.

22. A process for the preparation of a compound according to claim 1, comprising:
a) reacting a compound of formula (II):

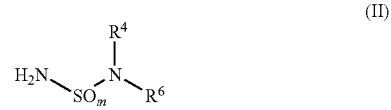

(II)

wherein $R^4$, $R^6$ and m are defined as in claim 1, with a strong base so as to form the corresponding amide anion and b) reacting an azalactone of formula (III):
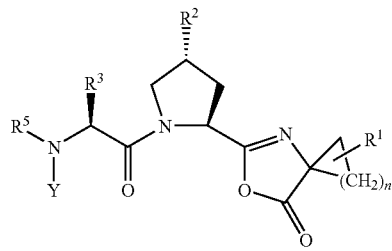
(III)
wherein $R^1$, $R^2$, $R^3$, $R^5$, Y and n are defined as in claim 1, with the amide anion formed in step a).
23. An azalactone intermediate compound of formula (III):
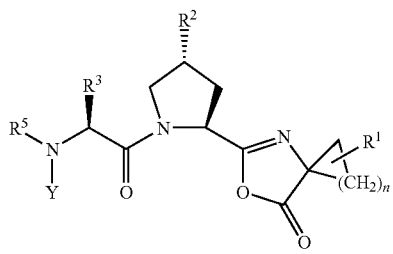
(III)
wherein $R^1$, $R^2$, $R^3$, $R^5$, Y and n are defined as in claim 1.
* * * * *